United States Patent [19]

Farge et al.

[11] 4,365,062
[45] Dec. 21, 1982

[54] CEPHALOSPORIN DERIVATIVES

[75] Inventors: Daniel Farge, Thiais; Claude Moutonnier, Le Plessis Robinson; Pierre Le Roy, Thiais; Jean-Francois Peyronel, Palaisseau, all of France

[73] Assignee: Rhone-Poulenc Industries, France

[21] Appl. No.: 152,153

[22] Filed: May 21, 1980

[30] Foreign Application Priority Data

May 23, 1979 [FR] France .................. 79 13097

[51] Int. Cl.³ .................................. C07D 501/24
[52] U.S. Cl. ............................ 544/22; 544/22; 544/30
[58] Field of Search ......................... 544/16, 22

[56] References Cited

U.S. PATENT DOCUMENTS 3,674,784   7/1972   Webber ........................ 544/22
3,769,277  10/1973   Long et al. .................... 544/16
3,823,139   7/1974   Underwood .................... 544/16
4,248,868   2/1981   Scartazzini et al. ............ 544/16

FOREIGN PATENT DOCUMENTS 1551075   8/1979   United Kingdom .

*Primary Examiner*—Paul M. Coughlan, Jr.
*Attorney, Agent, or Firm*—Stevens, Davis, Miller & Mosher

[57] ABSTRACT

New cephalosporins of the formula:

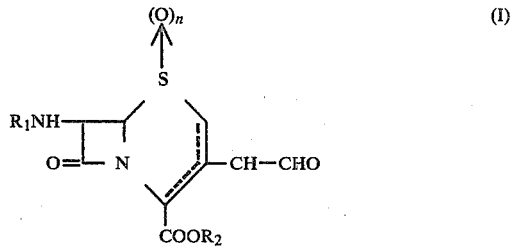

in which $n=0$ or 1, $R_1$ is a radical of the formula:

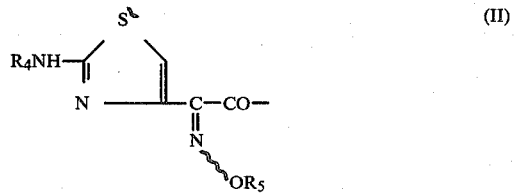

[in which $R_4$ is a protective radical and $R_5$ is hydrogen, alkyl, vinyl, cyanomethyl or a protective radical], or $R_1$ is a protective radical and $R_2$ is a protective radical or an enzymatically removable radical, or $R_1$ is an acyl radical which may be substituted in various ways and $R_2$ is a protective radical, in the 3-oxoethyl-bicyclooct-2-ene or -bicyclooct-3-ene or 3-oxoethylidene-bicyclooctane form if $n=0$, and in the 3-oxoethyl-bicyclooct-2-ene or 3-oxoethylidene-bicyclooctane form if $n=1$, are useful as intermediates for the preparation of 3-thiovinyl-cephalosporins useful as antibacterial agents.

10 Claims, No Drawings

CEPHALOSPORIN DERIVATIVES

The present invention relates to novel cephalosporins of the general formula

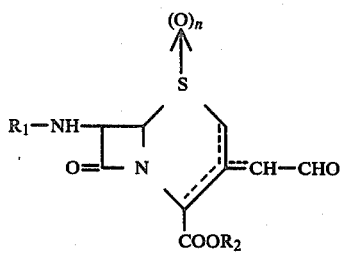

and to their preparation.

The product of the general formula (I), in which n is 0 or 1, is in the 3-oxoethyl-bicyclooct-2-ene or -bicyclooct-3-ene form or 3-oxoethylidene-bicyclooctane form if n=0, and in the 3-oxoethyl-bicyclooct-2-ene or 3-oxoethylidene-bicyclooctane form if n=1 (according to the Chemical Abstracts nomenclature) and (a) the symbol $R_1$ represents a radical of the general formula:

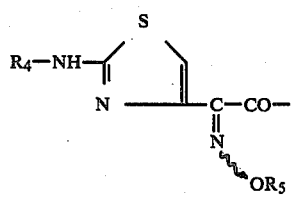

[in which $R_4$ is a protective radical (chosen from amongst tert.-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl) and $R_5$ is a hydrogen atom, an alkyl, vinyl or cyanomethyl radical or a protective group such as trityl, tetrahydropyranyl or 2-methoxy-prop-2-yl], a benzhydryl or trityl radical an acyl radical of the general formula

(in which $R_6$ is a hydrogen atom or an alkyl radical [which is optionally substituted by one or more halogen atoms or by a phenyl or phenoxy radical] or phenyl), a radical of the general formula

(in which $R_7$ is a branched unsubstituted alkyl radical or a branched or straight alkyl radical carrying one or more substituents [chosen from amongst halogen atoms and trialkylsilyl, phenyl, and phenyl substituted by one or more alkoxy, nitro or phenyl, radicals], vinyl, allyl or quinolyl) or a nitrophenylthio radical, or $R_1NH$— is replaced by a methyleneimino radical, in which the methylene radical is substituted by a dialkylamino group or aryl group (itself optionally substituted by one or more methoxy or nitro radicals) and the symbol $R_2$ represents an enzymatically easily removable radical of the general formula

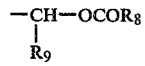

[in which $R_8$ represents an alkyl radical or the cyclohexyl radical and $R_9$ represents a hydrogen atom or an alkyl radical] or a protective radical chosen from amongst methoxymethyl, tert.-butyl, benzhydryl, p-nitrobenzyl or p-methoxybenzyl, or (b) the symbol $R_1$ represents an alkanoyl radical containing 1 to 8 carbon atoms, an alkanoyl radican containing 2 to 8 carbon atoms (substituted by chlorine or bromine atoms), an acyl radical of the general formula

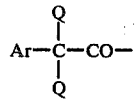

(in which each Q is H or methyl and Ar represents a thien-2-yl, thien-3-yl, fur-2-yl, fur-3-yl, pyrrol-2-yl or pyrrol-3-yl radical or a phenyl radical [optionally substituted by halogen atoms or by hydroxyl, alkyl (containing 1 to 3 carbon atoms) or alkoxy (containing 1 to 3 carbon atoms) radicals, of which at least one is situated in the meta- or in the para-position of the phenyl radical], an acyl radical of the general formula

in which X is oxygen or sulphur and Ar is defined as above or X represents sulphur and Ar represents pyrid-4-yl, an acyl radical corresponding to the general formula

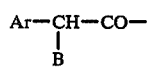

in which Ar is defined as above and B represents an amino radical which is protected [by a benzyloxycarbonyl, alkoxycarbonyl, cyclopentyloxycarbonyl, cyclohexyloxycarbonyl, benzhydryloxycarbonyl, trityl or 2,2,2-trichloro-ethoxycarbonyl group], a sulpho radical, a hydroxyl or carboxyl radical [optionally protected by esterification, respectively with an alkanoic acid or an alcohol (containing 1 to 6 carbon atoms)], or a 5-aminoadipyl radical [in which the amino group is protected by an alkanoyl radical (containing 1 to 3 carbon atoms and optionally substituted by a chlorine atom) and in which the carboxyl group is protected by a benzhydryl, 2,2,2-trichloroethyl, tert.-alkyl (containing 4 to 6 carbon atoms) or nitrobenzyl group], or $R_1NH$— is replaced by a cyclic imide group of a dicarboxylic acid, and the symbol $R_2$ represents a tert.-alkyl radical containing 4 to 6 carbon atoms, a tert.-alkenyl radical containing 6 or 7 carbon atoms, a tert.-alkynyl radical containing 6 or 7 carbon atoms, or a benzyl, methoxybenzyl, nitrobenzyl, 2,2,2-trichloroethyl, benzhydryl, succinimidomethyl or phthalimidomethyl radical.

It is to be understood that the alkyl or acyl portions or radicals which have been referred to above (or which will be referred to later) are (unless stated to the contrary) straight or branched and contain 1 to 4 carbon atoms.

It is also to be understood that the mixtures of the 3-oxoethyl-bicyclooct-2-ene and -bicyclooct-3-ene and 3-oxoethylidene-bicyclooctane isomers fall within the scope of the present invention.

Furthermore, it is to be understood that the —OR$_5$ group of the radical of the general formula (II) can be in the syn- or anti-position and that these isomers and their mixtures also fall within the scope of the present invention.

The syn-form can be represented by the formula

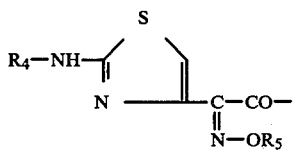
(IIa)

The anti-form can be represented by the formula

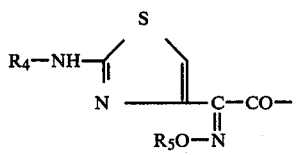
(IIb)

Amongst the meanings of R$_1$ defined above, the following may be mentioned especially: 2-methoxyimino-2-(2-tritylamino-thiazol-4-yl)-acetyl, 2-methoxyimino-2-(2-tert.-butoxycarbonylamino-thiazol-4-yl)-acetyl, 2-trityloxyimino-2-(2-tritylamino-thiazol-4-yl)-acetyl, 2-tetrahydropyranyloxyimino-2-(2-tritylamino-thiazol-4-yl)-acetyl, trityl, formyl, acetyl, chloroacetyl, trichloroacetyl, phenylacetyl, phenoxyacetyl, benzoyl, tert.-butoxycarbonyl, 2-chloro-1,1-dimethyl-ethoxycarbonyl, 2,2,2-trichloro-ethoxycarbonyl, 2,2,2-trichloro-1,1-dimethyl-ethoxycarbonyl, 2-cyano-1,1-dimethyl-ethoxycarbonyl, 2-trimethylsilyl-ethoxycarbonyl, benzyloxy-carbonyl, p-methoxybenzyloxycarbonyl, 3,5-dimethoxy-benzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio and p-nitrophenylthio.

As examples of methyleneimino radicals there may be mentioned: dimethylaminomethyleneimino, 3,4-dimethoxybenzylideneimino and 4-nitrobenzylideneimino.

I. According to the invention, the products of the general formula (I) for which n=0 can be obtained by hydrolysis of an enamine of the general formula:

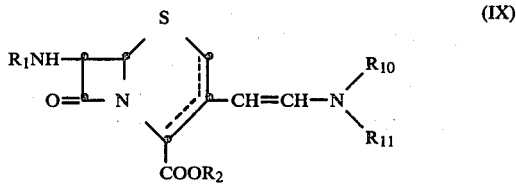
(IX)

(or of a mixture of its isomers), in which R$_1$ and R$_2$ are defined as above and R$_{10}$ and R$_{11}$, which are identical or different, represent alkyl radicals (optionally substituted by a hydroxyl, alkoxy, amino, alkylamino or dialkylamino radical) or phenyl radicals or form, together with the nitrogen atom to which they are attached, a saturated heterocyclic ring with 5 or 6 members, which optionally contains another hetero-atom chosen from amongst nitrogen, oxygen or sulphur, and which is optionally substituted by an alkyl radical, it being understood that the enamine of the general formula (IX) is in the bicyclooct-2-ene or bicyclooct-3-ene form and that the substituent on the carbon atom in the 3-position of the bicyclooctene exhibits the cis- or trans-stereoisomeric configuration.

In the text which follows, the trans-stereoisomeric configuration will be designated E and the cis-stereoisomeric configuration will be designated Z.

Preferably, an enamine of the general formula (IX), in which R$_{10}$ and R$_{11}$ represent a methyl radical, is hydrolysed.

In general, the process is carried out in an organic acid (for example formic acid or acetic acid) or an inorganic acid (for example hydrochloric acid or sulphuric acid) in the presence or absence of a solvent, in an aqueous or organic medium, at a temperature of between −20° C. and the reflux temperature of the reaction mixture, after which, where appropriate, the mixture is treated with an inorganic base (an alkali metal bicarbonate) or an organic base (a tertiary amine or pyridine).

If the reaction is carried out in an organic medium, the hydrolysis is effected by addition of water to the reaction mixture; if it is carried out in the presence of a solvent, it is not necessary that the solvent should be miscible with the acid aqueous phase; where it is not, contact is achieved by vigorous stirring.

Amongst the solvents which can be used, there may be mentioned the chlorinated solvents, ethyl acetate, tetrahydrofurane, acetonitrile, dimethylformamide and the alcohols.

Hydrolysis in an acid medium leads, where relevant, to addition salts of the products of the general formula (I) with the acids used, and these addition salts also form part of the invention.

2. According to the invention, the products of the general formula (I) for which n=1 can be obtained by oxidation of the products of the general formula (I) for which n=0 by any known method, in particular by application of the method described in German Patent Application No. 2,637,176.

The products of the general formula (IX) for which R$_{10}$ and R$_{11}$ have the definitions given above (except for representing alkyl substituted by hydroxyl, amino or alkylamino) can be obtained by the action of a product, optionally prepared in situ, of the general formula

(X)

{in which R$_{10}$ and R$_{11}$ are defined as above and R$_{12}$ and R$_{13}$, which are identical or different, represent either groups of the general formula

—X$_2$R$_{14}$ (XI)

(in which X$_2$ is an oxygen atom and R$_{14}$ represents an alkyl or phenyl radical), or one of R$_{12}$ and R$_{13}$ represents a radical of the general formula (XI), in which X$_2$ is oxygen or sulphur, and the other represents an amino radical of the general formula

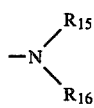 (XII)

[in which $R_{15}$ and $R_{16}$ are defined like $R_{10}$ and $R_{11}$ in the general formula (X)], or $R_{12}$ and $R_{13}$ each represent a radical of the general formula (XII)} on a cephalosporin derivative of the general formula

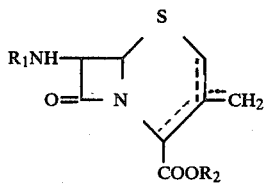 (XIII)

in which $R_1$ and $R_2$ are defined as above for the product of the general formula (I), and the derivative is in the 3-methyl-bicycloöct-2-ene or 3-methyl-bicycloöct-3-ene or 3-methylene-bicyclooctane form.

The reaction is in general carried out in an organic solvent, such as dimethylformamide, hexamethylphosphorotriamide, dimethylacetamide, acetonitrile or a mixture of solvents (e.g. dimethylformamide/tetrahydrofurane, dimethylformamide/dimethylacetamide, dimethylformamide/ether or dimethylformamide/dioxane) at a temperature between 20° C. and the reflux temperature of the reaction mixture.

If a product of the general formula (X) in which the radical (XII) is different from $-NR_{10}R_{11}$ is chosen, it is preferable to choose this product in such a way that the amine $HNR_{15}R_{16}$ is more volatile than $HNR_{10}R_{11}$.

The products of the general formula (IX) in, which $R_{10}$ and $R_{11}$, which are identical or different, represent alkyl radicals substituted by hydroxy, amino or alkyl-amino, can be obtained by transenamination from a product of the general formula (IX), in which $R_{10}$ and $R_{11}$ represent alkyl, preferably methyl, radicals.

The reaction is carried out by the action of an amine of the general formula

 (XIV)

(in which $R_{10}$ and $R_{11}$ have the corresponding definitions) on a product of the general formula (IX), and the conditions used are similar to those described above for the action of a product of the general formula (X) on a derivative of the general formula (XIII).

The products of the general formula (X) can be prepared according to the methods described by H. BREDERECK et al., Chem. Ber. 101, 41 (1968), Chem. Ber. 101, 3058 (1968) and Chem. Ber. 106, 3725 (1973).

The cephalosporin derivatives of the general formula (XIII), in which $R_1$ represents a radical of the general formula (II), can be prepared from products of the general formula

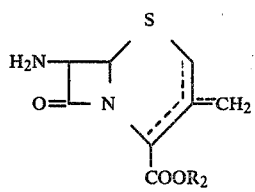 (XV)

[in which $R_2$ is defined as above and the position of the double bond is defined as for the product of the general formula (XIII)] by the action of an acid of the general formula

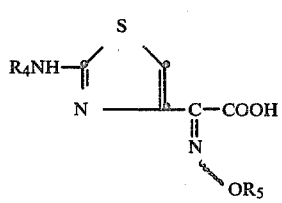 (XVI)

[in which $R_4$ and $R_5$ are defined as above, except for $R_5$ representing hydrogen], or of a reactive derivative of this acid. It is to be understood that the acid of the general formula (XVI), in the syn- or anti-form, or as a mixture of these forms, respectively gives the product of the general formula (XIII) in the syn- or anti-form or as a mixture of these forms.

In general, the condensation of the product of the general formula (XVI) in which the acid group is free, with the 7-amino-cephalosporin of the general formula (XV) is carried out in an organic solvent such as dimethylformamide, acetonitrile, tetrahydrofurane, methylene chloride or chloroform, in the presence of a condensation agent such as a carbodiimide (for example dicyclohexylcarbodiimide), N,N'-carbonyldiimidazole or 2-ethoxy-1-ethoxycarbonyl-1,2-dihydro-quinoline, at a temperature of between $-20°$ and $40°$ C.

If a reactive derivative of an acid of the general formula (XVI) is used, it is possible to employ the anhydride, a mixed anhydride or a reactive ester of the general formula

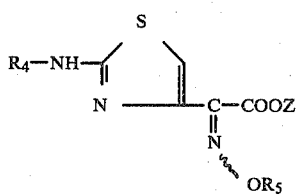 (XVII)

[in which $R_4$ and $R_5$ are defined as above and Z represents a succinimido, benzotriazol-1-yl, 4-nitrophenyl, 2,4-dinitrophenyl, pentachlorophenyl or phthalimido radical], or reactive derivatives such as a thiolo-ester defined below by the general formula (XLII), or an acid halide, for example the chloride of the acid of the general formula (XVI).

If the anhydride, a mixed anhydride or an acid halide (any of which may be prepared in situ) is employed, the condensation is carried out in an inert organic solvent such as an ether (for example tetrahydrofurane or dioxane), a chlorinated solvent (for example chloroform or methylene chloride), an amide (for example dimethylformamide or dimethylacetamide) or a ketone (for example acetone), or in mixtures of the above solvents, in the presence of an acid acceptor such as an epoxide (for example propylene oxide) or such as a nitrogen-containing organic base, e.g. pyridine, dimethylaminopyridine, N-methylmorpholine or a trialkylamine (for example triethylamine) or in an aqueous organic medium in the presence of an alkaline condensation agent such as sodium bicarbonate, and the temperature used is between $-40°$ and $+40°$ C.

It is also possible to employ a 7-aminocephalosporin of the general formula (XV) which has beforehand been silylated by applying the method described in German Patent Application No. 2,804,040.

If a reactive ester of the general formula (XVII), or a thiolo ester, is employed, the reaction is in general carried out in the presence of a trialkylamine for example triethylamine) in an organic solvent such as dimethylformamide, at a temperature of between 0° and 40° C.

The cephalosporin derivatives of the general formulae (XIII) and (XV), in which $R_2$ represents a radical of the general formula (V), can be obtained by esterification of the corresponding acid by any method which is in itself known for preparing an ester from an acid, without affecting the remainder of the molecule.

In general, an alkali metal salt or a tertiary amine salt of a product of the general formula

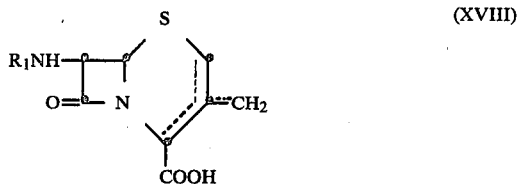

in which $R_1$ is defined as above, or

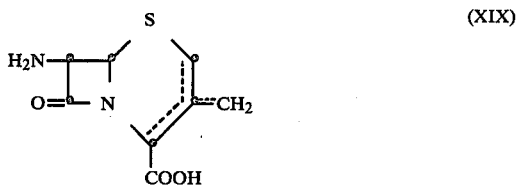

[in which the position of the double bond is defined as for the products of the general formula (XIII) and (XV)] is reacted with a halide of the general formula

in which $R_8$ and $R_9$ are defined as above and X represents a halogen atom, in an inert solvent such as dimethylformamide, at a temperature of between 0° and 30° C.

The products of the general formula (XX) can be prepared according to the method described in German Patent Application No. 2,350,230.

The introduction of the protective groups $R_1$ and/or $R_2$ of the products of the general formula (XIII), for which $R_1$ and $R_2$ are defined as above in (a) [with the exception of $R_1$ representing a radical of the general formula (II) and $R_2$ representing a radical of the general formula (V)] and of the products of the general formula (XV) for which $R_2$ is defined as above in (a) [except for representing a radical of the general formula (V)] can be effected into a cephalosporin, respectively of the general formula (XV), (XVIII) or (XIX), by application of one of the methods described in the following references:

if $R_1$ is a trityl radical: by analogy with the method described by J. C. Sheehan et al., J. Amer. Chem. Soc., 84, 2983 (1962);

if $R_1$ is a formyl radical: according to J. C. Sheehan et al., J. Amer. Chem. Soc. 80, 1156 (1958);

if $R_1$ is acetyl, chloroacetyl, trichloroacetyl, phenylacetyl, phenoxyacetyl or benzoyl: according to E. H. Flynn, Cephalosporins and Penicillins, Academic Press (1972);

if $R_1$ is a tert.-butoxycarbonyl radical: according to L. Moroder et al., Hoppe Seyler's Z. Physiol. Chem. 357, 1651 (1976);

if $R_1$ is 2,2,2-trichloro-1,1-dimethyl-ethoxycarbonyl: according to J. Ugi et al., Angew. Chem. Int. Ed. Engl. 17(5), 361 (1978);

if $R_1$ is 2,2,2-trichloro-ethoxycarbonyl, 2-chloro-1,1-dimethyl-ethoxycarbonyl, 2-cyano-1,1-dimethyl-ethoxycarbonyl, 2-trimethylsilyl-ethoxycarbonyl, benzyloxycarbonyl, p-methoxybenzyloxycarbonyl, 3,5-dimethoxybenzyloxycarbonyl, p-nitrobenzyloxycarbony or vinyloxycarbonyl: by the action of a chloroformate in an aqueous organic medium in the presence of an alkali metal bicarbonate, or according to Belgian Patent Application 788,885;

if $R_1$ is diphenylmethoxycarbonyl: by the action of the corresponding azidoformate in an aqueous organic medium, in the presence of an alkali metal bicarbonate;

if $R_1$ is 2-(biphenyl-4-yl)-isopropoxycarbonyl: by analogy with the method described in Helv. Chim. Acta, 51, 924 (1968);

if $R_1$ is quinol-8-yl-oxycarbonyl or allyloxycarbonyl: by the action of the corresponding carbonate in a basic aqueous organic medium;

if $R_1$ is o-nitrophenylthio or p-nitrophenylthio: by analogy with the method described by L. Zervas et al., J. Amer. Chem. Soc. 85, 3660 (1963);

if $R_1NH$ is replaced by dimethylaminomethyleneimino: by analogy with the method described by J. F. Fitt, J. Org. Chem. 42(15), 2639 (1977);

if $R_1NH$ is replaced by 4-nitro-benzylideneimino or 3,4-dimethoxy-benzylideneimino: according to the method described by R. A. Sirestone, Tetrahedron Lett., 375 (1972);

if $R_2$ is methoxymethyl: according to S. Seki et al., Tetrahedron Lett., 33, 2915 (1977);

if $R_2$ is tert.-butyl: according to R. J. Stedman, J. Med. Chem., 9, 444 (1966);

if $R_2$ is benzhydryl: according to Netherlands Patent Application 73/03263; and if $R_2$ is p-nitrobenzyl or p-methoxybenzyl: according to R. R. Chauvette et al., J. Org. Chem., 38(17), 2994 (1973).

The cephalosporin derivatives of the general formula (XIII), in which $R_1$ and $R_2$ are as defined above in (b), can be prepared by acylation of a 7-aminocephalosporin of the general formula (XV) according to the methods described in U.S. Pat. No. 4,065,620.

The acids of the general formula (XVI), in which $R_5$ is hydrogen, alkyl or trityl, can be prepared according to the method described in Belgian Pat. No. 850,662.

The acids of the general formula (XVI), in which $R_5$ is a vinyl radical can be prepared according to the method described in Belgian Pat. No. 869,079.

The acids of the general formula (XVI), in which $R_5$ is a cyanomethyl radical can be prepared according to the method described in German Patent Application No. 2,812,625.

The acids of the general formula (XVI), in which $R_5$ is a protective radical, can be prepared by protection of the oxime of such an acid, in which $R_5$ is hydrogen, by any known method which does not adversely affect the remainder of the molecule. In particular, protection is effected by the trityl, tetrahydropyranyl or 2-methoxyprop-2-yl groups.

The novel products of the general formula (I) are useful as intermediates for the preparation of 3-thiovinyl-cephalosporins of the general formula

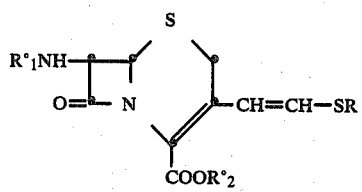

in which (α) the symbol R is chosen from amongst the following meanings:

(1) alkyl, L-2-amino-2-carboxy-ethyl and phenyl, (2) pyrid-2-yl, pyrid-3-yl or pyrid-4-yl and their N-oxides, (3) pyrimidin-2-yl; pyridazin-3-yl substituted in the 6-position (by an alkyl, methoxy, amino or acylamino radical), its N-oxide, and tetrazolo[4,5-b]pyridazin-6-yl, (4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl, in each case substituted in the 1-position (a) by an alkyl radical containing 1 to 4 carbon atoms which is unsubstituted or substituted by an alkoxy, alkylthio, phenyl, formyl, carbamyl, alkylcarbamyl, dialkylcarbamyl, acyl, alkoxycarbonyl or thiazolidin-2-yl radical, (b) by an allyl, 2,3-dihydroxypropyl, 1,3-dihydroxyprop-2-yl, 2-formyl-2-hydroxy-ethyl, 3-formyloxy-2-hydroxypropyl, 2,3-bis-formyloxy-propyl or 1,3-bis-formyloxyprop-2-yl radical, (c) by an alkyl radical which contains 2 to 4 carbon atoms and is substituted by hydroxyl, carbamyloxy, acyloxy (of which the acyl part can be substituted by an amino, alkylamino or dialkylamino radical), alkylsulphinyl, alkylsulphonyl, amino, alkylamino, dialkylamino, sulphoamino, alkylsulphonylamino, sulphamylamino, acylamino (of which the acyl part is optionally substituted by hydroxyl, amino, alkylamino or dialkylamino), alkoxycarbonylamino, ureido, alkylureido or dialkylureido (d) by a radical corresponding to one of the general formulae:

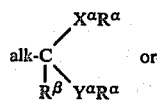

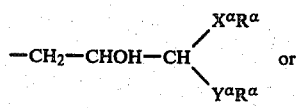

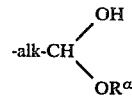

in which alk is an alkylene radical containing 1 to 4 carbon atoms, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) by an alkyl radical containing 1 to 5 carbon atoms, substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl, which is unsubstituted or substituted in the 3-position by alkoxycarbonyl, (7) a. 1,3,4-thiadiazol-5-yl which is unsubstituted or substituted by an alkyl, trifluoromethyl, alkoxy, alkylthio, hydroxyalkylthio, of which the alkyl part contains 2 to 4 carbon atoms, alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or b. 1,2,4-thiadiazol-5-yl substituted by an alkyl or alkoxy radical, (8) a. 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or b. oxazol-2-yl or 4-alkyl-oxazol-2-yl, or (9) tetrazol-5-yl which is unsubstituted or substituted in the 1-position by a. an alkyl radical containing 1 to 4 carbon atoms, which is unsubstituted or substituted by alkoxy, sulpho, carboxyl, formyl or sulphamyl, b. an alkyl radical which contains 2 to 4 carbon atoms and is substituted by hydroxyl, amino, alkylamino, dialkylamino, acylamino, carboxyalkylamino, sulphamylamino, sulphoamino, ureido, alkylureido or dialkylureido, c. an alkyl radical which contains 1 to 5 carbon atoms and is substituted by hydroxyimino or alkoxyimino, d. a phenyl, 2,3-dihydroxypropyl, 1,3-dihydroxyprop-2-yl, 2-formyl-2-hydroxyethyl, 3-formyloxy-2-hydroxypropyl, 2,3-bis-formyloxy-propyl or 1,3-bis-formyloxyprop-2-yl radical, or e. a radical of the general formula (XXIIa) in which $R^\beta$ is a hydrogen atom, or a radical of the general formula (XXIIb), the symbol $R^o{}_1$ represents a radical of the general formula (II), in which $R_5$ is hydrogen or alkyl, vinyl or cyanomethyl and $R_4$ represents a hydrogen atom, and the symbol $R^o{}_2$ represents a hydrogen atom or a radical of the general formula (V) or (β) the symbol R represents an alkyl or phenyl radical, the symbol $R^o{}_1$ is defined like $R_1$ above in (b), or represents an azidoacetyl or cyanoacetyl radical or a radical of the general formula (VI), in which Ar is substituted phenyl [the substituents being trifluoromethyl, cyano or nitro radicals, of which at least one is located in the meta- or in the para-position] or a radical of the general formula (VIII) [in which Ar is defined as above and B is amino, azido, cyano or carbamyl] or a 2-(sydnone-3)alkanoyl radical (of which the alkanoyl part contains 1 to 3 carbon atoms) or a radical of the general formula

 N—(CH$_2$)$_m$—CO—          (XXIII)

in which m is 0 to 2 and the symbol $R^o{}_2$ is defined like $R_2$ above in (b), or represents a hydrogen atom.

It is to be understood that in the products of the general formula (XXI), the substituent in the 3-position of the bicyclooctene exhibits the E or Z stereoisomeric configuration and, if $R^o{}_1$ is a radical of the general formula (II), this radical can be in the syn or anti forms. The products of the general formula (XXI) also exist as mixtures of these isomeric forms.

I. The 3-thiovinyl-caphalosporins of the general formula (XXI) can be prepared in the following manner:

A. An activated form of an acid $R'_3$ SO$_3$H or $R''_3$COOH, of the type

 (R'$_3$SO$_2$)$_2$O          (XXIVa)

 R'$_3$SO$_2$Hal          (XXIVb)

 (R''$_3$CO)$_2$O          (XXVa)

 R''$_3$COHal          (XXVb)

(in which R'$_3$ represents an alkyl, trifluoromethyl or trichloromethyl radical, or a phenyl radical which is optionally substituted by a halogen atom or by an alkyl or nitro radical, R''$_3$ is defined like R'$_3$ or represents an acylmethyl, 2-acylethyl, 2-acylpropyl, alkoxycarbonylmethyl, 2-alkoxycarbonylethyl or 2-alkoxycarbonylpropyl radical and Hal represents a halogen atom) is reacted with a product of the general formula (I), or with a mixture of its isomers, after which, where appropriate, the sulphoxide obtained is reduced and, where necessary, the protective groups are removed from the amine group of the radical of the general formula (II) and/or, where appropriate, from the acid group, to give a product of the general formula

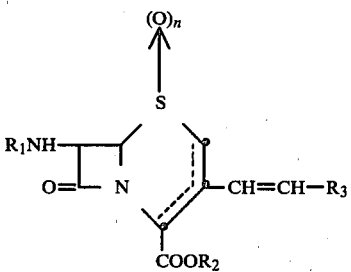

(XXVI)

{in which n is defined as above, R$_1$ is defined as above or represents a radical of the general formula (II), in which R$_4$ is a hydrogen atom, R$_2$ is defined as above or represents a hydrogen atom and R$_3$ represents a radical of the general formula:

 R'$_3$—SO$_2$O—          (XXVII)

or

R''$_3$—COO—          (XXVIII)

in which R'$_3$ and R''$_3$ are defined as above}, which is in the bicyclooct-2-ene or bicyclooct-3-ene form if n=0 or in the bicyclooct-2-ene form if n=1, and in which the substituent of the carbon atom in the 3-position of the bicyclooctene exhibits the E or Z stereoisomeric configuration.

The reaction is in general carried out in the presence of a tertiary base of the type:

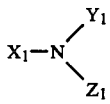          (XXIX)

where X$_1$, Y$_1$ and Z$_1$ represent alkyl or phenyl radicals, or optionally two of them form a ring with the nitrogen atom to which they are attached (for example, in the presence of triethylamine or dimethylaniline), in a chlorinated organic solvent (for example methylene chloride), in an ester (for example ethyl acetate), in an ether (for example dioxane or tetrahydrofurane), in an amide (for example dimethylacetamide or dimethylformamide in acetonitrile or in N-methylpyrrolidone, or directly in a basic solvent such as pyridine, or in an aqueous organic medium in the presence of an alkaline condensing agent (for example an alkali metal bicarbonate, sodium hydroxide or potassium hydroxide), at a temperature of between −78° C. and the reflux temperature of the reaction mixture).

Where appropriate, the reaction is carried out under nitrogen.

It is not absolutely necessary to have purified the product of the general formula (I) (or the mixture of isomers) beforehand in order to employ it/them in this reaction.

Furthermore, it is to be understood that if R$_1$ is a radical of the general formula (II), in which R$_5$ is a hydrogen atom, it is necessary to protect the oxime by a group such as has been indicated above, which group can subsequently be removed under the conditions indicated below.

The reduction of the S-oxide can be carried out under the conditions described in German Patent Application No. 2,637,176.

Where appropriate, the removel of the protective radicals from the amine group of the radical of the general formula (II) and from the acid group is carried out simultaneously or successively.

By way of example:

1. The removal of the protective groups of amines is effected as follows:

in the case of a tert.-butoxycarbonyl, trityl, p-methoxybenzyloxycarbonyl or formyl radical, by treatment in an acid medium. Preferably, trifluoroacetic acid is used and the process is carried out at a temperature of between 0° and 20° C., or anhydrous or aqueous formic acid, or para-toluenesulphonic or methanesulphonic acid, is used in acetone or acetonitrile at between 20° C. and the reflux temperature of the reaction mixture. Under these conditions, the product of the general formula (I) can be obtained in the form of the trifluoroacetate, the solvate with formic acid, the methanesulphonate or the para-toluenesulphonate, and from these the amine group can be liberated by any method which is in itself known for obtaining an amine from one of its salts without affecting the remainder of the molecule. In particular, the process is carried out by bringing the compound into contact with an ion exchange resin or by the action of an organic base.

In the case of a 2,2,2-trichloro-ethoxycarbonyl or p-nitrobenzyloxycarbonyl radical, by reduction (especially by treatment with zinc in acetic acid).

In the case of a chloroacetyl or trichloroacetyl radical, by applying the method described in the French Patent published under No. 2,243,199.

In the case of a benzyl, dibenzyl or benzyloxycarbonyl radical, by catalytic hydrogenation.

In the case of a trifluoroacetyl radical, by treatment in a basic medium.

2. The removal of the protective groups from the carboxyl radical is effected as follows:

in the case of a tert.-butyl, p-methoxybenzyl or benzyhydryl radical, by treatment in an acid medium, under the conditions described above for the removal of the protective trityl radical from an amino group. In the case of the benzyhydryl radical, the process can be carried out in the presence of anisole.

In the case of a methoxymethyl group, by treatment in a dilute acid medium.

In the case of a p-nitrobenzyl group, by reduction (especially by treatment with zinc in acetic acid, or by hydrogenolysis).

3. The removal of the protective group from the oxime is effected as follows:

in the case of a trityl or tetrahydropyranyl group: by acidolysis, for example with trifluoroacetic acid, aqueous or non-aqueous formic acid, or paratoluenesulphonic acid, and in the case of the 2-methoxy-prop-2-yl group: according to the method described in Belgian Pat. No. 875,379.

B. If appropriate, the protective radical $R_1$, or the radicals $R_1$ and $R_2$ simultaneously, are removed from a product of the general formula (XXVI) [in which $R_1$ is defined as above in (a) except for representing a radical of the general formula (II), or represents a 5-aminoadipyl radical of which the amine and acid groups are protected, or a radical of the general formula (VI) or (VII) as defined for $R_1$ in (b), and $R_2$ has the corresponding definitions], to give a product of the general formula (XXVI) in which $R_1$ represents hydrogen and $R_2$, $R_3$ and n are defined as above.

The elimination of the protective radical $R_1$ is effected by any known method for liberating an amine group without affecting the remainder of the molecule.

By way of example, the following methods may be mentioned:

if $R_1$ represents trityl, benzhydryl, trichloroacetyl, chloroacetyl, tert.-butoxycarbonyl, trichloroethoxycarbonyl, benzyloxycarbonyl, p-methoxybenzyloxycarbonyl or p-nitrobenzyloxycarbonyl: in accordance with the methods mentioned above for liberating the amino radical of the product of the general formula (XXVI); advantageously this is carried out by using p-toluenesulphonic acid in acetonitrile at a temperature of between 0° and 50° C.;

if $R_1$ represents formyl, 2-chloro-1,1-dimethylethoxycarbonyl, 2-cyano-1,1-dimethyl-ethoxycarbonyl, 3,5-dimethoxy-benzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, and if $R_1NH$ is replaced by dimethylaminomethyleneimino, 3,4-dimethoxy-benzylideneimino or 4-nitro-benzylideneimino: by hydrolysis in an acid medium;

if $R_1$ represents 2,2,2-trichloroethyl or 2,2,2-trichloro-1,1-dimethyl-ethoxycarbonyl: by treatment with zinc in acetic acid;

if $R_1$ represents acetyl, benzoyl, phenylacetyl, phenoxyacetyl or protected 5-amino-adipyl: in accordance with the method described in Belgian Patent 758,800;

if $R_1$ represents trimethylsilylethoxycarbonyl: in accordance with the method described by H. GERLACH, Helv. Chim. Acta 60 (8), 3039 (1977); and if $R_1$ represents p-nitrobenzyloxycarbonyl: by hydrogenolysis in the presence of palladium.

C. If appropriate, a product of the general formula (XXVI), in which $R_1$ is a hydrogen atom, or, where appropriate, a mixture of the isomers of this product, is acylated by means of an acid represented by the general formula $$R_1OH \qquad \text{(XXX)}$$

[in which $R_1$ represents a radical of the general formula (II) as defined above or is defined as above in (b)] or a reactive derivative of this acid, after which, if appropriate, the oxide obtained is reduced and, if appropriate, the protective radicals are removed, to give a product of the general formula (XXVI), in which n and $R_3$ are defined as above, $R_1$ is defined as above and $R_2$ has the corresponding definitions.

The process is carried out analogously to the method described above for obtaining a product of the general formula (XIII) from products of the general formulae (XV) and (XVI), or according to the methods quoted in U.S. Pat. No. 4,065,620.

Where appropriate, the reduction of the oxide, as well as the removal of the protective radicals from the amine group and from the acid group, can be carried out under the conditions described above.

D. If appropriate, a product of the general formula (XXVI) in which n=0, is oxidised to give a product of the general formula (XXVI) in which n=1.

The oxidation can be carried out by any known method which does not adversely affect the remainder of the molecule, especially by application of the method described in German Pat. No. 2,637,176.

E. If appropriate, a product of the general formula (XXVI), in which $R_2$ is a hydrogen atom, is esterified by any known method for preparing an ester from an acid without affecting the remainder of the molecule, to give a product of the general formula (XXVI) in which $R_2$ is a radical of the general formula (V). In particular, the reaction of an alkali metal salt or of a tertiary amine salt of the product of the general formula (XXVI) with a halide of the general formula (XX) is employed, under the conditions described above for the preparation of the products of the general formula (XIII) or (XV) in which $R_2$ is a radical of the general formula (V).

F. A thiourea of the general formula $$R_4NH-CSNH_2 \qquad \text{(XXXI)}$$

(in which $R_4$ is defined as above except for representing chloroacetyl or trichloroacetyl, or represents a hydrogen atom) is reacted with a product, or with a mixture of the isomers of the product, of the general formula

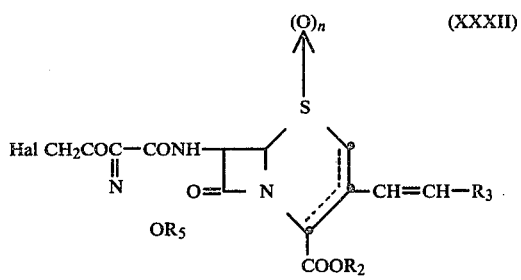

(XXXII)

[in which R₂ is defined as above in (a), R₃ and n are defined as above, R₅ is defined as above except for representing a vinyl radical and Hal represents a chlorine or bromine atom], after which, if appropriate, the sulphoxide obtained is reduced and, if appropriate, the protective radicals are removed to give a product of the general formula (XXVI), in which R₁ is a radical of the general formula (II) [in which R₄ and R₅ are defined as above].

The reaction is generally carried out in an aqueous, organic or aqueous-organic medium, for example in solvents or mixtures of solvents such as alcohols (methanol or ethanol), ketones (acetone), chlorinated solvents (chloroform or ethylene chloride), nitriles (acetonitrile), amides (dimethylformamide or dimethylacetamide), ethers (tetrahydrofurane or dioxane), esters (ethyl acetate) or acids (acetic acid or formic acid) in the presence or absence of a base such as sodium hydroxide, potassium hydroxide, alkali metal carbonates and bicarbonates, alkali metal salts of carboxylic acids (sodium formate or sodium acetate) or tertiary amines (triethylamine, trimethylamine or pyridine), at a temperature of between −30° and 60° C.

The reduction of the sulphoxide and the removal of the protective radicals are carried out under the conditions described above.

The products of the general formula (XXXII), in which R₅ is an alkyl or cyanomethyl radical, can be obtained by the action of an acid halide of the general formula

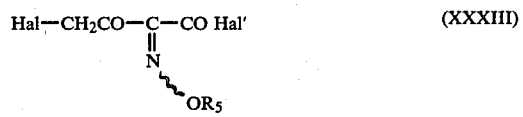

(XXXIII)

(in which Hal and Hal' are chlorine or bromine atoms and R₅ is an alkyl or cyanomethyl radical) on a 7-aminocephalosporin of the general formula (XXVI) in which R₂ has the definition given above in (a), followed, where appropriate, by reduction of the sulphoxide obtained (if n=1) and, where appropriate, by removal of the protective radicals.

The reaction is in general carried out in an aqueous organic medium, for example water/ether (tetrahydrofurane or dioxane), water/ketone (acetone) or water/chlorinated solvent (chloroform or methylene chloride), in the presence of an alkaline condensation agent such as an alkali metal bicarbonate (for example sodium bicarbonate), at a temperature of between −40° and +40° C.

It is also possible to proceed by analogy with the method described in French Patent Application No. 2,399,418.

The products of the general formula (XXXIII) can be obtained by halogenation of a product of the general formula

(XXXIV)

in which R₅ and Hal' are defined as above, by any method which is in itself known for the preparation of halogenated derivatives and which does not adversely affect the remainder of the molecule.

If it is desired to obtain a product of the general formula (XXXIII) in which Hal represents a bromine atom, bromine is used as the reactant in the presence of a catalyst, namely either using an acid catalyst such as hydrobromic acid, hydrochloric acid, the sulphonic acids (methanesulphonic acid, anhydrous p-toluenesulphonic acid or benzenesulphonic acid) or using ultraviolet light.

If it is desired to obtain a product of the general formula (XXXIII) in which Hal is a chlorine atom, chlorine is used as a reactant in the presence of a catalyst such as mentioned above, or sulphuryl chloride is used as a reactant.

The halogenation is carried out in an organic solvent such as a chlorinated solvent (for example methylene chloride, chloroform, carbon tetrachloride, dichloroethane or trichloroethane) or an ether (for example diethyl ether or dioxane), or in a mixture of these solvents, at a temperature between −40° C. and the reflux temperature of the reaction mixture.

The products of the general formula (XXXIV) can be prepared from the corresponding esters according to the method described in French Patent Application No. 2,414,508.

The esters can themselves be prepared by application of the method described by R. BUCOURT et al., Tetrahedron Letters, 34, 2233 (1978).

The products of the general formula (XXXII) in which R₅ is a hydrogen atom, can be obtained by treating a product of the general formula

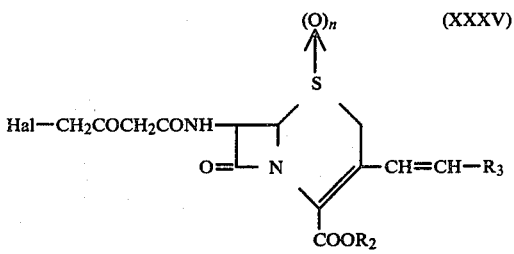

(XXXV)

in which R₂, R₃, Hal and n are defined as above, with a nitrosylating agent, by analogy with the method described in French Patent Application No. 2,399,418, followed, where appropriate, by reduction of the sulphoxide and removal of the protective radicals.

The products of the general formula (XXXII) in which R₅ is a protective radical can be obtained by protecting the oxime of a product of the general formula (XXXII), in which R₅ is a hydrogen atom.

The products of the general formula (XXXV) can be obtained from a 7-amino-cephalosporin of the general formula (XXVI), in which R₂ has the definition given above in (a), by treatment with a product of the general formula

   (XXXVI)

in which Hal is defined as above (which product may be formed in situ), using the conditions described above for condensing a product of the general formula (XXXIII) with a product of the general formula (XXVI), or by analogy with the method described in French Patent Application No. 2,399,418.

G. The 3-thiovinyl-cephalosporins of the general formula (XXI), in which R is defined as above in (α) or (β), except for containing a substituent of the general formula (XXIIc), can be prepared by the action of a thiol (which is free or in the form of an alkali metal salt or alkaline earth metal salt) of the general formula

   (XXXVII)

[in which the radical R which is defined as above is protected as an acetal (as defined by the general formulae (XXIIa) and (XXIIb)) if it is desired to obtain a cephalosporin of the general formula (XXI) in which R contains a formyl or acylalkyl radical] on a cephalosporin derivative, or a mixture of the isomers, of the general formula (XXVI) [in which $R_1$ is a radical of the general formula (II) as defined above and $R_2$ has the corresponding definitions, or $R_1$ is defined as above in (b) and $R_2$ has the corresponding definitions], followed, where appropriate, by reduction of the oxide obtained and by the removal of the protective radicals.

It is to be understood that if the radical R of the product of the general formula (XXXVII) is prone to interfere with the reaction, it is preferable to protect this group by any method which is in itself known and which does not adversely affect the remainder of the molecule (especially if R contains an amino, alkylamino, hydroxyl or carboxyl radical).

Where amino, alkylamino or carboxyl groups are concerned, protection is effected under the conditions described above.

Where hydroxyl groups are concerned, protection is effected by the radicals mentioned above in the case of the protection of the oxime, or protection is effected in the form of a cyclic acetal in the case of protection of the 2,3-dihydroxy-propyl or 1,3-dihydroxy-prop-2-yl radicals (for example in the form of 2,2-dimethyl-dioxolan-4-yl-methyl or 2,2-dimethyl-dioxan-5-yl radicals).

It is also to be understood that if $R_5$ represents a hydrogen atom, it is preferable to protect the oxime (under the conditions described above).

Furthermore it is to be understood that if the radical R of the product of the general formula (XXXVII) contains hydroxyl or sulpho radical, it is preferable to employ a product of the general formula (XXVI) in which n=0.

In general, the process is carried out in the presence of a base such as a pyridine or a tertiary organic base of the formula (XXIX): for example, diisopropylethylamine or diethylphenylamine is used.

The presence of such a base is not necessary if an alkali metal salt or alkaline earth metal salt of the thiol of the general formula (XXXVII) is employed.

The reaction is advantageously carried out in an organic solvent, such as dimethylformamide, tetrahydrofurane or acetonitrile or a mixture of the abovementioned solvents.

It is also possible to work in the presence of an alkali metal bicarbonate in a solvent such as mentioned above, if appropriate in the presence of water.

The process is carried out at a temperature of between $-20°$ C. and the reflux temperature of the reaction mixture, the chosen temperature varying depending on the thiol employed. Equally, depending on the thiol employed, the reaction time can vary from 5 minutes to 48 hours.

Where appropriate, the process is carried out under nitrogen.

Preferably, if it is desired to use a bicyclooct-3-ene of the general formula (I) in which $R_1$ represents a radical of the general formula (II), a product in which $R_2$ is other than hydrogen is employed.

It is immaterial whether the protective radical is removed from R before or after the reduction of the oxide, and before, simultaneously with, or after the removal of the other protective radicals.

The reduction of the oxide and the removal of the protective groups are carried out in accordance with the methods described above.

If the dihydroxypropyl radicals are protected in the form of cyclic acetals, the protective radicals are removed by acidolysis (with trifluoroacetic acid, aqueous or non-aqueous formic acid, or p-toluenesulphonic acid). If aqueous or non-aqueous formic acid is used, liberation of the hydroxyl radicals which have been protected in the form of a cyclic acetal can lead, at least partially, to the corresponding formic acid monoester or diester, which can be separated, where necessary, by chromatography.

The removal of the groups of the general formula (XXIIa) or (XXIIb) (if it is desired to obtain a product of the general formula (XXI) in which R contains a formyl or acylalkyl radical) is effected as follows:

in the presence of a sulphonic acid (for example methanesulphonic acid or p-toluenesulphonic acid) in an organic solvent (for example acetonitrile or acetone), optionally in the presence of water and optionally in the presence of an acetalisable reactant such as acetone, glyoxylic acid, benzaldehyde or pyruvic acid, at a temperature of between 20° C. and the reflux temperature of the reaction mixture, or, if the radical R is a 5,6-dioxo-1,4,5,6-tetrahydro-1,2,4-triazin-3-yl radical, by the action of aqueous formic acid (preferably containing less than 10% of water), in the presence or absence of silica, or by trans-acetalisation in the presence of an acetalisable reactant as defined above.

The thiols of the general formula (XXXVII), which can be employed in their tautomeric form, can be prepared by application of one of the following methods, depending on the meaning of the radical R:

if R is a pyrid-3-yl radical: according to the method described by H. M. WUEST and E. H. SAKAL, J. Am. Chem. Soc., 73, 1210 (1951);

if R is a pyrid-3-yl-1-oxide radical: according to the method described by B. BLANK et al., J. Med. Chem. 17, 1065 (1974);

if R is a pyrid-4-yl-1-oxide radical: according to the method described by R. A. Y. JONES et al., J. Chem. Soc. 2937 (1960);

if R is a pyridazin-3-yl radical substituted by alkyl or methoxy, or a N-oxide derivative of such a radical: according to the method described in Belgian Pat. No. 787,635;

if R is a pyridazin-3-yl radical substituted by amino, or a N-oxide derivative of such a radical: according to the method described in Belgian Pat. No. 579,291;

if R is a pyridazin-3-yl radical substituted by acylamino, or a N-oxide derivative of such a radical: by application of the methods described by M. KUMAGAI and M. BANDO, Nippon Kagaku Zasshi, 84, 995 (1963) and by T. HORIE and T. UEDA, Chem. Pharm. Bull., 11, 114 (1963);

if R is a tetrazolo[4,5-b]pyridazin-6-yl radical: according to the method described in Belgian Pat. No. 804,251; and if R is a 5,6-dioxo-1,4,5,6-tetrahydro-1,2,4-triazin-3-yl radical substituted in the 4-position or a 2-alkoxycarbonyl-1,3,4-triazol-5-yl radical substituted in the 1-position by a radical R$^\gamma$ chosen from amongst:

(a) an allyl radical, or an alkyl radical (which has 1 to 4 carbon atoms and is itself optionally substituted by an alkoxy, alkylthio, phenyl, carbamyl, alkylcarbamyl, dialkylcarbamyl, acyl, alkoxycarbonyl or thiazolidin-2-yl radical).

(b) a 2,3-dihydroxy-propyl radical or 1,3-dihydroxyprop-2-yl radical (optionally protected in the form of the cyclic acetal), (c) an alkyl radical [which has 2 to 4 carbon atoms and is itself substituted by hydroxyl, carbamyloxy, dialkylamino, alkylsulphinyl, alkylsulphonyl, alkylsulphonylamino, sulphamylamino, acylamino (which is optionally substituted), alkoxycarbonylamino, ureido, alkylureido or dialkylureido], (d) a radical of the general formula (XXIIa) or (XXIIb), or (e) a hydroxyiminoalkyl or alkoxyiminoalkyl radical: by reacting an alkyl oxalate with a thiosemicarbazide of the general formula:

NHCSNH—NH$_2$ (XXXVIII)

(in which R$^\gamma$ is defined as above), in the presence of an alkali metal alcoholate, for example sodium ethylate or sodium methylate, or potassium tert.-butylate, by applying the method described by M. PESSON and M. ANTOINE, Bull. Soc. Chim. France (1970), 1590.

It is not absolutely necessary to purify the product obtained (nor to liberate the protected radicals) in order to employ the product for the preparation of the products of the general formula (XXI).

The thiosemicarbazide of the general formula (XXXVIII) can be prepared in accordance with one of the methods described by K. A. JENSEN et al., Acta Chim. Scand., 22, 1 (1968), or by application of the method described by Y. KAZAROV and J. Y. POTOVSKII, Doklady Acad. Nauk. SSSR 134, 824 (1966), it being understood that if R$^\gamma$ contains an amino radical, the latter is protected.

The protection of the amino radical and the removal of the protective radical are carried out in accordance with the usual methods which do not adversely affect the remainder of the molecule. In particular, the tert.-butoxycarbonyl group, which can be removed by acid hydrolysis, is used.

If R is a 1,3,4-triazol-5-yl radical substituted in the 1-position by an alkyl, allyl or alkoxyalkyl radical, by an alkyl radical (having 1 to 4 carbon atoms) which is itself substituted as defined above in (a), with the exception of a thiazolidin-2-yl radical, by a radical as defined above in (c) or by an alkoxyiminoalkyl radical: by application of one of the methods described by M. PESSON and M. ANTOINE, Bull. Soc. Chim. France 1590 (1970).

If R is a 1,3,4-triazol-5-yl radical substituted in the 1-position by thiazolidin-2-yl-alkyl or hydroxyiminoalkyl: by the respective action of cysteamine or hydroxylamine on a 1-dialkoxyalkyl-5-mercapto-1,3,4-triazole, which can be obtained by application of the method described by M. KANAOKA, J. Pharm. Soc. Japan, 75, 1149 (1955), from a 4-dialkoxyalkyl-thiosemicarbazide.

If R is a 1,3,4-triazol-5-yl radical substituted in the 1-position by 2,3-dihydroxypropyl or 1,3-dihydroxyprop-2-yl (optionally protected in the form of a cyclic acetal), or R represents a radical of the general formula (XXIIa) or (XXIIb): by application of the method described by M. KANAOKA, J. Pharm. Soc. Japan, 75, 1149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by optionally substituted acyloxyalkyl: by acylation of, respectively, 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, of which the mercapto radical has beforehand been protected (for example according to the method of C. G. KRUSE et al., Tet. Lett. 1725 (1976)), by any method known for acylating an alcohol without affecting the remainder of the molecule, followed by liberation of the mercapto group in an acid medium.

If R is a 5,6-dioxo-1,4,5,6-tetrahydro-1,2,4-triazin-3-yl radical substituted in the 4-position, or 2-alkoxycarbonyl-1,3,4-triazol-5-yl or 1,3,4-triazol-5-yl radical substituted in the 1-position, by aminoalkyl or alkylaminoalkyl: by liberating the amine group of the corresponding product, protected, for example, by a tert.-butoxycarbonyl group.

If R is a 5,6-dioxo-1,4,5,6-tetrahydro-1,2,4-triazin-3-yl radical substituted in the 4-position, or 2-alkoxycarbonyl-1,3,4-triazol-5-yl or 1,3,4-triazol-5-yl radical substituted in the 1-position, by sulphoaminoalkyl: from the corresponding product substituted by a tert.-butoxycarbonylaminoalkyl radical, by analogy with the method described in Belgian Pat. No. 847,237.

If R is a 1,4-dialkyl-1,4,5-tetrahydro-1,2,4-triazin-3-yl radical or 1-alkyl-5,6-dioxo-1,4,5,6-tetrahydro-1,2,4-triazin-3-yl radical: according to the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: according to the method described by M. PESSON and M. ANTOINE, C.R. Acad. Sci., Ser C, 267, 25, 1726 (1968).

If R is a 1,2,3-triazol-5-yl radical: according to the method described in French Patent Application No. 2,215,942.

If R is a 1,3,4-triazol-5-yl radical: according to the method described by M. KANAOKA, J. Pharm. Soc. Jap. 75, 1149 (1955).

If R is a 1,3,4-triadiazol-5-yl radical optionally substituted by alkyl, alkoxy, alkylthio, alkylsulphonyl, amino, dialkylamino or acylamino: according to the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: according to the method described in German Patent Application No. 2,446,254.

If R is a 1,3,4-thiadiazol-5-yl radical substituted by a carboxyalkyl radical: by application of the method described in German Patent Application No. 1,953,861.

If R is a 1,3,4-thiadiazol-5-yl radical substituted by a trifluoromethyl radical: according to the method described in German Patent Application No. 2,162,575.

If R is a 1,3,4-thiadiazol-5-yl radical substituted by a carboxyl radical: according to the method described in Japanese Patent Application No. 77/48,666.

If R is a 1,3,4-thiadiazol-5-yl radical substituted by an acylaminoalkyl radical: according to the method described in Japanese Patent Application No. 76/80,857.

If R is a 1,3,4-thiadiazol-5-yl radical substituted by a hydroxyalkylthio radical: by application of the method described by G. NANNINI, Arz. Forsch. 27 (2), 343 (1977).

If R is a 1,2,4-thiadiazol-5-yl radical substituted by alkyl or alkoxy: according to the method described in German Patent Application No. 2,806,226 or according to Chem. Ber. 90, 184 (1957).

If R is a 1,3,4-oxadiazol-5-yl radical as described in the definition of the general formula (XXI) in 8a.: by application of the method described by E. HOGGARTH, J. Chem. Soc. 4811 (1952).

If R is an oxazol-2-yl or 4-alkyl-oxazol-2-yl radical: by application of the method described previously by C. BRADSHER, J. Org. Chem. 32, 2079 (1967).

If R is a tetrazol-5-yl radical optionally substituted in the 1-position by alkyl, hydroxyalkyl or phenyl: according to the methods described in Belgian Pat. No. 830,821.

If R is a tetrazol-5-yl radical substituted in the 1-position by alkoxyalkyl: by addition reaction of sodium azide with an isothiocyanatoalkoxyalkyl compound, in an organic solvent such as ethanol, at the reflux temperature of the reaction mixture.

The isothiocyanatoalkoxyalkyl compound can be obtained by application of the method described by E. Schmidt et al., Chem. Ber. 73, 286 (1940).

If R is a tetrazol-5-yl radical substituted in the 1-position by a carboxyalkyl radical: according to the method described in Belgian Pat. No. 858,112.

If R is a tetrazol-5-yl radical substituted in the 1-position by a sulphoalkyl radical: according to the method described in Belgian Pat. No. 856,498 or described by D. A. BERGES et al., J. Het. Chem. 15, 981 (1978).

If R is a tetrazol-5-yl radical substituted in the 1-position by an aminoalkyl, alkylaminoalkyl or dialkylaminoalkyl radical: by application of the method described in German Patent Application No. 2,738,711.

If R is a tetrazol-5-yl radical substituted in the 1-position by a sulphamylalkyl, sulphamylaminoalkyl or sulphoaminoalkyl radical: according to the method described in Belgian Pat. No. 856,636.

If R is a tetrazol-5-yl radical substituted by an acylaminoalkyl radical or a 1,3,4-thiadiazol-5-yl radical substituted by hydroxyl: according to the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (of which the mercapto radical has beforehand been protected), by treatment with an alkali metal isothiocyanate, with an alkyl isocyanate or with a dialkylcarbamyl halide, followed by liberation of the mercapto group under the conditions described in Belgian Pat. No. 847,237.

If R is a tetrazol-5-yl radical substituted in the 1-position by a carboxyalkylaminoalkyl radical: according to the method described in German Patent Application No. 2,715,597.

If R is a tetrazol-5-yl radical substituted in the 1-position by a 2,3-dihydroxypropyl radical: according to the method described in U.S. Pat. No. 4,064,242.

If R is a tetrazol-5-yl radical substituted in the 1-position by a 1,3-dihydroxy-prop-2-yl radical: by addition reaction of sodium azide with a 2,2-dimethyl-1,3-dioxolan-5-yl isothiocyanate (followed, where appropriate, by liberation of the hydroxyl groups).

If R is a tetrazol-5-yl radical substituted in the 1-position by a radical of the general formula (XXIIa) as described in the definition of the general formula (XXI) in 9e. or of the general formula (XXIIb) or a radical defined above in 9c. for the general formula (XXI): by the action of sodium azide on the corresponding isothiocyanate, by analogy with the method described by R. E. ORTH, J. Pharm. Sci. 52 (9), 909 (1963), it being understood that where R contains a hydroxyl or hydroxyiminoalkyl substituent, the alcohol or oxime function are protected, if appropriate, for example by a tetrahydropyranyl group.

(II°) The 3-thiovinyl-cephalosporins of the general formula (XXI), in which R does not contain a substituent of the general formula (XXIIc), can also be obtained as follows:

A. A product, or a mixture of isomers of the product, of the general formula (XXVI) [either as defined in B. for the preparation of the products of the general formula (XXVI), for which $R_1$ is a hydrogen atom, or in which $R_1$ is a hydrogen atom and $R_2$ has the corresponding definition] is treated with a thiol of the general formula (XXXVII) (or one of its alkali metal salts or alkaline earth metal salts), after which, if appropriate, the sulphoxide obtained (if n=1) is reduced and, if appropriate, the protective radicals of R are removed, to give a product of the general formula

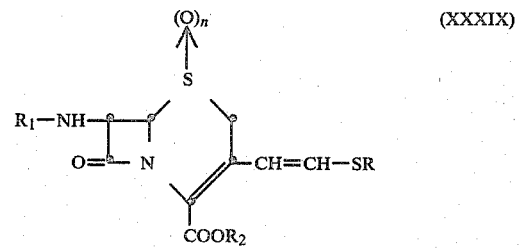

(XXXIX)

in which n is defined as above, $R_1$ and $R_2$ are defined as above and R assumes the corresponding definitions.

The reaction is carried out under the conditions described above for obtaining a product of the general formula (XXI) from a product of the general formula (XXVI) and from a thiol of the general formula (XXXVII).

It is to be understood that the radical R of the thiol is (where appropriate) protected as described above and that the removal of the protective radicals can be effected under the conditions described above. It is, however, preferable to retain the protective groups until the product of the general formula (XXI) is obtained.

B. A product of the general formula

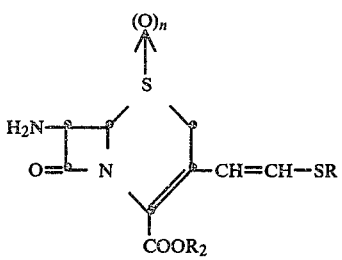

in which R, $R_2$ and n are defined as above, is prepared by removal of the radical $R_1$ from a product of the general formula (XXXIX), in which $R_1$ is other than a hydrogen atom, or, where appropriate, by simultaneous removal of the protective radicals $R_1$ and $R_2$ from this product.

The process is carried out under the conditions described above for the preparation of a product of the general formula (XXVI), in which $R_1$ is a hydrogen atom.

C. The 3-thiovinyl-cephalosporin of the general formula (XXI), in which R, $R^o{}_1$ and $R^o{}_2$ are defined as above, is then prepared by acylation of a 7-amino-cephalosporin of the general formula (XL) by means of an acid represented by the general formula $$R^o{}_1\text{—OH} \tag{XLI}$$

[in which $R^o{}_1$, which is defined as above, is optionally protected if it contains radicals which can interfere with the reaction], or by means of a reactive derivative of this acid, under the conditions described above for the preparation of the products of the general formula (XIII), after which the oxide obtained (if n=1) is reduced and the protective radicals are removed.

It is to be understood that:

the amino or alkylamino radicals which are present in certain radicals R must be protected and the carboxyl, hydroxyl, formyl or acylalkyl radicals contained in the radicals R can be protected.

The protection, and the removal of the protective radicals, are carried out under the conditions described above.

The reduction of the oxide and the removal of the other protective radicals are carried out under the conditions described above.

It is also to be understood that if R contains a hydroxyl, sulpho, sulphinyl or sulphonyl substituent, it is preferred to employ a product of the general formula (XL) in which n=0.

III°. The 3-thiovinyl-cephalosporins of the general formula (XXI), in which R does not contain a substituent of the general formula (XXIIc), can also be obtained by the action of a thiolo-ester of the general formula $$R'_1\text{—SR} \tag{XLII}$$

in which $R'_1$ either represents a radical of the general formula (II) or is defined like $R_1$ in b. and R is defined as above [it being understood that if it contains an amino or alkylamino substituent, this substituent is protected, if it contains a hydroxyl or carboxyl substituent, this substituent is free or protected and if it contains a formyl or acylalkyl substituent, this substituent is protected in the form of an acetal of the general formula (XXIIa) or (XXIIb)] on a 7-amino-cephalosporin of the general formula (XXVI), in which $R_1$ is a hydrogen atom and $R_2$ has the corresponding definition, followed by the reduction of the sulphoxide obtained, if n=1, and, where appropriate, by the removal of the protective radicals.

It is also to be understood that the radicals $R'_1$ which contain a group which is prone to interfere with the reaction are protected beforehand. The same is true of the oxime if $R'_1$ represents a radical of the general formula (II), in which $R_5$ is a hydrogen atom.

It is also preferable to employ a product in which $R'_1$ does not contain a halogen substituent.

As for the processes described above, if R contains a hydroxyl, sulpho, sulphinyl or sulphonyl substituent, it is preferred to employ a product of the general formula (XXVI) in which n=0.

The protection, and the removal of the protective radicals, are carried out under the conditions described above.

The reaction of the thiolo-ester with the 7-amino-cephalosporin of the general formula (XXVI) is in general carried out in the presence of an acid acceptor such as an organic base, more especially in the presence of a pyridine or of a tertiary organic base of the general formula (XXIX), especially triethylamine, N,N-diisopropyl-N-ethylamine, diethylphenylamine or N-methylmorpholine.

The reaction is advantageously carried out in an organic solvent such as an amide (for example dimethylformamide or dimethylacetamide), an ether (for example tetrahydrofurane or dioxane), a chlorinated solvent (for example chloroform or methylene chloride), a ketone (for example acetone) or a nitrile (for example acetonitrile) or in a mixture of these solvents. It is also possible to carry out the reaction in the presence of an alkali metal bicarbonate in one of the abovementioned solvents, optionally in the presence of water.

The reaction is carried out at a temperature of between $-20°$ C. and the reflux temperature of the reaction mixture. Optionally, the reaction is carried out under nitrogen.

The reduction of the S-oxide is carried out under the conditions described above.

The thiolo-esters of the general formula (XLII) can be prepared by the action of an acid, or of a reactive derivative of an acid, of the general formula $$R'_1\text{—OH} \tag{XLIa}$$

on a thiol of the general formula (XXXVII) (or on an alkali metal salt or alkaline earth metal salt of this thiol), followed, where appropriate, by removal of the protective radicals.

In the general formula (XLIa), $R'_1$ represents a radical of the general formula (II) in which $R_4$ and $R_5$ are other than hydrogen, or R'HD 1 is defined like $R_1$ in b.

It is to be understood that the amino or alkylamino substituents of $R'_1$ and R are protected and that the hydroxyl or carboxyl substituents are free or protected.

It is also to be understood that the radical R is protected in the form of an acetal if it is desired to prepare a product of the general formula (XXI) in which R contains a formyl or acylalkyl radical.

The reaction is carried out under the conditions described above for the preparation of a product of the general formula (XIII) from a product of the general formula (XV).

If it is desired to obtain a product in which R contains a carboxyl or sulpho radical, it is preferable to treat the corresponding thiol with a reactive derivative of the acid $R'_1OH$.

If it is desired to obtain a thiolo-ester in which $R'_1$ is a radical of the general formula (II), as described for $R^o_1$, it is possible to remove the tert.butoxycarbonyl radical, protecting the aminothioazole, by treatment in an anhydrous acid medium. Preferably, trifluoroacetic acid is employed and the reaction is carried out at between 0° and 20° C. The trityl radical protecting the oxime can be removed by acidolysis, for example with anhydrous trifluoroacetic acid.

Where necessary, the removal of the trityl group protecting a hydroxyl substituent of the thiolo-ester is effected under the conditions described above for the liberation of the oxime.

It is advantageous to remove the protective groups only after the reaction of the thiolo-ester with the product of the general formula (XXVI) in which $R_1$ is a hydrogen atom.

IV°. The 3-thiovinyl-cephalosporins of the general formula (XXI), in which $R^o_1$ represents a radical of the general formula (II) (as defined above, except for $R_5$ representing a vinyl radical), and R does not contain a substituent of the general formula (XXIIc), can be obtained by proceeding as follows:

A product of the general formula

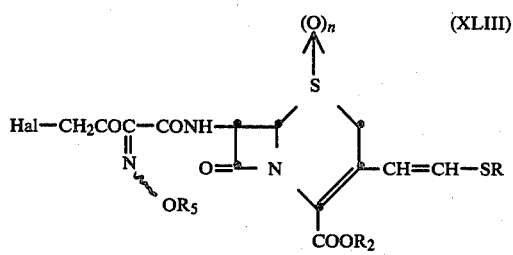

in which $R_5$ and R are defined as above and $R_2$, Hal and n are defined as previously, is prepared from a product of the general formula (XL) or from a product of the general formula

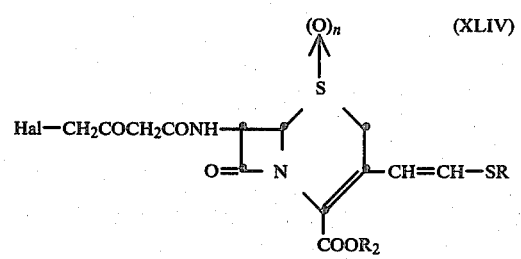

[in which Hal, $R_2$ and n are defined as above and R is defined as above], by application of the methods described previously for the preparation of the product of the general formula (XXXII).

If the product of the general formula (XLIII) is prepared from a product of the general formula (XL), the radical R is protected beforehand if it contains an amino or alkylamino radical, and is free or protected if it contains a hydroxyl, carboxyl, formyl or acylalkyl radical.

If the product of the general formula (XLIII) is prepared from a product of the general formula (XLIV), the radical R is protected beforehand if it contains an amino, alkylamino or formyl radical, and is free or protected if it contains a hydroxyl, carboxyl or acylalkyl radical.

The protection, and the removal of the protective radicals, are effected under the conditions described above.

A thiourea of the general formula (XXXI) is reacted with the product of the general formula (XLIII) under the conditions described above for the preparation of the products of the general formula (XXVI) from the products of the general formula (XXXII), after which, where appropriate, the sulphoxide obtained is reduced, and, where appropriate, the protective radicals are removed.

If it is desired to obtain a product of the general formula (XXI) in which R contains a formylalkyl or acylalkyl radical, this radical can be protected, as an acetal, in the form of a radical of the general formula (XXIIa) or (XXIIb) as defined above.

The reduction of the sulphoxide and the removal of the protective radicals are effected under the conditions described above.

The cephalosporin of the general formula (XLIV) can be prepared from a cephalosporin of the general formula (XXXV) by the action of a thiol of the general formula (XXXVII), by application of the method described for the preparation of the products of the general formula (XXI).

V°. The 3-thiovinyl-cephalosporins of the general formula (XXI) in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an alkyl radical containing 2 to 4 carbon atoms substituted by a carbamyloxy group or by an acyloxy group (of which the acyl part is optionally substituted by an amino, alkylamino or dialkylamino radical), and $R^o_1$ and $R^o_2$ have the corresponding definitions, which are functional derivatives of the product of the general formula (XXI) in which R is a — Ⓡ —alk'—OH radical chosen from amongst 5,6-dioxo-4-hydroxyalkyl-1,4,5,6-tetrahydro-1,2,4-triazin-3-yl, 1-hydroxyalkyl-1,3,4-triazol-5-yl or 2-alkyloxycarbonyl-1-hydroxylalkyl-1,3,4-triazol-5-yl and $R^o_1$ and $R^o_2$ are defined as above, can be obtained from a product of the general formula

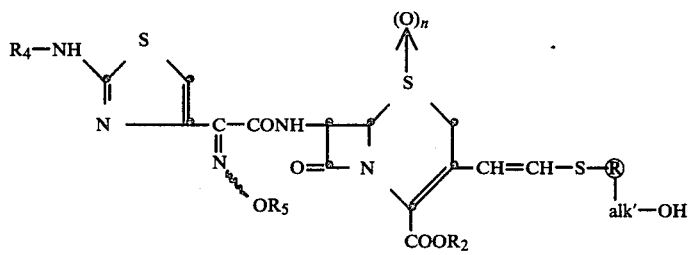

(XXXI')

in which $R_4$, $R_5$, $R_2$, Ⓡ —alk'—OH and n are defined as above, except for $R_4$ representing a hydrogen atom, by any method known for obtaining an ester or a carbamate from an alcohol without affecting the remainder of the molecule, followed, where appropriate, by reduction of the sulphoxide obtained and removal of the protective radicals.

position by an alkyl radical which contains 2 to 4 carbon atoms and is substituted by an acylamino, sulphamylamino, sulphoamino, ureido, alkylureido or dialkylureido group, and $R^o{}_1$ and $R^o{}_2$ have the corresponding definitions, which are all functional derivatives of the amine corresponding to them, can be obtained from a product of the general formula

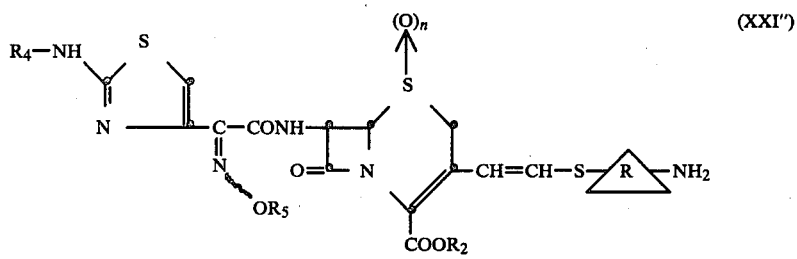

(XXI")

The esterification is carried out at a temperature of between −50° C. and the reflux temperature of the reaction mixture, especially by condensation of the anhydride of the acid (or of some other reactive derivative of the acid, for example the halide) in an inert organic solvent such as an ether (for example tetrahydrofurane), a chlorinated solvent (for example methylene chloride) or a mixture of these solvents, in the presence of a nitrogen-containing base such as pyridine, 4-dimethylamino-pyridine or a trialkylamine (triethylamine) or of an alkaline condensation agent (for example sodium bicarbonate), followed, where appropriate, by reduction of the S-oxide obtained and removal of the protective groups in accordance with the methods described above.

The carbamate is obtained by any known method which does not adversely affect the remainder of the molecule. In particular, the reaction of a chlorosulphonyl isocyanate or trichloroacetyl isocyanate in an inert organic solvent, for example tetrahydrofurane or acetonitrile, at a temperature of between −80° and 20° C., followed by removal of the protective groups, is employed.

VI. The 3-thiovinyl-cephalosporins of the general formula (XXI) in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an alkyl radical containing 2 to 4 carbon atoms substituted by a sulphoamino, alkylsulphonylamino, sulphamylamino, acylamino (of which the acyl part is optionally substituted by hydroxyl, amino, alkylamino or dialkylamino), alkoxycarbonylamino, ureido, alkylureido or dialkylureido group, or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1- in which $R_4$, $R_5$, $R_2$ and n are defined as above, except for $R_4$ representing a hydrogen atom, and —R—$NH_2$ represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an aminoalkyl radical of which the alkyl part contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical of which the alkyl part contains 2 to 4 carbon atoms, by any method which is in itself known for forming an amide, sulphamide, carbamate or urea group without affecting the remainder of the molecule, followed, where appropriate, by reduction of the sulphoxide and removal of the protective groups.

It is to be understood that the products which contain a sulpho, sulphonyl or sulphamyl group are preferably prepared from a product of the general formula (XXI") in which n=0.

Furthermore, if it is desired to prepare a product of which the radical R contains an amino or hydroxyl group, it is necessary to protect these radicals in the reactant used. Equally, if $R_5$ represents a hydrogen atom, it is necessary to protect the oxime.

If it is desired to prepare a product of the general formula (XXI) in which the radical R contains an alkylsulphonylamino, sulphamylamino, acylamino (substituted or unsubstituted), alkoxycarbonylamino or dialkylureido substituent, the reaction is advantageously effected by treatment with, respectively, the corresponding chlorosulphonyl derivative, acid chloride, chloroformate or dialkylcarbamyl chloride, under the conditions described above for the reaction of the acid chloride of the general formula (XVI) with the 7-aminocephalosporin of the general formula (XV).

If it is desired to prepare a product of the general formula (XXI) in which the radical R contains a sulphoamino, alkylsulphonylamino or (substituted or unsubstituted) acylamino substituent, the reaction can be effected by means of the anhydride of the corresponding acid, under the conditions described above for reacting the product of the general formula (XVI) in the form of an anhydride.

If it is desired to obtain a product of the general formula (XXI), in which R contains a (substituted or unsubstituted) acylamino radical, it is also possible to employ the corresponding acid, under the conditions described above for the use of the acid of the general formula (XVI).

If it is desired to obtain a product of the general formula (XXI) in which R contains a ureido or alkylureido radical, the corresponding product of the general formula (XXI″) is treated, respectively, with an alkali metal isocyanate or an alkyl isocyanate, in an aqueous-organic medium or organic medium (for example in tetrahydrofurane) at a temperature of between −20° and 60° C.

VII°. The 3-thiovinyl-cephalosporins of the general formula (XXI), in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by a thiazolidin-2-yl-alkyl radical, by a radical of the general formula (XXIIc) or by a hydroxyiminoalkyl or alkoxyiminoalkyl radical of which the iminoalkyl part contains 1 to 5 carbon atoms, or represents a tetrazol-5-yl radical substituted in the 1-position by a hydroxyiminoalkyl or alkoxyiminoalkyl radical of which the iminoalkyl part contains 1 to 5 carbon atoms, and $R^o{}_1$ and $R^o{}_2$ have the corresponding definitions, which are addition reaction derivatives of the product of the general formula (XXI) in which R is one of the heterocyclic radicals mentioned above, substituted by a formylalkyl radical (or by its hydrate form), can be obtained from a product of the general formula hydrogen is employed, it is advantageous to use solvents such as tetrahydrofurane, acetonitrile, alcohols or ketones. If a product of the general formula (XXI′″), in which $R_4$ and $R_2$ are hydrogen atoms, is employed, it is advantageous to carry out the reaction in solvents such as pyridine, dimethylsulphoxide or dimethylformamide.

If it is desired to prepare a product of the general formula (XXI) in which the radical R contains a substituent of the general formula (XXIIc), the reaction is carried out in an acid medium.

VIII. The 3-thiovinyl-cephalosporins of the general formula (XXI), in which $R^o{}_2$ represents a radical of the general formula (V), in which $R_8$ and $R_9$ are defined as above, can also be obtained by esterification of a product of the general formula (XXI), in which $R^o{}_2$ represents a hydrogen atom, and in which the amine group has been protected beforehand, by any method which is in itself known for preparing an ester from an acid without affecting the remainder of the molecule.

In particular, the reaction is carried out under the conditions described above for the preparation of products of the general formula (XIII) or (XV) in which $R_2$ is a radical of the general formula (V).

The products of the general formulae (XXVI), (XXXII) and (XXXV), in which n=1, can be obtained by oxidation of the corresponding products in which n=0, in accordance with the method described in German Patent Application No. 2,637,176.

The isomers of the products of the general formulae (I), (IX), (XXI), (XXVI), (XXXII), (XXXV), (XXXIX), (XL), (XLII), (XLIII) and (XLIV) can be separated by chromatography or by crystallisation.

The novel products according to the invention, and the products of the general formula (XXI), can optionally be purified by physical methods such as crystallisation or chromatography.

The cephalosporin derivatives of the general formula (XXI) as defined in (α), and their pharmaceutically acceptable salts, exhibit particularly valuable antibacterial properties. They exhibit a remarkable activity, in

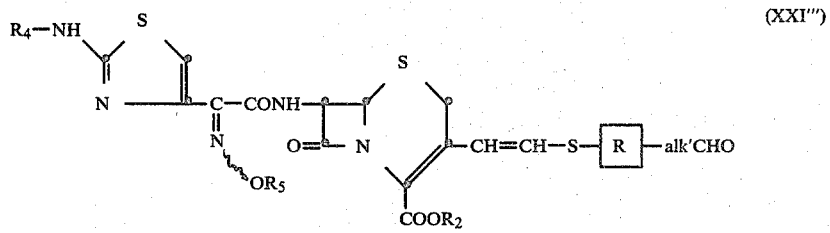

(XXI′″)

in which $R_2$, $R_4$ and $R_5$ are defined as above and —[R]—alk′CHO represents a 5,6-dioxo-4-formylalkyl-1,4,5,6-tetrahydro-1,2,4-triazin-3-yl, 1-formylalkyl-1,3,4-triazol-5-yl, 2-alkoxycarbonyl-1-formylalkyl-1,3,4-triazol-5-yl or 1-formylalkyl-tetrazol-5-yl radical, by addition reaction with, respectively, cysteamine, an alcohol, hydroxylamine or an alkoxyamine, in accordance with the known methods for forming addition reaction derivatives of carbonyl groups, followed, where appropriate, by removal of the protective radicals.

The reaction is in general carried out in an organic solvent at a temperature of between 20° C. and the reflux temperature of the reaction mixture.

The organic solvents are chosen in accordance with the solubility of the products. If a product of the general formula (XXI′″) in which $R_4$ and $R_2$ are other than vitro and in vivo, against Gram-positive and Gram-negative germs.

In vitro, they have proved active at a concentration of between 0.5 and 15 μg/cc against strains of staphylococci sensitive to penicillin G (*Staphylococcus aureus* Smith), at a concentration of between 1 and 30 μg/cc against strains of staphylococci resistant to penicillin G (*Staphylococcus aureus* MB 9), at a concentration of between 0.001 and 1 μg/cc against *Escherichia coli*, Monod strain, and at a concentration of between 0.06 and 30 μg/cc against *Klebsiella pneumoniae*. Furthermore, some of the compounds have proved active at a concentration of between 0.01 and 30 μg/cc against *Proteus morganii* and at a concentration of between 0.1 and 30 μg/cc against *Enterobacter aerogenes*.

In vivo, the compounds have proved active against experimental infections of mice with *Staphylococcus aureus* Smith (sensitive to penicillin G) at a dose of between 0.2 and 15 mg/kg per day, administered subcutaneously, and with *Escherichia coli* (Monod strain) at doses of between 0.001 and 10 mg/kg per day, administered subcutaneously.

Furthermore, the $LD_{50}$ of the products of the general formula (XXI) is between 1.5 g/kg and doses greater than 2.5 g/kg, for subcutaneous administration to mice.

The derivatives of the cephalosporin of the general formula (XXI) as defined in (β) are described, in respect of their antibacterial properties, or by way of intermediates for the preparation of antibiotic substances, in U.S. Pat. No. 4,065,620.

Products of particular interest are those of the general formula (I) in which (a) the symbol $R_1$ represents
a radical of the general formula (II),
a trityl radical,
a radical of the general formula (III), in which $R_6$ is an alkyl radical containing 1 or 2 carbon atoms (optionally substituted by a phenyl or phenoxy radical) or a phenyl radical, or
a radical of the general formula (IV) in which $R_7$ is a branched unsubstituted alkyl radical, and the symbol $R_2$ is a protective radical, or (b) the symbol $R_1$ is
an acyl radical of the general formula (VIII), in which Ar is a phenyl radical and B is a protected amino radical, and the symbol $R_2$ has the corresponding definition, and
n is 0 or 1,
in their bicyclooct-2-ene or bicyclooct-3-ene forms if n=0, and their bicyclooct-2-ene forms if n=1.

Amongst these products, particularly preferred products of the general formula (I) are those in which:

(a) the symbol $R_1$ is
a radical of the general formula (II) (in which $R_5$ is an alkyl or vinyl radical and $R_4$ is trityl),
a trityl radical,
a radical of the general formula (III) as defined above or
a radical of the general formula (IV) [in which $R_7$ is a branched unsubstituted alkyl radical containing 3 or 4 carbon atoms], and the symbol $R_2$ is a benzhydryl or p-nitrobenzyl radical, or (b) the symbol $R_1$ is
an acyl radical of the general formula (VIII), in which Ar is a phenyl radical and B is an amino radical protected by an alkoxycarbonyl group, of which the alkyl part contains 1 to 4 carbon atoms, and the symbol $R_2$ represents a benzhydryl or nitrobenzyl radical, and n is 0 or 1,
in their bicyclooct-2-ene or bicyclooct-3-ene forms, it being understood that the alkyl portions or radicals contain (unless stated to the contrary) 1 or 2 carbon atoms, and especially the following products:
2-benzhydryloxycarbonyl-7-tert.-butoxycarbonylamino-8-oxo-3-(2-oxoethyl)-5-thia-1-aza-bicyclo[4.2.0]oct-2-ene,
2-benzhydryloxycarbonyl-8-oxo-3-(2-oxoethyl)-7-tritylamino-5-thia-1-aza-bicyclo[4.2.0]oct-2-ene,
2-benzhydryloxycarbonyl-8-oxo-3-(2-oxoethyl)-7-phenylacetamido-5-thia-1-aza-bicyclo[4.2.0]oct-2-ene,
2-benzhydryloxycarbonyl-8-oxo-3-(2-oxoethyl)-7-phenoxyacetamido-5-thia-1-aza-bicyclo[4.2.0]oct-2-ene, and
2-benzhydryloxycarbonyl-7-[2-methoxyimino-2-(2-tritylamino-thiazol-4-yl)-acetamido]-8-oxo-3-(2-oxoethyl)-5-thia-1-aza-bicyclo[4.2.0]oct-2-ene.

The examples which follow and are given without implying a limitation, show how the invention can be put into practice.

In these examples, the products are referred to in accordance with the Chemical Abstracts nomenclature. It is to be understood that all the products according to the present invention exhibit the stereochemistry resulting from the partial general formula

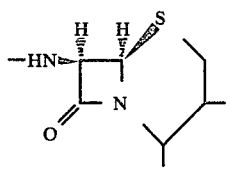

EXAMPLE 1

2-Benzhydryloxycarbonyl-7-tert.-butoxycarbonylamino-3-(2-dimethylamino-vinyl)-8-oxo-5-thia-1-aza-bicyclo[4.2.0]oct-2-ene (E-form) (2.7 g) is dissolved in tetrahydrofurane (54 cc). Distilled water (27 cc) and pure formic acid (2.7 cc) are added successively and the reaction mixture is stirred for 40 minutes at 25° C. After partially concentrating the reaction mixture under reduced pressure (20 mm Hg) at 30° C. and adding ethyl acetate (200 cc), the organic phase is separated off and washed with a saturated aqueous sodium chloride solution (2×100 cc). The organic phase is then dried over magnesium sulphate in the presence of decolorising charcoal, filtered and concentrated to dryness under reduced pressure (20 mm Hg) at 30° C. An orange-coloured froth (2.3 g) is obtained, which is used without additional purification.

A solution of some of the froth (1.02 g) obtained above, in methylene chloride (100 cc), is cooled at a temperature of between −5° C. and −10° C. A solution of 85% pure meta-chloroperbenzoic acid (0.35 g) in methylene chloride (40 cc) is added dropwise in the course of 20 minutes. After the addition, the reaction mixture is stirred for 10 minutes at between −5° and 0° C. and is then washed with a half-saturated aqueous sodium bicarbonate solution (50 cc) and with distilled water (3×50 cc). After drying over sodium sulphate, and filtering, the solvent is evaporated to dryness under reduced pressure (20 mm Hg) at 30° C. The residue is redissolved in methylene chloride (25 cc). Silica (0.56–0.2 mm) (5 g) is added. The mixture is concentrated to dryness under 400 mm Hg at 30° C. and the powder obtained is charged onto a column (column height=21 cm; diameter =2 cm) of silica (0.56–0.2 mm) (25 g) which has been prepared with an 80:20 (by volume) mixture of cyclohexane and ethyl acetate. Elution is carried out successively with the following mixtures (ratios by volume) of cyclohexane and ethyl acetate: 80:20 (100 cc), 70:30 (200 cc), 60:40 (400 cc), 50:50 (400 cc) and 40:60 (400 cc), 60 cc fractions being collected. Fractions 10 to 21 are concentrated to dryness under reduced pressure (20 mm Hg) at 30° C. 2-Benzhydryloxycarbonyl-7-tert.-butoxycarbonylamino-8-oxo-3-(2-oxoethyl)-5-oxide-5-thia-1-aza-bicyclo[4.2.0]oct-2-ene (0.2 g) is obtained in the form of an orange-coloured froth.

Rf=0.32; silica gel chromatographic plate; eluant: an 80:20 (by volume) mixture of cyclohexane and ethyl acetate.

Infrared spectrum (CHBr$_3$): characteristic bands (cm$^{-1}$) at 2720, 1800, 1720 and 1050.

Proton nuclear magnetic resonance spectrum (350 MHz, CDCl$_3$, δ in ppm): 1.47 (S, 9H, (CH$_3$)$_3$CO—); 3.37 and 3.57 (2d, AB, J=19 Hz, 2H:—CH$_2$CHO); 3.60 and 4.20 (2d, AB, J=18 Hz, 2H:—SO—CH$_2$); 4.56 (d, J=4 Hz, 1H:H in the 6-position); 5.24 (d, J=10 Hz, 1H:—CONH—); 5.82 (dd, J=10 and 4 Hz, 1H:H in the 7-position); 6.87 (S, 1H:—CH (C$_6$H$_5$)$_2$); 7.2 to 7.5 (hump, 10H:aromatics); 9.55 (d, J=1 Hz, 1H:—CHO).

2-Benzhydryloxycarbonyl-7-tert.-butoxycarbonylamino-3-(2-dimethylamino-vinyl)-8-oxo-5-thia-1-azabicyclo[4.2.0]octene (E-form) can be prepared in the following manner:

A solution of dimethoxydimethylaminomethane in anhydrous N,N-dimethylformamide (12 cc) is added, at 25° C., to a solution of 2-benzhydryloxycarbonyl-7-tert.-butoxycarbonylamino-3-methyl-8-oxo-5-thia-1-aza-bicyclo [4.2.0]oct-2-ene (2.4 g) in anhydrous N,N-dimethylformamide (12 cc) under an atmosphere of dry nitrogen. The reaction mixture is heated at 80° C. for 3 hours 20 minutes and then poured into a mixture of ethyl acetate (150 cc) and distilled water (150 cc). The aqueous phase is decanted and extracted with ethyl acetate (100 cc). The combined organic solutions are washed with distilled water (2×100 cc) and then dried over magnesium sulphate and filtered. Evaporation of the solvent under reduced pressure (20 mm Hg) at 30° C. gives a chestnutcoloured froth (2.7 g). Thin layer chromatography [silica gel; eluant: a 60:40 (by volume) mixture of cyclohexane and ethyl acetate] and the infrared spectrum indicate that the material is principally 2-benzhydryloxycarbonyl-7-tert.-butoxycarbonylamino-3-(2-dimethylaminovinyl)-8-oxo-5-thia-1-aza-bicyclo[4.2.0]oct-2-ene (E-form).

Rf=0.29; silica gel chromatographic plate [50:50 (by volume) mixture of cyclohexane and ethyl acetate].

2-Benzhydryloxycarbonyl-7-tert.-butoxycarbonylamino-3-methyl-8-oxo-5thia-1-aza-bicyclo[4.2.0]oct-2-ene can be prepared in the following manner:

A solution of diphenyldiazomethane (116.5 g) in acetonitrile (800 cc) is added dropwise, in the course of 45 minutes, at a temperature of between 25° and 30° C., to a solution of 7-tert.-butoxycarbonylamino-2-carboxy-3-methyl-8-oxo-5-thia-1-aza-bicyclo[4.2.0]oct-2-ene (188.6 g) in acetonitrile (2,100 cc). The reaction mixture is stirred for 16 hours at 22° C. and is then concentrated to dryness under reduced pressure (20 mm Hg) at 40° C. The residue is redissolved in ethyl acetate (2 liters) and the solution is washed with 2 N hydrochloric acid (700 cc) and then with a saturated aqueous sodium bicarbonate solution (700 cc) and a saturated aqueous sodium chloride solution (700 cc). The solution is dried over sodium sulphate, treated with decolorising charcoal, filtered, and then concentrated to dryness under reduced pressure (20 mm Hg) at 40° C. The residue is dissolved in boiling ethyl acetate (600 cc). Cyclohexane (1 liter) is added, and the mixture is heated to the reflux temperature and then allowed to cool. The crystals which have appeared are filtered off, washed with diethyl ether (3×250 cc) and then dried. 2-Benzhydryloxycarbonyl-7-tert.-butoxycarbonylamino-3-methyl-8-oxo-5-thia-1-aza-bicyclo[4.2.0]oct-2-ene (191 g) is obtained in the form of white crystals (m.p.=179° C.). On concentrating the mother liquor to 500 cc, a second fraction of product (32.6 g, m.p.=178° C.) is obtained.

7-tert.-Butoxycarbonylamino-2-carboxy-3-methyl-8-oxo-5-thia-1-aza-bicyclo[4.2.0]oct-2-ene can be obtained in the following manner:

7-Amino-2-carboxy-3-methyl-8-oxo-5-thia-1-azabicyclo[4.2.0]oct-2-ene (371 g) is dissolved in a solution of sodium bicarbonate (307 g) in a mixture of distilled water (2 liters) and dioxane (2 liters). A solution of di-tert.-butyl carbonate (421 g) in dioxane (2 liters) is added in the course of 10 minutes. The reaction mixture is stirred for 48 hours at 25° C. The suspension obtained is concentrated under reduced pressure (20 mm Hg) at 50° C. to a residual volume of about 2 liters, and is then diluted with ethyl acetate (1 liter) and distilled water (2 liters). The aqueous phase is decanted, washed with ethyl acetate (500 cc) and acidified to pH 2 with 6 N hydrochloric acid in the presence of ethyl acetate (1500 cc). The aqueous phase is extracted with ethyl acetate (2×1 liter). The combined organic phases are washed with a saturated sodium chloride solution (2×250 cc) and dried over sodium sulphate. After filtration, the solvent is evaporated under reduced pressure (20 mm Hg) at 50° C. 7-tert.-Butoxycarbonylamino-2-carboxy-3-methyl-8-oxo-5-thia-1-aza-bicyclo[4.2.0]oct-2-ene (486 g) is obtained in the form of yellow crystals (m.p.=190° C., with decomposition).

EXAMPLE 2

Distilled water (50 cc) and pure formic acid (8 cc) are added successively to a solution of crude 2-benzhydryloxycarbonyl-7-(D-α-tert.-butoxycarbonylamino-phenylacetamido)-3-(2-dimethylamino-vinyl)-8-oxo-5-thia-1-aza-bicyclo[4.2.0]oct-2-ene (9.3 g) in tetrahydrofurane (100 cc). The reaction mixture is stirred for 50 minutes at 25° C. and then concentrated partially under reduced pressure (20 mm Hg) at 30° C., and the residue is diluted with ethyl acetate (200 cc). The organic phase is decanted, washed successively with distilled water (100 cc), a saturated aqueous sodium bicarbonate solution (100 cc) and a saturated aqueous sodium chloride solution (100 cc) and then dried over magnesium sulphate and filtered. Evaporation of the solvent, to reduce the mixture to dryness under reduced pressure (20 mm Hg) at 30° C., followed by drying the residue under reduced pressure (5 mm Hg) gives a brown froth (9 g) of which the infrared spectrum indicates that it is principally 2-benzhydryloxycarbonyl-7-(D-α-tert.-butoxycarbonylaminophenylacetamido)-8-oxo-3-(2-oxoethyl)-5-thia-1-aza-bicyclo[4.2.0]oct-2-ene.

Rf=0.55; silica gel chromatographic plate; eluant: a 50:50 (by volume) mixture of cyclohexane and ethyl acetate. (Rf of the starting material=0.36).

Infrared spectrum (in CHCl$_3$ solution): characteristic bands at:

1780 cm$^{-1}$ (carbonyl group of the β-lactam)
1715 cm$^{-1}$ (several carbonyl bands: conjugated ester, carbamate, aldehyde)
1695 cm$^{-1}$ (carbonyl of the amide group).

The E-form of 2-benzhydryloxycarbonyl-7-(D-α-tert.-butoxycarbonylaminophenylacetamido)-3-(2-dimethylamino-vinyl)-8-oxo-5-thia-1-aza-bicyclo[4.2.0]oct-2-ene can be obtained in the following manner:

A solution of 2-benzhydryloxycarbonyl-7-[D-α-tert.-butoxycarbonylaminophenylacetamido]-3-methyl-8-oxo-5-thia-1-aza-bicyclo[4.2.0]oct-2-ene (6.14 g) in anhydrous N,N-dimethylformamide (90 cc), at 80° C., is treated, under a dry nitrogen atmosphere, with bisdimethylamino-tert.-butoxymethane (3.49 g) in N,N-dimethylacetamide (30 cc). Following the procedure of reference example 1, a brown froth (6.27 g) is obtained, which consists essentially of 2-benzhydryloxycarbonyl-7-(D-α-tert.-butoxycarbonylaminophenylacetamido)-3-(2-dimethylamino-vinyl)-8-oxo-5-thia-1-aza-bicyclo[4.2.0]oct-2-ene (E.form).

Infrared spectrum (CHBr$_3$): characteristic bands at
1760 cm$^{-1}$ (carbonyl of the β-lactam group)
1710 cm$^{-1}$ (carbonyl of the conjugated ester group)
1690 cm$^{-1}$ (carbonyl of the carbamate group)
1610 cm$^{-1}$ (carbon-carbon double bonds of the dienamine)

Rf=0.33 [silica gel chromatographic plate, using a 50:50 (by volume) mixture of cyclohexane and ethyl acetate].

2-Benzhydryloxycarbonyl-7-(D-α-tert.-butoxycarbonylaminophenylacetamido)-3-methyl-8-oxo-5-thia-1-aza-bicyclo[4.2.0]oct-2-ene can be prepared according to the method described in German Patent Application No. 2,333,256.

EXAMPLE 3

A solution of 2-benzhydryloxycarbonyl-7-tert.-butoxycarbonylamino-3-(2-dimethylamino-vinyl)-8-oxo-5-thia-1-aza-bicyclo[4.2.0]oct-2-ene (E-form) (1.07 g) in ethyl acetate (10 cc) is stirred for 1 hour at 25° C. with a 1 N aqueous hydrochloric acid solution (5 cc). The organic phase is decanted, washed with a saturated aqueous sodium chloride solution (4×50 cc) and then dried over magnesium sulphate and filtered. Evaporation of the solvent, to reduce the mixture to dryness, under reduced pressure gives a product (1 g), of which the infrared spectrum shows that the material is principally 2-benzhydryloxycarbonyl-7-tert.-butoxycarbonylamino 8-oxo-3-(2-oxoethyl)-5-thia-1-aza-bicyclo[4.2.0]oct-2-ene.

Rf=0.57 [silica gel chromatographic plate; eluant: a 60:40 (by volume) mixture of cyclohexane and ethyl acetate].

Infrared spectrum (solution in CHBr$_3$): characteristic bands (cm$^{-1}$) at 2840, 1785 and 1720.

Nuclear magnetic resonance spectrum (350 MHz, CHCl$_3$, δ in ppm, J in Hz): 1.47 (s, 9H:(CH$_3$)$_3$C—O—); 3.24 and 3.55 (AB, J=18, 2H:—SCH$_2$—); 3.50 and 3.66 (AB, J=16, 2H:—C$\underline{H}_2$CHO); 4.98 (d, J=4.5, 1H:H in the 6-position); 5.25 (d, J=9, 1H:—CONH—); 5.65 (dd, J=4.5 and 9, 1H:H in the 7-position); 6.87 (S, 1H:—CO$_2$C$\underline{H}$<); 7.2 to 7.5 (hump, 10H:aromatics); 9.54 (S, 1H:—CHO).

A solution of 2-benzhydryloxycarbonyl-7-tert.-butoxycarbonylamino-3-(2-oxo-ethyl)-8-oxo-5-thia-1-aza-bicyclo[4.2.0]oct-2-ene (0.5 g) and triethylamine (1.0 g) in methylene chloride (50 cc) is stirred for 20 minutes. The mixture is then washed twice with 0.1 N hydrochloric acid (100 cc) and thereafter with a saturated aqueous sodium bicarbonate solution (50 cc) and then an aqueous sodium chloride solution (50 cc), and is dried over sodium sulphate, filtered and concentrated to dryness under reduced pressure (20 mm Hg; 2.7 kPa). This gives a mixture (0.5 g) of the starting material and of 2-benzhydryloxycarbonyl-7-tert.-butoxycarbonylamino-3-(2-oxo-ethyl)-8-oxo-5-thia-1-aza-bicyclo[4.2.0]oct-3-ene, which can be characterised in the mixture by its 1H nuclear magnetic resonance spectrum (360 MHz, CDCl$_3$, δ in ppm, J in Hz): 4.96 (s, H$_2$); 6.06 (s, H$_4$); 6.78 (s, —COOC$\underline{H}$—); 9.33 (s, CHO).

2-Benzhydryloxycarbonyl-7-tert.-butoxycarbonylamino-3-(2-dimethylamino-vinyl)-8-oxo-5-thia-1-aza-bicyclo[4.2.0]oct-2-ene (E-form) can be obtained in the following manner:

A solution of 2-benzhydryloxycarbonyl-7-tert.-butoxycarbonylamino-3-methyl-8-oxo-5-thia-1-aza-bicyclo [4.2.0]oct-3-ene (1.0 g) in anhydrous N,N-dimethylformamide (100 cc) is heated at 80° C. under a nitrogen atmosphere. Bis-dimethylamino-tert.-butoxymethane (0.86 cc) is then added rapidly. The reaction mixture is kept at 80° C. for 5 minutes and is then poured into ethyl acetate (50 cc). After addition of distilled water (25 cc), the organic phase is decanted, washed with distilled water (4×25 cc), dried over magnesium sulphate and filtered. It is then concentrated to dryness under reduced pressure (20 mm Hg) at 30° C., and a product (1.10 g) consisting principally of 2-benzhydryloxycarbonyl-7-tert.-butoxycarbonylamino-3-(2-dimethylamino-vinyl)-8-oxo-5-thia-1-aza-bicyclo[4.2.0]oct-2-ene (E-form) is obtained as an orange-coloured froth.

Rf=0.29; silica gel chromatographic plate [using a 50:50 (by volume) mixture of cyclohexane and ethyl acetate].

Infrared spectrum (CHBr$_3$): characteristic bands (cm$^{-1}$) at 3430, 3350, 2820, 1765, 1715, 1690, 1615, 1540, 1505, 1495, 1465, 1370, 1240, 940, 745 and 600.

Ultraviolet and visible spectrum in ethanol: $\nu_{max}$=390 nm; ε=29,000 (c=2×10$^{-5}$ M).

Mass spectrum: molecular peak at 535; characteristic fragments m/e =378 and 379 (cleavage of the β-lactam).

Proton nuclear magnetic resonance spectrum (350 MHz, CDCl$_3$, δ in ppm, J in Hz): 1.48 (s, (CH$_3$)$_3$C—OCO—, 9H); 2.89 (s, (CH$_3$)$_2$N—, 6H); 3.17 (AB, J=14, —S—CH$_2$— cephem, 2H); 5.02 (d, J=4, H in the 6-position, 1H); 5.27 (dd, J=4 and 9, H in the 7-position, 1H); 5.60 (d, J=9, —OCONH—, 1H); 6.71 (d, J=14, —CH=CH—N<1H); 6.49 (d, J=14, —CH=CH—N<, 1H); 6.95 (s, —C$\underline{H}$(C$_6$H$_5$)$_2$, 1H); 7.2 to 7.5 (hump, aromatics, 10H).

2-Benzhydryloxycarbonyl-7-tert.-butoxycarbonylamino-3-methyl-8-oxo-5-thia-1-aza-bicyclo[4.2.0]oct-3-ene can be prepared by esterification of 7-tert.-butoxycarbonylamino-2-carboxy-3-methyl-8-oxo-5-thia-1-aza-bicyclo[4.2.0]oct-3-ene (3.2 g) by means of diphenyldiazomethane (2.1 g) in accordance with the procedure of Example 1. After recrystallisation from a 90:10 (by volume) mixture of cyclohexane and ethyl acetate, 2-benzhydryloxycarbonyl-7-tert.-butoxycarbonylamino-3-methyl-8-oxo-5-thia-1-aza-bicyclo[4.2.0]oct-3-ene (2.3 g) is obtained in the form of white crystals (melting point =161° C.).

7-Tert.-butoxycarbonylamino-2-carboxy-3-methyl-8-oxo-5-thia-1-aza-bicyclo[4.2.0]oct-3-ene can be prepared by conversion of 7-tert.-butoxycarbonylamino-2-methoxycarbonyl-3-methyl-8-oxo-5-thia-1-aza-bicyclo[4.2.0]oct-2-ene (8.28 g), using the method of R. B. Morin et al., J. Amer. Chem. Soc., 91(6), 1401 (1969). 7-Tert.-butoxycarbonylamino-2-carboxy-3-methyl-8-oxo-5-thia-1-aza-bicyclo[4.2.0]oct-3-ene (5.4 g) is obtained. M.p.=200° C. (with decomposition) (after recrystallisation from ethyl acetate).

Rf=0.59 [silica gel chromatographic plate; eluant: a 60:20:1:1 (by volume) mixture of ethyl acetate, acetone, water and formic acid].

7-Tert.-butoxycarbonylamino-2-methoxycarbonyl-3-methyl-8-oxo-5-thia-1-aza-bicyclo[4.2.0]oct-2-ene can be prepared by esterifying 7-tert.-butoxycarbonylamino-2-carboxy-3-methyl-8-oxo-5-thia-1-aza-bicyclo[4.2.0]oct-2-ene (16.7 g) (described in Example 1) with a solution of diazomethane in ether, according to R. B. Morin et al., J. Amer. Chem. Soc., 91(6), 1401 (1969). 7-Tert.-butoxycarbonylamino-2-methoxycarbonyl-3-methyl-8-oxo-5-thia-1-aza-bicyclo[4.2.0]oct-2-ene (13.6 g) is obtained in the form of white crystals (m.p.=148° C.).

Rf=0.45 [silica gel chromatographic plate; eluant: a 60:40 (by volume) mixture of cyclohexane and ethyl acetate].

EXAMPLE 4

A solution of 2-benzhydryloxycarbonyl-7-tert.-butoxycarbonylamino-3-(2-dimethylamino-vinyl)-8-oxo-5-thia-1-aza-bicyclo[4.2.0]oct-2-ene (E-form) (5.5 g) (obtained as described in Example 1) in pure formic acid (40 cc) is kept for 3 minutes at 0° C. and then diluted with ethyl acetate (300 cc), and this mixture is treated with distilled water (100 cc). After decanting, the organic phase is washed successively with distilled water (100 cc), a saturated aqueous sodium bicarbonate solution (100 cc) and a saturated aqueous sodium chloride solution (100 cc) and is then dried over magnesium sulphate and filtered. Evaporation of the solvent under reduced pressure gives an orange brown froth (5.1 g), the characteristics of which are identical to those of the product obtained in Example 3.

EXAMPLE 5

A solution of 2-benzhydryloxycarbonyl-7-[2-methoxyimino-2-(2-tritylamino-thiazol-4-yl)-acetamido] 3-methyl-8-oxo-5-thia-1-aza-bicyclo[4.2.0]oct-2-ene (syn isomer) (8.06 g) in anhydrous N,N-dimethylformamide (160 cc) is heated to 80° C. bis-Dimethylamino-tert.-butoxymethane (2.26 g) is added and the reaction mixture is kept at 80° C. for 5 minutes. It is then diluted with iced ethyl acetate (645 cc) and this mixture is washed with distilled water (4×250 cc) and then with a saturated aqueous sodium chloride solution (100 cc). The organic solution is dried over magnesium sulphate and filtered. Evaporation to dryness under reduced pressure (20 mm Hg) at 30° C. gives a brown froth (8.1 g), of which the infrared and nuclear magnetic resonance spectra show that it consists principally of the syn isomer, E-form, of 2-benzhydryloxycarbonyl-7-[2-methoxyimino-2-(2-tritylamino-thiazol-4-yl)-acetamido]-3-(2-dimethylamino-vinyl)-8-oxo-5-thia-1-aza-bicyclo[4.2.0]oct-2-ene.

Rf=0.18 [silica gel chromatographic plate; eluant: a 50:50 (by volume) mixture of cyclohexane and ethyl acetate].

Infrared spectrum (solution in CHBr$_3$): characteristic bands at 1765 cm$^{-1}$ (carbonyl group of the β-lactam) and 1610 cm$^{-1}$ (double bond of the enamine).

Nuclear magnetic resonance spectrum (350 MHz, CDCl$_3$, δ in ppm): 2.87 (s, 6H, (CH$_3$)$_2$N—); 2.98 and 3.15 (AB, J=14 Hz, 2H, —S—CH$_2$-cephem); 4.08 (s, 3H, =NOCH$_3$); 5.12 (d, J=4 Hz, 1H, H in the 6-position); 5.51 (dd, J=4 and 8 Hz, 1H, H in the 7-position); 6.42 and 6.54 (AB, J=14 Hz, 2H, H, trans-vinyl); 6.83 (s, 1H, H of the thiazole ring); 6.94 (s, 1H, —COOC$\underline{H}$(C$_6$H$_5$)$_2$); 7.01 (s, broad, 1H, (C$_6$H$_5$)$_3$CN$\underline{H}$—); 7.10 to 7.50 (15H aromatics); 7.63 (d, J=8 Hz, 1H, —CON$\underline{H}$—).

The froth (7.2 g) obtained above is redissolved in ethyl acetate (900 cc) and the solution is stirred with a 1 N aqueous hydrochloric acid solution (120 cc) for 1 hour at 25° C. The organic solution is then decanted, washed with a saturated sodium chloride solution (60 cc), dried over magnesium sulphate and filtered. The solvent is evaporated under reduced pressure (20 mm Hg) at 30° C. A yellowish froth (6.3 g) is obtained; its infrared and nuclear magnetic resonance spectra shows that it consists principally of the syn isomer of 2-benzhydryloxycarbonyl-7-[2-methoxyimino-2-(2-tritylamino-thiazol-4-yl)-acetamido]-8-oxo-3-(2-oxoethyl)-5-thia-1-aza-bicyclo[4.2.0]oct-2-ene.

Rf=0.35 [silica gel chromatographic plate; eluant: a 50:50 (by volume) mixture of cyclohexane and ethyl acetate].

Infrared spectrum (KBr tablet): characteristic bands at 1780 cm$^{-1}$ (carbonyl of the β-lactam); 1720 cm$^{-1}$ (carbonyl of the conjugated ester group); 1680 cm$^{-1}$ (carbonyl of the amide group).

Nuclear magnetic resonance spectrum (350 MHz, CDCl$_3$, δ in ppm): 3.26 and 3.57 (A B, J=19 Hz, 2H:—SCH$_2$-cephem); 3.51 and 3.67 (AB, J=14 Hz, 2H:—C$\underline{H}_2$CHO); 4.08 (S, 3H:=NOCH$_3$); 5.08 (d, J=4 Hz, 1H:H in the 6-position); 5.97 (dd, J=4 and 9 Hz, 1H:H in the 7-position); 6.73 (s, 1H, H in the thiazole ring); 6.83 (d, J=9 Hz, —CON$\underline{H}$—); 6.85 (s, 1H:—COOC$\underline{H}$(C$_6$H$_5$)$_2$); 6.99 (s, broad, 1H, (C$_6$H$_5$)$_3$CN$\underline{H}$); 7.20 to 7.45 (15 H aromatics); 9.57 (s, 1H, —C$\underline{H}$O).

2-Benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene, syn isomer can be prepared in the following manner:

A solution of 2-(2-tritylamino-thiazol-4-yl)-2-methoxyimino-acetic acid (syn isomer) (7.2 g) in methylene chloride (22.5 cc) is added, in a single shot, to a solution of 7-amino-2-benzhydryloxycarbonyl-3-methyl-8-oxo-5-thia-1-aza-bicyclo[4.2.0]oct-2-ene (3.15 g) in methylene chloride (31.5 cc). The temperature rises from 8° to 14° C. The mixture is kept stirred for one hour 15 minutes, during which the temperature rises to 20° C., and is then washed with 0.5 N hydrochloric acid (10 cc), distilled water (10 cc) and a saturated sodium bicarbonate solution (20 cc). The insoluble matter formed is filtered off, and the organic phase is washed again with distilled water (2×20 cc), dried over magnesium sulphate, filtered and concentrated to dryness under reduced pressure (20 mm Hg) at 40° C. The residue is chromatographed on a column (diameter: 3 cm, height: 33 cm) containing silica gel (125 g), elution being carried out with a 20:80 (by volume) mixture of ethyl acetate and cyclohexane (1.2 liters) and then with a 40:60 (by volume) mixture (1 liter), and 50 cc fractions of eluate being collected. Fractions 31 to 44 are evaporated and 2-benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene, syn isomer (2.8 g) is obtained in the form of a pale yellow solid.

7-Amino-2-benzhydryloxycarbonyl-3-methyl-8-oxo-5-thia-1-aza-bicyclo[4.2.0]oct-2-ene can be prepared according to the method described in Netherlands Patent Application 73/03,263.

EXAMPLE 6

Starting from 2-benzhydryloxycarbonyl-7-(D-α-tert.-butoxycarbonylaminophenylacetamido)-3-(2-dimethylamino-vinyl)-8-oxo-5-thia-1-aza-bicyclo[4.2.0]oct-2-ene (E-form) (66 g), and proceeding in accordance with the method described in Example 4, a brown froth (57.9 g) is obtained, having characteristics identical to those of the 2-benzhydryloxycarbonyl-7-(D-α-tert.-butoxy-carbonylaminophenylacetamido)-8-oxo-3-(2-oxo-ethyl)-5-thia-1-aza-bicyclo[4.2.0]oct-2-ene obtained in Example 2.

EXAMPLE 7

Starting from crude 3-(2-dimethylamino-vinyl)-2-(4-nitro-benzyloxycarbonyl)-8-oxo-7-phenoxyacetamido-5-thia-1-aza-bicyclo[4.2.0]oct-2-ene (E-form) (1 g) and working in accordance with the procedure described in Example 1, an orange froth (0.74 g) is obtained, which consists principally of 2-(4-nitro-benzyloxycarbonyl)-8-oxo-3-(2-oxo-ethyl)-7-phenoxyacetamido-5-thia-1-aza-bicyclo[4.2.0]oct-2-ene.

Infrared spectrum (CHBr$_3$)-characteristic bands at: 3400 cm$^{-1}$, —NH— and —OH (enol form); 2730 cm$^{-1}$,

of the aldehyde; 1780 cm$^{-1}$, carbonyl group of the β-lactam; 1720 cm$^{-1}$, carbonyl groups of the conjugated ester and of the aldehyde; 1690 cm$^{-1}$, carbonyl group of the amide; 1650 cm$^{-1}$, carbon-carbon double bonds of the enol form; 1520 and 1345 cm$^{-1}$, —C$_6$H$_4$NO$_2$.

Crude 3-(2-dimethylamino-vinyl)-2-(4-nitro-benzyloxycarbonyl)-8-oxo-7-phenoxyacetamido-5-thia-1-aza-bicyclo[4.2.0]oct-2-ene (E-form) can be obtained in the following manner:

A solution of 3-methyl-2-(4-nitro-benzyloxy-carbonyl)-8-oxo-7-phenoxyacetamido-5-thia-1-aza-bicyclo[4.2.0]oct-2-ene (17 g) in anhydrous N,N-dimethylformamide (100 cc) is heated at 80° C. under dry nitrogen and then treated with bis-dimethylamino-tert.-butoxymethane (10.8 cc) for 1 minute at 80° C. The reaction mixture is then diluted with ethyl acetate (400 cc) and distilled water (250 cc). The organic phase is decanted, washed with distilled water (2×250 cc) and with a saturated aqueous sodium chloride solution (250 cc), and is dried and filtered. The residue obtained after evaporating the solvent under reduced pressure (20 mm Hg) at 30° C. is redissolved in methylene chloride (50 cc) and the solution is poured dropwise into isopropyl ether (1,600 cc). The precipitate formed is filtered off, washed with isopropyl ether (4×100 cc) and dried under reduced pressure (10 mm Hg) at 25° C. An ochre powder (8.6 g) is obtained; its infrared and nuclear magnetic resonance spectra indicate that it contains principally 3-(2-dimethylamino-vinyl)-2-(4-nitro-benzyloxycarbonyl)-8-oxo-7-phenoxyacetamido-5-thia-1-aza-bicyclo[4.2.0]oct-2-ene (E-form).

Rf=0.3 [silica gel chromatographic plate; 40:60 (by volume) mixture of cyclohexane and ethyl acetate].

3-Methyl-2-(4-nitro-benzyloxycarbonyl)-8-oxo-7-phenoxyacetamido-5-thia-1-aza-bicyclo[4.2.0]oct-2-ene can be prepared according to the method described by E. H. Flynn, Cephalosporins and Penicillins, Academic Press New-York and London (1972) page 670.

EXAMPLE 8

2-Benzhydryloxycarbonyl-7-benzoylamino-3-(2-dimethylamino-vinyl)-8-oxo-5-thia-1-aza-bicyclo[4.2.0]oct-2-ene (E-form) (1 g) is dissolved in pure formic acid (10 cc) at 25° C. The solution obtained is poured into a mixture of ethyl acetate (100 cc) and distilled water (100 cc). The organic phase is decanted and washed successively with distilled water (100 cc), a saturated aqueous sodium chloride solution (100 cc), a saturated aqueous sodium bicarbonate solution (2×50 cc) and a saturated aqueous sodium chloride solution (100 cc). After drying over magnesium sulphate, the solution is filtered and concentrated to dryness under reduced pressure. An orange froth (0.9 g) is obtained, which consists principally of 2-benzhydryloxycarbonyl-7-benzoylamino-8-oxo-3-(2-oxo-ethyl)-5-thia-1-aza-bicyclo[4.2.0]oct-2-ene.

Rf=0.37 [silica gel chromatographic plate; eluant: a 50:50 (by volume) mixture of cyclohexane and ethyl acetate].

Infrared spectrum (KBr tablet): characteristic bands (cm$^{-1}$): 2720, CH of the aldehyde; 1770, carbonyl group of the β-lactam.

2-Benzhydryloxycarbonyl-7-benzoylamino-3-(2-dimethylamino-vinyl)-8-oxo-5-thia-1-aza-bicyclo[4.2.0]octene (E-form) can be obtained in the following manner:

bis-Dimethylamino-tert.-butoxymethane (10 g) is added, under a dry nitrogen atmosphere, to a solution of 2-benzhydryloxycarbonyl-7-benzoylamino-3-methyl-8-oxo-5-thia-1-aza-bicyclo[4.2.0]oct-2-ene (24 g) in anhydrous N,N-dimethylformamide (100 cc). The reaction mixture is stirred at 25° C. for 23 hours and is then poured into a mixture of ethyl acetate (300 cc) and an aqueous saturated sodium chloride solution (700 cc). The aqueous phase is decanted and extracted with ethyl acetate (250 cc). The organic phases are combined, washed with 1 N aqueous hydrochloric acid (250 cc), with distilled water (500 cc) and with a saturated aqueous sodium chloride solution (300 cc) and then dried over magnesium sulphate in the presence of decolorising charcoal, and filtered. The solvent is evaporated under reduced pressure (20 mm Hg) at 30° C. The residue is dissolved in methylene chloride (200 cc) and fixed to silica (50 g). The powder obtained is placed in a column (height 60 cm, diameter 5 cm) containing silica gel (415 g) in a 95:5 (by volume) mixture of cyclohexane and ethyl acetate. Elution is carried out with the following mixtures of cyclohexane and ethyl acetate: 95:5 (by volume) (5 liters), 90:10 (by volume) (5 liters), 80:20 (by volume) (5 liters), 70:30 (by volume) (7.5 liters) (so as to elute the impurities) and 60:40 (by volume) (8 liters) the latter being collected and concentrated to dryness. 2-Benzhydryloxycarbonyl-7-benzoylamino-3-(2-dimethylamino-vinyl)-8-oxo-5-thia-1-aza-bicyclo[4.2.0]oct-2-ene (E-form) (10.4 g) is obtained in the form of a yellow solid.

Rf=0.24 [silica gel chromatographic plate]; eluant: a 50:50 (by volume) mixture of cyclohexane and ethyl acetate.

Infrared spectrum (CHCl$_3$): characteristic bands (cm$^{-1}$) at 2800, 1760, 1740, 1660 and 1605.

Proton nuclear magnetic resonance spectrum (60 MHz, CDCl$_3$, δ in ppm, J in Hz): principal signals 2.85 (s, 6H, (CH$_3$)$_2$N—CH=CH—); 5.1 (d, J=4 Hz, 1H, H in the 6-position); 5.65 (dd, J=9 and 4 Hz, 1H, H in the 7-position); 6.8 (s, 1H, —C<u>H</u>(C$_6$H$_5$)$_2$); 7.05 to 8.2 (hump, aromatics and —CON<u>H</u>—).

UV spectrum (C$_2$H$_5$OH, C=1.9 10$^{-5}$ M, 1=1 cm); λ$_{max}$=392 nm, ε=16,000.

2-Benzhydryloxycarbonyl-7-benzoylamino-3-methyl-8-oxo-5-thia-1-aza-bicyclo[4.2.0]oct-2-ene can be prepared according to the method described in Polish Pat. Nos. 86,945 and 86,946.

EXAMPLE 9

A solution of 2-benzhydryloxycarbonyl-3-(2-dimethylamino-vinyl)-8-oxo-7-[2-(2-tritylamino-thiazol-4-yl)-2-vinyloxyimino-acetamido]-5-thia-1-aza-bicyclo[4.2.0]oct-2-ene (syn isomer, E-form) (2.5 g) in ethyl acetate (70 cc) is stirred in the presence of 1 N hydrochloric acid (50 cc) for 1 hour at 25° C. The organic phase is decanted, washed with a half-saturated sodium bicarbonate solution (2×50 cc) and a half-saturated sodium chloride solution (50 cc), dried over sodium sulphate, filtered and concentrated to dryness under 20 mm Hg (2.7 kPa) at 20° C. A brown froth (2.4 g) consisting principally of 2-benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]oct-2-ene, syn isomer, is obtained.

Infrared spectrum (KBr): characteristic bands (cm$^{-1}$) at 1785, 1725, 1685, 1640, 1530, 1495, 1450, 1000, 950, 755 and 700.

Proton nuclear magnetic resonance spectrum (350 MHz, CDCl$_3$, δ in ppm, J in Hz): 3.26 and 3.58 (2d, J=18, 2H, —SCH$_2$—); 3.53 and 3.69 (2d, J=18, 2H, —CH$_2$—);

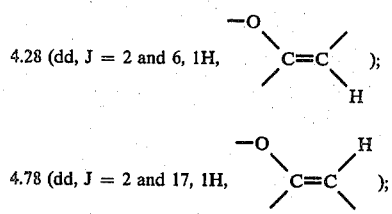

5.12 (d, J=4, 1H, H in the 6-position); 6.0 (dd, J=4 and 9, 1H, H in the 7-position); 6.8 (s, 1H, H of the thiazole); 6.90 (s, 1H, —COOCH<); 7.08 (dd, J=6 and 17, 1H, —CH=CH$_2$); 9.55 (s, 1H, —CHO).

2-Benzhydryloxycarbonyl-3-(2-dimethylamino-vinyl)-8-oxo-7-[2-(2-tritylamino-thiazol-4-yl)-2-vinyloxyimino-acetamido]-5-thia-1-aza-bicyclo[4.2.0]oct-2-ene (syn isomer, E-form) can be prepared in the following manner:

tert.-Butoxy-bis-dimethylaminomethane (0.7 cc) is added at 80° C., under nitrogen, to a solution of 2-benzhydryloxycarbonyl-3-methyl-8-oxo-7-[2-(2-tritylamino-thiazol-4-yl)-2-vinyloxyimino-acetamido]-5-thia-1-aza-bicyclo[4.2.0]oct-2-ene, syn isomer (2.5 g) in dimethylformamide (40 cc). The mixture is stirred for 10 minutes at 80° C. and is then poured into ethyl acetate (250 cc) and iced water (250 cc). The organic phase is decanted, washed with water (3×150 cc) and saturated aqueous sodium chloride (150 cc), dried over sodium sulphate, filtered and concentrated to dryness under 20 mm Hg (2.7 kPa) at 30° C. A brown froth (2.5 g) consisting principally of 2-benzhydryloxycarbonyl-3-(2-dimethylamino-vinyl)-8-oxo-7-[2-(2-tritylamino-thiazol-4-yl)-2-vinyloxyimino-acetamido]-5-thia-1-aza-bicyclo[4.2.0]oct-2-ene (syn isomer, E-form) is obtained.

Infrared spectrum (KBr): characteristic bands (cm$^{-1}$) at 1770, 1670, 1635, 1610, 1530, 1495, 1450, 1000, 945, 755 and 700.

Proton nuclear magnetic resonance spectrum (350 MHz, CDCl$_3$, δ in ppm, J in Hz): 2.90 (s, 6H, —N(CH$_3$)$_2$);

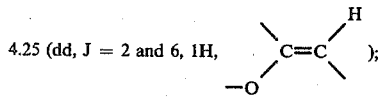

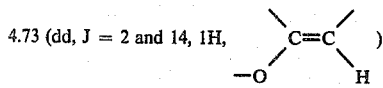

5.18 (d, J=4, 1H, H in the 6-position); 5.60 (dd, J=4 and 9, 1H, H in the 7-position); 6.53 and 6.75 (2d, J=16, 2 H, —CH=CH—); 6.88 (s, 1H, —COOCH<); 7.10 (dd, J=6 and 14, 1H, =NOCH=).

2-Benzhydryloxycarbonyl-3-methyl-8-oxo-7-[2-(2-tritylamino-thiazol-4-yl)-2-vinyloxyimino-acetamido]-5-thia-1-aza-bicyclo[4.2.0]oct-2-ene, syn isomer, is prepared by condensing 2-(2-tritylamino-thiazol-4-yl)-2-vinyloxyimino-acetic acid, syn isomer (4.6 g) with the benzhydryl ester of 7-ADCA (3.8 g) in the presence of N,N'-dicyclohexylcarbodiimide (2.3 g) and of 4-dimethylamino-pyridine (0.05 g) in methylene chloride (40 cc) for 4 hours at between 5° C. and 20° C. After chromatography over silica gel (200 g), using methylene chloride, the expected product (5 g) is obtained in the form of a yellow froth.

Infrared spectrum (KBr): characteristic bands (cm$^{-1}$) at 3400, 1785, 1725, 1690, 1640, 1525, 1495, 1450, 1040, 1000, 940, 755 and 700.

Proton nuclear magnetic resonance spectrum (350 MHz, CDCl$_3$, δ in ppm, J in Hz): 2.12 (s, 3H, —CH$_3$); 3.22 and 3.49 (2d, J=18, 2H, —CH$_2$—);

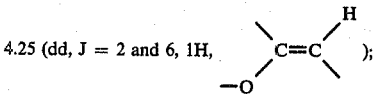

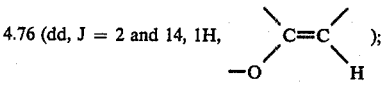

5.08 (d, J=4, 1H, H in the 6-position); 5.92 (dd, J=4 and 9, 1H, H in the 7-position); 6.83 (s, 1H, H of the thiazole); 6.93 (s, 1H, —COOCH<); 7.0 (s, 1H, —NH—C(C$_6$H$_5$)$_3$).

2-(2-Tritylamino-thiazol-4-yl)-2-vinyloxyimino-acetic acid, syn isomer, is prepared according to Belgian Pat. No. 869,079.

EXAMPLE 10

A solution of 2-benzhydryloxycarbonyl-3-(2-dimethylaminovinyl)-8-oxo-7-tritylamino-5-thia-1-aza-bicyclo[4.2.0]oct-2-ene (E-form) (23.5 g) in ethyl acetate (500 cc) is stirred with 1 N hydrochloric acid (250 cc) for 90 minutes at 25° C. The organic phase is decanted, washed with distilled water (3×250 cc), a saturated sodium bicarbonate solution (100 cc) and a half-saturated sodium chloride solution (250 cc), then dried over sodium sulphate and concentrated to dryness under reduced pressure (40 mm Hg) at 40° C. 2-Benzhydryloxycarbonyl-8-oxo-3-(2-oxo-ethyl)-7-tritylamino-5-thia-1-aza-bicyclo[4.2.0]oct-2-ene (21 g) is obtained in the form of an orange-coloured froth.

Proton nuclear magnetic resonance spectrum (350 MHz, CDCl$_3$, δ in ppm, J in Hz): 2.99 (d, J=9, 1H, >NH); 3.07 and 3.33 (2d, J=18, 2H, —SCH$_2$—); 3.50

(AB, J=14, 2H, —C$\underline{\text{H}}_2$CHO); 4.30 (d, J=4, 1H, H in the 6-position); 4.75 (dd, J=4 and 9, 1H, H in the 7-position); 6.82 (s, 1H, —CO$_2$CH(C$_6$H$_5$)$_2$); 7.20 to 7.60 (hump, 25H, aromatics); 9.46 (s, 1H, —C$\underline{\text{H}}$O).

tert.-Butoxy-bis-dimethylaminomethane (10.8 cc) is added to a solution of a mixture (21.8 g) of 2-benzhydryloxycarbonyl-3-methyl-8-oxo-7-tritylamino-5-thia-1-aza-bicyclo[4.2.0]oct-2-ene (40%) and its oct-3-ene isomer (60%) in dry N,N-dimethylformamide (120 cc) heated to 80° C. under nitrogen. After 5 minutes at 80° C., the reaction mixture is poured into ethyl acetate (500 cc). Distilled water (250 cc) is added, the mixture is stirred, and the organic phase is decanted, washed with distilled water (3×250 cc), then dried over magnesium sulphate and concentrated under reduced pressure (40 mm Hg) at 40° C. Examination, by thin layer chromatography, of the residue shows the presence of unchanged starting material. The product is redissolved in dry, N,N-dimethylformamide (100 cc), the solution is heated to 80° C. under nitrogen, and after addition of tert.-butoxy-bis-dimethylaminomethane (6 cc) the reaction mixture is kept at 80° C. for 5 minutes. It is then diluted with ethyl acetate (500 cc) and treated as above, to give an orange froth (24 g) consisting principally of 2-benzhydryloxycarbonyl-3-(2-dimethylamino-vinyl)-8-oxo-7-tritylamino-5-thia-1-aza-bicyclo[4.2.0]oct-2-ene (E-form).

Infrared spectrum (CHBr$_3$, characteristic bands in cm$^{-1}$): 3320, 2800, 1760, 1680, 1610, 1445, 760 and 705.

Proton nuclear magnetic resonance spectrum (CDCl$_3$, 350 MHz, δ in ppm, J in Hz): 2.84 (s, 6H, —N(CH$_3$)$_2$); 2.95 and 3.12 (2d, J=16, 2H, —SCH$_2$—); 3.36 (d, J=10, 1H, —NH—); 3.98 (d, J=4, 1H, H in the 6-position); 4.41 (dd, J=4 and 10, 1H, H in the 7-position); 6.46 and 6.72 (2d, J=14, —CH=CH—);

6.82 (s, 1H, C$\underline{\text{H}}$(C$_6$H$_5$)$_2$);

7.2 to 7.6 (hump, 25H aromatics).

The mixture of 2-benzhydryloxycarbonyl-3-methyl-8-oxo-7-tritylamino-5-thia-1-aza-bicyclo[4.2.0]oct-2-ene (40%) and its oct-3-ene isomer (60%) can be obtained in the following manner:

A solution of diphenyldiazomethane (12.3 g) in acetonitrile (200 cc) is added, in the course of 15 minutes, to a suspension of a mixture (28.8 g) of 2-carboxy-3-methyl-8-oxo-7-tritylamino-5-thia-1-aza-bicyclo[4.2.0]oct-2-ene (40%) and its oct-3-ene isomer (60%) in acetonitrile (500 cc), and the reaction mixture is then stirred for 2 hours at 25° C. The solvent is evaporated under reduced pressure (40 mm Hg) at 30° C. and the oily residue is redissolved in ethyl acetate (500 cc). The solution is washed successively with normal hydrochloric acid (until colourless), with a saturated sodium bicarbonate solution (3×100 cc), with water (100 cc) and with a saturated sodium chloride solution (100 cc), and is then dried and concentrated to dryness, to give a mixture (35.4 g) of 2-benzhydryloxycarbonyl-3-methyl-8-oxo-7-tritylamino-5-thia-1-aza-bicyclo[4.2.0]oct-2-ene (40%) and its oct-3-ene isomer (60%), in the form of a cream-coloured froth.

Infrared spectrum (CHBr$_3$): characteristic bands (cm$^{-1}$) at 3340, 1765, 1730, 1620, 1590, 1490, 1445, 745 and 700.

Proton nuclear magnetic resonance spectrum (CDCl$_3$, 350 MHz, δ in ppm, J in Hz): 1.73 (s, —CH$_3$ of the oct-3-ene); 2.04, s, —CH$_3$ of the oct-2-ene); 3.05 and 3.30 (2d, AB, J=18, —SCH$_2$— of the oct-2-ene); 4.20 (2d, J=4, H in the 6-position of the oct-2-ene and oct-3-ene); 4.60 (2dd, J=4 and 10, H in the 7-position of the oct-2-ene and oct-3-ene); 4.80 (s, H in the 2-position of the oct-3-ene); 5.75 (s broad, H in the 4-position of oct-2-ene); 6.78 (s, —CO$_2$C$\underline{\text{H}}$(C$_6$H$_5$)$_2$ of the oct-3-ene); 6.89 (s, —CO$_2$C$\underline{\text{H}}$(C$_6$H$_5$)$_2$ of the oct-2-ene); 7.2 to 7.50 (aromatics).

2-Carboxy-3-methyl-8-oxo-7-tritylamino-5-thia-1-aza-bicyclo[4.2.0]octene (40%) and its oct-3-ene isomer (60%) can be obtained in the following manner:

Triethylamine (55.6 cc) is added to a suspension of 7-amino-2-carboxy-3-methyl-8-oxo-5-thia-1-aza-bicyclo[4.2.0]oct-2-ene (42.8 g) in dry N,N-dimethylformamide (250 cc), and after cooling the mixture to −20° C. a solution of chlorotriphenylmethane (55.8 g) in chloroform (250 cc) is added in the course of 2 hours. The reaction mixture is stirred for 24 hours at 25° C. and then poured into normal hydrochloric acid (400 cc). After filtration, the organic phase is separated off, concentrated to half its volume under reduced pressure (40 mm Hg) at 40° C., and taken up in ethyl acetate (400 cc). The aqueous phase is extracted with ethyl acetate (400 cc), and the combined organic phases are washed with normal hydrochloric acid (2×250 cc) and then extracted with a half-saturated sodium bicarbonate solution (4×500 cc). These combined aqueous phases are washed with ethyl acetate (300 cc), then acidified to pH 3 with 12 N hydrochloric acid and extracted with ethyl acetate (2×500 cc). The combined organic solutions are washed with a saturated sodium chloride solution (250 cc), dried over sodium sulphate and concentrated to dryness under reduced pressure (40 mm Hg) at 40° C. The residue is caused to solidify by adding isopropyl ether (250 cc). The solid is filtered off, washed with isopropyl ether (100 cc) and dried. A mixture (22.2 g) of 2-carboxy-3-methyl-8-oxo-7-tritylamino-5-thia-1-aza-bicyclo[4.2.0]oct-2-ene (40%) and its oct-3-ene isomer (60%) is obtained in the form of a cream-coloured solid.

Infrared spectrum (CHBr$_3$); characteristic bands (cm$^{-1}$) at 3320, 3300, 2400, 1765, 1730, 1625, 1595, 1490, 1450, 750 and 710.

Proton nuclear magnetic resonance spectrum (CDCl$_3$, 350 MHz, δ in ppm, J in Hz): 1.84 (s, —CH$_3$ of the oct-3-ene); 2.16 (s, —CH$_3$ of the oct-2-ene); 3.10 and 3.40 (2d, J=10, —SCH$_2$— of the oct-2-ene); 4.2 (2d, J=4, H in the 6-position of the oct-2-ene and oct-3-ene); 4.6 (2dd, J=4 and 10, H in the 7-position of the oct-2-ene and oct-3-ene); 4.73 (s, H in the 2-position of the oct-3-ene); 5.77 (s broad, H in the 4-position of the oct-3-ene); 7.2 to 7.5 (aromatics).

EXAMPLE 11

1 N Hydrochloric acid (90 cc) is added to a solution of 2-benzhydryloxycarbonyl-3-(2-dimethylamino-vinyl)-8-oxo-7-phenylacetamido-5-thia-1-aza-bicyclo[4.2.0]oct-2-ene, E-form (5.0 g) in ethyl acetate (130 cc). The mixture is stirred for one hour and the aqueous phase is then decanted. The organic phase is washed with a saturated sodium bicarbonate solution (2×75 cc) and then with a saturated sodium chloride solution (75 cc), dried over sodium sulphate and evaporated to dryness under reduced pressure (20 mm Hg, 2.7 kPa). This gives 2-benzhydryloxycarbonyl-3-(2-oxo-ethyl)-8-oxo-7-phenylacetamido-5-thia-1-aza-bicyclo[4.2.0]oct-2-ene (4.7 g) in the form of a cream-coloured froth.

Infrared spectrum (KBr): characteristic bands (cm$^{-1}$) at 3410, 2740, 1780, 1720, 1700, 1690 and 1600.

Proton nuclear magnetic resonance spectrum (350 MHz, CDCl$_3$, δ in ppm, J in Hz): 3.13 and 3.43 (2d, J=18, 2H, —SCH$_2$—); 3.37 and 3.62 (2d, J=16, 2H, —CH$_2$—CHO);

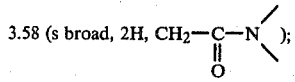

3.58 (s broad, 2H, CH$_2$—C—N$\diagup\diagdown$);

4.90 (d, J=4, 1H, H$_6$); 5.81 (dd, J=4 and 9, 1H, H$_7$); 6.12 (d, J=9, >NH); 6.78 (s, 1H, —COOC$\underline{H}$<); 9.47 (s, 1H, —CHO).

A solution of 2-benzhydryloxycarbonyl-3-formyl-methyl-8-oxo-7-phenylacetamido-5-thia-1-aza-bicyclo[4.2.0]oct-2-ene (0.5 g) and triethylamine (1.0 g) in methylene chloride (50 cc) is stirred for 20 minutes. The organic phase is washed with 0.1 N hydrochloric acid (2×100 cc), then with a saturated sodium bicarbonate solution (50 cc) and finally with a saturated sodium chloride solution (50 cc). It is dried over sodium sulphate, filtered and concentrated to dryness under reduced pressure (20 mm Hg, 2.7 kPa). This gives a mixture (0.5 g) of the starting material and of 2-benzhydryloxycarbonyl-3-(2-oxo-ethyl)-8-oxo-7-phenylacetamido-5-thia-1-aza-bicyclo[4.2.0]oct-3-ene, which can be characterised in the mixture by its proton nuclear magnetic resonance spectrum (350 MHz, CDCl$_3$, δ in ppm, J in Hz): 4.95 (s, H$_2$); 5.13 (d, J=4, H$_6$); 5.56 (dd, J=4 and 9, H$_7$); 4.98 (s, H$_4$); 9.32 (s, —CHO).

2-Benzhydryloxycarbonyl-3-(2-dimethylaminovinyl)-8-oxo-7-phenylacetamido-5-thia-1-aza-bicyclo[4.2.0]oct-2-ene, E-form, can be obtained in the following manner:

2-Benzhydryloxycarbonyl-3-methyl-8-oxo-7-phenylacetamido-5-thia-1-aza-bicyclo[4.2.0]oct-2-ene (4.6 g) (prepared according to Netherlands Patent Application No. 7,303,263) is dissolved in dimethylformamide (44 cc) at 80° C. A solution of ethoxy-bis-(dimethylamino)methane (2.68 g) in dimethylformamide (2.67 cc) is added in the course of 30 minutes. The resulting solution is then poured into a mixture of water (100 cc), ice (100 cc) and ethyl acetate (300 cc). The organic phase is decanted, washed with water (2×200 cc) and then with a saturated sodium chloride solution (100 cc), dried over sodium sulphate, filtered and evaporated to dryness under reduced pressure (40° C., 20 mm Hg, 2.7 kPa). This gives 2-benzhydryloxycarbonyl-3-(2-dimethylaminovinyl)-8-oxo-7-phenylacetamido-5-thia-1-aza-bicyclo[4.2.0]oct-2-ene, E-form (5.0 g) in the form of a brown oil.

Infrared spectrum (CHBr$_3$); characteristic bands in cm$^{-1}$ at 3320, 1680, 1755, 1610 and 1540.

Proton nuclear magnetic resonance spectrum (350 MHz, CDCl$_3$, δ in ppm, J in Hz): 2.72 (s, 6H, —N(CH$_3$)$_2$); 2.30 and 3.15 (2d, J=18, 2H, —SCH$_2$—);

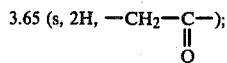

3.65 (s, 2H, —CH$_2$—C—);

4.93 (d, J=4, 1H, H$_6$); 5.34 (dd, J=4 and 8, 1H, H$_7$); 6.01 (d, J=12, 1H, —C$\underline{H}$=CH—N<); 6.11 (d, J=12, 1H, —CH=C$\underline{H}$—N<); 6.66 (s, 1H, —CH<(benzhydryl)); 7.2 to 7.5 (m, 15H, aromatic); 7.56 (d, J=8, 1H, >NH).

EXAMPLE 12

A 1 N hydrochloric acid solution (28 cc) is added to a solution of 2-benzhydryloxycarbonyl-3-(2-dimethylamino-vinyl)-8-oxo-7-phenoxyacetamido-5-thia-1-aza-bicyclo[4.2.0]oct-2-ene, E-form (1.5 g) in ethyl acetate (40 cc), and the emulsion thus obtained is stirred for one hour. The aqueous phase is decanted and the organic phase is washed with a saturated sodium bicarbonate solution (2×25 cc) and then with a saturated sodium chloride solution (25 cc), dried over magnesium sulphate and evaporated to dryness under reduced pressure (20 mm Hg, 2.7 kPa). This gives 2-benzhydryloxycarbonyl-8-oxo-3-(2-oxo-ethyl)-7-phenoxyacetamido-5-thia-1-aza-bicyclo[4.2.0]oct-2-ene (1.3 g) in the form of a cream-coloured froth.

Infrared spectrum (KBr): characteristic bands (cm$^{-1}$) at 3410, 2740, 1780, 1720, 1700, 1690, 1600, 1590, 1520, 1475, 1455, 1240, 755 and 700.

Proton nuclear magnetic resonance spectrum (350 MHz, CDCl$_3$, δ in ppm, J in Hz): 3.27 and 3.57 (2d, J=18, 2H, —S—CH$_2$—); 3.50 and 3.72 (2d, J=16, 2H, —CH$_2$CHO); 4.57 (s, 2H, —OCH$_2$CO—); 5.04 (d, J=5, 1H, H in the 6-position); 5.96 (dd, J=5 and 9, 1H, H in the 7-position); 6.88 (s, 1H, —COOC$\underline{H}$<); 9.60 (s, 1H, —C$\underline{H}$O).

2-Benzhydryloxycarbonyl-3-(2-dimethylaminovinyl)-8-oxo-7-phenoxyacetamido-5-thia-1-aza-bicyclo[4.2.0]oct-2-ene, E-form, can be obtained in the following manner:

bis-Dimethylamino-butoxymethane (7.8 g) is added, in the course of 30 seconds, to a solution of 2-benzhydryloxycarbonyl-3-methyl-8-oxo-7-phenoxyacetamido-5-thia-1-aza-bicyclo[4.2.0]oct-2-ene (21 g) in dimethylformamide 400 cc), which has been heated to 80° C. The solution becomes greenish brown. After 5 minutes at 80° C., the solution is poured into a mixture of water (500 cc), ice (500 g) and ethyl acetate (1500 cc). The organic phase is washed with water (2×1000 cc) and then with a saturated sodium chloride solution (500 cc), dried over magnesium sulphate and concentrated to dryness under reduced pressure (20 mm Hg, 2.7 kPa). The residue is dissolved in ethyl acetate (75 cc), the solution is poured into ethyl ether (250 cc) and the mixture is filtered; the filtrate is concentrated to dryness under reduced pressure (20 mm Hg, 2.7 kPa), the residue is dissolved in ethyl acetate (50 cc) and the solution is poured into isopropyl ether (250 cc). The precipitate formed is filtered off and then dried. This gives 2-benzhydryloxycarbonyl-3-(2-dimethylamino-vinyl)-8-oxo-7-phenoxyacetamido-5-thia-1-aza-bicyclo[4.2.0]oct-2-ene, E-form (11 g) in the form of a yellow solid.

Infrared spectrum (KBr): characteristic bands (cm$^{-1}$) at 3320, 1765, 1690, 1615, 1540, 1500, 1460, 1240, 760 and 705.

Proton nuclear magnetic resonance spectrum (350 MHz, CDCl$_3$, δ in ppm, J in Hz): 2.90 (s, 6H>N—CH$_3$); 2.93 and 3.18 (2d, J=14, 2H, —S—CH$_2$—); 4.62 (s, broad, 2H, —OCH$_2$—CO—); 5.11 (d, J=4, 1H, H in the 6-position); 5.43 (dd, J=4 and 8, 1H, H in the 7-position); 6.42 (d, J=14, 1H, —C$\underline{H}$=CH—N<); 6.57 (d, J=14, 1H, —CH=C$\underline{H}$—N<); 6.85 (s, 1H, —COOC$\underline{H}$<); 7.92 (d, J=8, 1H, —CON$\underline{H}$—).

II. The reference examples which follow show how the products of the invention can be employed as intermediates for the preparation of cephalosporins of the general formula (XXI).

REFERENCE EXAMPLE 1

A solution of formic acid (50 cc) in water (500 cc) is added to a solution of 2-benzhydryloxycarbonyl7-tert.-butoxycarbonylamino-3-(2-dimethylaminovinyl)-8-oxo-5-thia-1-aza-bicyclo[4.2.0]oct-2-ene (E-form) (113.7 g) in tetrahydrofurane (1 liter). The homogeneous solution is stirred at 20° C. for 20 minutes and is then concentrated to a quarter of its volume under reduced pressure (20 mm Hz) at 20° C. The concentrate is taken up in ethyl acetate (2 liters) and this mixture is washed with a 5% strength sodium bicarbonate solution (2×500 cc), water (2×500 cc) and a saturated sodium chloride solution (2×500 cc), dried over sodium sulphate, filtered and evaporated to dryness at 20° C. under reduced pressure (20 mm Hg). A crude product (112.4 g) is obtained, which is dissolved in anhydrous pyridine (250 cc), and the solution is treated, at 5° C., with tosyl chloride (57.2 g). After 30 minutes at 5° C. and 1 hour at 20° C., the solution is poured into a mixture of water and crushed ice (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength sodium bicarbonate solution (2×750 cc) and water (4×750 cc), dried over sodium sulphate and concentrated to dryness under reduced pressure (20 mm Hg) at 20° C. A product (121 g) consisting principally of 2-benzhydryloxycarbonyl-7-tert.-butoxycarbonylamino-8-oxo-3-(2-tosyloxyvinyl)-5-thia-1-aza-bicyclo[4.2.0]oct-2-ene (a mixture of the E- and Z-forms) is obtained in the form of a crude brown froth.

A solution of 85% strength m-chloroperbenzoic acid (55.22 g) in methylene chloride (600 cc) is added dropwise, in the course of 2 hours, to a solution, cooled to −10° C., of the product prepared under the conditions described above (180.56 g) in methylene chloride (1.4 liters). The mixture is washed with a 5% strength sodium bicarbonate solution (1.5 liters) and with water (2×1.5 liters), dried over sodium sulphate and concentrated to a volume of 300 cc at 20° C. under reduced pressure (20 mm Hg). This solution is chromatographed on a column (column diameter: 9.2 cm; height: 145 cm) of Merck silica gel (0.05–0.2 mm) (3 kg). Elution is carried out successively with the following mixtures of cyclohexane and ethyl acetate: 80:20 (by volume) (15 liters) and 70:30 (by volume) (32 liters), 600 cc fractions being collected. Fractions 27 and 28 are combined and concentrated to dryness; the Z-form of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (5.56 g) is obtained.

Infra-red spectrum (CHBr$_3$): characteristic bands (cm$^{-1}$) at 3420, 1800, 1720, 1505, 1380, 1370, 1195, 1180, 1050, 1010 and 730.

Proton nuclear magnetic resonance spectrum (350 MHz, CDCl$_3$, δ in ppm, J in Hz): 1.49 (s, 9H, —C(CH$_3$)$_3$); 2.44 (s, 3H, —CH$_3$); 3.36 and 4.04 (2 d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —CH=CH OSO$_2$—); 6.46 (d, J=7, 1H, =CH OSO$_2$—);

6.89 (s, 1H, —COOCH—);

7.77 (d, J=9, 2H, H in the ortho-position of the tosyl group).

A mixture of the Z- and E-forms (26 g) is obtained from fractions 29 to 34.

Finally, the E-form of the product (43 g) is obtained from fractions 35 to 58:

Infra-red spectrum (CHBr$_3$): characteristic bands (cm$^{-1}$) at 3420, 1800, 1720, 1505, 1380, 1370, 1195, 1180, 1075, 935 and 745.

Proton nuclear magnetic resonance spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2 d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —CH=CH OSO$_2$—);

6.83 (s, 1H, —COOCH—);

7.08 (d, J=13, 1H, =CH OSO$_2$—); 7.73 (d, J=9, 2H, H in the ortho-position of the tosyl group).

(a) A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (Z-form) (5.44 g), dimethylformamide (40 cc), 1-methyl-2-mercapto-tetrazole (1.88 g) and N-ethyl-N,N-diisopropylamine (2.8 cc) is heated at 60° C. for 1 hour, whilst stirring under nitrogen. The mixture is then diluted with ethyl acetate (250 cc) and this mixture is washed successively with water (3×100 cc), 0.1 N hydrochloric acid (100 cc), a 2% strength sodium bicarbonate solution (2×100 cc) and a half-saturated sodium chloride solution (2×100 cc), dried over sodium sulphate, filtered and concentrated to dryness under reduced pressure (20 mm Hg) at 20° C. The residue is fixed on silica gel (20 g) and is charged onto a column (column diameter:3 cm, height:12 cm) of Merck silica gel (0.05–0.2 mm) (80 g). Elution is carried out with the following mixtures of cyclohexane and ethyl acetate:90:10 (by volume) (250 cc), 80:20 (by volume) (500 cc), 70:30 (by volume (1,000 cc), 60:40 (by volume) (2,000 cc) and 40:60 (by volume) (2,000 cc), 125 cc fractions being collected. Fractions 34 to 45 are collected and concentrated to dryness and 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) (3.44 g) is obtained in the form of a light brown froth.

Infra-red spectrum (CHBr$_3$): characteristic bands (cm$^{-1}$) at 3410, 1800, 1720, 1500, 1370, 1230, 1045, 755 and 740.

Proton nuclear magnetic resonance spectrum (350 MHz, CDCl$_3$, δ in ppm, J in Hz): 1.48 (s, 9H, (CH$_3$)$_3$C—); 3.81 (s, 3H, >NCH$_3$); 3.38 and 4.03 (2 d, J=18, 2H, —SCH$_3$—); 4.58 (d, J=4.5, 1H, H in the 6-position); 5.75 (d, J=9, 1H, —CONH—); 5.85 (dd, J=4.5 and 9, 1H, H in the 7-position); 6.70 (d, J=9.5, 1H, —CH=CH—S—); 6.79 (d, J=9.5, 1H, =CHS—);

6.98 (s, 1H, —COOCH—).
            |

A mixture of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) (3.11 g), acetonitrile (50 cc) and p-toluenesulphonic acid monohydrate (1.9 g) is stirred for 16 hours at 25° C. The mixture is then concentrated under reduced pressure (20 mm Hg) at 20° C. and the residue is stirred with ethyl acetate (100 cc) and a 5% strength sodium bicarbonate solution (100 cc). The organic phase is decanted, washed with a 5% strength sodium bicarbonate solution (50 cc) and a half-saturated sodium chloride solution (2×50 cc), dried over sodium sulphate, filtered and concentrated to dryness under reduced pressure (20 mm Hg at 20° C.). This gives 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (Z-form) (1.55 g) in the form of a crude brown froth.

$R_f=0.21$ (silica gel chromatographic plate, solvent: a 85:15 (by volume) mixture of dichloroethane and methanol).

Dicyclohexylcarbodiimide (0.71 g) is added to a solution, cooled to 4° C., of syn-2-methoxyimino-2-(2-tritylamino-thiazol-4-yl)-acetic acid (2.89 g) in methylene chloride (10 cc). The solution is stirred for 40 minutes at 4' C. and then for 30 minutes at 20° C., and is filtered.

To this filtered solution, cooled to −30° C., is added a solution of 7-amino-2-benzhydryloxycarbonyl-3-8 2-(1-methyl-tetrazol-5-yl)-thiovinyl]-8-oxo-5-oxide-5-thia-1-aza-bicyclo[4.2.0]oct-2-ene (Z-form) (1.55 g) in methylene chloride (13 cc) containing triethylamine (0.46 cc). The cooling bath is removed and the mixture is stirred for 1 hour 50 minutes at 20° C. It is then concentrated under reduced pressure (20 mm Hg) at 20° C. and the residue is taken up in ethyl acetate (100 cc). This organic phase is washed with water (3×50 cc), 0.05 N hydrochloric acid (50 cc), a 1% strength sodium bicarbonate solution (50 cc) and half-saturated aqueous sodium chloride (2×50 cc), dried over sodium sulphate, filtered and concentrated to dryness under reduced pressure (20 mm Hg) at 20° C. The concentrate is redissolved in a 10:90 (by volume) mixture of cyclohexane and ethyl acetate (25 cc) and the solution is chromatographed on a column (column diameter: 5 cm; height: 33 cm) of Merck silica gel (0.04–0.06 mm) (300 g). Elution is carried out with a 10:90 (by volume) mixture of cyclohexane and ethyl acetate (3 liters) under a nitrogen pressure of 0.4 bar, 110 cc fractions being collected. After concentrating fractions 9 to 17 to dryness, and drying this product, 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, Z-form) (0.98 g) is obtained in the form of a yellow froth.

Infra-red spectrum ($CHBr_3$): characteristic bands ($cm^{-1}$) at 3380, 1805, 1725, 1680, 1515, 1050, 755 and 740.

Proton nuclear magnetic resonance spectrum (350 MHz, $CDCl_3$, δ in ppm, J in Hz): 3.81 (s, 3H, >$NCH_3$); 3.89 and 4.01 (2 d, J=19, 2H, —S—$CH_2$—); 4.10 (s, 3H, —$OCH_3$); 4.66 (d, J=4, 1H, H in the 6-position); 6.24 (dd, J=4 and 10, 1H, H in the 7-position); 6.72 and 6.76 (2 d, J=10, 2H, —C<u>H</u>=C<u>H</u>S—);

6.98 (s, 1H, —COOCH—);
            |

6.72 (s, 1H, H in the 5-position of the thiazole); 7.07 (s, 1H, ($C_6H_5)_3$C—N<u>H</u>—).

Phosphorus trichloride (0.17 cc) is added to a solution, cooled to −10° C., of 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, Z-form) (0.93 g) in methylene chloride (10 cc) and dimethylacetamide (0.39 cc) and the mixture is stirred for 45 minutes at the same temperature. It is then diluted with ethyl acetate (200 cc) and this mixture is washed with 2% strength sodium bicarbonate solution (2×50 cc) and a saturated sodium chloride solution (2×50 cc), dried over sodium sulphate, filtered and concentrated to dryness under reduced pressure (20 mm Hg) at 20° C. The residue is fixed on Merck silica gel (0.05–0.2 mm) (5 g) and the powder is charged onto a column (diameter: 2 cm, height: 8 cm) of Merck silica gel (0.05–0.2 mm) (15 g). Elution is carried out successively with the following mixtures of cyclohexane and ethyl acetate: 75:25 (by volume) (100 cc), 50:50 (by volume) (250 cc) and 25:75 (by volume) (250 cc), 60 cc fractions being collected. Fractions 3 to 7 are concentrated to dryness under reduced pressure (20 mm Hg) at 25° C. and 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-thia-1-aza-bicyclo[4.2.0]oct-2-ene (syn isomer, Z-form) (0.74 g) is obtained in the form of a yellow froth.

Infra-red spectrum ($CHBr_3$): characteristic bands ($cm^{-1}$) at 3400, 1790, 1725, 1685, 1515, 1370, 1050, 755 and 740.

Proton nuclear magnetic resonance spectrum (350 MHz, $CDCl_3$, δ in ppm, J in Hz): 3.56 and 3.69 (2 d, J=17.5, 2H, —$SCH_2$—); 3.81 (s, 3H, >$NCH_3$); 4.09 (s, 3H, —$OCH_3$); 5.13 (d, J=4, 1H, H in the 6-position); 5.99 (dd, J=4 and 10, 1H, H in the 7-position); 6.76 (AB, J=11, 2H, —CH=CH S—); 6.9 (d, J=10, 1H, —CONH—);

6.97 (s, 1H, —COOCH—);
            |

7.01 (s, 1H, ($C_6H_5)_3$CNH—).

2-Benzhydryloxycarbonyl-7-[2-methoxyimino-2-(2-tritylamino-thiazol-4-yl)-acetamido]-3-[2-(1-methyltetrazol-5-yl)-thiovinyl]-8-oxo-5-thia-1-aza-bicyclo[4.2.0]oct-2-ene (syn isomer, Z-form) (0.67 g) is dissolved in trifluoroacetic acid (3.6 cc) and anisole (0.07 cc). The mixture is stirred for 1 hour at 5° C. and then for 30 minutes at 20° C., and is concentrated to dryness under reduced pressure (20 mm Hg) at 20° C. The residue is redissolved in trifluoroacetic acid (2 cc) and the solution is poured, with stirring, into ethyl ether (10 cc). After filtering and drying, 7-[2-(2-amino-thiazol-4-yl)-2-methoxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, Z-form) trifluoroacetate (0.33 g) is obtained.

Rf=0.50 [silica gel chromatographic plate, solvent: a 50:20:10:10 (by volume) mixture of ethyl acetate, acetone, acetic acid and water].

Infra-red spectrum (KBr): characteristic bands (cm$^{-1}$) at 3300, 1785, 1675, 1180, 1140 and 1050.

Proton nuclear magnetic resonance spectrum (350 MHz, DMSO d$_6$, δ in ppm, J in Hz): 3.8 and 3.85 (AB, J=17.5, 2H, —SCH$_2$—); 3.93 (s, 3H, >NCH$_3$); 4.0 (s, 3H, —OCH$_3$); 5.26 (d, J=4, 1H, H in the 6-position); 5.85 (dd, J=4 and 10, H in the 7-position); 6.75 (d, J=11, 1H, =C$\underline{H}$=CH—S—); 6.87 (s, 1H, H in the 5-position of the thiazole); 6.91 (d, J=11, 1H, =CH—S—); 9.34 (d, J=10, 1H, —CONH—).

(b) A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (40.73 g), dimethylformamide (300 cc), 1-methyl-5-mercapto-tetrzole (13.94 g) and N-ethyl-N,N-diisopropylamine (20.9 cc) is heated at 60° C. for 1½ hours, whilst stirring under nitrogen. It is then diluted with ethyl acetate (2 liters) and the mixture is washed successively with water (3×1 liter), 0.1 N hydrochloric acid (1 liter), a 1% strength sodium bicarbonate solution (1 liter) and a half-saturated sodium chloride solution (2×1 liter), dried over sodium sulphate, filtered and concentrated to dryness at 30° C. under reduced pressure (20 mm Hg). 2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (35.7 g) is obtained in the form of a brown froth.

Infra-red spectrum (CHBr$_3$): characteristic bands (cm$^{-1}$) at 3410, 1800, 1715, 1505, 1370, 1050, 945, 760 and 745.

Proton nuclear magnetic resonance spectrum (350 MHz, CDCl$_3$, δ in ppm, J in Hz): 1.47 (s, 9H, (CH$_3$)$_3$C—); 3.32 and 4.15 (2 d, J=17.5, 2H, —SCH$_2$—); 3.94 (s, 3H, >NCH$_3$); 4.56 (d, J=4, 1H, H in the 6-position); 5.72 (d, J=10, 1H, —CONH—); 5.83 (dd, J=4 and 10, 1H, H in the 7-position);

6.97 (s, 1H, —COOCH—);

7.05 (d, J=16, 1H, —C$\underline{H}$=CHS—); 7.58 (d, J=16, 1H, =CHS—).

A mixture of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (34.87 g), acetonitrile (560 cc) and p-toluenesulphonic acid monohydrate (21.31 g) is stirred for 16 hours at 25° C. The mixture is then concentrated at 20° C. under reduced pressure (20 mm Hg) and the residue is taken up in ethyl acetate (1 liter). The solution is neutralised by stirring with a 5% strength sodium bicarbonate solution (500 cc) and is decanted, washed with a half-saturated sodium chloride solution (3×500 cc), dried over sodium sulphate, filtered and concentrated to dryness under reduced pressure (20 mm Hg) at 20° C. 7-Amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (19.59 g) is obtained in the form of a crude brown froth.

Rf=0.27 [silica gel chromatographic plate, solvent: a 85:15 (by volume) mixture of dichloroethane and methanol].

(α) Dicyclohexylcarbodiimide (8.90 g) is added to a solution, cooled to 4° C., of syn-2-methoxyimino-2-(2-tritylamino-thiazol-4-yl)-acetic acid (36.59 g) in methylene chloride (135 cc). After stirring for 40 minutes at 4° C. and 30 minutes at 20° C., the solution is filtered.

To this filtered solution, cooled to −30° C., is added, with stirring, a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (19.59 g) in methylene chloride (165 cc) containing triethylamine (5.8 cc). The cooling bath is removed and stirring is continued for 1½ hours. The mixture is then concentrated at 20° C. under reduced pressure (20 mm Hg), the residue is taken up in ethyl acetate (1 liter) and the solution is washed successively with water (2×500 cc), 0.1 N hydrochloric acid (500 cc), a 2% strength sodium bicarbonate solution (2×250 cc) and a half-saturated sodium chloride solution (2×500 cc), dried over sodium sulphate and concentrated to dryness at 20° C. under reduced pressure (20 mm Hg). The residue is fixed on Merck silica gel (0.05–0.2 mm) (100 g) and the powder obtained is charged onto a column (column diameter: 6 cm, height: 61 cm) of Merck silica gel (0.05–0.2 mm) (700 g). Elution is carried out successively with the following mixtures of cyclohexane and ethyl acetate: 80:20 (by volume) (1.5 liters), 70:30 (by volume) (1.5 liters), 60:40 (by volume) (3 liters), 50:50 (by volume) (3 liters), 40:60 (by volume) (6 liters) and 30:70 (by volume) (7.5 liters), 600 cc fractions being collected. After evaporating fractions 27 to 37 to dryness at 20° C. under reduced pressure (20 mm Hg), and drying the residue, 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form) (15.52 g) is obtained.

Infra-red spectrum (CHBr$_3$): characteristic bands (cm$^{-1}$) at 3390, 1805, 1725, 1685, 1520, 1375, 1210, 1050, 945, 755 and 740.

Proton nuclear magnetic resonance spectrum (350 MHz, CDCl$_3$, δ in ppm, J in Hz): 3.28 and 4.06 (2 d, J=17.5, 2H, —SCH$_2$—); 3.91 (s, 3H, >NCH$_3$); 4.06 (s, 3H, —OCH$_3$); 4.60 (d, J=4, 1H, H in the 6-position); 6.14 (dd, J=4 and 10, 1H, H in the 7-position); 6.71 (s, 1H, H in the 5-position of the thiazole);

6.94 (s, 1H, —COOCH—);

6.99 (d, J=16, 1H, —C$\underline{H}$=CHS—); 7.56 (d, J=16, 1H, =CHS—).

Phosphorus trichloride (2.8 cc) is added to a solution, cooled to −10° C., of 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form (15.17 g) in methylene chloride (160 cc) and dimethylacetamide (6.4 cc), and the mixture is stirred for 1 hour at the same temperature. It is then concentrated to about 20 cc (at 20° C. under 25 mm Hg), this material is diluted with ethyl acetate (1 liter) and the solution is washed successively with a 5% strength sodium bicarbonate solution (2×500 cc) and a half-saturated sodium chloride solution (2×500 cc). After drying over sodium sulphate and filtering, the solution is concentrated at 20° C. under reduced pressure (20 mm Hg). The residue is fixed on Merck silica gel (0.05–0.2 mm) (50 g) and the powder obtained is charged onto a column (diameter: 6 cm, height: 37 cm)

of Merck silica gel (0.05-0.2 mm) (250 g). Elution is carried out successively with the following mixtures of cyclohexane and ethyl acetate: 75:25 (by volume) (1 liter), 50:50 (by volume) (2 liters) and 25:75 (by volume) (2 liters), 600 cc fractions being collected. After evaporation of fractions 4 to 6 at 25° C. under reduced pressure (20 mm Hg), 2-benzhydryloxycarbonyl-7-[2-methoxyimino-2-(2-tritylamino-thiazol-4-yl)-acetamido]-3-[2-(1-methyltetrazol-5-yl)-thiovinyl]-8-oxo-5-thia-1-aza-bicyclo[4.2.0]oct-2-ene (syn isomer, E-form) (9.8 g) is obtained in the form of a yellow froth.

Infra-red spectrum (CHBr$_3$): characteristic bands (cm$^{-1}$) at 3390, 1785, 1720, 1680, 1515, 1370, 1205, 1040, 940, 760 and 735.

Proton nuclear magnetic resonance spectrum (350 MHz, CDCl$_3$, δ in ppm, J in Hz): 3.60 and 3.70 (AB, J=18, 2H, —SCH$_2$—); 3.95 (s, 3H, >NCH$_3$); 4.10 (s, 3H, —OCH$_3$); 5.10 (d, J=4, 1H, H in the 6-position); 5.95 (dd, J=4 and 10, 1H, H in the 7-position); 6.72 (s, 1H, H in the 5-position of the thiazole);

6.95 (s, 1H, —COOCH—);

7.02 (d, J=16, 1H, —CH=CHS—); 7.04 (d, J=10, 1H, —CONH—); 7.05 (s, 1H, —NH—); 7.37 (d, J=16, =CHS—).

2-Benzhydryloxycarbonyl-7-[2-methoxyimino-2-(2-tritylamino-thiazol-4-yl)-acetamido]-3-[2-(1-methyltetrazol-5-yl)-thiovinyl]-8-oxo-5-thia-1-aza-bicyclo[4.2.0]-oct-2-ene (syn isomer, E-form) (9.32 g) is dissolved in trifluoroacetic acid (50 cc) and anisole (1 cc). The mixture is stirred for 1 hour at 4° C. and 30 minutes at 20° C. and is then concentrated at 20° C. under reduced pressure (0.05 mm Hg). The concentrate is taken up in ethyl acetate (2×200 cc), the mixture being evaporated each time at 20° C. under reduced pressure (20 mm Hg). The residue is triturated in diethyl ether (100 cc). After filtration and drying, a cream-coloured solid (4.87 g) containing 80% of the expected product and 20% of the N-tritylated product (the percentages being based on nuclear magnetic resonance measurements) is obtained.

The above solid is dissolved in trifluoroacetic acid (35 cc) and the solution obtained is poured, with stirring, into diethyl ether (175 cc). After filtration and drying, 7-[2-(2-amino-thiazol-4-yl)-2-methoxyimino-acetamido]-2-carboxy-3-[2-(1-methyl-tetrazol-5-yl)thiovinyl]-8-oxo-5-thia-1-aza-bicyclo[4.2.0]oct-2ene (syn isomer, E-form) trifluoroacetate (4.57 g) is obtained.

Rf=0.49 [silica gel chromatographic plate, solvent: a 50:20:10:10 (by volume) mixture of ethyl acetate, acetone, acetic acid and water].

Infra-red spectrum (KBr): characteristic bands (cm$^{-1}$) at 3320, 1780, 1675, 1200, 1140, 1040 and 950.

Proton nuclear magnetic resonance spectrum (350 MHz, DMSO d$_6$, δ in ppm, J in Hz): 3.66 and 3.86 (2 d, J=17, 2H, —SCH$_2$—); 3.90 (s, 3H, >NCH$_3$); 4.0 (s, 3H, —OCH$_3$); 5.20 (d, J=4, 1H, H in the 6-position); 5.80 (dd, J=4 and 9, 1H, H in the 7-position); 6.83 (s, 1H, H in the 5-position of the thiazole); 7.0 (d, J=16, 1H, —CH=CHS—); 7.1 (d, J=16, 1H, =CHS—); 9.7 (d, J=9, 1H, —CONH—).

(β) 2-(2-Tritylamino-thiazol-4-yl)-2-trityloxyiminoacetic acid (syn isomer) (6.2 g) is added to a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (4.4 g) in methylene chloride (100 cc), the mixture is cooled to 4° C. and 4-dimethylaminopyridine (0.1 g) and dicyclohexylcarbodiimide (1.89 g) are introduced successively, whilst stirring. The cooling bath is removed and the mixture is stirred for 1½ hours at 20° C. It is then filtered and the filtrate is concentrated at 20° C. under reduced pressure (20 mm Hg), the residue is taken up in ethyl acetate (500 cc) and the solution is washed with 1 N hydrochloric acid (250 cc), a 2% strength sodium bicarbonate solution (2×100 cc), water (2×100 cc) and a saturated sodium chloride solution (100 cc), dried over sodium sulphate and concentrated to dryness at 20° C. under reduced pressure (20 mm Hg). The residue is fixed on Merck silica gel (0.05-0.2 mm) (20 g) and the powder is charged onto a column (column diameter: 2.6 cm, height: 30 cm) of silica gel (70 g) which has been prepared with an 80:20 (by volume) mixture of cyclohexane and ethyl acetate; elution is carried out successively with the following mixtures of cyclohexane and ethyl acetate: 80:20 (by volume) (500 cc), 70:30 (1,000 cc) and 60:40 (1,200 cc), 60 cc fractions being collected.

Fractions 33 to 42 are evaporated to dryness under reduced pressure (20 mm Hg) at 20° C.; 2-benzhydryloxycarbonyl-3-[2-(1-methyl-tetrazol-5-yl)-thiovinyl]-8-oxo-5-oxide-7-[2-(2-tritylamino-thiazol-4-yl)-2-trityloxyimino-acetamido]-5-thia-1-aza-bicyclo[4.2.0]-oct-2-ene (syn isomer, E-form) (2 g) is obtained in the form of a cream-coloured powder.

Infra-red spectrum (CHBr$_3$): characteristic bands (cm$^{-1}$) at 3390, 1800, 1720, 1680, 1655, 1525, 1490, 1450, 750 and 700.

Proton nuclear magnetic resonance spectrum (350 MHz, CDCl$_3$, δ in ppm, J in Hz): 3.72 and 3 (2d, J=18, 2H, —S—CH$_2$—); 3.96 (s, 3H, ≦NCH$_3$); 4.44 (d, J=4, 1H, H in the 6-position); 5.35 (dd, J=4 and 9, 1H, H in the 7-position); 6.40 (s, 1H, H in the 5-position of the thiazole); 6.95 (d, J=16, 1H, —CH=CHS—);

6.97 (s, 1H, —COOCH—);

7.60 (d, J=16, 1H, =CHS—).

Phosphorus trichloride (0.302 cc) is added, whilst stirring, to a solution, cooled to −10° C. of 2-benzhydryloxycarbonyl-3-[2-(1-methyl-tetrazol-5-yl)-thiovinyl]-8-oxo-5-oxide-7-[2-(2-tritylamino-thiazol-4-yl)-2-trityloxyimino-acetamido]-5-thia-1-aza-bicyclo[4.2.0]oct-2-ene (syn isomer, E-form), (2 g) in methylene chloride (17 cc) and dimethylacetamide (0.64 cc). After 10 minutes at the same temperature, the mixture is diluted with ethyl acetate (500 cc) and the solution is washed with a 5% strength sodium bicarbonate solution (2×100 cc) and a saturated sodium chloride solution (2×100 cc), dried over sodium sulphate, filtered and concentrated to dryness at 20° C. under reduced pressure (20 mm Hg). The residue is taken up in methylene chloride (10 cc) and the solution is chromatographed on a column (column diameter: 4 cm, height: 20 cm) of silica gel (0.04-0.06 mm) (150 g), which has been prepared with a 65:35 (by volume) mixture of cyclohexane and ethyl acetate. Elution is carried out with 2 liters of the same mixture under a pressure of 40 kPa, 120 cc fractions being collected.

Fractions 6 to 21 are concentrated to dryness under reduced pressure (20 mm Hg) at 20° C.; 2-benzhydryloxycarbonyl-3-[2-(1-methyl-tetrazol-5-yl)-thiovinyl]-8-oxo-7-[2-(2-tritylamino-thiazol-4-yl)-2- trityloxyimino-acetamido]-5-thia-1-aza-bicyclo[4.2.-0]oct-2-ene (syn isomer, E-form) (0.85 g) is obtained in the form of a cream-coloured powder.

Infra-red spectrum (CHBr$_3$): characteristic bands (cm$^{-1}$) at 3400, 1790, 1715, 1690, 1510, 1490, 1450, 950, 750 and 710.

Proton nuclear magnetic resonance spectrum (350 MHz, CDCl$_3$, δ in ppm, J in Hz): 3.43 and 3.50 (2d, J=18, 2H, —S—CH$_2$—); 3.94 (s, 3H, >NCH$_3$); 5.09 (d, J=4, 1H, H in the 6-position); 6.10 (dd, J=4 and 9, 1H, H in the 7-position); 6.41 (s, 1H, H in the 5-position of the thiazole); 6.71 (s, 1H, (C$_6$H$_5$)$_3$ CN$\underline{H}$—);

6.95 (s, 1H, —COOC$\underline{H}$—);

6.97 (d, J=16, 1H, —C$\underline{H}$=CHS—).

A solution of 2-benzhydryloxycarbonyl-3-[2-(1-methyl-tetrazol-5-yl)-thiovinyl]-8-oxo-7-[2-(2-tritylamino-thiazol-4-yl)-2-trityloxyimino-acetamido]-5-thia-1-aza-bicyclo[4.2.0]oct-2-ene (syn isomer, E-form) (0.85 g) in tetrahydrofurane (10 cc) is treated with 50% strength by volume aqueous formic acid (10 cc) for 30 minutes at 50° C. The mixture is concentrated to dryness under reduced pressure (20 mm Hg) at 20° C., the residue is taken up in ethanol (20 cc) at 60° C., the solution is allowed to cool, and the crystals which have appeared are filtered off, washed with diethyl ether (2×10 cc) and dried. 7-[2-(2-Amino-thiazol-4-yl)-2-hydroxyimino-acetamido]-2-carboxy-3-[2-(1-methyl-tetrazol-5-yl)thiovinyl]-8-oxo-5-thia-1-aza-bicyclo[4.2.0]oct-2-ene (syn isomer, E-form) (0.24 g) is obtained in the form of a yellow powder.

Infra-red spectrum (KBr): characteristic bands (cm$^{-1}$) at 3440, 3360, 3200, 1785, 1720, 1680, 1610 and 1405.

Proton nuclear magnetic resonance spectrum (350 MHz, DMSO d$_6$. δ in ppm, J in Hz); 3.65 and 3.91 (2d, J=18, 2H, —S—CH$_2$—); 4.97 (s, 3H, >NCH$_3$); 5.25 (d, J=4, 1H, H in the 6-position); 5.90 (dd, J=4 and 9, 1H, H in the 7-position); 6.76 (s, 1H, H in the 5-position of the thiazole); 6.96 (d, J=14, 1H, —C$\underline{H}$=CHS—); 7.07 (d, J=14, 1H, =CHS—); 9.50 (d, J=9, 1H, —CONH—).

(c) A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (mixture of the E- and Z-forms) (4.06 g) (obtained as described in Reference Example 2) in acetonitrile (150 cc) is stirred with p-toluenesulphonic acid monohydrate (2.28 g) at 20° C. for 16 hours. The mixture is concentrated under reduced pressure (20 mm Hg) at 20° C. to a volume of 10 cc and is diluted with ethyl acetate (150 cc), and this mixture is washed with a 2% strength sodium bicarbonate solution (100 cc) and then with saturated aqueous sodium chloride (2×150 cc), dried over sodium sulphate and concentrated to dryness under reduced pressure (20 mm Hg) at 20° C. 7-Amino-2-benzhydryloxycarbonyl-8-oxo-5-oxide-3-(2-tosyloxyvinyl)-5-thia-1-aza-bicyclo[4.2.0]oct-2-ene (mixture of the E- and Z-forms) (3.5 g) is obtained in the form of a crude brown solid.

Infra-red spectrum (KBr): characteristic bands (cm$^{-1}$) at 3430, 3360, 1780, 1725, 1370, 1180, 1170, 1070, 745 and 700.

Proton nuclear magnetic resonance spectrum (350 MHz, CDCl$_3$, δ in ppm, J in Hz): 2.43 (s, 3H, —CH$_3$); 3.12 and 3.75 (2d, J=18, 2H, —SCH$_2$—); 4.36 (d, J=4, 1H, H in the 6-position); 4.74 (d, J=4, 1H, H in the 7-position); 6.87 (d, J=12, 1H, —C$\underline{H}$=CH—OSO$_2$—); 6.90 (s, 1H, COOCH<); 6.99 (d, J=12, 1H, =CH—OSO$_2$—); 7.40 and 7.71 (2d, J=9, —C$_6$H$_4$—).

Dicyclohexylcarbodiimide (1.85 g) is added, with stirring, to a solution, cooled to +4° C., of syn-2-methoxyimino-2-(2-tritylamino-thiazol-4-yl)-acetic acid (7.97 g) in methylene chloride (100 cc). The solution is stirred for 40 minutes at +4° C. and then for 30 minutes at 20° C., and is filtered.

A solution of crude 7-amino-2-benzhydryloxycarbonyl-8-oxo-5-oxide-3-(2-tosyloxyvinyl)-5-thia-1-aza-bicyclo[4.2.0]oct-2-ene (mixture of the E- and Z-forms) (3.47 g) in methylene chloride (30 cc) containing triethylamine (0.84 cc) is added rapidly to the preceding filtered solution, cooled to −30° C. The cooling bath is removed at the end of the addition and the reaction mixture is stirred for 1 hour 50 minutes at 20° C. It is then concentrated to dryness at 20° C. under reduced pressure (20 mm Hg) and the residue is taken up in ethyl acetate (250 cc). The organic phase is washed with water (3×100 cc), 0.05 N hydrochloric acid (100 cc), a 1% strength sodium bicarbonate solution (100 cc) and half-saturated aqueous sodium chloride (2×100 cc), dried over sodium sulphate, filtered and concentrated to dryness under reduced pressure (20 mm Hg at 20° C.). The residue is taken up in ethyl acetate (20 cc), cyclohexane (20 cc) is added, the mixture is filtered and the solution is chromatographed on a column (column diameter: 6 cm, height: 30 cm) of Merck silica gel (0.04–0.06 mm) (300 g). Elution is carried out with a 40:60 (by volume) mixture of cyclohexane and ethyl acetate (4 liters) under a pressure of 40 kPa, 125 cc fractions being collected. Fractions 6 to 25 are concentrated under reduced pressure (20 mm Hg at 20° C.) and 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (4.8 g) is obtained in the form of a cream-coloured froth.

On carrying out a second chromatography identical to the above, the Z-isomer (1.21 g) is obtained from fractions 12 to 16 and the E-isomer (1.49 g) from fractions 22 to 40; fractions 17 to 21 contain a mixture of the E- and Z-isomers (0.8 g).

Z-isomer:

Infra-red spectrum (CHBr$_3$): characteristic bands (cm$^{-1}$) at 3380, 1800, 1720, 1680, 1510, 1375, 1190, 1175, 1045, 1000 and 735.

Proton nuclear magnetic resonance spectrum (350 MHz, CDCl$_3$, δ in ppm, J in Hz): 2.03 (s, 3H, —C$_6$H$_4$—CH$_3$); 3.36 and 4.07 (2 d, J=19, 2H, —SCH$_2$—); 4.09 (s, 3H, —OCH$_3$); 4.52 (d, J=4, 1H, H in the 6-position); 6.16 (dd, J=4 and 9, 1H, H in the 7-position); 6.43 (AB, J=8, 2H, —C$\underline{H}$=C$\underline{H}$—); 6.86 (s, 1H, >CHO—CO—); 6.71 (s, 1H, H in the 5-position of the thiazole); 7.75 (d, J=9, 2H, H in the ortho-position of the tosyl group).

E-isomer:

Infra-red spectrum (CHBr$_3$): characteristic bands (cm$^{-1}$) at 3380, 1800, 1725, 1685, 1515, 1380, 1190, 1180, 1070, 1050, 755 and 735.

Proton nuclear magnetic resonance spectrum (350 MHz, CDCl$_3$, δ in ppm, J in Hz): 2.45 (s, 3H, —C$_6$H$_4$C$\underline{H}_3$); 3.19 and 3.77 (2 d, J=18, 2H, —SCH$_2$—); 4.08 (s, 3H, —OCH$_3$); 4.6 (d, J=4, H in the 6-position); 6.18 (dd, J=4 and 9, H in the 7-position); 6.72 (s, 1H, H in the 5-position of the thiazole); 6.93 (d, J=12, 1H, —C$\underline{H}$=CH—OSO$_2$—); 7.11 (d, J=12, 1H, —CH=CH—OSO$_2$—); 6.90 (s, 1H, —COOCH—); 7.73 (d, J=9, 2H, H in the ortho-position of the tosyl group).

2-Benzhydryloxycarbonyl-7-[2-methoxyimino-2-(2-tritylamino-thiazol-4-yl)-acetamido]-3-(2-tosyloxyvinyl)-8-oxo-5-thia-1-aza-bicyclo[4.2.0]oct-2-ene (syn isomer, E-form) (3 g) is dissolved in methylene chloride (30 cc); N,N-dimethylacetamide (1.2 cc) is added. The solution is placed under an atmosphere of dry nitrogen, cooled to −10° C., and treated with phosphorus trichloride (0.9 g). The reaction mixture is then stirred for 90 minutes at a temperature of between −10° and −5° C., after which it is diluted with ethyl acetate (250 cc), and this mixture is washed with a saturated aqueous sodium bicarbonate solution (150 cc) and a saturated sodium chloride solution (2×100 cc). After drying over magnesium sulphate and filtering, the organic solution is concentrated to dryness under reduced pressure (20 mm Hg) at 30° C.; the residue is taken up in methylene chloride (20 cc) and the solution is chromatographed on a column (height: 25 cm, diameter: 5 cm) containing silica (0.04–0.063 mm) (240 g). Elution is carried out with a 60:40 (by volume) mixture of cyclohexane and ethyl acetate (2 liters), 100 cc fractions being collected. Fractions 8 to 13 are concentrated to dryness under reduced pressure (20 mm Hg) at 30° C. 2-Benzhydryloxycarbonyl-7-[2-methoxyimino-2-(2-tritylamino-thiazol-4-yl)-acetamido]-3-(2-tosyloxyvinyl)-8-oxo-5-thia-1-aza-bicyclo[4.2.0]oct-2-ene (syn isomer, E-form) (1.7 g) is obtained.

Rf=0.52; silica gel chromatographic plate; eluant: a 50:50 (by volume) mixture of cyclohexane and ethyl acetate.

Infra-red spectrum (CHBr$_3$): characteristic bands (cm$^{-1}$) at 3400, 1790, 1725, 1685, 1520, 1375, 1190, 1180, 1075, 1050, 755 and 740.

Proton nuclear magnetic resonance spectrum (350 MHz, CDCl$_3$, δ in ppm, J in Hz): 2.42 (s, 3H, —CH$_3$ of the tosyl group); 3.33 and 3.42 (AB, J=19, 2H, —SCH$_2$—); 4.07 (s, 3H, —OCH$_3$); 5.03 (d, J=4, 1H, H in the 6-position); 5.87 (dd, J=4 and 9, 1H, H in the 7-position); 6.71 (s, 1H, H in the 5-position of the thiazole); 6.87 (s, 1H, —CO$_2$CH<); 6.87 (d, J=10, 1H, —C$\underline{H}$=CH—OSO$_2$—); 7.0 (s broad, 1H, NH— of the thiazole); 7.78 (d, J=9, 1H, —CONH—).

(α) A mixture of 2-benzhydryloxycarbonyl-7-[2-methoxyimino-2-(2-tritylamino-thiazol-4-yl)-acetamido]-8-oxo-3-(2-tosyloxy-vinyl)-5-thia-1-aza-bicyclo[4.2.0]oct-2-ene (syn isomer, E-form) (0.57 g) (obtained as described in Reference Example 3), dimethylformamide (15 cc) and 1-(2-hydroxyethyl)-5-mercapto-tetrazole (0.17 g) is heated to 60° C. under nitrogen. A solution of N-ethyl-N,N-diisopropylamine (0.1 cc) in dimethylformamide (5 cc) is added dropwise to this mixture in the course of 15 minutes, whilst stirring. After 3½ hours at 60° C., the mixture is diluted with ethyl acetate (100 cc) and this mixture is washed with distilled water (5×50 cc), dried over sodium sulphate, filtered and concentrated to dryness under reduced pressure (20 mm Hg) at 20° C. The residue is dissolved in methylene chloride (5 cc) and the solution is chromatographed on a column (column diameter: 2 cm, height: 15 cm) of Merck silica gel (0.04–0.06 mm) (80 g). Elution is carried out with a 25:75 (by volume) mixture of cyclohexane and ethyl acetate (300 cc) under a pressure of 40 kPa, 60 cc fractions being collected.

In fraction 1, some starting material (0.06 g) is obtained. Fractions 2 to 4 are concentrated to dryness under reduced pressure (20 mm Hg at 20° C.) and 2-benzhydryloxycarbonyl-3-{2-[1-(2-hydroxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form), (0.4 g) is obtained.

Infrared spectrum (KBr): characteristic bands (cm$^{-1}$) at 3400, 1785, 1720, 1580, 1525, 1370, 1210, 1035, 940, 755 and 700.

Proton nuclear magnetic resonance spectrum (350 MHz, CDCl$_3$, δ in ppm, J in Hz): 3.57 and 3.67 (AB, J=18, 2H, —SCH$_2$—); 4.07 (s, 3H, —OCH$_3$); 4.1 and 4.35 (2t, 4H, —CH$_2$CH$_2$O—); 5.09 (d, J=4, 1H, H in the 6-position); 5.94 (dd, J=4 and 9, 1H, H in the 7-position); 6.74 (s, 1H, H in the 5-position of the thiazole); 6.95 (s, 1H, —COOCH<); 6.97 (s, 1H, (C$_6$H$_5$)$_3$CN$\underline{H}$—); 7.00 (d, J=16, 1H, —C$\underline{H}$=CHS—).

2-Benzhydryloxycarbonyl-3-{2-[1-(2-hydroxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.39 g) is dissolved in formic acid (7 cc), and the solution is diluted with water (4 cc) and heated for 30 minutes at 50° C. It is then allowed to cool, filtered, and concentrated to dryness under reduced pressure (0.05 mm Hg) at 20° C. The residue is triturated in diisopropyl ether (10 cc) and after filtration and drying the formic acid solvate of 7-[2-(2-amino-thiazol-4-yl)-2-methoxyiminoacetamido]-2-carboxy-3-{2-[1-(2-hydroxyethyl)-tetrazol-5-yl]-thiovinyl}-8-oxo-5-thia-1-aza-bicyclo[4.2.0]oct-2-ene (syn isomer, E-form) (0.2 g) is obtained in the form of a pale yellow solid.

The preceding product (0.9 g) (in the form of the solvate) is treated with ethanol (50 cc) under reflux, a small amount of insoluble matter is removed by filtration and the filtrate is allowed to cool for 2 hours at 20° C. and 2 hours at 4° C. and is then filtered. The preceding product (0.41 g) is obtained in the form of its internal salt.

Infrared spectrum (KBr): characteristic bands (cm$^{-1}$) at 3350, 1770, 1720, 1675, 1530, 1390, 1040 and 940.

Proton nuclear magnetic resonance spectrum (350 MHz, DMSO d$_6$, δ in ppm, J in Hz): 3.63 and 3.87 (AB, J=19, 2H, —SCH$_2$—); 3.77 and 4.41 (2t, 4H, —CH$_2$CH$_2$O—); 3.84 (s, 3H, —OCH$_3$); 5.19 (d, J=4, 1H, H in the 6-position); 5.89 (dd, J=4 and 9, 1H, H in the 7-position); 6.73 (s, 1H, H in the 5-position of the thiazole); 6.94 (d, J=16, 1H, —C$\underline{H}$=CHS—); 7.25 (d, J=16, 1H, =CHS—); 9.61 (d, J=9, 1H, —CONH—).

(β) 2-Benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (1.5 g) is dissolved in a mixture of formic acid (30 cc) and distilled water (10 cc). The solution is heated at 50° C. for 30 minutes. After cooling, the precipitate is filtered off and the filtrate is concentrated to dryness under reduced pressure (10 mm Hg) at 30° C. The residue is triturated with diethyl ether (50 cc). The solidified product is filtered off, washed with diethyl ether (2×25 cc) and then dried under reduced pressure (5 mm Hg) at 25° C. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]-oct-2-ene (syn isomer, E-form) (0.75 g) is obtained as a solvate with formic acid.

Rf=0.57; silica gel chromatographic plate; eluant: a 50:20:10:10 (by volume) mixture of ethyl acetate, acetone, water and acetic acid.

Infra-red spectrum (KBr): characteristic bands (cm$^{-1}$) at 3400, 3340, 3000, 2820, 2200, 1775, 1720, 1670, 1630, 1370, 1190, 1165 and 1070.

Proton nuclear magnetic resonance spectrum (350 MHz, DMSO d$_6$, δ in ppm, J in Hz): 2.42 (s, 3H, —CH$_3$ of the tosyl group); 3.55 and 3.78 (AB J=19, 2H, —SCH$_2$—); 3.83 (s, 3H, —OCH$_3$); 5.14 (d, J=4, 1H, H in the 6-position); 5.75 (dd, J=4 and 9, 1H, H in the 7-position); 6.65 (d, J=12, 1H, —CH=CH—OSO$_2$—); 6.73 (s, 1H, H in the 5-position of the thiazole); 7.18 (s broad, —NH$_3^+$); 9.58 (d, J=9, 1H, —CONH—).

A solution of the formic acid solvate of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.1 g) and of thiophenol (0.02 g) in anhydrous N,N-dimethylformaide (1 cc) is cooled to 0° C. A solution of N,N-diisopropyl N-ethylamine (0.069 g) in N,N-dimethylformamide (3 cc) is added dropwise. The reaction mixture is heated again and stirred for 1 hour at 25° C. Evaporation of the solvent under reduced pressure (10 mm Hg) at 30° C. gives a residue (0.19 g), the chromatographic examination of which [silica gel chromatographic plate; eluant: a 50:20:10:10 (by volume) mixture of ethyl acetate, acetone, water and acetic acid] shows the formation of 7-[2-(2-amino-thiazol-4-yl)-2-methoxyiminoacetamido]-2-carboxy-8-oxo-3-(2-phenylthiovinyl)-5-thia-1-aza-bicyclo[4.2.0]oct-2-ene (syn isomer, E-form): Rf=0.62.

(d) A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (mixture of the E- and Z-forms) (13.58 g), dimethylformamide (40 cc), trimethylchlorosilane (0.13 cc), 2-methyl-5-mercapto-1,3,4-thiadiazole (2.91 g) and N-ethyl-N,N-diisopropylamine (3.85 cc) is stirred at 20° C., under nitrogen, for 17 hours. The mixture is diluted with ethyl acetate (500 cc) and this mixture is washed successively with water (4×250 cc), 0.1 N hydrochloric acid (250 cc), a 2% strength sodium bicarbonate solution (2×250 cc), water (500 cc) and saturated aqueous sodium chloride (2×250 cc), dried over sodium sulphate, filtered and concentrated to dryness under reduced pressure (20 mm Hg) at 20° C. The residue is fixed on Merck silica gel (0.05-0.2 mm) (50 g) and the powder is charged onto a column (column diameter: 4 cm, height: 47 cm) of Merck silica gel (0.05-0.2 mm) (200 g). Elution is carried out with the following mixtures of cyclohexane and ethyl acetate: 80:20 (by volume) (500 cc), 60:40 (by volume) (2,000 cc) and 40:60 (by volume) (8,000 cc), 125 cc fractions being collected. Fractions 38 to 80 are collected and concentrated to dryness at 20° C. under reduced pressure (20 mm Hg). 2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) (7.91 g) is obtained in the form of a light brown froth.

Infra-red spectrum (CHBr$_3$): characteristic bands (cm$^{-1}$) at 3420, 1805, 1720, 1505, 1370, 1050, 940, 760 and 745.

Proton nuclear magnetic resonance spectrum (350 MHz, CDCl$_3$, δ in ppm, J in Hz):

E-form: 1.5 (s, 9H, (CH$_3$)$_3$C—); 2.75 (s, 3H, —CH$_3$); 3.30 and 4.15 (2d, J=18, 2H, —SCH$_2$—); 4.55 (d, J=4.5, 1H, H in the 6-position); 5.7 to 5.9 (mt, 2H, —CONH— and H in the 7-position);

6.97 (s, 1H, —COOCH—);

7.15 (d, J=16, 1H, —CH=CHS—); 7.53 (d, J=16, 1H, =CHS—).

Z-form: 1.5 (s, 9H, (CH$_3$)$_3$C—); 2.74 (s, 3H, —CH$_3$); 3.45 and 4.11 (2d, J=18, 2H, —SCH$_2$—); 4.55 (d, J=4.5, 1H, H in the 6-position); 5.7 to 5.9 (mt, 2H, —CONH— and H in the 7-position); 6.78 (d, J=10, 1H, —CH=CHS—); 6.88 (d, J=10, 1H, =CHS—);

6.95 (s, 1H, —COOCH—).

A mixture of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]-oct-2-ene (mixture of the E- and Z-forms) (7.67 g), acetonitrile (120 cc) and p-toluenesulphonic acid monohydrate (4.57 g) is stirred for 16 hours at 20° C. The mixture is diluted with ethyl acetate (300 cc) and this mixture is washed with a saturated sodium bicarbonate solution (200 cc) and a half-saturated sodium chloride solution (3×200 cc), dried over sodium sulphate, filtered and concentrated to dryness under reduced pressure (20 mm Hg) at 20° C. 7-Amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (4.32 g) is obtained in the form of a crude brown froth.

Rf=0.17 [silica gel chromatographic plate, eluant: 85:15 (by volume) mixture of dichloroethane and methanol].

Dicyclohexylcarbodiimide (1.90 g) is added to a solution, cooled to 5° C., of syn-2-methoxyimino-2-(2-tritylamino-thiazol-4-yl)-acetic acid (7.81 g) in methylene chloride (30 cc). The solution is stirred for 40 minutes at 5° C. and then for 30 minutes at 20° C., and filtered.

To this solution, cooled to −30° C., is added a solution of 7-amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) (4.32 g) in methylene chloride (25 cc) containing triethylamine (1.25 cc). The cooling bath is removed and the mixture is stirred for 1 hour 50 minutes at 20° C. It is then concentrated under reduced pressure (20 mm Hg) at 20° C., the residue is taken up in ethyl acetate (300 cc) and this solution is washed successively with water (3×100 cc), 0.1 N hydrochloric acid (100 cc), a 1% strength sodium bicarbonate solution (100 cc) and half-saturated aqueous sodium chloride (2×100 cc), dried over sodium sulphate and concentrated to dryness under reduced pressure (20 mm Hg) at 20° C. The residue is fixed on Merck silica gel (0.05-0.2 mm) (30 g) and the powder is charged onto a column (column diameter: 3 cm, height: 54 cm) of Merck silica gel (0.05-0.2 mm) (130 g). Elution is carried out successively with the following mixtures of cyclohexane and ethyl acetate: 80:20 (by volume) (500 cc), 60:40 (by volume) (1,000 cc), 40:60 (by volume) (2,000 cc) and 20:80 (by volume) (3,000 cc), 125 cc fractions being collected. After evaporation of fractions 32 to 49 under reduced pressure (20 mm Hg at 20° C.), 2-benzhydryloxycarbonyl-7-[2-methoxyimino-2-(tritylamino-thiazol-4-yl)-acetamido]-3-[2-(2-methyl-1,3,4-thiadiazol-5-yl)-thiovinyl]-8-oxo-5- oxide-5-thia-1-aza-bicyclo[4.2.0]oct-2-ene (syn isomer, mixture of the E- and Z-forms) (3.2 g) is obtained in the form of a light brown froth.

Infra-red spectrum (CHBr₃): characteristic bands (cm⁻¹) at 3390, 1805, 1725, 1685, 1520, 1375, 1050, 940, 755 and 740.

Proton nuclear magnetic resonance spectrum (350 MHz, CDCl₃, δ in ppm, J in Hz): the following principal signals are observed: 2.74 and 2.75 (2 s, total 3H, —CH₃); 4.09 (s, 3H, =NOCH₃); 6.73 (s, 1H, H in the 5-position of the thiazole).

Phosphorus trichloride (0.54 cc) is added to a solution, cooled to −10° C., of 2-benzhydryloxycarbonyl-7-[2-methoxyimino-2-(2-tritylamino-thiazol-4-yl)-3-[2-(2-methyl-1,3,4-thiadiazol-5-yl)-thiovinyl]-8-oxo-5-oxide-5-thia-1-aza-bicyclo[4.2.0]oct-2-ene (syn isomer, mixture of the E-and Z-forms) (2.99 g) in methylene chloride (30 cc) and dimethylacetamide (1.25 cc), and the mixture is stirred for 30 minutes at the same temperature. It is then diluted with ethyl acetate (500 cc) and this mixture is washed successively with a 2% strength sodium bicarbonate solution (2×100 cc) and a half-saturated sodium chloride solution (2×200 cc), dried over sodium sulphate, filtered and concentrated under reduced pressure (20 mm Hg) at 20° C. The residue is fixed on Merck silica gel (0.05–0.2 mm) (10 g) and the powder is charged onto a column (column diameter: 3 cm, height: 23 cm) of Merck silica gel (0.05–0.2 mm) (50 g). Elution is carried out successively with the following mixtures of cyclohexane and ethyl acetate: 75:25 (by volume) (500 cc), 50:50 (by volume) (750 cc) and 25:75 (by volume) (1,000 cc), 125 cc fractions being collected. Fractions 9 to 14 are concentrated to dryness under reduced pressure (20 mm Hg) at 20° C.; 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) (1.55 g) is obtained in the form of a yellow froth.

Infra-red spectrum (CHBr₃); characteristic bands (cm⁻¹) at 3400, 1790, 1720, 1685, 1515, 1370, 1045, 755 and 740.

Proton nuclear magnetic resonance spectrum (350 MHz, CDCl₃, δ in ppm, J in Hz): the following principal signals are observed: 2.77 (s, 3H, —CH₃); 4.09 (s, 3H, =NOCH₃); 6.77 (s, 1H, H in the 5-position of the thiazole).

2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) (1.47 g) is dissolved in trifluoroacetic acid (8 cc) and anisole (0.15 cc). The mixture is stirred for 1 hour at +5° C. and 30 minutes at 20° C. and is then poured, with stirring, into diethyl ether (35 cc). The product is filtered off and dried, and 7-[2-(2-amino-thiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) trifluoroacetate (1 g) is obtained.

Rf=0.50 [silica gel chromatographic plate, solvent: a 50:20:10:10 (by volume) mixture of ethyl acetate, acetone, acetic acid and water].

Infra-red spectrum (KBr): characteristic bands (cm⁻¹) at 3380, 3300, 1780, 1675, 1200, 1140, 1050 and 945.

Proton nuclear magnetic resonance spectrum (350 NMz, CDCl₃, δ in ppm, J in Hz):

E-form: 2.74 (s, 3H, —CH₃); 3.69 and 3.83 (2 d, J=17, 2H, —SCH₂—); 3.91 (s, 3H, —OCH₃); 5.23 (d, J=4, 1H, H in the 6-position); 5.82 (dd, J=4 and 10, 1H, H in the 7-position); 6.85 (s, 1H, H in the 5-position of the thiazole); 7.16 and 7.32 (2d, J=16, 2H, —CH=CHS—); 9.75 (d, J=10, 1H, —CONH—);

Z-form: 3.88 and 3.92 (2d, J=17, 2H, —SCH₂—); 6.91 (AB limit, 2H, —CH=CH—).

2-Benzhydryloxycarbonyl-7-tert.-butoxycarbonylamino-3-(2-dimethylaminovinyl)-8-oxo-5-thia-1-aza-bicyclo[4.2.0]oct-2-ene (E-form) can be obtained in the following manner:

2-Benzhydryloxycarbonyl-7-tert.-butoxycarbonylamino-3-methyl-8-oxo-5-thia-1-aza-bicyclo[4.2.0]oct-2-ene (90.5 g) is dissolved in anhydrous N,N-dimethylformamide (400 cc). The solution obtained is heated at 80° C. under an atmosphere of nitrogen. A solution, preheated to 80° C., of bis-dimethylamino-tert.-butoxymethane (36.1 g) in anhydrous N,N-dimethylformamide (60 cc) is then added rapidly. The reaction mixture is kept at 80° C. for 5 minutes and then poured into ethyl acetate (3 liters). After addition of distilled water (1 liter), the organic phase is decanted, washed with distilled water (4×1 liter), dried over sodium sulphate and filtered in the presence of decolorising charcoal. The filtrate is concentrated to dryness under reduced pressure (20 mm Hg) at 30° C., and 2-benzhydryloxycarbonyl-7-tert.-butoxycarbonylamino-3-(2-dimethylaminovinyl)-8-oxo-5-thia-1-aza-bicyclo[4.2.0]oct-2-ene (E-form) (101 g) is obtained in the form of an orange-coloured froth.

Rf=0.29; silica gel chromatographic plate [using a 50:50 (by volume) mixture of cyclohexane and ethyl acetate].

REFERENCE EXAMPLE 2 bis-(Dimethylamino)-ethoxymethane (0.91 g) is added to a solution of 2-benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene (syn isomer) (2.5 g) in dimethylformamide (50 cc), which has been heated to 80° C. The solution becomes brownish green. It is left at 80° C. for 20 minutes and then cooled rapidly and poured into ethyl acetate (200 cc) and the mixture is washed with water (3×80 cc) and with a saturated sodium chloride solution (50 cc). The ethyl acetate phase contains, in solution, the intermediate product 2-benzhydryloxycarbonyl-3-(2-dimethylamino-vinyl)-8-oxo-7-[2-methoxyimino-2-(2-tritylamino-thiazol-4-yl)-acetamido]-5-thia-1-aza-bicyclo-[4.2.0]oct-2-ene (described in Example 22), which can be used directly for the next stage. This solution is stirred at 20° C. for one hour in the presence of 1 N hydrochloric acid (37.5 cc). The aqueous phase is removed, and the organic phase is washed with a saturated sodium bicarbonate solution (20 cc) and then with a saturated sodium chloride solution (20 cc). The organic phase is dried over magnesium sulphate, filtered in the presence of decolorising charcoal and then concentrated to dryness under reduced pressure (20 mm Hg) at 40° C. The residue is dissolved in anhydrous pyridine (10 cc). The solution is cooled to 5° C. in an ice bath, tosyl chloride (0.87 g) is added and the reaction mixture is allowed to return to 20° C. After 1½ hours, the mixture is poured onto iced water (200 cc). The precipitated formed is filtered off, washed with water (2×20 cc) and then dissolved in ethyl acetate (50 cc). This solution is washed with a saturated sodium bicarbonate solution (20 cc) and a saturated sodium chloride solution (20 cc), dried over magnesium sulphate, filtered in the presence of decolorising charcoal and concentrated to dryness under reduced pressure (20 mm Hg) at 40° C. The residue which contains 2-benzhydryloxycarbonyl-7-[2-methoxyimino-2-(2-tritylaminothiazol-4-yl)-acetamido]-8-oxo-3-(2-tosyloxy-vinyl)-5-thia-1-aza-bicyclo[4.2.0]oct-2-ene (syn isomer, mixture of the E- and Z-forms) is dissolved in methylene chloride (13 cc) and the solution obtained is cooled to −10° C. in an ice/methanol bath. A solution of 85% pure m-chloroperbenzoic acid (0.226 g) in methylene chloride (10 cc) is added in the course of 15 minutes. The reaction mixture is left at between −10° C. and +5° C. for 20 minutes and is then washed twice with a saturated sodium bicarbonate solution (20 cc), dried over magnesium sulphate, filtered in the presence of decolorising charcoal and concentrated to dryness under reduced pressure (20 mm Hg) at 40° C.

The residue is chromatographed over a column (diameter: 1.7 cm, height: 21 cm) containing silica gel (26 g). Elution is carried out with ethyl acetate/cyclohexane mixtures (120, 240, 200 and 120 cc, with respective compositions of 20:80, 30:70, 40:60 and 60:40 by volume), and 20 cc fractions of eluate are collected. Fractions 17 to 34 are evaporated and 2-benzhydryloxycarbonyl-7-[2-methoxyimino-2-(2-tritylaminothiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (0.88 g) is isolated.

(a) A mixture of 2-benzhydryloxycarbonyl-7-[2-methoxyimino-2-(2-trithylamino-thiazol-4-yl)-acetamido]-8-oxo-5-oxide-3-(2-tosyloxyvinyl)-5-thia-1-aza-bicyclo[4.2.0]oct-2-ene (syn-isomer, mixture of the E- and Z-forms) (8.03 g), dimethylformamide (80 cc), methylmercaptan (1.59 g) and N-ethyl-N,N-diisopropylamine (1.53 cc) is heated at 40° C. for 5 hours in an autoclave. The mixture is diluted with ethyl acetate (500 cc) washed with water (3×250 cc), 0.1 N hydrochloric acid (100 cc), a 1% strength sodium bicarbonate solution (100 cc) and a half-saturated sodium chloride solution (2×200 cc), dried over sodium sulphate and concentrated to dryness under reduced pressure (20 mm Hg) at 20° C.

The residue is dissolved in a 50:50 (by volume) mixture of cyclohexane and ethyl acetate (100 cc) and the solution is chromatographed over a column of Merck silica gel (0.04–0.06 mm) (300 g) (column diameter: 6 cm, height: 36 cm). Elution is carried out with a 50:50 (by volume) mixture of cyclohexane and ethyl acetate (8 liters) under a pressure of 40 kPa, and 125 cc fractions are collected. Fractions 25 to 57 are combined and evaporated to dryness under reduced pressure (20 mm Hg) at 20° C. 2-Benzhydryloxycarbonyl-7-[2-methoxyimino-2-(2-tritylamino-thiazol-4-yl)-acetamido]-3-(2-methylthiovinyl)-8-oxo-5-oxide-5-thia-1-aza-bicyclo[4.2.0]oct-2-ene (syn isomer, mixture of the E- and Z-forms) (3.7 g) is collected in the form of a cream-coloured froth.

Infrared spectrum (CHBr$_3$): characteristic bands (cm$^{-1}$) at 3380, 1800, 1720, 1680, 1515, 1370, 1205, 1045, 835, 750 and 740.

Proton nuclear magnetic resonance spectrum (350 MHz, CDCl$_3$, δ in ppm, J in Hz): 2.17 (s, 3H, —CH$_3$ E-form); 2.35 (s, 3H, —CH$_3$ Z-form); 3.23 and 3.98 (AB, J=18, 2H, —SCH$_2$— E-form); 3.44 and 4.3 (AB, J=18, 2H, —SCH$_2$— Z-form); 4.09 (s, 3H, —OCH$_3$); 4.58 (d, J=9, 1H, H in the 6-position); 6.12 (dd, J=4 and 9, 1H, H in the 7-position); 6.17 (d, J=10, 1H, —C$\underline{H}$=CH—S—CH$_3$, Z-form); 6.65 (d, J=15, 1H, —C$\underline{H}$=CH—S—CH$_3$, E-form); 6.88 (d, J=10, 1H, =C$\underline{H}$—S—CH$_3$, Z-form); 7.15 (d, J=15, 1H, =C$\underline{H}$—S—CH$_3$, E-form); 6.72 (s, 1H, H in the 5-position of the thiazole); 6.98 (s, 1H, —COOCH); 7.07 (s broad, 1H, (C$_6$H$_5$)$_3$CN$\underline{H}$—).

A solution of 2-benzhydryloxycarbonyl-7-[2-methoxyimino-2-(2-tritylamino-thiazol-4-yl)-acetamido]-3-(2-methylthiovinyl)-8-oxo-5-oxide-5-thia-1-aza-bicyclo[4.2.0]oct-2-ene (syn isomer, mixture of E- and Z-forms) (2.30 g) in methylene chloride (25 cc) and dimethylacetamide (1.04 cc) is treated with phosphorus trichloride (0.46 cc) at −10° C. for 30 minutes. The mixture is diluted with ethyl acetate (500 cc), washed with a 2% strength sodium bicarbonate solution (2×100 cc) and a half-saturated sodium chloride solution (2×100 cc), dried over sodium sulphate, filtered and concentrated to dryness under reduced pressure (20 mm Hg) at 20° C.

The residue is dissolved in methylene chloride (10 cc) and the solution is chromatographed on a column of Merck silica gel (0.04–0.06 mm) (150 g) (column diameter: 4 cm, height: 20 cm). Elution is carried out with a 60:40 (by volume) mixture of cyclohexane and ethyl acetate (2 liters) under a pressure of 40 kPa, and 125 cc fractions are collected. Fractions 4 to 8 are concentrated under reduced pressure (20 mm Hg) at 20° C.; 2-benzhydryloxycarbonyl-7-[2-methoxyimino-2-(2-tritylaminothiazol-4-yl)-acetamido]-3-(2-methylthiovinyl)-8-oxo-5-thia-1-aza-bicyclo[4.2.0]oct-2-ene (syn isomer, mixture of the E- and Z-forms) (1.32 g) is obtained in the form of a cream-coloured froth.

Infra-red spectrum (CHBr$_3$): characteristic bands (cm$^{-1}$) at 3390, 1780, 1715, 1680, 1515, 1370, 1200, 1050, 1035, 750 and 740.

Proton nuclear magnetic resonance spectrum (350 MHz, CDCl$_3$, δ in ppm, J in Hz): 2.18 (s, 3H, —CH$_3$ E-form); 2.31 (s, 3H, —CH$_3$ Z-form); 3.44 (AB, J=18, 2H, —SCH$_2$— E-form); 3.80 (AB, J=18, 2H, —SCH$_2$— Z-form); 4.08 (s, 3H, —OCH$_3$); 5.06 (d, J=4, 1H, H in the 6-position); 5.80 (dd, J=4 and 9, 1H, H in the 7-position E-form); 5.90 (dd, J=4 and 9, 1H, H in the 7-position, Z-form); 6.14 (d, J=11, 1H, —C$\underline{H}$=CHS— Z-form); 6.64 (d, J=16, 1H, —C$\underline{H}$=CHS—, E-form); 6.70 (d, J=11, 1H, =CHS—, Z-form); 6.79 (s, 1H, H in the 5-position of the thiazole);

6.93 (s, 1H, —COOCH—);

6.98 (d, J=16, 1H, =CHS—, E-form).

2-Benzhydryloxycarbonyl-7-[2-methoxyimino-2-(2-tritylamino-thiazol-4-yl)-acetamido]-3-(2-methylthiovinyl)-8-oxo-5-thia-1-aza-bicyclo[4.2.0]oct-2-ene (syn isomer, mixture of the E- and Z-forms) (1.26 g) is dissolved in formic acid (35 cc), water (13 cc) is added and the mixture is heated for 15 minutes at 50° C. It is allowed to cool and is filtered and concentrated to dryness under reduced pressure (20 mm Hg at 20° C.). The residue is triturated in diethyl ether (20 cc), filtered off, washed with ether (20 cc) and dried. 7-[2-(2-Amino-thiazol-4-yl)-2-methoxyimino-acetamido]-2-carboxy-3-(2-methylthiovinyl)-8-oxo-5-thia-1-aza-bicyclo[4.2.0]oct-2-ene (syn isomer, mixture of the E- and Z-forms)

(0.63 g) is obtained as the solvate with formic acid, in the form of a cream-coloured powder.

Rf=0.34 and 0.48 [silica gel chromatographic plate, solvent: ethyl acetate/acetone/formic acid/water, 60:20:1:1 (by volume)].

Infra-red spectrum (KBr): characteristic bands (cm$^{-1}$) at 3320, 1770, 1675, 1530 and 1035.

Proton nuclear magnetic resonance spectrum (350 MHz, DMSO d$_6$, δ in ppm, J in Hz) E-form: 2.34 (s, 3H, —SCH$_3$); 3.61 and 3.77 (AB, J=18, 2H, —SCH$_2$—); 3.86 (s, 3H, —OCH$_3$); 5.14 (d, J=4, 1H, H in the 6-position); 5.62 (dd, J=4 and 9, 1H, H in the 7-position); 6.77 (s, 1H, H in the 5-position of the thiazole); 6.85 (d, J=16, 1H, —C<u>H</u>=CH—S—); 7.04 (d, J=16, 1H, =CH—S—); 9.57 (d, J=9, 1H, —CONH—) Z-form: in particular, the following signals are observed: 2.25 (s, 3H, —SCH$_3$), 6.74 (d, J=13, 1H, —C<u>H</u>=CH—S—CH$_3$) and 6.89 (d, J=13, 1H, =CHS—).

Thiophenol (0.90 cc), followed by N-ethyl-N,N-diisopropylamine (1.53 cc) is added to a solution of 2-benzhydryloxcarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (8.03 g) in dimethylformamide (80 cc) cooled to +2° C., under nitrogen. The mixture is stirred for 2 hours at 20° C. and is then diluted with ethyl acetate (320 cc), washed with water (3×200 cc), 0.1 N hydrochloric acid (100 cc), a 5% strength sodium bicarbonate solution (150 cc) and a saturated sodium chloride solution (2×150 cc), dried over sodium sulphate and concentrated to dryness under reduced pressure (20 mm Hg) at 20° C. The product is dissolved in methylene chloride (35 cc) and chromatographed over a column (diameter: 6 cm, height: 30 cm) of Merck silica gel (0.04–0.06 mm) (250 g). Elution is carried out with a 55:45 (by volume) mixture of cyclohexane and ethyl acetate (4 liters) under a pressure of 0.4 bar, 100 cc fractions being collected. Fractions 12 to 32 are evaporated under reduced pressure (20 mm Hg) at 20° C. and 2-benzhydryloxycarbonyl-7-[2-methoxyimino-2-(2-tritylamino-thiazol-4-yl)-acetamido]-8-oxo-5-oxide-3-(2-phenylthiovinyl)-5-thia-1-aza-bicyclo[4.2.0]oct-2-ene (syn isomer, mixture of the E- and Z-forms) (4.8 g) is obtained in the form of a yellow froth.

Infra-red spectrum (CHBr$_3$): characteristic bands (cm$^{-1}$) at 3380, 2820, 1795, 1720, 1680, 1580, 1475, 1445 and 1440.

Proton nuclear magnetic resonance spectrum (350 MHz, CDCl$_3$, δ in ppm, J in Hz): 3.93 and 3.13 (AB, J=19, 2H, —SCH$_2$—, E-form); 4.32 and 5.0 (AB, J=19, 2H, —SCH$_2$—, Z-form); 4.05 (s, 3H, —OCH$_3$, E-form); 4.07 (s, 3H, —OCH$_3$, Z-form); 4.51 (d, 1H, J=4, H in the 6-position, E-form); 4.56 (d, 1H, J=4, H in the 6-position, Z-form); 6.10 (dd, J=4 and 9, 1H, H in the 7-position, E-form); 6.14 (dd, J=4 and 9, 1H, H in the 7-position, Z-form); 6.41 (d, J=11, 1H, —C<u>H</u>=CH—S—, Z-form); 6.6 (d, J=16, 1H, —C<u>H</u>=CH—S—, E-form); 6.71 (s, 1H, H in the 5-position of the thiazole, E-form); 6.72 (s, 1H, H in the 5-position of the thiazole, Z-form); 6.93 (s, —CO$_2$CH<); 7.09 (s, —NH— thiazole).

Phosphorus trichloride (0.98 cc) is added to a solution, cooled to −10° C., of 2-benzhydryloxycarbonyl-7-[2-methoxyimino-2-(2-tritylamino-thiazol-4-yl)-acetamido]-8-oxo-5-oxide-3-(2-phenylthiovinyl)-5-thia-1-aza-bicyclo[4.2.0]oct-2-ene (syn isomer, mixture of the E- and Z-forms) (4.8 g) in methyl chloride (51 cc) and dimethylacetamide (2.02 cc). The mixture is stirred for 1 hour at −10° C. and is then taken up in ethyl acetate (300 cc), and this solution is washed with a 5% strength sodium bicarbonate solution (2×150 cc) and a saturated sodium chloride solution (150 cc), dried over sodium sulphate and concentrated to dryness under reduced pressure (20 mm Hg at 20° C.). The product is dissolved in methylene chloride (30 cc) and the solution is chromatographed over a column (column diameter: 5 cm, height: 30 cm) containing Merck silica gel (0.02–0.06 mm) (250 g). Elution is carried out with a 65.35 (by volume) mixture of cyclohexane and ethyl acetate (2 liters) under a pressure of 0.4 bar, 100 cc fractions being collected. Fractions 10 to 16 are evaporated; 2-benzhydryloxycarbonyl-7-[2-methoxyimino-2-(2-tritylamino-thiazol-4-yl)-acetamido]-8-oxo-3-(2-phenylthiovinyl)-5-thia-1aza-bicyclo[4.2.0]oct-2-ene (syn isomer, mixture of the E- and Z-forms) (2.6 g) is obtained in the form of a cream-coloured froth.

Proton nuclear magnetic resonance spectrum (350 MHz, CDCl$_3$, δ in ppm, J in Hz): 3.42 and 3.52 (AB, J=19, 2H, —SCH$_2$—, E-form); 3.50 and 3.88 (AB, J=19, 2H, —SCH$_2$—, Z-form); 4.07 (s, 3H, —OCH$_3$, E-form); 4.09 (s, 3H, —OCH$_3$, Z-form); 5.07 (d, J=4, 1H, H in the 6-position, E-form); 5.10 (d, J=4, 1H, H in the 6-position, Z-form); 5.87 (dd, J=4 and 9, 1H, H in the 7-position, E-form); 5.93 (dd, J=4 and 9, 1H, H in the 7-position, Z-form); 6.41 (d, J=11, 1H, —C<u>H</u>=CH—S—, Z-form); 6.70 (d, J=16, 1H, —C<u>H</u>=CH—S—, E-form); 6.76 (s, H in the 5-position of the thiazole);

6.95 (s, —CO$_2$CH—);

6.95 (d, J=11, 1H, —CH=C<u>H</u>—S—, Z-form); 7.22 (d, J=16, 1H, —CH=C<u>H</u>—S, E-form); 7.01 (s broad, —NH— thiazole).

2-Benzhydryloxycarbonyl-7-[2-methoxyimino-2-(2-tritylamino-thiazol-4-yl)-acetamido]-8-oxo-3-(2-phenylthiovinyl)-5-thia-1-aza-bicyclo[4.2.0]oct-2-ene (syn isomer, mixture of the E- and Z-forms) (2.6 g) is dissolved in formic acid (40 cc) and the solution is diluted with water (12.5 cc) and heated at 50° C. for 20 minutes. It is then cooled, the insoluble matter is removed by filtration and the filtrate is evaporated to dryness at 20° C. under reduced pressure (0.05 mm Hg). The residue is triturated in ethyl ether (50 cc), filtered off, washed with ether (50 cc) and dried. 7-[2-(2-Aminothiazol-4-yl)-2-methoxyimino-acetamido]-2-carboxy-3-(2-phenylthiovinyl)-8-oxo-5-thia-1-aza-bicyclo[4.2.0]oct-2-ene (syn isomer, mixture of the E- and Z-forms) (1.3 g) is obtained as a solvate with formic acid in the form of a yellow powder.

Infra-red spectrum (KBr): characteristic bands (cm$^{-1}$) at 3320, 1775, 1680, 1530, 1380, 1045, 945, 745 and 690.

Proton nuclear magnetic resonance spectrum (DMSO d$_6$, 350 MHz, δ in ppm, J in Hz): 3.65 and 3.94 (AB, J=18, 2H, —SCH$_2$—, E-form); 3.84 (s, 3H, —OCH$_3$); 5.17 (d, J=4, 1H, H in the 6-position, E-form); 5.22 (d, J=4, 1H, H in the 6-position, Z-form); 5.73 (dd, J=4 and 9, 1H, H in the 7-position, E-form); 6.61 (d, J=11, 1H, —C<u>H</u>=CH—S—, Z-form); 6.80 (d, J=11, 1H, —CH=C<u>H</u>—S—, Z-form); 6.98 (d, J=15, 1H, —C<u>H</u>=CH—S—, E-form); 7.06 (d, J=15, 1H, —CH=C<u>H</u>—S—, E-form); 6.74 (s, H in the 5-position of the thiazole), 7.18 (broad signal, —NH$_3$+ and —CO$_2$H); 8.11 (s, HCO$_2$−); 9.58 (d, J=9, 1H, —CONH—).

REFERENCE EXAMPLE 3

2-Mercapto-pyridine-N-oxide (0.43 g) and N,N-diisopropylethylamine (0.6 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (3.4 g) (obtained as described in reference example 1c) in dry N,N-dimethylformamide (85 cc) and the mixture is stirred for 30 minutes at 25° C. A further amount of 2-mercaptopyridine-N-oxide (0.43 g) and of N,N-diisopropylethylamine (0.6 cc) is added and the mixture is stirred for a further 10 minutes at 25° C., after which it is diluted with ethyl acetate (250 cc). The mixture is washed with water (2×200 cc) followed by 0.1 N hydrochloric acid (200 cc) and a saturated sodium chloride solution (200 cc); after drying over magnesium sulphate, the solvent is evaporated under reduced pressure (30 mm Hg) at 40° C. The residue (3.5 g) is added to a further amount (0.5 g) of product obtained in the same way and the mixture is chromatographed over Merck silica gel (0.04–0.06 mm) (80 g) (column diameter: 5 cm), elution being carried out with 10 liters of a 98:2 (by volume) mixture of ethyl acetate and methanol under a pressure of 50 kPa, and 120 cc fractions being collected. Unchanged starting material (1.1 g) is recovered from fractions 2 to 4. Fractions 45 to 75 are concentrated to dryness under reduced pressure (30 mm Hg) at 40° C. and 2-benzhydryloxycarbonyl-7-[2-methoxyimino-2-(2-tritylamino-thiazol-4-yl)-acetamido]-8-oxo-3-[2-(pyrid-2-yl-1-oxide)-thiovinyl]-5-thia-1-aza-bicyclo[4.2.0]oct-2-ene (syn isomer, E-form) (1.6 g) is obtained in the form of a grey froth.

Infra-red spectrum (CHBr$_4$): characteristic bands (cm$^{-1}$) at 3390, 1780, 1720, 1680, 1585, 1510, 1465, 1420, 1040, 945 and 750.

Proton nuclear magnetic resonance spectrum (350 MHz, CDCl$_3$, δ in ppm, J in Hz): 3.60 and 3.69 (AB, J=18, 2H, —SCH$_2$—); 4.08 (s, 3H, =NOCH$_3$); 5.12 (d, J=4, 1H, H in the 6-position); 5.97 (dd, J=4 and 9, 1H, H in the 7-position); 6.57 (d, J=16, 1H, —CH=C-HS—); 6.76 (s, 1H, H of the thiazole); 7.0 (s, 2H, —CH(C$_6$H$_5$)$_2$ and (C$_6$H$_5$)$_3$CNH—); 7.1 to 7.5 (hump, aromatic); 8.25 (d, J=9, 1H, —CONH—).

2-Benzhydryloxycarbonyl-7-[2-methoxyimino-2-(2-tritylamino-thiazol-4-yl)-acetamido]-8-oxo-3-[2-(pyrid-2-yl-1-oxide)-thiovinyl]-5-thia-1-aza-bicyclo[4.2.0]oct-2-ene (syn isomer, E-form) (2.3 g) is dissolved in formic acid (54 cc). The solution is diluted with distilled water (21 cc) and stirred for 20 minutes at 50° C. It is then filtered hot and the solvents are evaporated under reduced pressure (10 mm Hg) at 40° C. The residue is triturated with ethanol (50 cc). The mixture is evaporated to dryness under reduced pressure (30 mm Hg) at 40° C. The operation is repeated once. The residue is taken up in ethanol (50 cc) and the solid is filtered off, washed with ethanol (15 cc) and then with ethyl ether (2×25 cc) and is dried under reduced pressure (10 mm Hg) at 25° C. 7-[2-(2-Amino-thiazol-4-yl)-acetamido]-2-carboxy-8-oxo-3-[2-(pyrid-2-yl-1-oxide)-thiovinyl]-5-thia-1-aza-bicyclo[4.2.0]oct-2-ene (syn isomer, E-form) (0.98 g) is obtained in the form of a grey powder.

Infra-red spectrum (KBr), characteristic bands (cm$^{-1}$) at 3330, 1770, 1670, 1540, 1470, 1420, 1040, 950 and 760.

Proton nuclear magnetic resonance spectrum (350 MHz, DMSO d$_6$, δ in ppm, J in Hz): 3.75 and 4.16 (AB, J=18, 2H, —SCH$_2$—); 3.88 (s, 3H, =NOCH$_3$); 5.24 (d, J=4, 1H, H in the 6-position); 5.73 (dd, J=4 and 9, 1H, H in the 7-position); 6.78 (s, 1H, H of the thiazole); 7.05 and 7.32 (AB, J=16, 2H, —CH=CH—S—); 7.63 (d, J=7, 1H, H in the 3-position of the pyridine group); 7.1 to 7.5 (hump, 4H, H in the 4- and 5-position of pyridine-+—NH$_2$); 7.63 (d, J=7, 1H, H in the 3-position of pyridine); 8.32 (d, J=6, 1H, H in the 6-position of pyridine); 9.64 (d, J=9, 1H, —CONH—).

REFERENCE EXAMPLE 4

3-Mercapto-6-methyl-pyridazine-1-oxide (0.738 g) and N,N-diisopropylethylamine (0.89 cc) are added successively at 22° C., under a nitrogen atmosphere and with stirring, to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (4.9 g) (obtained as described in reference example 1c) in dimethylformamide (40 cc). The mixture is stirred for 15 minutes at 25° C. and is then diluted with ethyl acetate (600 cc) washed successively with water (2×120 cc), 0.1 N hydrochloric acid (120 cc), a 2% strength sodium bicarbonate solution (2×120 cc) and a half-saturated sodium chloride solution (2×120 cc), dried over sodium sulphate, filtered and concentrated to dryness at 20° C. under reduced pressure (20 mm Hg). The residue is taken up in ethyl acetate (10 cc) and the solution is filtered over a column (column diameter: 2.4 cm) of Merck silica gel (0.05–0.2 mm) (50 g). Elution is carried out with ethyl acetate (500 cc), successively collecting a colourless fraction 1 (100 cc), pale yellow fraction 2 (20 cc) and a fraction 3 (360 cc). The latter is concentrated to dryness at 20° C. under reduced pressure (20 mm Hg). This gives 2-benzhydryloxycarbonyl-7-[2-methoxyimino-2-(2-tritylaminothiazol-4-yl)-acetamido]-3-[2-(6-methyl-pyridazin-3-yl-1-oxide)-thiovinyl]-8-oxo-5-thia-1-aza-bicyclo[4.2.0]oct-2-ene (syn isomer, E-form) (4 g) in the form of a brownish-orange froth.

Infra-red spectrum (KBr): characteristic bands (cm$^{-1}$) at 3400, 1780, 1720, 1680, 1530, 1495, 1450, 1330, 1210, 1050, 1040, 1000, 945, 810, 755 and 700.

Proton nuclear magnetic resonance spectrum (350 MHz, CDCl$_3$, δ in ppm, J in Hz): 2.45 (s, 3H, —CH$_3$); 3.62 and 3.77 (2d, J=18, 2H, —SCH$_2$—); 4.09 (s, 3H, —OCH$_3$); 5.08 (d, J=4, 1H, H in the 6-position); 5.93 (dd, J=4 and 9, 1H, H in the 7-position); 6.03 (s, 1H, (C$_6$H$_5$)$_3$CNH—); 6.76 (s, 1H, H of the thiazole);

6.95 (s, 1H, —COOCH—).

A solution of 2-benzhydryloxycarbonyl-7-[2-methoxyimino-2-(2-tritylamino-thiazol-4-yl)-acetamido]-3-[2-(6-methyl-pyridazin-3-yl-1-oxide)-thiovinyl]-8-oxo-5-thia-1-aza-bicyclo[4.2.0]oct-2-ene (syn isomer, E-form) (3.9 g) in a mixture of formic acid (60 cc) and distilled water (25 cc) is stirred at 50° C. for 30 minutes. The mixture is then cooled to about 20° C. and filtered, and the filtrate is concentrated to dryness at 30° C. under reduced pressure (0.05 mm Hg). The residue is taken up in ethanol (50 cc), the mixture is concentrated to dryness at 20° C. under reduced pressure (20 mm Hg) and this operation is repeated twice. The solid which remains is treated with ethanol (40 cc) under reflux for 5 minutes and the suspension is then cooled to about 20° C. and filtered. After drying, 7-[2-(2-amino-thiazol-4-yl)-2-methoxyimino-acetamido]-2-carboxy-3-[2-(6-methyl-pyridazin-3-yl-1-oxide)-thiovinyl]-8-xo-5-thia-1-aza-bicyclo[4.2.0]oct-2-ene (syn isomer, E-form) (1.96 g) is obtained in the form of a yellow powder.

Infra-red spectrum (KBr): characteristic bands (cm$^{-1}$) at 3420, 3320, 3230, 1765, 1675, 1655, 1620, 1535, 1325, 1210, 1040, 1000 and 810.

Proton nuclear magnetic resonance spectrum (350 MHz, DMSO d$_6$, δ in ppm, J in Hz): 2.33 (s, 3H, —CH$_3$); 3.70 and 3.97 (2d, J=18, 2H, —SCH$_2$—); 3.86 (s, 3H, —OCH$_3$); 5.23 (d, J=4, 1H, H in the 6-position); 5.81 (dd, J=4 and 9, 1H, H in the 7-position); 6.76 (s, 1H, H of the thiazole); 7.18 to 7.20 (hump, 5H, —CH=CH— and —NH$_3$+); 7.31 and 7.86 (2d, J=7, H of the pyridazine); 9.62 (d, J=9, 1H, —CONH—).

REFERENCE EXAMPLE 5

5,6-Dioxo-4-methyl-3-thioxo-perhydro-1,2,4-triazine (0.7 g) and N,N-diisopropylethylamine (0.77 cc) are added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4 g) (obtained as described in reference example 1c) in dry N,N-dimethylformamide (40 cc). The reaction mixture is heated for 90 minutes at 60° C. and is then diluted with ethyl acetate (200 cc) and washed with distilled water (4×100 cc). After drying over magnesium sulphate, filtering and evaporating to dryness under reduced pressure (30 mm Hg) at 40° C., the residue is chromatographed over Merck silica gel (0.04–0.06 mm) (column diameter: 4 cm), elution being carried out under 50 kPa with ethyl acetate (3 liters) and 100 cc fractions being collected; fractions 11 to 29 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.8 g) is obtained.

Infra-red spectrum (CHBr$_3$): characteristic bands (cm$^{-1}$) at 3360, 3200, 2820, 1795, 1710, 1680, 1590, 1515, 1490, 1450, 1040 and 760.

Proton nuclear magnetic resonance spectrum (350 MHz, CDCl$_3$, δ in ppm, J in Hz): 3.30 (s, 3H, —CH$_3$ of the triazine); 3.30 and 4.0 (AB, J=18, —S(O)CH$_2$—); 3.88 (s, 3H, =NOCH$_3$); 4.65 (d, J=4, 1H, H in the 6-position); 6.02 (dd, J=4 and 9, 1H, H in the 7-position); 6.32 (d, J=16, 1H, —CH=CH—S—); 6.68 (s, 1H, H of the thiazole); 6.92 (s, 1H, —CH(C$_6$H$_5$)$_2$); 7.15 to 7.55 (hump, aromatic+—CONH—+(C$_6$H$_5$)$_3$CNH—+—CH=CHS—).

Phosphorus trichloride (0.53 cc) is added to a solution, cooled to −30° C., of 2-benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylaminothiazol-4-yl)-acetamido]-8-oxo-5-oxide-5-thia-1-aza-bicyclo[4.2.0]oct-2-ene (syn isomer, E-form) (2.8 g) in methylene chloride (30 cc) and N,N-dimethylacetamide (1.1 cc) and the reaction mixture is stirred for 2 hours at between −15° and −10° C., after which it is diluted with ethyl acetate (250 cc). It is washed with a saturated sodium bicarbonate solution (2×100 cc) and then with a saturated sodium chloride solution (250 cc), dried over magnesium sulphate and filtered, and the solvent is evaporated under reduced pressure (30 mm Hg) at 40° C. The residue is chromatographed over silica gel (0.04–0.06 mm) (120 g) (column diameter: 4 cm, height: 20 cm), elution being carried out with a 20:80 (by volume) mixture of cyclohexane and ethyl acetate (2 liters) under a pressure of 50 kPa, and 100 cc fractions being collected. Fractions 4 to 16 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.75 g) is obtained in the form of a cream-coloured solid.

Infra-red spectrum (CHBr$_3$): characteristic bands (cm$^{-1}$) at 3380, 1785, 1710, 1680, 1515, 1490, 1445, 1040, 940, 755 and 740.

Proton nuclear magnetic resonance spectrum (350 MHz, CDCl$_3$, δ in ppm, J in Hz): 3.41 (s, 3H, —CH$_3$ of the triazine); 3.58 and 3.68 (AB, J=18, 2H, —SCH$_2$—); 4.04 (s, 3H, =NOCH$_3$); 5.10 (d, J=4, 1H, H in the 6-position); 5.95 (dd, J=4 and 9, 1H, H in the 7-position); 6.74 (s, 1H, H of the thiazole); 6.84 (d, J=17, 1H, —CH=CH—S—); 6.96 (s, 1H, —CH(C$_6$H$_5$)$_2$); 7.03 (d, J=9, 1H, —CONH—); 7.15 to 7.55 (hump, aromatics+(C$_6$H$_5$)$_3$CNH—+—CH=CHS—); 10.8 (s, 1H, —NH— of the triazine).

2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.7 g) is dissolved in formic acid (24 cc); after addition of distilled water (16 cc), the reaction mixture is heated for 25 minutes at 50° C. and is then filtered hot and concentrated to dryness under reduced pressure (10 mm Hg) at 40° C. The solid is triturated with ethanol (40 cc) and the mixture is evaporated to dryness under reduced pressure (30 mm Hg) at 40° C.; this operation is repeated once, and the residue obtained is then taken up in ethanol (30 cc). The insoluble matter is filtered off, washed with ethanol (10 cc) and ether (2×50 cc) and dried under reduced pressure (10 mm Hg) at 25° C. 7-[2-(2-Aminothiazol-4-yl)-2-methoxyimino-acetamido]-2-carboxy-3-[2-(5,6-dioxo-4-methyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.85 g) is obtained in the form of a cream-coloured solid.

Rf=0.37; silica gel chromatographic plate; eluant: 3:2:2 (by volume) ethyl acetate/water/acetic acid.

Infra-red spectrum (KBr): characteristic bands (cm$^{-1}$) at 3300, 3260, 2600, 1770, 1705, 1680, 1630, 1585, 1530, 1375, 1040 and 950.

Proton nuclear magnetic resonance spectrum (350 MHz, DMSO d$_6$, δ in ppm, J in Hz): 3.35 (s, 3H, —CH$_3$ of the triazine); 3.65 and 3.88 (AB, J=18, 2H, —SCH$_2$—); 3.87 (s, 3H, =NOCH$_3$); 5.22 (d, J=4, 1H, H in the 6-position); 5.80 (dd, J=4 and 9, 1H, H in the 7-position); 6.75 (s, 1H, H of the thiazole); 6.83 (d, J=16, —CH=CH—S—); 7.11 (d, J=16, 1H, —CH=CH—S—); 7.20 (s broad, 3H, —NH$_3$+); 9.58 (d, J=9, 1H, —CONH—).

REFERENCE EXAMPLE 6

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.8 g) (obtained as described in reference example 1c), dimethylformamide (58 cc), 4-(2-methoxyethyl)-5,6-dioxo-3-thioxoperhydro-1,2,4-triazine (1.3 g) and diisopropylethylamine (0.819 mg) is stirred at 60° C. for 80 minutes, under nitrogen. The mixture is cooled to 20° C. and diluted with ethyl acetate (300 cc), and the organic phase is washed 4 times with water (a total of 100 cc), dried over magnesium sulphate, filtered and concentrated to dryness at 20° C. under reduced pressure (20 mm Hg). The residue, dissolved in ethyl acetate (250 cc) is filtered over a column of silica gel (32 g) and eluted with ethyl acetate (500 cc). The eluate is evaporated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (5.4 g) in the form of a beige solid.

Infra-red spectrum (KBr): characteristic bands (cm$^{-1}$) at 3400, 2830, 1800, 1720, 1690, 1590, 1525, 1495, 1450, 1370, 1210, 1110, 1040, 945, 755 and 700.

Proton nuclear magnetic resonance spectrum (350 MHz, CDCl$_3$, δ in ppm, J in Hz): 3.32 (s, 3H, —CH$_2$OC$\underline{H}_3$); 3.60 (t, J=5, 2H, —CH$_2$O—); 4.05 (t, J=5, 2H, —CH$_2$N<); 3.34 and 4.1 (dd, J=18, 2H, —S(O)CH$_2$—); 4.00 (s, 3H, =NOCH$_3$); 4.66 (d, J=4, 1H, H in the 6-position); 6.08 (dd, J=4 and 9, 1H, H in the 7-position); 6.71 (s, 1H, H of the thiazole); 6.85 (d, J=16, 1H, —C$\underline{H}$=CHS—); 6.97 (s, 1H, —COOCH).

Dimethylacetamide (2.06 cc), followed by phosphorus trichloride (0.91 cc) is added to a solution, cooled to −10° C., of 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (5.3 g) in methylene chloride (53 cc). The solution is stirred for 2 hours at −10° C. and is then diluted with ethyl acetate (750 cc); this solution is washed with a saturated sodium bicarbonate solution (2×100 cc), and a saturated sodium chloride solution (2×100 cc), dried over magnesium sulphate and concentrated to 50 cc under reduced pressure (20 mm Hg) at 20° C., and isopropyl ether (200 cc) is added. The solid formed is isolated by filtration, washed with isopropyl ether (20 cc) and dried. This gives a cream-coloured solid (4.2 g). This solid, dissolved in a 70:30 (by volume) mixture of ethyl acetate and cyclohexane, is chromatographed over a column (column diameter 6 cm, height 20 cm) of Merck silica gel (0.04–0.06 mm). Elution is carried out with a 70:30 (by volume) mixture of ethyl acetate and cyclohexane (1,500 cc) under a pressure of 40 kPa, 75 cc fractions being collected. Fractions 9 to 19 are concentrated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.9 g) in the form of a cream-coloured solid.

Infra-red spectrum (KBr): characteristic bands (cm$^{-1}$) at 3400, 2820, 1785, 1720, 1690, 1590, 1525, 1495, 1450, 1370, 1210, 1110, 1040, 945, 755 and 705.

Proton nuclear magnetic resonance spectrum (350 MHz, CDCl$_3$, δ in ppm, J in Hz): 3.34 (s, 3H, —CH$_2$OC$\underline{H}_3$); 3.65 (t, J=5, 2H, —CH$_2$O—);

4.11 (t, J=5, 2H, —CH$_2$N$\diagdown^{\diagup}$);

3.60 and 3.68 (2d, J=18, 2H, —SCH$_2$—); 4.06 (s, 3H, =NOCH$_3$); 5.11 (d, J=4, 1H, H in the 6-position); 5.95 (dd, J=4 and 9, 1H, H in the 7-position); 6.76 (s, 1H, H of the thiazole); 6.86 (d, J=16, 1H, —C$\underline{H}$=CHS—); 6.93 (d, J=9, 1H, —CONH—);

6.97 (s, 1H, —COOCH—).

2-Benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.8 g) is dissolved in formic acid (50 cc), water (25 cc) is added and the mixture is heated for 15 minutes at 50° C., with stirring. The mixture is then diluted with water (25 cc), cooled, filtered and concentrated to dryness at 40° C. under 0.05 mm Hg. The residue is taken up three times in ethanol (50 cc), and each time the mixture is evaporated to dryness under reduced pressure (0.05 mm Hg). The residue is taken up in ethanol (200 cc) under reflux, the mixture is filtered hot on a glass frit, the residue is again taken up in ethanol (100 cc) under reflux and the mixture again filtered hot, the two combined filtrates are concentrated to 20 cc and cooled to 0° C., and the solid obtained is filtered off and dried. This gives 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (1.45 g), in the form of a yellow solid.

Infra-red spectrum (KBr): characteristic bands (cm$^{-1}$) at 3480, 2830, 1775, 1710, 1680, 1635, 1590, 1535, 1380, 1110, 1040 and 940.

Proton nuclear magnetic resonance spectrum (350 MHz, DMSO d$_6$, δ in ppm, J in Hz): 3.36 (s, 3H, —CH$_2$OC$\underline{H}_3$); 3.56 (t, J=5, 2H, —C$\underline{H}_2$O—); 4.10 (t, J=5, 2H, —CH$_2$N<); 3.62 and 3.73 (2d, J=18, 2H, —SCH$_2$—); 3.96 (s, 3H, =NOCH$_3$); 5.18 (d, J=4, 1H, H in the 6-position); 5.81 (dd, J=4 and 9, 1H, H in the 7-position); 6.78 (s, 1H, H of the thiazole); 6.87 (d, J=15, 1H, —C$\underline{H}$=CH—S—); 7.29 (d, J=15, 1H, —CH=C$\underline{H}$—S—); 6.70 (s, broad, 3H, —NH$_3^+$); 9.55 (d, J=9, 1H, —CONH—);

12.64 (s, 1H, =N NHCO— or =N N =C—).
                                              |
                                              OH 4-(2-Methoxyethyl)-5,6-dioxo-3-thioxo-perhydro-1,2,4-triazine can be prepared in accordance with Belgian Pat. No. 830,455.

REFERENCE EXAMPLE 7

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10 g) (obtained as described in reference example 1c), dimethylformamide (50 cc), 4-(2,2-dimethoxyethyl)-5,6-dioxo-3-thioxo-perhydro-1,2,4-triazine (2.56 g) and N,N-diisopropylethylamine (1.9 cc) is stirred at 60° C. under nitrogen for 2 hours 30 minutes. It is then diluted with ethyl acetate (600 cc) and this mixture is washed with water (2×125 cc), 1 N hydrochloric acid (150 cc), a half-saturated sodium bicarbonate solution (2×150 cc) and a half-saturated sodium chloride solution (2×150 cc), dried over sodium sulphate, filtered and concentrated to dryness under reduced pressure (20° C., 20 mm Hg; 2.7 kPa). The residue, dissolved in methylene chloride (30 cc), is chromatographed over a column (column diameter: 7 cm, height: 35 cm) of Merck silica gel (0.02–0.06 mm). Elution is carried out with a 40:60 (by volume) mixture of cyclohexane ethyl acetate (7 liters) under a pressure of 40 kPa, 100 cc fractions being collected. Fractions 27 to 46 are concentrated to dryness at 20° C. under reduced pressure (20 mm Hg; 2.7 kPa). 2-Benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.5 g) is obtained in the form of a beige-coloured froth.

Infra-red spectrum (KBr): characteristic bands in cm$^{-1}$ at 3380, 3250, 1795, 1720, 1685, 1520, 1490, 1445, 1040, 940, 760 and 700.

Proton nuclear magnetic resonance spectrum (350 MHz, CDCl$_3$, δ in ppm, J in Hz): 3.34 and 4.12 (2d, J=18, 2H, —SCH$_2$—); 3.40 (s, 6H, —CH(OC$\underline{H}_3$)$_2$); 3.94 to 4.06 (m, 5H, —OCH$_3$ and >NCH$_2$—); 4.60 to 4.68 (m, 2H, H in the 6-position and —C$\underline{H}$(OCH$_3$)$_2$); 6.07 (dd, J=4 and 9, 1H, H in the 7-position); 6.70 (s, 1H, H of the thiazole); 6.82 (d, J=16, 1H, —C$\underline{H}$=CHS—);

6.96 (s, 1H, —COOCH—).
|

A solution of 2-benzhydryloxycarbonyl-3-{2-[4-(2,2-dimethoxyethyl)-5,6-dioxo-1,4,5,6-tetrahydro-1,2,4-thiazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.5 g) and dimethylacetamide (3 cc) in methylene chloride (100 cc) is treated with phosphorus trichloride (1.40 cc) at −10° C., whilst stirring; phosphorus trichloride (0.7 cc) is added after 1 hour 30 minutes and the same amount is added again after a further 2 hours. The mixture is diluted with ethyl acetate (600 cc) and this mixture is washed with a 2% strength sodium bicarbonate solution (2×150 cc) and a half-saturated sodium chloride solution (2×150 cc), dried over sodium sulphate, filtered and concentrated to dryness at 20° C. under a pressure of 20 mm Hg (2.7 kPa). The residue is taken up in ethyl acetate (50 cc) and the solution is chromatographed over a column (column diameter: 3 cm, height: 25 cm) of Merck silica gel (0.05–0.2 mm) (100 g). Elution is carried out with ethyl acetate (1 liter), 200 cc fractions being collected. Fractions 3, 4 and 5 are concentrated to dryness (20 mm Hg; 2.7 kPa) at 20° C. 2-Benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (7.5 g) is obtained in the form of an orange-coloured froth.

Infra-red spectrum (CHBr$_3$): characteristic bands in cm$^{-1}$ at 3380, 1780, 1720, 1680, 1515, 1490, 1445, 755 and 740.

Proton nuclear magnetic resonance spectrum (350 MHz, CDCl$_3$, δ in ppm, J in Hz): 3.40 (s, 6H, —CH(OCH$_3$)$_2$); 3.54 and 3.66 (2d, J=18, 2H, —SCH$_2$—); 3.98 (d, J=5, 2H, >NC$\underline{H}_2$—); 4.02 (s, 3H, =NOCH$_3$); 4.65 (t, J=5, 1H, —C$\underline{H}$(OCH$_3$)$_2$); 5.08 (d, J=4, 1H, H in the 6-position); 5.92 (dd, J=4 and 9, 1H, H in the 7-position); 6.73 (s, 1H, H of the thiazole); 6.83 (d, J=16, 1H, —C$\underline{H}$=CHS—); 6.95 (s, 1H, —COOCH—).

1. (a) A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.05 g) in 98% strength formic acid (20 cc) is kept at 50° C. for 30 minutes. The mixture is then concentrated to dryness at 50° C. under a pressure of 0.05 mm Hg (0.007 kPa), the residue is taken up in acetone (50 cc), this mixture is concentrated to dryness at 30° C. under reduced pressure (20 mm Hg; 2.7 kPa) and this operation is repeated a second time.

The solid obtained is treated with acetone (50 cc) at 60° C. for 10 minutes whilst stirring, the cooled suspension is filtered and the residue is dried, giving 7-[2-(2-amino-thiazol-4-yl)-2-methoxyimino-acetamido]-2-carboxy-3-{2-[5,6-dioxo-4-formylmethyl-1,4,5,6-tetrahydro-1,2,4-triazin-3-yl]-thiovinyl}-8-oxo-5-thia-1-aza-bicyclo[4.2.0]oct-2-ene (syn isomer, E-form) (0.51 g).

Infra-red spectrum (KBr): characteristic bands in cm$^{-1}$ at 3500, 2300, 1770, 1715, 1680, 1540, 1050 and 950.

Proton nuclear magnetic resonance spectrum (350 MHz, CF$_3$COOD, δ in ppm, J in Hz): 3.87 (AB limit, 2H, —SCH$_2$—); 4.30 (s, 3H, —OCH$_3$); 5.20 (s broad, 2H, >NCH$_2$—); 5.38 (d, J=4, 1H, H in the 6-position); 6.03 (d, J=4, 1H, H in the 7-position); 7.22 (d, J=16, 1H, —C$\underline{H}$=CHS—); 7.50 (s, 1H, H of the thiazole); 7.72 (d, J=16, 1H, =CHS—); 9.74 (s broad, 1H, —CHO).

Proton nuclear magnetic resonance spectrum (350 MHz, CF$_3$COOD+D$_2$O, δ in ppm, J in Hz): 3.82 (AB limit, 2H, —SCH$_2$—); 4.26 (s, 3H, —OCH$_3$); 5.10 (s broad, 2H, >NCH$_2$—); 5.31 (d, J=4, 1H, H in the 6-position); 5.96 (d, J=4, 1H, H in the 7-position); 7.06 (d, J=16, 1H, —C$\underline{H}$=CHS—); 7.43 (s, 1H, H of the thiazole); 7.56 (d, J=16, 1H, =CHS—); 9.67 (s broad, 1H, —CHO).

(b) It is also possible to proceed as follows.

A mixture of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1 g), pure formic acid (40 cc), water (1.27 cc) and Merck silica gel (0.05–0.2 mm) (6 g) is heated at 50° C. for 30 minutes, whilst stirring. The mixture is concentrated to dryness at 30° C. under 20 mm Hg (2.7 kPa) and the powder obtained is deposited on a column (column diameter: 2 cm, height: 17 cm) of Merck silica gel (0.05–0.2 mm) (20 g). Elution is carried out with a 3:1:1 (by volume) mixture of ethyl acetate/formic acid/water, 10 cc fractions being collected. Fractions 3 to 26 are concentrated to dryness at 27° C. under 0.05 mm Hg (0.007 kPa). The yellow solid obtained is triturated in ether (60 cc), the mixture is filtered, the residue is dried and 7-[2-(2-amino-thiazol-4-yl)-2-methoxyimino-acetamido]-2-carboxy-3-

[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.4 g) is obtained, the nuclear magnetic resonance characteristics and infrared characteristics of this product being identical to those of the product described in (a).

2. A mixture of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.297 g), water (10 cc) and sodium bicarbonate (0.042 g) is stirred under nitrogen until all has dissolved, and the solution is filtered and lyophilised. The sodium salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) as the aldehyde hydrate (0.28 g) is obtained.

Infra-red spectrum (KBr): characteristic bands in cm$^{-1}$ at 3420, 3200, 1760, 1710, 1670, 1600, 1530, 1040 and 945.

Proton nuclear magnetic resonance spectrum (350 MHz, DMSO d$_6$+D$_2$O, δ in ppm, J in Hz): 3.54 (AB limit, 2H, —SCH$_2$—); 5.06 (d, J=4, 1H, H in the 6-position); 5.08 (s, 1H, —CH(OH)$_2$); 5.63 (d, J=4, 1H, H in the 7-position); 6.44 (d, J=16, 1H, —C$\underline{H}$=CHS—); 6.76 (s, 1H, H of the thiazole); 7.24 (d, J=16, 1H, =CHS—); 9.60 (s, 0.05H, —CHO).

The nuclear magnetic resonance spectrum of this sodium salt, as the aldehyde hydrate, recorded in CF$_3$COOD, shows that in solution in this solvent the product is in the aldehyde form [spectrum identical to that described in 1. (a)].

4-(2,2-Dimethoxyethyl)-5,6-dioxo-3-thioxo-perhydro-1,2,4-triazine can be prepared as follows:

A solution of sodium methylate is prepared by dissolving sodium (4.15 g) in methanol (140 cc), and 4-(2,2-dimethoxyethyl)-thiosemicarbazide (32.3 g) and ethyl oxalate (26.3 g) are added. The mixture is refluxed, with stirring, for 4 hours and is then allowed to cool. After standing overnight, the suspension obtained is filtered and the precipitate is washed with ether (3×25 cc). The solid is dissolved in water (40 cc) and after cooling to about 4° C. the solution is acidified to pH 3 by means of 4 N hydrochloric acid and left at 4° C. for 30 minutes. After filtering and drying, 4-(2,2-dimethoxyethyl)-5,6-dioxo-3-thioxo-perhydro-1,2,4-triazine (12 g) is obtained in the form of a white solid. Instantaneous m.p. (Kofler)=172° C. (with decomposition).

Infra-red spectrum (KBr): characteristic bands in cm$^{-1}$ at 3280, 3250, 1695, 1380, 1130 and 1050.

Proton nuclear magnetic resonance spectrum (80 MHz, DMSO d$_6$, δ in ppm, J in Hz): 3.30 (s, 6H, —CH(OCH$_3$)$_2$); 4.38 (d, J=5.5, 2H, >NCH$_2$—); 4.94 (t, J=5.5, 1H, —C$\underline{H}$(OCH$_3$)$_2$).

4-(2,2-Dimethoxyethyl)-thiosemicarbazide can be prepared as follows:

2,2-Dimethoxyethyl isothiocyanate (37.7 g) is added in the course of 1 hour to a solution of hydrazine hydrate (14.35 g) in ethanol (40 cc), whilst stirring at a temperature of between 5° and 9° C. After 12 hours at 4° C., the mixture is concentrated to dryness at 20° C. under reduced pressure (20 mm Hg; 2.7 kPa). The yellow syrup obtained crystallises after seeding. The solid is dissolved in hot methanol (50 cc) and the solution is filtered and diluted with diethyl ether (200 cc). After about ten hours at 4° C., the mixture is filtered and 4-(2,2-dimethoxyethyl)-thiosemicarbazide (32.3 g) is obtained in the form of a white solid.

Instantaneous m.p. (Kofler)=69° C.

REFERENCE EXAMPLE 8

2-Benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) is prepared as described in reference example 7 from the tosylate (15.06 g) and 4-(2,2-diethoxyethyl)-5,6-dioxo-3-thioxo-perhydro-1,2,4-triazine (8 g) in the presence of N,N-diisopropylethylamine (2.85 cc) in dimethylformamide (75 cc). Chromatography is carried out on a column (column diameter: 5 cm, height: 40 cm) of Merck silica gel (0.05-0.2 mm) (250 g), elution being effected with a 30:70 (by volume) mixture of cyclohexane and ethyl acetate (5 liters). The expected product (8.35 g) is obtained in the form of a brown-red froth.

Proton nuclear magnetic resonance spectrum (350 MHz, CDCl$_3$, δ in ppm, J in Hz): 1.15 (t, J=7, 6H, —CH$_3$); 3.38 (d, J=18, 1H, —SCH—); 3.50 and 3.72 (2 q AB, J=9 and 7, 4H, —OCH$_2$—); 3.90 to 4.20 (hump, 6H, >OCH$_3$ and —SCH—); 4.65 (d, J=4, 1H, H in the 6-position); 4.72 (t, J=5, 1H, —CH(O Et)$_2$); 6.04 (dd, J=4 and 9, 1H, H in the 7-position); 6.70 (s, 1H, H of the thiazole); 6.85 (d, J=16, 1H, —C$\underline{H}$=CHS—);

6.97 (s, 1H, —COOCH—); 11.94 (s broad, 1H, =NNHCO— or

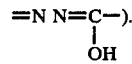

A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.30 g) in methylene chloride (100 cc) and dimethylacetamide (2.88 cc) is treated with phosphorus trichloride (1.33 cc) at −10° C. for 2 hours. The product is treated as described in Example 4(a), by chromatography on a column (column diameter: 4 cm, height: 44 cm) of Merck silica gel (0.05-0.2 mm) (200 g) and elution with a 30:70 (by volume) mixture of cyclohexane and ethyl acetate (2 liters). 2-Benzhydryloxycarbonyl-3-{2-[4-(2.2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.3 g) is obtained in the form of a yellow-orange froth. The product is purified by dissolving it in ethyl acetate (20 cc) and adding isopropyl ether (100 cc); this gives a cream-coloured solid (4.5 g).

Infra-red spectrum (CHBr$_3$): characteristic bands in cm$^{-1}$ at 3390, 1785, 1720, 1685, 1585, 1515, 1495, 1445, 1050, 940, 750 and 740.

Proton nuclear magnetic resonance spectrum (350 MHz, CDCl$_3$, δ in ppm, J in Hz): 1.18 (t, J=7, 6H, —CH$_3$); 3.52 and 3.75 (2 q AB, J=7 and 10, 4H, —OCH$_2$—); 3.60 (d, J=18, 1H, —SCH=), 3.97 to 4.06 (hump, 6H, —OCH$_3$, >NCH$_2$—, —SCH=); 4.76 (t, J=5, 1H, —CH(O Et)$_2$); 5.09 (d, J=4, 1H, H in the 6-position); 5.92 (dd, J=4 and 9, 1H, H in the 7-position); 6.75 (s, 1H, H of the thiazole); 6.85 (d, J=16, 1H, —C<u>H</u>=CHS—); 6.92 (d, J=9, 1H, —CON<u>H</u>—);

6.92 (s, 1H, —COOC<u>H</u>—); 11.30 (s broad, 1H, =NN<u>H</u>CO— or

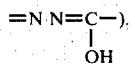

A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (1 g) in pure formic acid (25 cc) is heated at 50° C. for 30 minutes. It is then concentrated to dryness at 40° C. under 20 mm Hg (2.7 kPa), the residue is taken up in acetone (20 cc), the mixture is concentrated to dryness at 20° C. under 20 mm Hg (2.7 kPa), the operation is repeated twice, the residue is triturated in acetone (40 cc), this mixture is heated under reflux for 10 minutes, whilst stirring, and the suspension is cooled and filtered. A yellow powder (0.6 g) is obtained, which is purified as follows:

The preceding product (50 mg) is dissolved in pure formic acid (5 cc), Merck silica gel (0.05–0.2 mm) (2.5 g) is added and the mixture is concentrated to dryness at 30° C. under 0.05 mm Hg (0.007 kPa). The powder is deposited on a column (column diameter: 2.5 cm, height: 3 cm) of silica gel (5 g) and elution is carried out with a 3:2:2 (by volume) mixture of ethyl acetate/acetic acid/water (100 cc), 10 cc fractions being collected. Fractions 2 to 7 are concentrated to dryness (30° C., under 0.05 mm Hg; 0.007 kPa) and 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (30 mg) is obtained in the form of a cream-coloured powder, of which the infra-red characteristics and nuclear magnetic resonance characteristics are identical to those of the product of reference example 7.

4-(2,2-Diethoxyethyl)-5,6-dioxo-3-thioxo-perhydro-1,2,4-triazine can be prepared as follows:

4-(2,2-Diethoxyethyl)-thiosemicarbazide (18.6 g) and diethyl oxalate (13.15 g) are added successively to a solution of sodium (2.07 g) in dry methanol (70 cc) and the mixture is refluxed under nitrogen for 4 hours. The cooled mixture is diluted with water (300 cc) and ethyl acetate (150 cc) and then acidified to pH=2 with concentrated hydrochloric acid whilst cooling to 4° C. The mixture is allowed to settle out, the aqueous phase is extracted with ethyl acetate (3×100 cc), and the organic phase is washed with a saturated sodium chloride solution (3×100 cc), dried over sodium sulphate, filtered and concentrated to dryness at 20° C. under 20 mm Hg (2.7 kPa). A thick yellow oil (22.6 g) consisting principally of 4-(2,2-diethoxyethyl)-5,6-dioxo-3-thioxoperhydro-1,2,4-triazine is obtained.

4-(2,2-Diethoxyethyl)-thiosemicarbazide can be prepared as follows:

Hydrazine hydrate (27.3 cc) is added over the course of 1 hour to a solution of 2,2-diethoxyethyl isothiocyanate (94 g) in ethanol (150 cc), at 4° C. The mixture is stirred for a further 20 minutes at 4° C. and is then filtered; the desired product (86 g) is obtained as a white solid, m.p.=96° C.

REFERENCE EXAMPLE 9

4-Carbamylmethyl-5,6-dioxo-3-thioxo-perhydro-1,2,4-triazine (1.5 g) and N,N-diisopropylethylamine (0.65 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-azabicyclo[4.2.0]oct-2-ene (syn isomer, E-form) (3.7 g) (obtained as described in reference example 1c), in dry N,N-dimethylformamide (70 cc). The reaction mixture is heated for 3 hours at 60°–65° C. under nitrogen, then diluted with ethyl acetate (300 cc), and washed with distilled water (3×100 cc). After drying over magnesium sulphate and filtration, the solvent is evaporated under reduced pressure (35 mm Hg; 9.4 kPa) at 40° C., and the expected crude product (3.1 g) is obtained.

The crude product (3.7 g) obtained in accordance with the working method described above is chromatographed on a column (column diameter: 4 cm, height: 30 cm) of Merck silica gel (0.04–0.06 mm), elution being carried out under a pressure of 40 kPa with ethyl acetate, and 200 cc fractions being collected. Fractions 11 to 32 are evaporated to dryness under reduced pressure (35 mm Hg; 9.4 kPa) at 40° C. This gives 2-benzhydryloxycarbonyl-3-[2-(4-carbamylmethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g).

Infra-red spectrum (CHBr₃): characteristic bands in cm⁻¹ at 3450, 3390, 3190, 2820, 1780, 1720, 1685, 1590, 1475, 1450, 1050, 945, 755 and 700.

Proton nuclear magnetic resonance spectrum (350 MHz, CDCl₃, δ in ppm, J in Hz): 3.62 and 3.68 (AB, J=16, 2H, —SCH₂—); 3.83 (s, 3H, =NOCH₃); 4.41 (s broad, 2H, —C<u>H</u>₂ CONH₂); 5.22 (d, J=5, 1H, H in the 6-position); 5.75 (dd, J=5 and 9, 1H, H in the 7-position); 6.71 (s, 1H, H of the thiazole); 6.85 and 6.95 (AB, J=16, —=CH—S—); 6.94 (s, 1H, —CH(C₆H₅)₂); 7.15 to 7.50 (Mt. 25H, aromatics); 7.71 and 8.80 (2s, 2×1H, —CON<u>H</u>₂); 9.58 (d, J=9, 1H, —CON<u>H</u>-C₇);

12.65 (s, 1H, =NN=C—OH or =N—NH—C—).
                    |              ‖
                                   O

2-Benzhydryloxycarbonyl-3-[2-(4-carbamylmethyl-5,6-dioxo-1,4,5,6-tetrahydro-1,2,4-triazin-3-yl)-thio-vinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g) is dissolved in formic acid (47 cc). After addition of distilled water (30 cc), the reaction mixture is heated for 30 minutes at 50° C. and then diluted with distilled water (17 cc) and filtered. The filtrate is concentrated under reduced pressure (5 mm Hg; 0.67 kPa) at 40° C. The residue is triturated with anhydrous ethanol (50 cc), which is evaporated under reduced pressure (30 mm Hg; 4 kPa) at 40° C.; this operation is repeated twice more. The residue is taken up in anhydrous ethanol (50 cc). The insoluble matter is filtered off and washed with anhydrous ethanol (25 cc) and ether (2×50 cc) and then dried under reduced pressure (5 mm Hg; 0.67 kPa) at 20° C. This gives 7-[2-(2-amino-thiazol-4-yl)-2-methoxyimino-acetamido]-3-[2-(4-carbamylmethyl-5,6-dioxo-1,4,5,6-tetrahydro-1,2,4-triazin-3-yl)-thiovinyl]-2-carboxy-8- oxo-5-thia-1-aza-bicyclo[4.2.0]oct-2-ene (syn isomer, E-form) (1.3 g) in the form of a beige powder.

Infra-red spectrum (KBr): characteristic bands in cm$^{-1}$ at 3410, 3320, 3200, 3100, 2000, 1770, 1710, 1680, 1630, 1590, 1380, 1040 and 945.

Proton nuclear magnetic resonance spectrum (350 MHz, DMSO d$_6$, δ in ppm, J in Hz): 3.63 and 3.83 (AB, J=18, 2H, —SCH$_2$—); 3.87 (s, 3H, =NOCH$_3$); 4.45 (s broad, 2H, —C$\underline{H}_2$—CONH$_2$); 5.20 (d, J=4, 1H, H in the 6-position); 5.78 (dd, J=4 and 9, 1H, H in the 7-position); 6.75 (s, 1H, H of the thiazole); 6.90 and 7.08 (2d, J=16, 2×1H, —CH=CH—S—); 7.32 (s broad, 2H, —NH$_2$ of the thiazole); 7.70 (s broad, 2H, —CONH$_2$); 9.60 (d, J=9, 1H, —CONH—C$_7$);

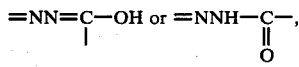

δ>12 ppm.

4-Carbamylmethyl-5,6-dioxo-3-thioxo-perhydro-1,2,4-triazine can be prepared in the following manner:

4-Ethoxycarbonylmethyl-thiosemicarbazide (8.33 g) (GANTE and LANTSCH, Chem. Ber., 97, 989 (1964)) are suspended in a saturated solution (250 cc) of ammonia in ethanol, and the reaction mixture is stirred at 25° C. for 22 hours. The insoluble matter is filtered off and washed with alcohol (2×25 cc) and ether (2×50 cc); after drying, 4-carbamylmethyl-thiosemicarbazide (6.2 g), m.p.=188° C., is obtained.

4-Carbamylmethyl-5,6-dioxo-3-thioxo-perhydro-1,2,4-triazine (3.8 g) is obtained by condensing 4-carbamylmethyl-thiosemicarbazide (6.8 g) and ethyl oxalate (6.7 g) in accordance with the method of M. PESSON and M. ANTOINE, Bull. Soc. Chim. France 1590 (1970).

Infra-red spectrum (KBr): characteristic bands in cm$^{-1}$ at 3550, 3480, 3430, 3270, 3100, 2000, 1710, 1690, 1670, 1365 and 1200.

REFERENCE EXAMPLE 10

A solution of the sodium salt of 4-N,N-dimethylcarbamylmethyl-5,6-dioxo-3-thioxo-perhydro-1,2,4-triazine (4 g) in N,N-dimethylformamide (240 cc) is treated with formic acid (0.60 cc) and then heated to 60° C. under nitrogen. 2-Benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (8 g) is then added, followed by a solution of N,N-diisopropylethylamine (2.8 cc) in N,N-dimethylformamide (20 cc) added dropwise in the course of 10 minutes. The mixture is stirred for 2 hours at 20° to 60° C. and is then diluted with distilled water (600 cc) and extracted with ethyl acetate (2×250 cc). The organic extracts are washed successively with an 0.1 N hydrochloric acid solution (200 cc), a half-saturated sodium bicarbonate solution (200 cc) and a half-saturated sodium chloride solution (200 cc) and are then dried over magnesium sulphate. The residue obtained by concentrating to dryness under reduced pressure (30 mm Hg; 4 kPa) at 30° C. is chromatographed on a column (height: 30 cm, diameter: 5 cm) of silica gel (0.04–0.06 mm), elution being carried out under 50 kPa with ethyl acetate (2.5 liters) and then with a 95:5 (by volume) mixture of ethyl acetate and methanol (1.5 liters). Fractions 32 to 37 (each of 100 cc) are combined and concentrated to dryness. This gives 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in the form of a salmon-coloured solid.

Infra-red spectrum (CHBr$_3$): characteristic bands (cm$^{-1}$) at 3380, 3200, 1800, 1725, 1685, 1670, 1590, 1520, 1495, 1450, 1040, 945, 755 and 740.

A solution, cooled to −10° C., of 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.4 g) in methylene chloride (48 cc) is treated with N,N-dimethylacetamide (1.47 cc) and then with phosphorus trichloride (0.44 cc), after which the mixture is stirred for 3 hours at about −10° C. The reaction mixture is then diluted with methylene chloride (100 cc) and poured into a half-saturated sodium bicarbonate solution (100 cc). The organic phase is washed with a half-saturated sodium chloride solution (100 cc), dried over magnesium sulphate and then concentrated to dryness under reduced pressure (30 mm Hg; 4 kPa) at 30° C. The residue is chromatographed over a column (column diameter: 2.2 cm, height: 30 cm) of silica gel (0.04–0.06 mm), elution being carried out with ethyl acetate (600 cc) and 25 cc fractions being collected. Fractions 10 to 21 are combined and concentrated to dryness. 2-Benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.3 g) is obtained.

Infra-red spectrum (CHBr$_3$): characteristic bands (cm$^{-1}$) at 3400, 1790, 1730, 1690, 1670, 1590, 1520, 1500, 1460, 1050, 760 and 740.

Proton nuclear magnetic resonance spectrum (350 MHz, CDCl$_3$, δ in ppm, J in Hz): 2.97 and 3.40 (2s, 2×3H, —CON(CH$_3$)$_2$); 3.60 and 3.75 (2d, J=18, 2H, —SCH$_2$—); 4.08 (s, 3H, =NOCH$_3$); 4.73 (s broad, 2H, —CH$_2$CON<); 5.08 (d, J=4, 1H, H in the 6-position); 5.93 (dd, J=4 and 9, 1H, H in the 7-position); 6.77 (s, 1H, H in the 5-position of the thiazole); 6.88 (d, J=16, 1H, —C$\underline{H}$=CH—S—); 6.92 (s, 1H, —CO$_2$C$\underline{H}$(C$_6$H$_5$)$_2$); 7.0 to 7.6 (hump, 27H, aromatics, —CONH— and —CH=C$\underline{H}$S—); 7.81 (s broad, 1H, —NH— of the trityl);

11.25 (s broad, 1H, —N=C—OH or —N—C— of the triazine).
  |                | |
  |                H O Distilled water (9 cc) is added to a solution of 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]-oct-2-ene (syn isomer, E-form) (1.3 g) in 98% strength formic acid (15 cc) and the reaction mixture is heated at 50° C. for 45 minutes. After filtration to remove the insoluble matter, the solution is concentrated to dryness under reduced pressure (10 mm Hg; 1.33 kPa) at 40° C. The residue is taken up, and triturated, in ethanol (20 cc), which is then concentrated under reduced pressure (30 mm Hg; 4 kPa) at +° C. The solid is taken up in ethanol (25 cc) and filtered off, after which it is washed successively with ethanol (3×5 cc) and ethyl ether (3×10 cc) and dried. 7-[2-(2-Amino-thiazol-4-yl)-acetamido]-2-carboxy-3-{2-[4-(N,N-dimethylcarbamylmethyl)-5,6-dioxo-1,4,5,6-tetrahydro-1,2,4-triazin-5-yl]-thiovinyl}-5-thia-1-aza-bicyclo[4.2.0]oct-2-ene (syn isomer, E-form) (0.62 g) is obtained.

Infra-red spectrum (KBr): characteristic bands (cm$^{-1}$) at 3420, 3320, 3210, 1780, 1720, 1690, 1660, 1530, 1040 and 945.

Proton nuclear magnetic resonance spectrum (350 MHz, DMSO d$_6$, δ in ppm, J in Hz): 2.88 and 3.08 (2s, 2×3H, —CON(CH$_3$)$_2$); 3.61 and 3.82 (2d, J=18, 2H, —SCH$_2$—); 3.85 (s, 3H, =NOCH$_3$); 4.80 (s broad, 2H, —CH$_2$CON<); 5.21 (d, J=4, 1H, H in the 6-position); 5.79 (dd, J=4 and 9, 1H, H in the 7-position); 6.75 (s, 1H, H of the thiazole); 6.88 and 7.10 (2d, J=16, 2H, —CH=CH—S—); 7.19 (s broad, 2H, —NH$_2$); 9.60 (d, J=9, 1H, —CONH—C$_7$);

12.73 (s, 1H, —N=C—OH or —NH—C— of the triazine).
            |                    ||
            |                    O The sodium salt of 4-(N,N-dimethylcarbamylmethyl)-5,6-dioxo-4-thioxo-perhydro-1,2,4-triazine can be obtained by the method of M. PESSON and M. ANTOINE, Bull. Soc. Chim. Fr. (1970) 1590, by the action of ethyl oxalate on 4-(N,N-dimethylcarbamylmethyl)-thiosemicarbazide in methanol in the presence of sodium methylate.

Infra-red spectrum (KBr): characteristic bands (cm$^{-1}$) at 3200, 1696, 1640, 1580 and 1530.

REFERENCE EXAMPLE 11

A solution of 2-benzhydryloxycarbonyl-7-[2-methoxyimino-2-(tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (18.2 g), 5,6-dioxo-4-ethoxycarbonylmethyl-3-thioxo-perhydro-1,2,4-triazine (8.4 g) and diisopropylethylamine (3.11 cc) in dimethylformamide (182 cc) is heated at 80° C. for 1 hour 20 minutes. The mixture is then cooled, diluted with ethyl acetate (2,000 cc) and washed with a saturated sodium bicarbonate solution (3×100 cc) and a saturated sodium chloride solution (2×100 cc), dried over magnesium sulphate, filtered and concentrated to dryness under reduced pressure (20 mm Hg; 2.7 kPa). The residue is chromatographed on a column (column diameter: 4.9 cm, height: 31 cm) of Merck silica gel (0.06-0.2 mm) (313 g) and elution is carried out with a 20:80 (by volume) mixture of cyclohexane and ethyl acetate (2,000 cc) and then with ethyl acetate (2,200 cc), 100 cc fractions being collected. Fractions 10 to 40 are concentrated to dryness under reduced pressure (20 mm Hg; 2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (6.15 g) is thus obtained in the form of a yellow froth.

Infra-red spectrum (KBr): characteristic bands (cm$^{-1}$) at 3400, 1795, 1720, 1685, 1590, 1515, 1490, 1445, 1210, 1040, 935, 750 and 700.

Proton nuclear magnetic resonance spectrum (350 MHz, CDCl$_3$, δ in ppm, J in Hz): 1.28 (t, J=7, 3H, —CH$_2$CH$_3$);

O
                  ||
3.32 and 4.50 (2d, J = 18, 2H, —SCH$_2$—);

4.02 (s, 3H, —OCH$_3$); 4.23 (q, J=7, 2H, —O—CH$_2$CH$_3$); 4.60 (s, 2H, >NCH$_2$COO—); 4.63 (d, J=4, 1H, H in the 6-position); 6.05 (dd, J=4 and 9, 1H, H in the 7-position); 6.70 (s, 1H, H of the thiazol); 6.76 (d, J=16, 1H, —CH=CHS—); 6.95 (s, 1H, —COOCH<);

11.54 (s, 1H, =N—NHCO— or =N—N=C—).
                                      |
                                      OH

Phosphorus trichloride (1 cc) is added to a solution, cooled to −10° C., of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (6 g) and dimethylacetamide (2.27 cc) in methylene chloride (60 cc), and the mixture is kept at −10° C. for 1 hour 20 minutes. It is then diluted with ethyl acetate (750 cc) and this mixture is washed with a saturated sodium bicarbonate solution (3×100 cc) and a saturated sodium chloride solution (2×100 cc) and evaporated to dryness under reduced pressure (20 mm Hg; 2.7 kPa). The residue is chromatographed over a column (column diameter: 2.1 cm, height: 18 cm) of Merck silica gel (0.06-0.2 mm) (35 g) and elution is carried out with ethyl acetate (0.5 liter), 30 cc fractions being collected. Fractions 2 to 7 are concentrated to dryness under 20 mm Hg (2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.2 g) is thus obtained in the form of a yellow froth.

Infra-red spectrum (KBr): characteristic bands (cm$^{-1}$) at 3400, 1780, 1720, 1685, 1590, 1525, 1490, 1445, 1210, 1035, 940, 750 and 700.

Proton nuclear magnetic resonance spectrum (350 MHz, CDCl$_3$, δ in ppm, J in Hz): 1.28 (t, J=7, 3H, —CH$_2$CH$_3$); 3.55 and 3.64 (2d, J=18, 2H, —SCH$_2$—); 4.06 (s, 3H, —OCH$_3$); 4.26 (q, J=7, 2H, —OCH$_2$CH$_3$); 4.63 (s, 2H, >N—CH$_2$COO—); 5.09 (d, J=4, 1H, H in the 6-position); 5.94 (dd, J=4 and 9, 1H, H in the 7-position); 6.72 (s, 1H, H of the thiazole); 6.75 (d, J=16, 1H, —CH=CHS—); 6.94 (s, 1H, —COOCH<);

11.05 (s, 1H, =N—NHCO— or =N—N=C—).
                                     |
                                     OH

A solution of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5 g) in 98% strength formic acid (100 cc) and distilled water (30 cc) is heated at 50° C. for 15 minutes. The mixture is cooled, diluted with water (70 cc) and filtered, and the filtrate is concentrated to dryness under reduced pressure (20 mm Hg; 2.7 kPa). The residue is taken up in ethanol (3×50 cc) and is each time concentrated to dryness under reduced pressure (20 mm Hg; 2.7 kPa);

the solid obtained is then suspended in refluxing ethanol (50 cc), cooled, filtered off and dried in vacuo (20 mm Hg; 2.7 kPa). This gives 7-[2-(2-amino-thiazol-4-yl)-2-methoxyimino-acetamido]-2-carboxy-3-[2-(5,6-dioxo-4-ethoxycarbonylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1.9 g) in the form of a yellow solid.

Infra-red spectrum (KBr): characteristic bands ($cm^{-1}$) at 3340, 3220, 3130, 1780, 1725, 1690, 1590, 1530, 1040 and 945.

Proton nuclear magnetic resonance spectrum (350 MHz, DMSO $d_6$, δ in ppm, J in Hz): 1.22 (t, J=7, 3H, C$\underline{H}_3$—CH$_2$—); 3.60 and 3.85 (2d, J=18, 2H, —SCH$_2$—); 3.85 (s, 3H, —OCH$_3$); 4.15 (q, J=7, 2H, —OC$\underline{H}_2$—CH$_3$); 4.66 (s, 2H, >N—CH$_2$CO—); 5.18 (d, J=4, 1H, H in the 6-position); 5.77 (dd, J=4 and 9, 1H, H in the 7-position); 6.72 (s, 1H, H of the thiazole); 6.87 (d, J=16, 1H, —C$\underline{H}$=CHS—); 7.08 (d, J=16, 1H, —CH=C$\underline{H}$S—) 7.15 (s broad, 2H, —NH$_2$); 9.58 (d, J=9, 1H, —CONH—);

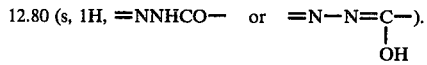

12.80 (s, 1H, =NNHCO— or =N—N=C—).
                                      |
                                      OH 5,6-Dioxo-4-ethoxycarbonylmethyl-3-thioxo-perhydro-1,2,4-triazine can be obtained as follows:

A solution of ethyl isothiocyanoacetate in anhydrous ethanol (185 cc) is added, in the course of 5 minutes, to a suspension of ethyl hydrazino-oxalate (24.4 g) in anhydrous ethanol (185 cc) at 25° C. The mixture dissolves, after which a white precipitate again forms. The mixture is kept stirred for 20 hours under nitrogen, after which a solution prepared from sodium (8.5 g) in ethanol (185 cc) is added in the course of 15 minutes and the mixture is heated under reflux for 4 hours. The red-brown suspension obtained is concentrated to dryness under reduced pressure (20 mm Hg; 2.7 kPa) and the residue is dissolved by adding 4 N hydrochloric acid (100 cc) and ethyl acetate (2,000 cc). The insoluble matter is filtered off and the organic phase is washed with a saturated sodium chloride solution (4×250 cc), dried over magnesium sulphate, filtered and concentrated to dryness under reduced pressure (20 mm Hg; 2.7 kPa). This gives a red-brown gum (43 g) which is dissolved in a saturated sodium bicarbonate solution (300 cc). The brown solution obtained is washed with isopropyl ether (3×100 cc) and brought to pH 1 with the requisite amount of 1 N hydrochloric acid, and is extracted with ethyl acetate (500 cc). The organic phase is washed with a saturated sodium chloride solution (2×50 cc), dried over magnesium sulphate, filtered in the presence of decolorising charcoal and concentrated to dryness under reduced pressure (20 mm Hg; 2.7 kPa). This gives 5,6-dioxo-4-ethoxycarbonylmethyl-3-thioxoperhydro-1,2,4-triazine (9.5 g) in the form of a brown solid.

Infra-red spectrum (KBr): characteristic bands ($cm^{-1}$) at 3500-2800, 1740, 1700, 1645, 1380, 1235 and 1200.

Proton nuclear magnetic resonance spectrum (80 MHz, DMSO $d_6$, δ in ppm, J in Hz): 1.38 (t, J=7, 3H, —CH$_2$C$\underline{H}_3$); 4.30 (q, J=7, 2H, —C$\underline{H}_2$CH$_3$); 5.03 (s, 2H, >N-CH$_2$CO—); 12.50 (s, 1H, —NHCO—).

Ethyl isothiocyanoacetate can be prepared according to D. HOPPE and R. FOLLMANN, Chem. Ber. 109 3047 (1976).

REFERENCE EXAMPLE 12

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]-oct-2-ene (syn isomer, E-form) (10.04 g) (obtained as described in reference example 1c), dimethylformamide (200 cc), 4-allyl-5,6-dioxo-3-thioxoperhydro-1,2,4-triazine (2.22 g) and N,N-diisopropylethylamine (2.1 cc) is stirred for 3 hours under nitrogen at 60° C. The mixture is then diluted with ethyl acetate (600 cc), and this mixture is washed with water (2×200 cc) and half-saturated aqueous sodium chloride (2×100 cc), dried over sodium sulphate, filtered and concentrated to dryness at 20° C. under 20 mm Hg. The residue is taken up in methylene chloride (50 cc), Merck silica gel (0.05–0.2 mm) (20 g) is added and the mixture is concentrated to dryness at 20° C. under 20 mm Hg. The powder is deposited on a column (column diameter; 6.1 cm) of Merck silica gel (0.05–0.2 mm) (200 g). Elution is carried out with a 20:80 (by volume) mixture of cyclohexane and ethyl acetate (2 liters), a 10:90 (by volume) mixture of cyclohexane and ethyl acetate (1 liter) and then with ethyl acetate (2 liters), 120 cc fractions being collected. Fractions 8 to 28 are concentrated to dryness at 20° C. under 20 mm Hg. 3-[2-(4-Allyl-5,6-dioxo-1,4,5,6-tetrahydro-1,2,4-triazin-3-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.7 g) is obtained in the form of an orange-coloured froth.

Infra-red spectrum (CHBr$_3$): characteristic bands ($cm^{-1}$) at 3380, 1800, 1720, 1670, 1515, 1045 and 940.

Proton nuclear magnetic resonance spectrum (350 MHz, DMSO $d_6$, δ in ppm, J in Hz): 3.60 and 4.29 (2d, J=18, 2H, —SCH$_2$—); 3.85 (s, 3H, —OCH$_3$); 4.45 (d, J=5, 2H, >NCH$_2$-); 5.05 (d, J=4, 1H, H in the 6-position); 5.17 to 5.27 (Mt, 2H, =CH$_2$); 5.78 to 5.92 (2 Mt, 2H, H in the 7-position and —C$\underline{H}$=CH$_2$); 6.78 (s, 1H, H of the thiazole); 6.95 (d, J=16, 1H, —C$\underline{H}$=CHS—); 6.97 (s, 1H, —COOCH<); 7.09 (d, J=16, 1H, =CHS—); 8.78 (s, 1H, —NHC(C$_6$H$_5$)$_3$); 9.04 (d, J=9, 1H, —CONH—)

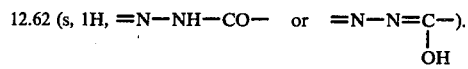

12.62 (s, 1H, =N—NH—CO— or =N—N=C—).
                                     |
                                     OH

Phosphorus trichloride (0.40 cc) is added to a mixture, cooled to −10° C., of 3-{2-[4-(all-3-yl)-5,6-dioxo-1,4,5,6-tetrahydro-1,2,4-triazin-3-yl]-thiovinyl}2-benzhydryloxycarbonyl-7-[2-methoxyimino-2-(2-tritylamino-1,3-thiazol-4-yl)-acetamido]-8-oxo-5-oxide-5-thia-1-aza-bicyclo[4.2.0]oct-2-ene (syn isomer, E-form) (2.34 g) and dimethylacetamide (0.85 cc) in methylene chloride (23 cc), and the mixture is stirred for 30 minutes at −10° C. It is then poured into ethyl acetate (250 cc) and this mixture is washed with water (50 cc), a saturated sodium bicarbonate solution (50 cc) and a saturated sodium chloride solution (2×50 cc), dried over sodium sulphate, filtered and concentrated to dryness at 30° C. under 20 mm Hg. The residue, dissolved in methylene chloride (10 cc), is fixed on Merck silica gel (0.05–0.2 mm) (10 g) and deposited on a column (column diameter: 1.4 cm) of silica gel (30 g). Elution is carried out with a 20:80 (by volume) mixture of cyclohexane and ethyl acetate (500 cc), 60 cc fractions being collected. Fractions 2 to 4 are evaporated to dryness at 20° C. under reduced pressure (20 mm Hg). 3-{2-[4-(all -3-yl)-5,6-dioxo-1,4,5,6-tetrahydro-1,2,4-triazin-3-yl]-thiovinyl}-2-benzhydryloxycarbonyl-7-[2-methox-yimino-2-(2-tritylamino-thiazol-4-yl)-acetamido]-8-oxo-5-thia-1-aza-bicyclo[4.2.0]oct-2-ene (syn isomer, E-form) (1.34 g) is obtained in the form of a yellow froth.

Infra-red spectrum (CHBr$_3$): characteristic bands (cm$^{-1}$) at 3380, 1780, 1720, 1680, 1515, 1490, 1445, 1040, 940, 750 and 735.

Proton nuclear magnetic resonance spectrum (350 MHz, CDCl$_3$, δ in ppm, J in Hz): 3.57 and 3.66 (2d, J=18, 2H, —SCH$_2$—); 4.03 (s, 3H, —OCH$_3$); 4.52 (d, J=4, 2H, >NCH$_2$—); 5.09 (d, J=4, 1H, H in the 6-position); 5.26 to 5.38 (2d, 2H, =CH$_2$); 5.78 to 5.88 (mt, 1H, —CH=CH$_2$); 5.92 (dd, J=4 and 9, 1H, H in the 7-position); 6.74 (s, 1H, H of the thiazole); 6.86 (d, J=16, —CH=CHS—); 6.96 (s, 1H, —COOCH<); 7.05 (d, J=9, 1H, —CONH—);

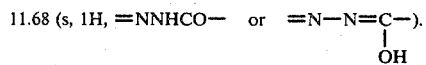

3-{2-[4-(all-3-yl)-5,6-dioxo-1,4,5,6-tetrahydro-1,2,-4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form (1.34 g) is dissolved in formic acid (13 cc), water (6.5 cc) is added and the mixture is heated at 50° C. for 30 minutes, whilst stirring. After cooling, the mixture is filtered and the solution is concentrated to dryness at 30° C. under reduced pressure (0.05 mm Hg). The residue is taken up in ethanol (50 cc), the solvent is driven off under reduced pressure (20 mm Hg) at 20° C. and this operation is repeated 3 times. The residue is treated with ethanol (100 cc) under reflux, a slight amount of insoluble matter is removed by filtration, and the filtrate is concentrated to 50 cc at 30° C. under reduced pressure (20 mm Hg) and then cooled for 1 hour at +40° C. After filtering off and drying the precipitate, 3-{2-[4-(all-3-yl)-5,6-dioxo-1,4-,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-azabicyclo[4.2.0]oct-2-ene (syn isomer, E-form)(0.37 g) is obtained in the form of a yellow powder.

Infra-red spectrum (KBr): characteristic bands (cm$^{-1}$) at 3600, 2300, 1775, 1710, 1680, 1535, 1040 and 945.

Proton nuclear magnetic resonance spectrum (350 MHz, DMSO d$_6$, δ in ppm, J in Hz): 3.63 and 3.80 (2d, J=18, 2H, —SCH$_2$—); 3.88 (s, 3H, —OCH$_3$); 4.48 (d, J=4, 2H, >NCH$_2$-); 5.19 to 5.27 (mt, 3H, =CH$_2$ and H in the 6-position); 5.74 to 5.92 (mt, 2H, —CH=CH$_2$ and H in the 7-position); 6.74 (s, 1H, H of the thiazole); 6.91 (d, J=16, 1H, —CH=CHS—); 7.09 (d, J=16, 1H, =CHS—); 7.18 (s, —NH$_3$+); 9.60 (d, J=9, 1H, —CONH—);

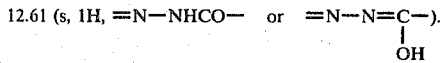

4-Allyl-5,6-dioxo-3-thioxo-perhydro-1,2,4-triazine can be prepared according to the method described in Belgian Pat. No. 830,455.

REFERENCE EXAMPLE 13

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.-0]oct-2-ene (syn isomer, E-form) (5.02 g), dimethylformamide (93 cc), 4-(2,2-dimethyl-dioxolan-4-yl-methyl)5,6-dioxo-3-thioxo-perhydro-1,2,4-triazine (1.5 g) and N,N-diisopropylethylamine (1.05 cc) is stirred at 60° C., under nitrogen, for 3 hours. It is then diluted with ethyl acetate (200 cc) and this mixture is washed with water (4×200 cc), dried over sodium sulphate, filtered and concentrated to dryness at 20° C. under 20 mm Hg (2.7 kPa). The residue is fixed on Merck silica gel (0.06–0.2 mm) (10 g) and the powder is deposited on a column (column diameter: 2.5 cm, height: 40 cm) of Merck silica gel (0.06–0.2 mm) (100 g). Elution is carried out with ethyl acetate (1.3 liters), 60 cc fractions being collected. Fractions 6 to 20 are concentrated to dryness at 20° C. under 20 mm Hg (2.7 kPa) and 2-benzhydryloxycarbonyl-3-{2-[4-(2,2-dimethyl-dio xolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-oxide-5-thia-1-azabicyclo[4.2.0]oct-2-ene (syn isomer, E-form) (2.48 g) is obtained in the form of a yellow froth.

Proton nuclear magnetic resonance spectrum (350 MHz, CDCl$_3$, δ in ppm, J in Hz): 1.32 and 1.43 (2s, 6H, —C(CH$_3$)$_2$);

3.74 (t, J=6, 2H, —CH$_2$O—); 3.84 (s, 3H, =NOCH$_3$); 3.95 (t, J=6, 2H, >N—CH$_2$—); 4.38 (quintuplet, J=6, 1H, >CH—O—); 4.65 (d, J=4, 1H, H in the 6-position); 6.06 (dd, J=4 and 9, 1H, H in the 7-position); 6.71 (s, 1H, H of the thiazole); 6.84 (d, J=16, 1H, —CH=CHS—); 6.96 (s, 1H, —COOCH<); 11.60 (s, 1H, =N—NHCO—).

A solution of 2-benzhydryloxycarbonyl-3-{2-[4-(2,2-dimethyl-dioxolan-4-yl-methyl)-5,6--dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form (2.48 g) in methylene chloride (22.9 cc) and dimethylacetamide (0.85 cc) is treated with phosphorus trichloride (0.4 cc) at −10° C. for 40 minutes. The mixture is poured into ethyl acetate (250 cc) and this mixture is washed successively with saturated sodium bicarbonate solution (200 cc), water (2×100 cc) and a saturated sodium chloride solution (100 cc), dried over sodium sulphate, filtered and concentrated to dryness at 20° C. under 20 mm Hg (2.7 kPa). The residue is taken up in methylene chloride (20 cc), Merck silica gel (0.06–0.2 mm) (10 g) is added, the mixture is concentrated to dryness at 20° C. under 20 mm Hg and the powder obtained is deposited on a column (column diameter: 1.5 cm, height: 15 cm) of Merck silica gel (0.06–0.2 mm) (40 g). Elution is carried out with methylene chloride (500 cc), 60 cc fractions being collected. Fractions 2 to 7 are combined and concentrated to dryness at 20° C. under 20 mm Hg, and 2-benzhydryloxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.-0]oct-2-ene (syn isomer, E-form) (1.4 g) is obtained in the form of a yellow froth.

A mixture of 2-benzhydryloxycarbonyl-3-{2-[4-(2,2-dimethyl-dioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.4 g), formic acid (13 cc) and water (6.5 cc) is heated at 50° C. for 30 minutes. It is then cooled to 20° C., filtered and concentrated to dryness at 30° C. under 0.05 mm Hg (0.007 kPa). The residue is taken up in ethanol (100 cc), the solvent is driven off at 20° C. under 20 mm Hg (2.7 kPa) and the operation is repeated twice. The yellow solid is taken up in boiling ethanol (100 cc), the mixture is filtered, the filtrate is concentrated to 50 cc at 20° C. (20 mm Hg; 2.7 kPa) and then filtered, and the solid is washed with diethyl ether (20 cc) and dried. 7-[2-(2-Amino-thiazol-4-yl)2-methoxyimino-acetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-aza-bicyclo[4.2.0]oct-2-ene (syn isomer, E-form) (0.49 g) is obtained.

The nuclear magnetic resonance shows that this product contains about 25% of formic acid ester of one or other of the alcohol groups.

Infra-red spectrum (KBr): characteristic bands (cm$^{-1}$) at 3650–2200, 1770, 1710, 1680, 1590, 1530, 1045 and 945.

Proton nuclear magnetic resonance spectrum (350 MHz, DMSO d$_6$+D$_2$O, δ in ppm, J in Hz):

diol: 3.87 (s, 3H, =NOCH$_3$); 5.20 (d, J=4, 1H, H in the 6-position); 5.75 (d, J=4, H in the 7-position); 6.74 (s, 1H, H of the thiazole); 6.95 and 7.10 (2d, J=16, 2H, —CH=CH—S—);

formic acid ester: 3.87 (s, 3H, =NOCH$_3$); 5.18 (d, J=4, 1H, H in the 6-position); 5.75 (d, J=4, 1H, H in the 7-position); 6.74 (s, 1H, H of the thiazole); 6.93 and 7.08 (2d, J=16, 2H, —CH=CHS—); 8.22 (s, 1H, HCOO—).

4-(2,2-Dimethyl-dioxolan-4-yl-methyl)-5,6-dioxo-3-thioxo-perhydro-1,2,4-triazine can be prepared in the following manner:

A solution of sodium (1.12 g) in anhydrous methanol (50 cc) is prepared, 4-(2,2-dimethyl-dioxolan-4-yl-methyl)-thiosemicarbazide (10 g) is added under nitrogen, whilst stirring at 25° C., diethyl oxalate (6.6 cc) is then introduced dropwise in the course of 10 minutes, and the mixture is heated under reflux for 2 hours. It is then allowed to cool to 20° C., diluted with diethyl ether (1 liter) and filtered, and after drying a white solid (3.7 g) is obtained. The product is taken up in methylene chloride (200 cc) and the mixture is stirred in the presence of 1 N hydrochloride acid (10 cc). The organic phase is decanted, washed with saturated aqueous sodium chloride (2×50 cc), dried over sodium sulphate and concentrated to dryness at 20° C. under 20 mm Hg (2.7 kPa). The oil which remains is taken up in methylene chloride (50 cc), crystallisation is started by scratching, and the mixture is left at 4° C. for 3 hours. After filtration and drying, 4-(2,2-dimethyl-dioxolan-4-yl-methyl)-5,6-dioxo-3-thioxo-perhydro-1,2,4-triazine (1.5 g) is obtained in the form of white crystals.

Infra-red spectrum (KBr): characteristic bands (cm$^{-1}$) at 3600–3100, 1680, 1575, 1535, 1210 and 1060.

Proton nuclear magnetic resonance spectrum (80 MHz, DMSO d$_6$, δ in ppm, J in Hz): 1.30 and 1.42 (2s, 6H, >C(CH$_3$)$_2$); 3.95 (m, 2H, —CH$_2$O—);

4.50 (m, 3H, —CHO— and —N—CH$_2$—).

4-(2,2-Dimethyl-dioxolan-4-yl-methyl)-thiosemicarbazide can be prepared in the following manner:

A mixture of methyl N-(2,2-dimethyl-dioxolan-4-yl-methyl)-dithiocarbamate (23.6 g) prepared according to U.S. Pat. No. 4,064,242, absolute ethanol (500 cc) and hydrazine hydrate (5.6 g) is heated under reflux for 2 hours 30 minutes. It is then concentrated to dryness at 20° C. under 20 mm Hg (2.7 kPa) and the residue is taken up in diethyl ether (100 cc). After filtration and drying, 4-(2,2-dimethyl-dioxolan-4-yl-methyl)-thiosemicarbazide (15.2 g) is obtained in the form of a creamcoloured solid melting at 145° C.

Infra-red spectrum (KBr): characteristic bands (cm$^{-1}$) at 3340, 3200, 1630, 1555, 1510, 1380, 1370, 1240, 1210 and 1060.

Proton nuclear magnetic resonance spectrum (80 MHz, CDCl$_3$, δ in ppm, J in Hz): 1.38 and 1.48 (2s, 6H, >C(CH$_3$)$_2$); 3.72 (dd, J=5 and 6, 2H, —CH$_2$N<); 3.90 s, 2H, —NH$_2$); 4.10 (dd, J=6 and 7, 2H, —CH$_2$O—); 4.38 (m, 1H, >CHO—); 7.78 (t, J=5, 1H, —CH$_2$NH—);

7.98 (s, 1H, —NH—N).

REFERENCE EXAMPLE 14

A solution of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.58 g) (obtained as described in reference example 1c) and of the sodium salt of 5,6-dioxo-4-(2-hydroxyethyl)-3-thioxo-perhydro-1,2,4-triazine (0.31 g) in N,N-dimethylformamide (10 cc) is heated for 4 hours at 30°–60° C. The reaction mixture is cooled and diluted with ethyl ether (150 cc) and the precipitate is filtered off, washed with ether (2×25 cc) and dried. Crude 7-[2-(2-amino-thiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.6 g) is obtained in the form of an amorphous beige powder.

Rf=0.42; silica gel chromatographic plate; eluant: a 60:20:20 (by volume) mixture of ethyl acetate, acetic acid and water.

The product can be purified as follows: it is redissolved in a dilute sodium hydroxide solution (50 cc) (pH=8) and the mixture is then brought to pH 5 by means of dilute hydrochloric acid; after filtering off a small amount of insoluble matter; the solution obtained is chromatographed on a column (diameter: 2.4 cm) of XAD-2 resin, with successive elution of the impurities with distilled water (1 liter) and then of the pure product with a 95:5 (by volume) mixture of water and ethanol (1 liter). After concentration under reduced pressure (5 mm Hg) at 30° C., and drying, 7-[2-(2-aminothiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.-

0]oct-2-ene (syn isomer, E-form) (0.2 g) is obtained in the form of light yellow crystals.

Proton nuclear magnetic resonanace spectrum (350 MHz, DMSO d6, δ in ppm, J in Hz): 3.60 (t, J=5, 2H, N—CH2—CH2OH); 3.84 (s, 3H, =NOCH3); 3.92 (t, J=5, 2H, >N—CH2CH2OH); 5.10 (d, J=4, 1H, H in the 6-position); 5.65 (dd, J=4 and 9, 1H, H in the 7-position); 6.39 (d, J=16, 1H, —CH=CH—S—); 6.73 (s, 1H, H in the 5-position of the thiazole); 7.17 (s broad, 2H, —NH2); 7.37 (d, J=16, 1H, —CH=CH—S—); 9.54 (d, J=9, 1H, —CONH—C7).

7-[2-(2-Amino-thiazol-4-yl)-2-methoxyimino-acetamido]-2-carboxy-3-{2-[5,6-dioxo-4-(2-hydroxyethyl)1,4,5,6-tetrahydro-1,2,4-triazin-3-yl]-thiovinyl}8-oxo-5-thia-1-aza-bicyclo[4.2.0]oct-2-ene (syn isomer, E-form) (0.13 g) is dissolved in a N/100 sodium bicarbonate solution (21 cc). The solution is frozen at −80° C. and lyophilised. The sodium salt of 7-[2-(2-aminothiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.145 g) is obtained in the form of a white lyophilisate.

Rf=0.28; silica gel chromatographic plate; eluant: a 60:20:20 (by volume) mixture of ethyl acetate:acetic acid and water.

Proton nuclear magnetic resonance spectrum (350 MHz, DMSO d6, δ in ppm, J in Hz): 3.50 (AB not resolved, 2H, —SCH2—); 3.60 (t, J=6, 2H, >NCH2CH2OH); 3.91 (t, J=6, 2H, >N—CH2CH2OH); 3.87 (s, 3H, =NOCH3); 5.07 (d, J=4, 1H, H in the 6-position); 5.60 (dd, J=4 and 9, 1H, H in the 7-position); 6.31 (d, J=16, 1H, —CH=CH—S—); 6.71 (s, 1H, H in the 5-position of the thiazole); 7.17 (s broad, 2H, —NH2); 7.36 (d, J=16, 1H, —CH=CHS—); 9.54 (d, J=9, 1H, —CONH—).

5,6-Dioxo-4-(2-hydroxyethyl)-3-thioxo-perhydro-1,2,4-triazine can be prepared by applying the method described by M. PESSON and M. ANTOINE, Bull. Soc. Chim. France 1590 (1970), and working as follows:

4-(Hydroxyethyl)-thiosemicarbazide (5 g) and ethyl oxalate (5.5 cc) are added to a solution of sodium methylate (prepared from sodium (0.85 g)) in methanol (37 cc), and the mixture is heated under reflux for 3 hours. After it has cooled, the precipitate is filtered off and washed with methanol (2×5 cc). The crude sodium salt is obtained, and is then taken up in distilled water (25 cc); the solution is filtered, and acidified to pH 2 with 1 N hydrochloric acid. The precipitate is filtered off, washed with water and dried in air. 5,6-Dioxo-4-(2-hydroxyethyl)-3-thioxo-perhydro-1,2,4-triazine (2.4 g) (m.p.=230° C.) is obtained.

The sodium salt can be prepared by treating 5,6-dioxo-4-(2-hydroxyethyl)-3-thioxo-perhydro-1,2,4-triazine (4.73 g), in anhydrous methanol, with sodium 2-ethylhexanoate. This gives 4.7 g of the sodium salt.

Infra-red spectrum (KBr): principal bands (cm−1) at 3420, 3200, 3070, 1655, 1575, 1560, 1395, 1205, 1080, 1045 and 835.

4-(2-Hydroxyethyl)-thiosemicarbazide can be obtained according to the method described by Y. KAZAKOV and I. Y. POTOVSKII, Doklady Acad. Nauk. SSSR, 134, 824 (1960).

7-[2-(2-Amino-thiazol-4-yl)-2-methoxyimino-acetamido]-2-carboxy-8-oxo-3-(2-tosyloxyvinyl)-5-thia-1-azabicyclo[4.2.0]oct-2-ene (syn isomer, E-form) can be prepared in the following manner:

A solution of 2-benzhydryloxycarbonyl-7-[2-methoxyimino-2-(2-tritylamino-thiazol-4-yl)-acetamido]8-oxo-3-(2-tosyloxyvinyl)-5-thiaz-1-aza-bicyclo[4.2.0]oct-2-ene (syn isomer, E-form) (5.93 g) in a mixture of pure formic acid (80 cc) and water (25 cc) is heated at 50° C. for 30 minutes. The mixture is then cooled to 20° C., filtered and concentrated to dryness at 30° C. under 20 mm Hg (2.7 kPa). The residue is taken up in acetone (150 cc), the mixture is concentrated to dryness at 20° C. under 20 mm Hg (2.7 kPa), the operation is repeated twice more and the residue is then triturated in ether (75 cc) and filtered off. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (3.4 g) is obtained in the form of a yellow powder.

REFERENCE EXAMPLE 15

A mixture of 2-benzhydryloxycarbonyl-7-[2-methoxyimino-2-(2-tritylamino-thiazol-4-yl)-acetamido]-8-oxo-5-oxide-4-(2-tosyloxyvinyl)-5-thia-1-aza-bicyclo[4.2.-0]oct-2-ene (syn isomer, E-form) (10.04 g) (obtained as described in reference example 1c), dimethylformamide (200 cc), 4-(2-acetamidoethyl)-5,6-dioxo-3-thioxoperhydro-1,2,4-triazine (2.76 g) and diisopropylethylamine (2.1 cc) is stirred at 60° C. for 3 hours, under nitrogen. The cooled mixture is then diluted with ethyl acetate (800 cc) and the organic phase is washed with water (1.2 liters), dried over sodium sulphate, filtered and concentrated to dryness under reduced pressure (20 mm Hg) at 20° C. The residue is triturated in ether (150 cc), the insoluble matter is filtered off, and after drying 3-{2-[4-(2-acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)acetamido]-8-oxo-5-oxide-5-thia-1-aza-bicyclo[4.2.-0]oct-2-ene (syn isomer, E-form) (9.5 g) is obtained in the form of a light brown solid.

Infra-red spectrum (CHBr3): characteristic bands (cm−1) at 3370, 1795, 1710, 1680, 1520, 1495, 1445, 750 and 735.

Proton nuclear magnetic resonance spectrum (350 MHz, DMSO d6, δ in ppm, J in Hz): 1.75 (s, 3H, —COCH3); 3.65 and 3.90 (2d, J=18, 2H, —SCH2—); 3.86 (s, 3H, —OCH3); 3.88 (t, 2H, >NCH2—); 5.26 (d, J=4, 1H, H in the 6-position); 5.78 (dd, J=4 and 9, 1H, H in the 7-position); 6.73 (s, 1H, H of the thiazole); 6.92 (d, J=16, 1H, —CH=CHS—);

6.95 (s, 1H, —COOCH—);

7.0 (d, J=16, 1H, =CHS—); 7.78 (t, J=6, —NHCOCH3); 8.81 (s, 1H, —NHC(C6H5)3); 9.60 (d, J=9, 1H, —CONH—);

12.60 (s, 1H, =N—NHCO— or =N—N=C—).
                                           |
                                           OH

Dimethylacetamide (3.4 cc) followed by phosphorus trichloride (1.49 cc) is added to a solution, cooled to −10° C., of 3-{2-[4-(2-acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylaminothiazol-4-yl)-acetamido]-8-oxo-5-oxide-5-thia-1-azabicyclo[4.2.0]oct-2-ene (syn isomer, E-form) (9.03 g) in methylene chloride (85 cc). The mixture is stirred for 2 hours at −10° C. and is then diluted with methylene chloride (500 cc), and this mixture is washed with a half-saturated sodium bicarbonate solution (250 cc) and a saturated sodium chloride solution (250 cc), dried over sodium sulphate and concentrated to dryness under reduced pressure (20 mm Hg) at 20° C. The chestnut-coloured solid obtained is dissolved in a mixture of ethyl acetate, methylene chloride and methanol (120:120:80 cc) and the solution is chromatographed over a column (column diameter: 4 cm) of Merck silica gel (0.04–0.06 mm). Elution is carried out with a 95:5 (by volume) mixture of ethyl acetate and methanol (1.5 liters) under a pressure of 40 kPa, 125 cc fractions being collected. Fractions 6 to 10 are concentrated to dryness under reduced pressure (20 mm Hg) at 20° C. 3-{2-[4-(2-Acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]8-oxo-5-thia-1-aza-bicyclo[4.2.0]oct-2-ene (syn isomer, E-form) (3.33 g) is obtained in the form of a beige solid.

Infra-red spectrum (CHBr$_3$): characteristic bands (cm$^{-1}$) at 3380, 1785, 1710, 1680, 1520, 1495, 1445, 755 and 740.

Proton nuclear magnetic resonance spectrum (350 MHz, DMSO d$_6$, δ in ppm, J in Hz): 1.75 (s, 3H, —COCH$_3$); 3.32 (mt, 2H, —CH$_2$NHCO—); 3.62 and 4.30 (2d, J=18, 2H, —SCH$_2$—); 3.86 (t, 2H, >NCH$_2$—); 3.86 (s, 3H, —OCH$_3$); 5.05 (d, J=4, 1H, H in the 6-position); 5.85 (dd, J=4 and 9, 1H, H in the 7-position); 6.80 (s, 1H, H of the thiazole); 6.96 (d, J=16, 1H, —CH=CHS—); 6.97 (s, 1H, —COOCH—); 7.12 (d, J=16, 1H, =CHS—); 7.98 (t, J=6, 1H, —NH COCH$_3$); 8.75 (s, 1H, —NHC(C$_6$H$_5$)$_3$); 9.04 (d, J=9, 1H, —CONH—);

12.60 (s, 1H, =N—NHCO— or =N—N=C—).
$\quad\quad\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad\quad\quad$ OH 3-{2-[4-(2-acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.15 g) is dissolved in formic acid (80 cc), water (30 cc) is added and the mixture is heated at 60° C. for 30 minutes, whilst stirring. It is then cooled, filtered and concentrated to dryness under reduced pressure (0.05 mm Hg) at 50° C. The residue is taken up in ethanol (250 cc), the mixture is concentrated to dryness under reduced pressure (20 mm Hg) at 30° C., the operation is repeated and the solid is then taken up in ethanol (40 cc) whilst stirring at 40° C. After cooling, filtering and drying, 3-{2-[4-(2-acetamidoethyl)-5,6-dioxo-1,4,5,6-tetrahydro-1,2,4-triazin-3-yl]-thiovinyl}-7-[2-(2-amino-thiazol-4-yl)-2-methoxyiminoacetamido]-2-carboxy-8-oxo-5-thia-1-aza-bicyclo[4.2.0]oct-2-ene (syn isomer, E-form) (1.56 g) is obtained in the form of a yellow powder.

Infra-red spectrum (KBr): characteristic bands (cm$^{-1}$) at 3500, 2500, 1775, 1710, 1685 to 1630, 1540, 1045 and 950.

Proton nuclear magnetic resonance spectrum (350 MHz, DMSO d$_6$, δ in ppm, J in Hz): 1.90 (s, 3H, —CH$_3$); 3.48 (m, 2H, —CH$_2$NH—); 3.62 and 3.73 (2d, J=18, 2H, —SCH$_2$—); 4.0 (s, 3H, —OCH$_3$); 5.15 (d, J=4, 1H, H in the 6-position); 5.82 (dd, J=4 and 9, 1H, H in the 7-position); 6.78 (s, 1H, H of the thiazole); 6.86 (d, J=16, 1H, —CH=CHS—); 7.31 (d, J=16, 1H, =CHS—); 7.73 (s, 3H, —NH$_3^+$); 9.50 (d, J=9, 1H, —CONH—);

12.54 (s broad, 1H, —CONHN= or —C=N—N=).
$\quad\quad\quad\quad\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad\quad\quad\quad\quad$ OH A portion of the preceding product (0.128 g) is dissolved in an 0.1 M sodium bicarbonate solution (2 cc), and the resulting solution is filtered and lyophilised. The sodium salt of 3-{2-[4-(acetamidoethyl)-5,6--dioxo-1,4,5,6-tetrahydro-1,2,4-triazin-3-yl]-thiovinyl}-7-[2-(2-amino-thiazol-4-yl)-2-methoxyiminoacetamido]-2-carboxy-8-oxo-5-thia-1-aza-bicyclo[4.2.-0]oct-2-ene (syn isomer, E-form) (0.127 g) is obtained.

4-(2-Acetamidoethyl)-5,6-dioxo-3-thioxo-perhydro-1,2,4-triazine (3.61 g) is obtained from 4-(2-acetamidoethyl)-thiosemicarbazide (4.41 g) and ethyl oxalate (3.4 cc) in the presence of sodium methylate, by application of the method described by M. PESSON and M. ANTOINE, Bull. Soc. Chim. France 1590 (1970). The product has the following properties: instantaneous m.p. [Kofler]>260° C.; infra-red spectrum (KBr): characteristic bands (cm$^{-1}$) at 3365, 3050, 2000, 1710, 1630, 1600–1580, 1545, 1350, 1330 and 1200; proton nuclear magnetic resonance spectrum (80 MHz, DMSO d$_6$, δ in ppm, J in Hz): 1.7 (s, 3H, —CH$_3$); 3 to 3.7 (mt, —CH$_2$NHCO— and H$_2$O); 4.3 (t, 2H, >N CH$_2$—); 7.85 (t, 1H, —NHCO—); 12.5 (m, 2H, —NH— of the ring).

The thiosemicarbazide starting material can be obtained in the following manner:

A solution of methyl N-(2-acetamidoethyl)-dithiocarbamate (57.7 g) and hydrazine hydrate (14.6 cc) in absolute ethanol (300 cc) is heated under reflux for 2 hours. The mixture is then cooled to 4° C. and is filtered, and the insoluble matter is dried at 30° C. under 0.05 mm Hg. 4-(2-Acetamidoethyl)-thiosemicarbazide (39.5 g) is obtained in the form of white crystals (instantaneous m.p. [Kofler]=171° C.).

Infra-red spectrum (KBr): characteristic bands (cm$^{-1}$) at 3280, 3180, 1650, 1560 to 1535, 1360 and 1280.

REFERENCE EXAMPLE 16

A mixture of 2-benzhydryloxycarbonyl-7-[2-methoxyimino-2-(2-tritylamino-thiazol-4-yl)-acetamido]8-oxo-5-oxide-3-(2-tosyloxyvinyl)-5-thia-1-aza-bicyclo[4.2.-0]oct-2-ene (syn isomer, E-form) (6.02 g) (obtained as described in reference example 1c), dimethylformamide (60 cc), 2-acetamidomethyl-5-mercapto-1,3,4-thiadiazole (2.27 g) and diisopropylethylamine (1.15 cc) is stirred for 2 hours 30 minutes at 60° C. under nitrogen. The cooled mixture is diluted with ethyl acetate (250 cc), and this mixture is washed with water (150 cc), 0.1 N hydrochloric acid (100 cc), a saturated sodium bicarbonate solution (100 cc) and water (2×100 cc), dried over sodium sulphate, filtered and concentrated to dryness at 20° C. under reduced pressure (20 mm Hg). The residue, fixed on Merck silica gel (0.05–0.2 mm) (20 g), is deposited on a column (column diameter: 2.5 cm) of silica gel (0.05–0.2 mm) (70 g). Elution is carried out with ethyl acetate (2.5 liters), 100 cc fractions being collected. Fractions 9 to 23 are evaporated to dryness at 20° C. under reduced pressure (20 mm Hg) and 3-[2-(2-acetamidomethyl-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-oxide-5- thia-1-aza-bicyclo[4.2.0]oct-2-ene (syn isomer, E-form) (3 g) is obtained in the form of a brown froth.

Infra-red spectrum (KBr): characteristic bands (cm$^{-1}$) at 3400, 1795, 1720, 1670, 1525, 1495, 1450, 1370, 1040, 940, 750 and 700.

Proton nuclear magnetic resonance spectrum (350 MHz, CDCl$_3$, δ in ppm, J in Hz): 1.97 (s, 3H, —COCH$_3$); 3.30 and 4.15 (2d, J=18, 2H, —SCH$_2$—); 4.08 (s, 3H, —OCH$_3$); 4.64 (d, J=4, 1H, H in the 6-position); 4.72 (AB, 2H, —CH$_2$NHCO—); 6.14 (dd, J=4 and 9, 1H, H in the 7-position); 6.72 (s, 1H, H of the thiazole);

6.97 (s, 1H, —COOCH—).

Dimethylacetamide (1.1 cc) and phosphorus trichloride (0.519 cc) are added to a solution, cooled to −10° C., of 3-[2-(2-acetamidomethyl-1,3,4-thiadiazol-5-yl)thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) in methylene chloride (29 cc), and the mixture is then stirred for 1 hour at −10° C. Thereafter it is poured into ethyl acetate (250 cc) and this mixture is washed with a saturated sodium bicarbonate solution (250 cc) and with water (2×100 cc), dried over sodium sulphate, filtered and concentrated to dryness at 20° C. under reduced pressure (20 mm Hg). The residue is dissolved in methylene chloride (10 cc) and the solution is chromatographed on a column (column diameter: 4 cm) of Merck silica gel (0.04–0.06 mm). Elution is carried out with a 80:20 (by volume) mixture of ethyl acetate and cyclohexane (2.5 liters) under a pressure of 40 kPa, 100 cc fractions being collected. Fractions 11 to 21 are evaporated to dryness at 20° C. under reduced pressure (20 mm Hg) and 3-[2-(2-acetamido-1,3,4-thiadiazol-5-yl)-thiovinyl]-2-benzhydryloxycarbonyl-7-[2-methoxyimino-2-(2-tritylamino-thiazol-4-yl)-acetamido]8-oxo-5-thia-1-aza-bicyclo[4.2.0]oct-2-ene (syn isomer, E-form) (2.1 g) is obtained in the form of a yellow froth.

Infra-red spectrum (KBr): characteristic bands (cm$^{-1}$) at 3400, 3280, 1785, 1720, 1670, 1530, 1495, 1450, 1370, 1040, 945, 755 and 700.

Proton nuclear magnetic resonance spectrum (350 MHz, CDCl$_3$, δ in ppm, J in Hz): 2.0 (s, 3H, —COCH$_3$); 3.58 and 3.68 (2d, J=18, 2H, —SCH$_2$—); 4.08 (s, 3H, —OCH$_3$); 4.75 (d, J=5, 2H, —CH$_2$NHCO—); 5.10 (d, J=4, 1H, H in the 6-position); 5.97 (dd, J=4 and 9, 1H, H in the 7-position); 6.55 (t, J=5, 1H, —NHCO—); 6.76 (s, 1H, H of the thiazole); 7.0 (s, 1H, —COOCH<); 7.05 (s, 1H, —NH—C(C$_6$H$_5$)$_3$); 7.18 (d, J=16, 1H, —CH=CHS—).

3-[2-(2-Acetamidomethyl-1,3,4-thiadiazol-5-yl)thiovinyl]-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is dissolved in formic acid (21 cc), water (12 cc) is added and the mixture is heated at 50° C. for 30 minutes. It is then cooled to about 20° C., filtered and concentrated to dryness at 50° C. under reduced pressure (0.05 mm Hg), the residue is taken up in ethanol (50 cc) and the solvent is driven off at 20° C. under reduced pressure (20 mm Hg); this operation is repeated twice, after which the residue is taken up in ethanol (50 cc) under reflux. The mixture is filtered hot to remove a small amount of insoluble matter, and the filtrate is concentrated to 20 cc under reduced pressure (20 mm Hg) at 20° C. and filtered. After drying, 3-[2-(2-acetamidomethyl-1,3,4-thiadiazol-5-yl)-thiovinyl]-7-[2-(2-aminothiazol-4-yl)-2-methoxyimino-acetamido]-2-carboxy-8-oxo-5-thia-1-aza-bicyclo[4.2.0]oct-2-ene (syn isomer, E-form) (0.75 g) is obtained in the form of a cream-coloured powder.

Infra-red spectrum (KBr): characteristic bands (cm$^{-1}$) at 3320, 1770, 1660, 1540, 1380 and 1040.

Proton nuclear magnetic resonance spectrum (350 MHz, DMSO d$_6$, δ in ppm, J in Hz): 1.90 (s, 3H, —COCH$_3$); 3.68 and 3.92 (2d, J=18, 2H, —S—CH$_2$—); 3.87 (s, 3H, —OCH$_3$); 4.22 (d, J=4, 1H, H in the 6-position); 4.60 (AB limit, 2H, —CH$_2$NHCO—); 5.82 (dd, J=4 and 9, 1H, H in the 7-position); 6.75 (s, 1H, —OCH$_3$); 7.15 (d, J=16, 1H, —CH=CHS—); 7.20 (s, 3H, —NH$_3$+); 7.25 (d, J=16, 1H, =CHS—); 9.63 (d, J=9, 1H, —CONH—).

2-Acetamidomethyl-5-mercapto-1,3,4-thiadiazole can be prepared by application of the method described in Japanese Pat. No. 76/80857.

REFERENCE EXAMPLE 17

A mixture of 2-benzhydryloxycarbonyl-7-[2-methoxyimino-2-(2-tritylamino-thiazol-4-yl)-acetamido]8-oxo-5-oxide-3-(2-tosyloxyvinyl)-5-thia-1-aza-bicyclo[4.2.0]oct-2-ene (syn isomer, E-form) (10 g), dimethylformamide (200 cc) and the sodium salt of 1-(2,2-dimethoxyethyl)-5-mercapto-tetrazole (5.75 g) is stirred for 24 hours at 50° C. under nitrogen. It is then diluted with ethyl acetate (200 cc) and water (200 cc), and the organic phase is decanted, washed with water (3×200 cc) and saturated aqueous sodium chloride (100 cc), filtered and concentrated to dryness under 20 mm Hg (2.7 kPa) at 20° C. The residue is chromatographed on a column (column diameter: 6 cm, height: 30 cm) of Merck silica gel (0.04–0.06 mm). Elution is carried out with a 50:50 (by volume) mixture (3.8 liters) and a 25:75 (by volume) mixture (4.6 liters) of cyclohexane and ethyl acetate, 120 cc fractions being collected. Fractions 40 to 69 are concentrated to dryness under 20 mm Hg (2.7 kPa) at 20° C., and 2-benzhydryloxycarbonyl-3-{2-[1-(2,2-dimethoxyethyl)-tetrazol-5yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.4 g) is obtained in the form of a brown froth, which is used, as obtained, in the subsequent operations.

A solution of 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.37 g) in methylene chloride (25 cc) and dimethylacetamide (1.31 cc) is treated with phosphorus trichloride (0.58 cc) at −8° C. for 30 minutes, whilst stirring. The mixture is diluted with methylene chloride (75 cc), and this mixture is washed with a half-saturated sodium bicarbonate solution (2×50 cc) and water (2×50 cc), dried over sodium sulphate, filtered and concentrated to dryness under 20 mm Hg (2.7 kPa) at 20° C. The residue is chromatographed on a column (column diameter: 4 cm, height: 20 cm) of Merck silica gel (0.04–0.06 mm). Elution is carried out with a 50:50 (by volume) mixture of cyclohexane and ethyl acetate (1.8 liters), under a pressure of 40 kPa, 60 cc fractions being collected. Fractions 16 to 24 are evaporated to dryness and 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.1 g) is obtained in the form of a cream-coloured froth.

Infra-red spectrum (KBr): characteristic bands (cm$^{-1}$) at 3400, 1790, 1725, 1690, 1520, 1500, 1450, 1210, 1050, 1040, 945, 755 and 705.

Proton nuclear magnetic resonance spectrum (350 MHz, DMSO d$_6$, δ in ppm, J in Hz): 3.31 (s, 6H, >C(OCH$_3$)$_2$); 3.65 and 3.91 (2d, J=18, 2H, —SCH$_2$—); 3.83 (s, 3H, =NOCH$_3$); 4.48 (d, J=6, 2H, >NCH$_2$CH<); 4.70 (t, J=6, >NCH$_2$CH<); 5.23 (d, J=4, H$_6$); 5.78 (dd, J=4 and 9, H$_7$); 6.74 (s, H of the thiazole); 6.96 (s, —COOCH<); 7.02 and 7.08 (2d, J=16, 2H, —CH=CH—S—); 8.79 (s, —NH—); 9.60 (d, J=9, —NHCO—).

A solution of 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.06 g) in formic acid (42 cc) is heated for 30 minutes at 50° C. It is then concentrated to dryness under 0.05 mm Hg (0.007 kPa) at 30° C., the residue is taken up in acetone (100 cc), the mixture is again concentrated to dryness, under 20 mm Hg (2.7 kPa) at 20° C., and this operation is repeated 4 times. The yellow solid obtained is treated with acetone (30 cc) under reflux, and the mixture is allowed to cool and filtered. After drying the product, 7-[2-(2-amino-thiazol-4-yl)-2-methoxyimino-acetamido]-2-carboxy-3{2-[1-(2,2-dimethoxyethyl)-tetrazol-5-yl]-thiovinyl}-8-oxo-5-thia-1-aza-bicyclo[4.2.0]oct-2-ene (syn isomer, E-form) (0.43 g) is obtained in the form of a yellow powder.

Infra-red spectrum (KBr): characteristic bands (cm$^{-1}$) at 3350, 1780, 1680, 1655, 1620, 1530, 1120, 1040 and 940.

Proton nuclear magnetic resonance spectrum (350 MHz, CF$_3$CO$_2$D, δ in ppm, J in Hz): 3.61 (s, 6H, >C(OCH$_3$)$_2$); 3.92 (s broad, 2H, —SCH$_2$—); 4.31 (s, 3H, =NOCH$_3$); 4.73 (d, J=6, 2H, >NCH$_2$—); 5.0 (t, J=6, 1H, —CH$_2$—CH<); 5.38 (d, J=4, H$_6$); 6.05 (dd, J=4 and 9, H$_7$); 7.16 and 7.88 (2d, J=16, —CH=CH—); 7.50 (s, H of the thiazole).

The sodium salt of 1-(2,2-dimethoxyethyl)-5-mercapto-tetrazole can be prepared in the following manner:

A solution of sodium azide (65 g) in 95% strength ethanol (1,680 cc) is heated under reflux. A solution of 2,2-dimethoxyethyl isothiocyanate (147.2 g) in 95% strength ethanol (320 cc) is added dropwise, with stirring, in the course of 1 hour 30 minutes, and the mixture is heated under reflux for 12 hours. It is then concentrated to dryness at 40° C. under 20 mm Hg (2.7 kPa), the residue is taken up in acetone (600 cc), the mixture is filtered and diethyl ether (1 liter) is added. The crystallisation is started, and a further amount of diethyl ether (2.5 liters) is added. The batch is left at 20° C. for 24 hours and is then filtered. After drying, the sodium salt of 1-(2,2-dimethoxyethyl)-5-mercapto-tetrazole, in the form of the hydrate (208.2 g), is obtained.

Infra-red spectrum (KBr): characteristic bands (cm$^{-1}$) at 3480, 3220, 2840, 1660, 1400, 1290, 1115, 1070, 1025 and 790.

REFERENCE EXAMPLE 18 p-Toluenesulphonyl chloride (0.65 g) is added to a solution, cooled to −15° C., of 2-benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]-oct-2-ene (syn isomer) (2.4 g) obtained as described above) in methylene chloride (30 cc), after which a solution of triethylamine (0.44 cc) in methylene chloride (5 cc) is added dropwise in the course of 10 minutes. The mixture is stirred for 30 minutes at −15° C., the temperature is allowed to return to +20° C. in the course of 1 hour, and the mixture is then diluted with methylene chloride (50 cc) washed with a saturated sodium bicarbonate solution (3×50 cc) and with water (3×50 cc), dried over sodium sulphate, filtered and concentrated to dryness under 20 mm Hg (2.7 kPa) at 30° C.

The residue is taken up in ethyl acetate (5 cc), and diisopropyl ether (50 cc) is added, the mixture is stirred for 10 minutes and filtered, and after drying, a beige powder (1.6 g) is obtained, which consists principally of 2-benzhydryloxycarbonyl-8-oxo-3-(2-tosyloxyvinyl)-7-[2-(2-tritylamino-thiazol-4-yl)-2-vinyloxyimino-acetamido]-5-thia-1-aza-bicyclo[4.2.0]oct-2-ene and -oct-3-ene (a mixture of the E- and Z-forms).

Infra-red spectrum (KBr): characteristic bands (cm$^{-1}$) at 1790, 1725, 1690, 1640, 1525, 1495, 1450, 1195, 1180, 1075, 1005, 950, 755 and 705.

Proton nuclear magnetic resonance spectrum (350 MHz, CDCl$_3$, δ in ppm, J in Hz): 2.45 (s, 3H, —CH$_3$); 3.40 and 3.55 (2d, J=18, 2H, —SCH$_2$—);

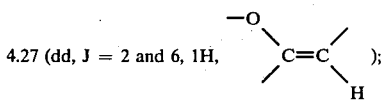

4.27 (dd, J = 2 and 6, 1H, >C=C< );

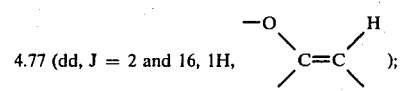

4.77 (dd, J = 2 and 16, 1H, >C=C< );

5.09 (d, J=4, 1H, H in the 6-position); 5.94 (dd, J=4 and 9, 1H, H in the 7-position); 6.81 (s, 1H, H of the thiazole); 6.91 (s, 1H, —COOCH<); 7.07 (dd, J=6 and 16, 1H, —CH=CH$_2$); 7.74 (d, J=8, 2H, H of the sulphonyl group).

A solution of 85% strength m-chloroperbenzoic acid (0.33 g) in methylene chloride (7 cc) is added dropwise, in the course of 10 minutes, to a solution, cooled to −10° C., of 2-benzhydryloxycarbonyl-8-oxo-3-(2-tosyloxyvinyl)-7-[2-(2-tritylamino-thiazol-4-yl)-2-vinyloxyimino-acetamido[-5-thia-1-aza-bicyclo[4.2.0]oct-2-ene and oct-3-ene (syn isomer, mixture of the E- and Z-forms) (1.6 g) in methylene chloride (5 cc). The mixture is stirred for 1 hour at −10° C. and is then diluted with methylene chloride (30 cc), and this mixture is washed with a saturated sodium bicarbonate solution (2×50 cc) and a half-saturated sodium chloride solution (50 cc), dried over sodium sulphate, filtered and concentrated to dryness under 20 mm Hg (2.7 kPa) at 30° C. The residue is chromatographed on a column (column diameter: 1 cm, height: 10 cm) of Merck silica gel (0.06–0.2 mm) (20 g). Elution is carried out with methylene chloride (500 cc), a 97:3 (by volume) mixture (1 liter) and a 95:5 (by volume) mixture (1.5 liters) of methylene chloride and ethyl acetate, 25 cc fractions being collected. Fractions 14 to 24 are evaporated to dryness under 20 mm Hg (2.7 kPa) at 20° C. 2-Benzhydryloxycarbonyl-8-oxo-5-oxide-3-(2-tosyloxyvinyl)-7-[2-(2-tritylamino-thiazol-4-yl)-2-vinyloxyiminoacetamido]-5-thia-1-aza-bicyclo[4.2.0]oct-2-ene (syn isomer, E-form) (0.45 g) is obtained.

Infra-red spectrum (KBr): characteristic bands (cm$^{-1}$) at 1800, 1725, 1690, 1635, 1520, 1495, 1450, 1195, 1180, 1070, 1050, 1000, 945, 740 and 700.

Proton nuclear magnetic resonance spectrum (350 MHz, CDCl$_3$, δ in ppm, J in Hz); 2.45 (s, 3H, —CH$_3$); 3.19 and 3.77 (2d, J=18, 2H, —SCH$_2$—);

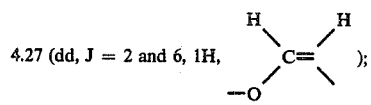

4.27 (dd, J = 2 and 6, 1H, 4.62 (d, J=4, 1H, H in the 6-position);

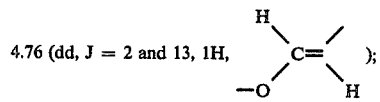

4.76 (dd, J = 2 and 13, 1H, 6.20 (dd, J=4 and 9, 1H, H in the 7-position); 6.80 (s, 1H, H of the thiazole); 6.90 (s, 1H, —COOCH<); 6.92 and 7.10 (2d, J=12, 2H, —CH=CH—); 7.05 (dd, J=6 and 13, 1H, =NOCH=); 7.73 (d, J=8, 2H, H in the ortho-position of the —OSO$_2$— group).

A mixture of 2-benzhydryloxycarbonyl-8-oxo-5-oxide-3-(2-tosyloxyvinyl)-7-[2-(2-tritylamino-thiazol-4-yl)-2-vinyloxyimino-acetamido]-5-thia-1-aza-bicyclo[4.2.0]oct-2-ene (syn isomer, E-form) (0.4 g), dimethylformamide (5 cc), 5-mercapto-1-methyl-tetrazole (0.1 g) and N,N-diisopropylethylamine (0.15 cc) is heated at 60° C. for 4 hours. It is then taken up in ethyl acetate (50 cc) and the organic phase is washed with water (50 cc), 0.1 N hydrochloric acid (50 cc), a half-saturated sodium bicarbonate solution (50 cc) and a saturated sodium chloride solution (50 cc), dried over sodium sulphate, filtered and concentrated to dryness under 20 mm Hg (2.7 kPa) at 30° C. The residue is chromatographed on a column (column diameter: 1.5 cm, height: 15 cm) of Merck silica gel (0.06–0.2 mm) (50 g). Elution is carried out with a 90:10 (by volume) mixture of methylene chloride and ethyl acetate (2.5 liters) under a pressure of 40 kPa, 25 cc fractions being collected. Fractions 18 to 42 are concentrated to dryness under 20 mm Hg (2.7 kPa) at 20° C. This gives 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (0.15 g), having the following characteristics:

Infra-red spectrum (KBr): characteristic bands (cm$^{-1}$) at 3340, 2940, 2860, 1800, 1730, 1690, 1640, 1575, 1525, 1500, 1450, 1215, 1045, 1005, 950, 765 and 760.

Proton nuclear magnetic resonance spectrum (350 MHz, CDCl$_3$, δ in ppm, J in Hz): 3.31 and 4.05 (2d, J=18, 2H, —SCH$_2$—); 3.92 (s, 3H, —CH$_3$);

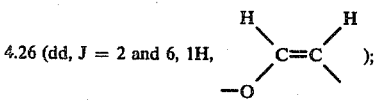

4.26 (dd, J = 2 and 6, 1H,

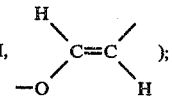

4.76 (dd, J = 2 and 14, 1H, 4.67 (d, J=4, 1H, H in the 6-position); 6.18 (dd, J=4 and 9, 1H, H in the 7-position); 6.78 (s, 3H, H of the thiazole); 6.95 (s, 1H, —COOH<); 7.0 (d, J=15, 1H, —CH=CHS—); 7.05 (dd, J=4 and 6, 1H, —OCH=); 7.10 (s, 1H, >—CNH—); 7.58 (d, J=15, 1H, —CH=C-HS—).

A solution of 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (3 g) in methylene chloride (31.7 cc) and dimethylacetamide (1.22 cc) is treated with phosphorus trichloride (0.554 cc) at −10° C. for 20 minutes. The mixture is poured into ethyl acetate (250 cc) and this mixture is washed with a saturated sodium bicarbonate solution (250 cc), water (250 cc) and a saturated sodium bicarbonate solution (250 cc), dried over sodium sulphate, filtered and concentrated to dryness under 20 mm Hg (2.7 kPa) at 20° C. The product is fixed on Merck silica gel (0.06–0.2 mm) (10 g) and is chromatographed on a column (column diameter: 1.5 cm) of Merck silica gel (0.06–0.2 mm) (30 g.). Elution is carried out with an 80:20 (by volume) mixture (250 cc), a 70:30 (by volume) mixture (250 cc) and a 60:40 (by volume) mixture (250 cc) of cyclohexane and ethyl acetate, 60 cc fractions being collected. Fractions 5 to 10 are concentrated to dryness under 20 mm Hg (2.7 kPa) at 20° C., and 2-benzhydryloxycarbonyl-3-[2-(1-methyl-tetrazol-5-yl)-thiovinyl]-8-oxo-7-[2-(2-tritylamino-thiazol-4-yl)-2-vinyloxyimino-acetamido]-5-thia-1-aza-bicyclo[4.2.0]oct-2-ene (syn isomer, E-form) (1.92 g) is obtained in the form of a cream-coloured froth.

Rf=0.58 [silica gel chromatographic plate, eluant: a 50:50 (by volume) mixture of cyclohexane and ethyl acetate].

A mixture of 2-benzhydryloxycarbonyl-3-[2-(1-methyl-tetrazol-5-yl)-thiovinyl]-8-oxo-7-[2-(2-tritylamino-thiazol-4-yl)-2-vinyloxyimino-acetamido]-5-thia-1-aza-bicyclo[4.2.0]oct-2-ene (syn isomer, E-form) (1.92 g), formic acid (15 cc) and water (7 cc) is stirred at 50° C. for 15 minutes. It is then filtered and concentrated to dryness under 0.05 mm Hg (0.007 kPa) at 30° C. The oil which remains is taken up in ethanol (100 cc), the solvent is driven off under 20 mm Hg (2.7 kPa) at 20° C., and this operation is repeated a second time. The residue is taken up in ethanol (100 cc), and the mixture is heated under reflux, whilst stirring, and is cooled and filtered. After drying, 7-[2-(2-amino-thiazol-4-yl)-2-vinyloxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, E-form) (0.72 g) is obtained in the form of a yellow powder.

Infra-red spectrum (KBr): characteristic bands (cm$^{-1}$) at 3340, 1770, 1680, 1620, 1530 and 1380.

Proton nuclear magnetic resonance spectrum (350 MHz, DMSO d$_6$, δ in ppm, J in Hz): 3.64 and 3.89 (2d, J=18, 2H, —SCH$_2$—); 4.0 (s, 3H, —CH$_3$);

4.22 (dd, J = 2 and 6, 1H, 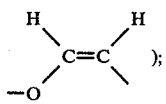 );

4.65 (dd, J = 2 and 14, 1H, 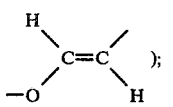 );

5.22 (d, J=4, 1H, H in the 6-position); 5.82 (dd, J=4 and 9, 1H, H in the 7-position); 6.75 (s, 1H, H of the thiazole); 6.95 (d, J=16, 1H, —C$\underline{H}$=CHS—); 6.96 (dd, J=6 and 14, 1H, —OC$\underline{H}$=CH$_2$); 7.13 (d, J=16, 1H, =C$\underline{H}$S—); 9.83 (d, J=9, 1H, —CONH—).

REFERENCE EXAMPLE 19

A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (54.3 g) (obtained as described in reference example 2) and hydrated p-toluenesulphonic acid (30.4 g) in acetonitrile (1.4 liters) is stirred at 35° C. for 2 hours. It is then concentrated to dryness at 30° C. under 20 mm Hg (2.7 kPa), the residue is taken up in ethyl acetate (1 liter) and this solution is washed with a half-saturated sodium bicarbonate solution (2×500 cc) and a half-saturated sodium chloride solution (2×500 cc), dried over sodium sulphate and concentrated to dryness at 20° C. under 20 mm Hg (2.7 kPa). The residue is triturated in ether (200 cc). 7-Amino-2-benzhydryloxycarbonyl-8-oxo-5-oxide-3-(2-tosyloxyvinyl)-5-thia-1-aza-bicyclo[4.2.0]oct-2-ene (E-form) (28.13 g) is obtained in the form of a light brown powder.

Rf=0.32; silica gel chromatographic plate [using an 85:15 (by volume) mixture of methylene chloride and methanol].

A mixture of 7-amino-2-benzhydryloxycarbonyl-8-oxo-5-oxide-3-(2-tosyloxyvinyl)-5-thia-1-aza-bicyclo[4.2.0]oct-2-ene (E-form) (1.16 g), dimethylformamide (35 cc), 5-[2-methoxyimino-2-(2-tritylamino-thiazol-4-yl)-acetylthio]-2-methyl-1,3,4-thiadiazole (syn isomer) (1.67 g) and N,N-diisopropylethylamine (0.35 cc) is stirred for 1 hour at 60° C. under nitrogen. The mixture is diluted with ethyl acetate (140 cc) and the solution is washed with water (3×70 cc), dried over sodium sulphate, filtered and concentrated to dryness at 20° C. under 20 mm Hg (2.7 kPa). The residue is taken up in methylene chloride (25 cc), Merck silica gel (0.06–0.2 mm) (5 g) is added, the mixture is concentrated to dryness at 20° C. under 20 mm Hg (2.7 kPa) and the powder is deposited on a column (column diameter: 2 cm) of Merck silica gel (0.06–0.2 mm) (35 g). Elution is carried out successively with the following mixtures of cyclohexane and ethyl acetate: 80:20 (by volume) (100 cc), 60:40 (by volume) (250 cc), 40:60 (by volume) (500 cc), and 20:80 (by volume) (500 cc) and with pure ethyl acetate (500 cc), 60 cc fractions being collected. Fractions 17 to 26 are concentrated to dryness at 20° C. under 20 mm Hg (2.7 kPa) and 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, E-form) (0.56 g) is obtained in the form of a pinkish froth.

Infra-red spectrum (CHBr$_3$): characteristic bands (cm$^{-1}$) at 3380, 1800, 1725, 1680, 1515, 1490, 1445, 1045, 935 and 750.

Proton nuclear magnetic resonance spectrum (350 MHz, CDCl$_3$, δ in ppm, J in Hz): 2.72 (s, 3H, —CH$_3$); 3.28 and 4.08 (2d, J=18, 2H, —SCH$_2$—); 4.07 (s, 3H, —OCH$_3$); 4.60 (d, J=4, 1H, H in the 6-position); 6.16 (dd, J=4 and 9, 1H, H in the 7-position); 6.71 (s, 1H, H of the thiazole);

6.95 (s, 1H, —COOC$\underline{H}$—);

7.07 (s, 1H, —N$\underline{H}$ C(C$_6$H$_5$)$_3$); 7.23 and 7.33 (2d, J=16, —CH=CH—).

Phosphorus trichloride (0.93 cc) is added at −8° C., with stirring, to a solution of 2-benzhydryloxycarbonyl-7-[2-methoxyimino-2-(2-tritylamino-thiazol-4-yl)-acetamido]-3-[2-(2-methyl-1,3,4-thiadiazol-5-yl)thiovinyl]-8-oxo-5-oxide-5-thia-1-aza-bicyclo[4.2.0]oct-2-ene (syn isomer, E-form) (5.11 g) and dimethylacetamide (2.1 cc) in methylene chloride (50 cc). The mixture is stirred for 1 hour at −8° C. and is then diluted with ethyl acetate (1 liter), and this mixture is washed with a half-saturated sodium bicarbonate solution (2×250 cc) and a half-saturated sodium chloride solution (2×250 cc), dried over sodium sulphate and concentrated to dryness at 20° C. under 20 mm Hg (2.7 kPa). The product, dissolved in a 40:60 (by volume) mixture of cyclohexane and ethyl acetate (50 cc), is chromatographed on a column (column diameter: 5 cm) of Merck silica gel (0.04–0.06 mm) (150 g). Elution is carried out with the preceding mixture (3 liters) under a pressure of 4 kPa, 125 cc fractions being collected. Fractions 10 to 20 are concentrated to dryness at 20° C. under 20 mm Hg (2.7 kPa). 2-Benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (2.69 g) is obtained in the form of a yellow froth.

Infra-red spectrum (CHBr$_3$): characteristic bands (cm$^{-1}$) at 3390, 1785, 1720, 1685, 1515, 1495, 1445, 1045, 940 and 755.

Proton nuclear magnetic resonance spectrum (350 MHz, CDCl$_3$, δ in ppm, J in Hz): 2.75 (s, 3H, —CH$_3$); 3.60 and 3.69 (2d, J=18, 2H, —SCH$_2$—); 4.09 (s, 3H, —OCH$_3$); 5.09 (d, J=4, 1H, H in the 6-position); 5.93 (dd, J=4 and 9, 1H, H in the 7-position); 6.75 (s, 1H, H of the thiazole);

6.98 (s, 1H, —COOC$\underline{H}$—);

7.0 (s, 1H, —NH—C(C$_6$H$_5$)$_3$); 7.22 (d, J=14, 1H, —C$\underline{H}$=CHS—).

A mixture of 2-benzhydryloxycarbonyl-7-[2-methoxyimino-2-(2-tritylamino-thiazol-4-yl)-acetamido]3-[2-(2-methyl-1,3,4-thiadiazol-5-yl)-thiovinyl]-8-oxo-5-thia-1-aza-bicyclo[4.2.0]oct-2-ene (syn isomer, E-form) (2.37 g) in formic acid (30 cc) containing water (14 cc) is stirred at 50° C. for 15 minutes. It is allowed to cool, diluted with water (16 cc) and filtered. The filtrate is concentrated to dryness at 30° C. under 0.05 mm Hg (0.007 kPa) and the residue is taken up in ethanol (3×50 cc), the mixture being concentrated to dryness each time. The solid obtained is stirred in ethanol (35 cc) for 25 minutes at 50° C. and is then filtered off, washed with ethyl ether (2×20 cc) and dried. 7-[2-(2-Amino-thiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, E-form) (1.18 g) is obtained in the form of a yellow powder.

Infra-red spectrum (KBr): characteristic bands (cm$^{-1}$) at 3400, 3200, 3100, 2200, 1775, 1675, 1530, 1045 and 940.

Proton nuclear magnetic resonance spectrum (350 MHz, DMSO $d_6$, δ in ppm, J in Hz): 2.74 (s, 3H, —CH$_3$); 3.67 and 3.94 (2d, J=18, 2H, —SCH$_2$—); 3.86 (s, 3H, —OCH$_3$); 5.21 (d, J=4, 1H, H in the 6-position); 5.80 (2d, J=4 and 9, 1H, H in the 7-position); 6.75 (s, 1H, H of the thiazole); 7.12 and 7.17 (2d, J=16, 2H, —CH=CHS—); 7.20 (s, 2H, —NH$_2$); 9.63 (d, J=9, 1H, —CONH—).

5-[2-Methoxyimino-2-(2-tritylamino-thiazol-4-yl)acetylthio]-2-methyl-1,3,4-thiadiazole (syn isomer) can be prepared in the following manner:

N,N'-Dicyclohexylcarbodiimide (4.96 g) is added as a single shot, with stirring, to a suspension, cooled to 4° C., of [2-methoxyimino-2-(2-tritylamino-thiazol-4-yl)]-acetic acid (syn isomer) (8.88 g) and 5-mercapto-2-methyl-1,3,4-thiadiazole (2.64 g) in ethyl acetate (200 cc). The suspension is stirred for 4 hours at 4° C. and is then filtered, and the filtrate is washed with water (2×200 cc), a half-saturated sodium bicarbonate solution (2×100 cc) and a saturated sodium chloride solution (100 cc), dried over sodium sulphate, filtered, concentrated to 20 cc at 20° C. under 20 mm Hg (2.7 kPa), and again filtered. The filtrate is diluted with petroleum ether (200 cc) and the mixture is filtered, a yellow powder (6.2 g), corresponding to a crude form of the expected product, being collected.

Purification is carried out in the following manner: the preceding product is treated with cyclohexane (200 cc) under reflux, the mixture is filtered hot, the filtrate is concentrated to 30 cc (at 20° C. under 20 mm Hg; 2.7 kPa), the concentrate is filtered and 5-[2-methoxyimino-2-(2-tritylamino-thiazol-4-yl)-acetylthio]2-methyl-1,3,4-thiadiazole, syn isomer, (4.5 g) is collected.

Proton nuclear magnetic resonance spectrum (80 MHz, CDCl$_3$, δ in ppm, J in Hz): 2.85 (s, 3H, —CH$_3$); 4.08 (s, 3H, =NOCH$_3$); 6.60 (s, 1H, H of the thiazole).

Infra-red spectrum (CHBr$_3$): characteristic bands (cm$^{-1}$) at 1695, 1605, 1580, 1530, 1490, 1450, 1050 and 900.

REFERENCE EXAMPLE 20

Thiourea (0.18 g) is added to a solution of 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.4 g) in ethanol (25 cc), tetrahydrofurane (25 cc) and water (5 cc) and the solution is stirred for 4 hours at 20° C. It is then concentrated to dryness under reduced pressure (20 mm Hg, 2.7 kPa). The residue is triturated with water (10 cc), the mixture is brought to pH 7 with a sodium bicarbonate solution, and the precipitate is filtered off, washed with water (5 cc) and dried. A light beige solid (1.3 g) is obtained, which is dissolved in chloroform (10 cc). The solution obtained is added dropwise to isopropyl ether (100 cc), whilst stirring. The insoluble matter formed is filtered off and redissolved in tetrahydrofurane (25 cc), the solution formed is filtered in the presence of decolorising charcoal and the filtrate is concentrated to a volume of 5 cc under reduced pressure (20 mm Hg, 2.7 kPa). Ethyl acetate (25 cc) is added to this solution. The solid formed is filtered off, washed with ethyl acetate (10 cc) and dried. 2-Benzhydryloxycarbonyl-7-[2-hydroxyimino-2-(2-aminothiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.9 g) is thus obtained in the form of a beige solid.

Infra-red spectrum (Br): characteristic bands (cm$^{-1}$) at 3380, 3200, 3100, 1785, 1720, 1685, 1630, 1535, 1500, 1445, 1210, 950, 760, 745 and 705.

Proton nuclear magnetic resonance spectrum (350 MHz, DMSO $d_6$, δ in ppm, J in Hz): 2.71 (s, 3H, —CH$_3$ Het); 3.72 and 3.98 (2 d, J=18, 2H, —SCH$_2$—); 5.28 (d, J=4, 1H, H in the 6-position); 5.90 (dd, J=4 and 9, 1H, H in the 7-position); 6.80 (s, 1H, H of the thiazole); 6.98 (s, 1H, —COOCH<); 7.05 (d, J=16, 1H, —CH=CHS—); 7.26 (d, J=16, 1H, —CH=CHS—); 9.65 (d, J=9, 1H, —CONH—); 11.85 (s broad, 1H, =NOH).

2-Benzhydryloxycarbonyl-7-[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.3 g) is dissolved in 98% strength formic acid (6 cc). Distilled water (6 cc) is added and the mixture is heated at 60° C. for 15 minutes. The cloudy solution is cooled and is filtered in the presence of decolorising charcoal, and the filtrate is evaporated to dryness under reduced pressure (20 mm Hg, 2.7 kPa). Ethanol (10 cc) is added to the residue, the mixture is concentrated to dryness under reduced pressure (20 mm Hg, 2.7 kPa), this operation is repeated twice, the suspension of the residue in ethanol (10 cc) is then heated under reflux and cooled, and the product is filtered off and dried under reduced pressure (0.5 mm Hg, 0.07 kPa). This gives 2-carboxy-7-[2-hydroxyimino-2-(2-amino-thiazol-4-yl)-acetamido]-3-[2-(2-methyl-1,3,4-thiadiazol-5-yl)thiovinyl]-8-oxo-5-thia-1-aza-bicyclo[4.2.0]oct-2-ene (syn isomer, E-form), (0.07 g) in the form of a yellow solid.

Infra-red spectrum (KBr): characteristic bands (cm$^{-1}$) at 3600, 2200, 1770, 1660, 1630, 1530, 1390 and 950.

Proton nuclear magnetic resonance spectrum (350 MHz, DMSO $d_6$, δ in ppm, J in Hz): 2.74 (s, 3H, —CH$_3$ Het); 3.64 and 3.90 (2 d, J=18, 2H, —SCH$_2$—); 5.20 (d, J=4, 1H, H in the 6-position); 5.80 (dd, J=4 and 9, 1H, H in the 7-position); 6.65 (s, 1H, H of the thiazole). 7.08 (s broad, 2H, —NH$_2$); 7.10 and 7.20 (2 d, J=14, 2H, —CH=CH—S—); 9.46 (d, J=9, 1H, —CONH—); 11.28 (s broad, 1H, =NOH).

2-Benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) can be prepared in the following manner:

2-Benzhydryloxycarbonyl-7-(4-bromo-3-oxo-butyramido)-3-[2-(2-methyl-1,3,4-thiadiazol-5-yl)-thiovinyl]8-oxo-5-thia-1-aza-bicyclo[4.2.0]oct-2-ene (E isomer) (1.8 g) is suspended in a mixture of tetrahydrofurane (23 cc) and water (4.7 cc) at 10° C. Acetic acid (7.8 cc) is then added, the mixture is cooled to 0° C. with ice, a solution of sodium nitrite (0.187 g) in water (2.3 cc) is added and the reactin mixture is allowed to return to 20° C. in the course of 4 hours. The resulting solution is diluted with iced water (150 cc). The precipitate is filtered off and dissolved in ethyl acetate (100 cc), and the organic phase is washed with a saturated sodium bicarbonate solution (2×25 cc) and a saturated sodium chloride solution (2×25 cc), dried over magnesium sulphate, filtered and concentrated to dryness under reduced pressure (20 mm Hg, 2.7 kPa). This gives 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.5 g) in the form of a brown solid.

Infra-red spectrum (KBr): characteristic bands (cm$^{-1}$) at 1785, 1715, 1685, 1540, 1495, 1455, 1205, 950, 760, 745 and 700.

Proton nuclear magnetic resonance spectrum (350 MHz, CDCl$_3$, δ in ppm, J in Hz): 2.76 (s, 3H, —CH$_3$ Het); 4.53 (s, 2H, —COCH$_2$Br); 5.12 (d, J=4, 1H, H in the 6-position); 5.85 (dd, J=4 and 9, 1H, H in the 7-position); 7.01 (s, 1H, —COOCH<); 9.43 (d, J=9, 1H, —CONH—); 16.50 (s broad, 1H, =NOH).

A solution of bromine (5.79 g) in methylene chloride (3.53 cc) is added dropwise to a solution of diketene (3.04 g) in methylene chloride (3.53 cc) in the course of 35 minutes, at −30° C. The solution is then stirred at the same temperature for 30 minutes. One-tenth of this solution is taken and added dropwise to a stirred solution of 7-amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) (1.38 g) and bis-trimethylsilyl-acetamide (1.11 cc) in ethyl acetate (20 cc) in the course of 10 minutes at −15° C., and the solution is then stirred at the same temperature for 30 minutes. Thereafter, water (20 cc) is added and the organic phase is decanted, washed with a saturated sodium chloride solution (3×10 cc), dried over magnesium sulphate, filtered and concentrated to dryness under reduced pressure (20 mm Hg; 2.7 kPa). This gives 2-benzhydryloxycarbonyl-7-(4-bromo-3-oxo-butyramido)-3-[2-(2-methyl-1,3,4-thiadiazol-5-yl)-thiovinyl]-8-oxo-5-thia-1-aza-bicyclo[4.2.0]oct-2-ene (E isomer) (1.9 g) in the form of a brown solid.

Infra-red spectrum (KBr): characteristic bands (cm$^{-1}$) at 1780, 1720, 1680, 1535, 1490, 1450, 1250, 940, 760 and 700.

Proton nuclear magnetic resonance spectrum (350 MHz, CDCl$_3$, δ in ppm, J in Hz): 2.75 (s, 3H, —CH$_3$ of the heterocyclic ring); 3.58 and 3.84 (2 d, J=19, 2H, —SCH$_2$—); 3.75 (s, 2H, —COCH$_2$CO—); 4.03 (s, 2H, —CH$_2$Br); 5.04 (d, J=4, 1H, H in the 6-position); 5.85 (dd, J=4 and 9, 1H, H in the 7-position); 6.98 (s, 1H, —COOCH<).

7-Amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) can be prepared in the following manner:

A solution of p-toluenesulphonic acid monohydrate (8.43 g) in acetonitrile (46 cc) is added, in the course of 3 minutes, to a suspension of 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.2 g) in acetonitrile (138 cc) at 35° C. The mixture becomes homogeneous, and is kept at 38° C. for 40 minutes, after which it is poured into a solution of sodium bicarbonate (7.44 g) in water (600 cc). The mixture is extracted with ethyl acetate (300 cc, followed by 3×100 cc). The organic phases are combined, washed with a saturated sodium bicarbonate solution (100 cc) and then with a saturated sodium chloride solution (2×100 cc), dried over magnesium sulphate, filtered and concentrated to dryness under reduced pressure (20 mm Hg, 2.7 kPa). This gives 7-amino-2-benzhydryloxycarbonyl-3-[2-(2-methyl-1,3,4-thiadiazol-5-yl)thiovinyl]-8-oxo-5-thia-1-aza-bicyclo[4.2.0]oct-2-ene (E isomer) (6.8 g) in the form of a brown gummy material.

Infra-red spectrum (KBr): characteristic bands (cm$^{-1}$) at 3400, 3340, 1780, 1720, 1670, 1560, 1500, 1455, 950, 760, 745 and 700.

Proton nuclear magnetic resonance spectrum (80 MHz, CDCl$_3$, δ in ppm, J in Hz): 2.72 (s, 3H, —CH$_3$ of the heterocyclic ring); 3.46 (s broad, 2H, —SCH$_2$—); 4.77 (d, J=4, 1H, H in the 6-position); 5.00 (d, J=4, 1H, H in the 7-position); 7.00 (s, 1H, —COOCH<); 7.18 (s broad, 2H, —CH=CH—).

2-Benzhydryloxycarbonyl-7-tert.-butoxycarbonylamino-3-[2-(2-methyl-1,3,4-thiadiazol-5-yl)-thiovinyl]8-oxo-5-thia-1-aza-bicyclo[4.2.0]oct-2-ene (E isomer) can be prepared as follows:

Phosphorus trichloride (4.7 cc) is added, in the course of 5 minutes, to a solution of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) (17 g) and dimethylacetamide (10.9 cc) in methylene chloride (170 cc) at −10° C., and the mixture is kept at this temperature for one hour. It is then diluted with ethyl acetate (2,000 cc) at 0° C., and this mixture is washed with a saturated sodium bicarbonate solution (three×250 cc) and a saturated sodium chloride solution (250 cc), dried over magnesium sulphate, filtered and evaporated to dryness under reduced pressure. The residue is chromatographed on a column (column diameter: 4.5 cm; height: 37 cm) of Merck silica gel (0.063–0.2 mm) (291 g), elution being carried out with a 92.5:7.5 (by volume) mixture of methylene chloride and ethyl acetate (3 liters) and 100 cc fractions being collected. Fractions 12 to 29, containing the product, are evaporated to dryness under reduced pressure (20 mm Hg, 2.7 kPa). This gives 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.25 g) in the form of a light yellow solid.

Infra-red spectrum (KBr): characteristic bands (cm$^{-1}$) at 3370, 1790, 1715, 1700, 1520, 1160, 945, 740 and 700.

Proton nuclear magnetic resonance spectrum (80 MHz, CDCl$_3$, δ in ppm, J in Hz): 1.50 (s, 9H, (CH$_3$)$_3$C—); 2.75 (s, 3H, —CH$_3$ of the heterocyclic ring); 3.68 (s broad, 2H, —SCH$_2$—); 5.03 (d, J=4, 1H, in the 6-position); 5.28 (d, J=9, 1H, —CONH—); 5.65 (dd, J=4 and 9, 1H, H in the 7-position); 7.00 (1H, s, —COOCH<).

2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) can be prepared as follows:

A solution of 2-benzhydryloxycarbonyl-7-tert.-butoxycarbonylamino-8-oxo-5-oxide-3-(2-tosyloxyvinyl)5-thia-1-aza-bicyclo[4.2.0]oct-2-ene (E isomer) (20 g), 2-methyl-1,3,4-thiadiazoline-5-thione (4.87 g) and diisopropyl ethylamine (5.04 cc) in dimethylformamide (200 cc) is heated to 60° C. for 2 hours. The mixture is poured onto iced water (2,000 cc), the mixture is extracted with ethyl acetate (2,000 cc followed by 500 cc), and the organic phases are combined, washed with a saturated sodium bicarbonate solution (250 cc), distilled water (4×250 cc) and a saturated sodium chloride solution (250 cc), dried over magnesium sulphate, filtered in the presence of decolorising charcoal and concentrated to dryness under reduced pressure (30 mm Hg, 4 kPa) at 30° C. This gives 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) (17 g) in the form of a green-brown gummy material. This material is redissolved in ethyl acetate (60 cc), reprecipitated by means of isopropyl ether (600 cc), filtered off and dried. The expected product is thus obtained in the form of a yellow powder.

Infra-red spectrum (KBr): characteristic bands (cm$^{-1}$) at 3410, 1795, 1720, 1500, 1160, 1050, 940, 755, 740 and 700.

Proton nuclear magnetic resonance spectrum (350 MHz, CDCl$_3$, δ in ppm, J in Hz): 1.50 (s, 9H, (CH$_3$)$_3$C—); 2.75 (s, 3H, —CH$_3$ Het);

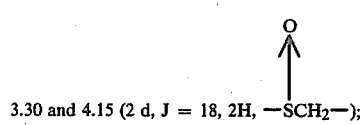

3.30 and 4.15 (2 d, J = 18, 2H, —SCH$_2$—);

4.55 (d, J=4, 1H, H in the 6-position); 5.7 to 5.9 (m, 2H, —CONH— and H in the 7-position); 6.97 (s, 1H, —COOCH<); 7.53 (d, J=16, 1H, —CH=CHS—).

REFERENCE EXAMPLE 21

7-Amino-2-carboxy-3-[2-(1-methyl-tetrazol-5-yl)thiovinyl]-8-oxo-5-thia-1-aza-bicyclo[4.2.0]oct-2-ene (E-form) (0.51 g) is dissolved in a mixture of water (10 cc), sodium bicarbonate (0.63 g) and acetone (7.5 cc). The solution is cooled to −8° C. and a solution of 4-bromo-2-methoxyimino-3-oxo-butyryl chloride, syn isomer (0.363 g) in acetone (5 cc) is added. The mixture is again stirred for 50 minutes whilst the temperature is allowed to rise from −8° C. to +5° C. The mixture is then filtered, the acetone is evaporated at 20° C. under 20 mm Hg (2.7 kPa), the residue is diluted with water (50 cc), this solution is washed with ethyl acetate (50 cc), the aqueous phase is diluted with water (100 cc), ethyl acetate (150 cc) is added and the mixture is acidified to pH 2.3 by means of a 4 N hydrochloric acid solution. The organic layer is washed with a half-saturated sodium chloride solution (100 cc), dried over sodium sulphate and concentrated to dryness at 20° C. under 20 mm Hg (2.7 kPa).

The solution of the product thus obtained, in ethanol (5 cc), is added, at 20° C., to a solution of thiourea (0.11 g) in ethanol (5 cc) and water (10 cc). The mixture is stirred for 35 minutes at 20° C., the pH is then adjusted to 6 by adding sodium bicarbonate, the mixture is acidified by adding formic acid (1 cc) and concentrated to dryness at 20° C. under 20 mm Hg (2.7 kPa), and the residue is taken up in ethanol (3×50 cc), the mixture being evaporated to dryness each time at 20° C. under 20 mm Hg. The residue is then extracted with ethanol (250 cc) under reflux, the mixture is filtered, the filtrate is concentrated to 25 cc at 20° C. under 20 mm Hg (2.7 kPa), this residue is left for 15 minutes at 5° C. and is then again filtered, and the solid is washed with ethanol (5 cc) and ether (2×10 cc). 7-[2-(2-Aminothiazol-4-yl)-2-methoxyimino-acetamido]-2-carboxy-3-[2(1-methyl-tetrazol-5-yl)-thiovinyl]-8-oxo-5-thia-1-azabicyclo[4.2.0]oct-2-ene (syn isomer, E-form) (0.28 g) is obtained in the form of a yellow powder, the characteristics of which are identical to those of the product described above in reference example 4.

7-Amino-2-carboxy-3-[2-(1-methyl-tetrazol-5-yl)thiovinyl]-8-oxo-5-thia-1-aza-bicyclo[4.2.0]oct-2-ene (E-form) can be obtained in the following manner:

A mixture of 7-amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) (3 g) in formic acid (105 cc) and water (40 cc) is treated at 50° C. for 30 minutes. It is then concentrated to dryness at 20° C. under 0.05 mm Hg (0.007 kPa), the residue is taken up in ethanol (2×100 cc), the mixture being concentrated to dryness each time at 20° C. under 20 mm Hg (2.7 kPa), and the solid obtained is triturated in ethanol (50 cc), filtered off and washed with diethyl ether (2×25 cc). 7-Amino-2-carboxy-3-[2-(1-methyl-tetrazol-5-yl)thiovinyl]-8-oxo-5-thia-1-aza-bicyclo[4.2.0]oct-2-ene (E-form) is obtained as the formate (1.5 g).

Proton nuclear magnetic resonance spectrum (350 MHz, DMSO d$_6$, δ in ppm, J in Hz): 3.64 and 3.89 (2d, J=18, 2H, —SCH$_2$—); 4.02 (s, 3H, —CH$_3$); 5.15 (d, J=4, 1H, H in the 6-position); 5.77 (dd, J=4 and 9, 1H, H in the 7-position); 6.97 and 7.13 (2d, J=16, 2H, —CH=CH—); 9.07 (d, J=9, 1H, —CONH—).

7-Amino-2-benzhydryloxycarbonyl-3-[2-(1-methyltetrazol-5-yl)-thiovinyl]-8-oxo-5-thia-1-aza-bicyclo[4.2.0]oct-2-ene (E-form) can be obtained in the following manner:

2-Benzhydryloxycarbonyl-7-tert.-butoxycarbonylamino-3-[2-(1-methyl-tetrazol-5-yl)-thiovinyl]-8-oxo-5-thia-1-aza-bicyclo[4.2.0]oct-2-ene (E-form) (8 g), dissolved in acetonitrile (80 cc) is treated with p-toluenesulphonic acid hydrate (4.9 g) under the conditions described above. After this treatment, 7-amino-2-benzhydryloxycarbonyl-3-[2-(1-methyl-tetrazol-5-yl)thiovinyl]-8-oxo-5-thia-1-aza-bicyclo[4.2.0]oct-2-ene (E-form) (5.7 g) is obtained in the form of a light brown solid.

Infra-red spectrum (KBr): characteristic bands (cm$^{-1}$) at 1775, 1710, 1495, 1455, 1210, 755 and 705.

A solution of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (13.8 g) in methylene chloride (250 cc) and dimethylacetamide (7.65 g) is treated with phosphorus tribromide (11.9 g) at −20° C. for 10 minutes. The mixture is poured into a saturated potassium bicarbonate solution (250 cc), with vigorous stirring, and the organic phase is washed with a saturated sodium chloride solution (100 cc), dried over sodium sulphate, filtered and concentrated to dryness at 20° C. under 20 mm Hg (2.7 kPa). The residue is chromatographed on a column (column diameter: 3 cm, height: 32 cm) of Merck silica gel (0.06–0.2 mm) (260 g). Elution is carried out with a 70:30 (by volume) mixture of cyclohexane and ethyl acetate (1.5 liters), 100 cc fractions being collected. Fractions 7 to 14 are concentrated to dryness at 20° C. under 20 mm Hg (2.7 kPa) and 2-benzhydryloxycarbonyl-7-tert.-butoxycarbonylamino-3-[2-(1-methyl-tetrazol-5-yl)-thiovinyl]-8-oxo-5-thia-1-azabicyclo[4.2.0]oct-2-ene (E-form) (8.5 g) is obtained in the form of a yellow powder.

Infra-red spectrum (KBr): characteristic bands (cm$^{-1}$) at 3340, 1790, 1705, 1690, 1510, 1160, 940, 730 and 700.

4-Bromo-2-methoxyimino-3-oxo-butyryl chloride, syn isomer, can be prepared in the following manner:

Dimethylformamide (2 drops) is added to a solution, at 20° C., of 2-methoxyimino-3-oxo-butyric acid, syn isomer (4.08 g) in diethyl ether (50 cc), after which oxalyl chloride (2 cc) dissolved in diethyl ether (5 cc) is added dropwise in the course of 15 minutes. The mixture is stirred for 1 hour at 20° C., dimethylformamide (1 drop) is added again and the reaction is continued for 15 minutes. The mixture is concentrated to dryness at 20° C. under 20 mm Hg (2.7 kPa) and the residue is taken up in petroleum ether (2×30 cc), the solvent being evaporated each time at 20° C. under 20 mm Hg (2.7 kPa). The 2-methoxyimino-3-oxo-butanoyl chloride, syn isomer, thus obtained is dissolved in methylene chloride (50 cc) and a 5.4 N solution of hydrogen chloride in ether (0.2 cc), and bromine (1.14 cc), are added to this solution at 20° C. The mixture is stirred for 20 hours at 20° C. and then concentrated to dryness at 20° C. under 20 mm Hg (2.7 kPa), and a brown oil (5.42 g) consisting principally of 4-bromo-2-methoxyimino-3-oxobutyryl chloride, syn isomer, is obtained.

Proton nuclear magnetic resonance spectrum (60 MHz, CDCl$_3$, δ in ppm, J in Hz): 4.25 (s, 3H, —OCH$_3$); 4.34 (s, 2H, —CH$_2$—).

2-Methoxyimino-3-oxo-butyric acid, syn isomer, can be prepared in the following manner:

A mixture of ethyl 2-methoxyimino-3-oxo-butyrate, syn isomer (52 g), ethanol (300 cc) and 1 N sodium hydroxide solution (330 cc) is heated under reflux for 15 hours. The mixture is concentrated by evaporation of ethanol at 20° C. under a pressure of 20 mm Hg (2.7 kPa) and is then extracted with methylene chloride (150 cc). The aqueous phase is treated with animal charcoal (1 g), filtered, saturated with sodium chloride, cooled to 4° C. and acidified to pH2 with 2 N hydrochloric acid in the presence of methylene chloride (200 cc). It is then re-extracted with the same solvent (2×100 cc), followed by ethyl acetate (6×200 cc). The organic phases are dried over sodium sulphate and concentrated to dryness separately at 20° C. under 20 mm Hg (2.7 kPa). The residues are combined and treated with isopropyl ether (80 cc) for 4 hours, with very vigorous stirring. The crystals obtained are filtered off and dried, and 2-methoxyimino-3-oxo-butyric acid, syn isomer (8.9 g) is thus obtained.

Infrared spectrum (CHCl$_3$): characteristic bands (cm$^{-1}$) at 3400, 2830, 2300, 1730, 1695, 1370 and 1035.

Proton nuclear magnetic resonance spectrum (60 MHz, CDCl$_3$, δ in ppm, J in Hz): 2.48 (s, 3H, CH$_3$CO—); 4.18 (s, 3H, —OCH$_3$); 11.2 (s, 1H, —COOH).

Ethyl 2-methoxyimino-3-oxo-butyrate, syn isomer, is prepared according to R. BUCOURT et al., Tetrahedron Letters, 34, 2233 (1978).

REFERENCE EXAMPLE 22

A solution of N,N-diisopropylethylamine in dry N,N-dimethylformamide (50 cc) is added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer) (E-form) (5.5 g) and of 5,6-dioxo-4-(2-hydroxyethyl)-3-thioxo-perhydro-1,2,4-triazine (2.08 g) in dry N,N-dimethylformamide (150 cc) in the course of 15 minutes, at 60° C. The reaction mixture is stirred for 3 hours at 60° C. and then diluted with ethyl acetate (600 cc). The organic phase is washed with a saturated sodium chloride solution (150 cc) and then with distilled water (3×150 cc), after which it is dried over magnesium sulphate. After filtration and concentration to dryness under reduced pressure (30 mm Hg; 4 kPa) at 40° C., the residue is chromatographed on Merck silica gel (0.04–0.06 mm) (column diameter: 6 cm, height: 30 cm), elution being carried out with a 15:85 (by volume) mixture of cyclohexane and ethyl acetate (7.5 liters) under a pressure of 40 kPa. The eluate is collected in fractions of about 100 cc. Fractions 24 to 70 are combined and concentrated to dryness under reduced pressure (30 mm Hg; 4 kPa) at 40° C. This gives 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]8-oxo-5-thia-1-aza-bicyclo[4.2.0]oct-2-ene (syn isomer, E-form) (3.31 g) in the form of a light yellow solid.

Rf=0.33 [silica gel chromatographic plate, eluant: a 10:90 (by volume) mixture of cyclohexane and ethyl acetate].

Infra-red spectrum (CHBr$_3$): characteristic bands in cm$^{-1}$ at 3380, 1785, 1715, 1680, 1585, 1520, 1495, 1450, 1050, 940, 755 and 740.

Proton nuclear magnetic resonance spectrum (350 MHz, CDCl$_3$, δ in ppm, J in Hz): 3.44 and 3.60 (AB, J=18, 2H, —SCH$_2$—); 3.81 (mf, 2H, —CH$_2$OH); 4.00 (s, 3H, =NOCH$_3$); 5.00 (d, J=4, 1H, H in the 6-position); 5.90 (dd, J=4 and 9, 1H, H in the 7-position); 6.70 (s, 1H, H of the thiazole); 6.81 (d, J=15, 1H, —CH=CH—S—); 6.90 (s, 1H, —CH (C$_6$H$_5$)$_2$); 5.72 to 7.6 (mf, aromatics, —CONH—, —CH=CHS—, (C$_6$H$_5$)$_3$CNH—).

A solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.5 g), in dry tetrahydrofurane (250 cc) is cooled to −50° C. and treated with chlorosulphonyl isocyanate (11 cc). The mixture is stirred for 55 minutes, whilst allowing the temperature to rise slowly to −5° C., and a saturated sodium bicarbonate solution (150 cc) and ethyl acetate (250 cc) are then added. The aqueous phase is extracted with ethyl acetate (100 cc) and the combined organic extracts are washed with a saturated sodium chloride solution (2×100 cc) and then dried over magnesium sulphate and filtered. After evaporation of the solvent under reduced pressure (30 mm Hg; 4 kPa) at 40° C., and drying, 2-benzhydryloxycarbonyl-3-{2-[4-(2-carbamyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)acetamido]-8-oxo-5-thia-1-aza-bicyclo[4.2.0]oct-2-ene (syn isomer, E-form) (2.6 g) is obtained in the form of a yellow powder.

Infra-red spectrum (KBr): characteristic bands in cm$^{-1}$ at 3350, 2600, 1785, 1720, 1685, 1530, 1490, 1450, 755 and 700.

Proton nuclear magnetic resonance spectrum (350 MHz, DMSO d$_6$, δ in ppm, J in Hz): 3.30 and 3.64 (2d, J=18, 2H, —SCH$_2$—); 3.84 (s, 3H, =NOCH$_3$); 4.03 and 4.11 (2t, J=5, 2×2H, >NCH$_2$CH$_2$OCO—); 5.24 (d, J=4, 1H, H in the 6-position); 5.77 (dd, J=4 and 9, 1H, H in the 7-position); 6.71 (s, 1H, H of the thiazole); 6.94 (s, 1H, —CH(C$_6$H$_5$)$_2$); 6.93 and 7.02 (AB, J=16, 2H, —CH=CH—S—); 7.15 to 7.60 (Mt, 25H, aromatics); 8.25 to 8.80 (2s, 2H, —OCONH$_2$); 9.60 (d, J=9, 1H, —CONH-C$_7$);

12.60 (s, 1H, —N=C—OH or =N—NHC— of the triazine).
              |              ‖
                             O A solution of 2-benzhydryloxycarbonyl-3-{-2-[4-(2-carbamyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.6 g) in formic acid (47 cc) is diluted with distilled water (20 cc) and the mixture is heated at 50° C. for 20 minutes and then diluted with a further amount of distilled water (27 cc); after filtering off the insoluble matter, the filtrate is concentrated to dryness under reduced pressure (5 mm Hg; 0.67 kPa) at 30° C. The residue is triturated with anhydrous ethanol (50 cc), which is then evaporated under reduced pressure (30 mm Hg; 4 kPa) at 40° C. This operation is repeated twice more, and the residue is then taken up in ethanol (40 cc), filtered off, washed with ether (2×50 cc) and dried. 7-[2-(2-Amino-thiazol-4-yl)-2-methoxyimino-acetamido]3-{2-[4-(2-carbamyloxyethyl)-5,6-dioxo-1,4,5,6-tetrahydro-1,2,4-triazin-3-yl]-thiovinyl}-2-carboxy-8-oxo-5-thia-1-aza-bicyclo[4.2.0]oct-2-ene (syn isomer, E-form) (1.5 g) is obtained in the form of a cream-coloured powder.

Infra-red spectrum (KBr): characteristic bands in cm$^{-1}$ at 3550, 2200, 1770, 1710, 1680, 1050 and 940.

Proton nuclear magnetic resonance spectrum (350 MHz, DMSO d$_6$, δ in ppm, J in Hz): 3.62 and 3.82 (2d, J=18, 2H, —SCH$_2$—); 3.86 (s, 3H, =NOCH$_3$); 4.06 and 4.15 (2t, J=5, 2×2H, >NCH$_2$CH$_2$O—); 5.21 (d, J=9, 1H, H in the 6-position); 5.78 (dd, J=4 and 9, 1H, H in the 7-position); 6.50 (s broad, 2H, —OCONH$_2$); 6.75 (s, 1H, H of the thiazole); 6.92 and 7.08 (2d, J=16, 2H, —CH=CH—S—); 7 to 7.50 (s broad, 2H, —NH$_2$ of the thiazole); 9.66 (d, J=9, 1H, —CONH-C$_7$);

12.62 (s, 1H, —N=C—OH or =HNH—C—).
              |              ‖
                             O

REFERENCE EXAMPLE 23

5,6-Dioxo-4-(2-hydroxyethyl)-perhydro-1,2,4-triazine (7 g) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (18 g) (obtained as described in reference example 1c) in dry N,N-dimethylformamide (490 cc) at 65° C., after which a solution of N,N-diisopropylethylamine (2.32 g) in dry N,N-dimethylformamide (160 cc) is introduced dropwise in the course of 10 minutes. The reaction mixture is stirred for 3 hours at 65° C. and then diluted with ethyl acetate (2 liters) and washed with distilled water (4×500 cc). The organic phase is dried over magnesium sulphate and concentrated under reduced pressure (35 mm Hg; 4.7 kPa) at 40° C. The residue is chromatographed on Merck silica gel (0.2–0.04 mm) (column diameter: 4 cm) (200 g), elution being carried out with a 20:80 (by volume) mixture of cyclohexane and ethyl acetate and fractions of about 250 cc being collected. Fractions 6 to 41 are concentrated to dryness under reduced pressure (35 mm Hg; 4.7 kPa) at 40° C. 2-Benzhydryloxycarbonyl-3-{2-[5,6-dioxo-4-(2-hydroxyethyl)-1,4,5,6-tetrahydro-1,2,4-triazin-3-yl]thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (17.16 g) is obtained in the form of a light brown powder.

Infra-red spectrum (KBr): characteristic bands in cm$^{-1}$ at 1800, 1720, 1685, 1525, 1495, 1450, 1045, 945, 755 and 700.

Proton nuclear magnetic resonance spectrum (350 MHz, DMSO d$_6$, δ in ppm, J in Hz): 3.60 and 4.28 (2d, J=17.5, 2×1H, —S(O)CH$_2$-); 3.57 and 3.88 (2 Mt, 2×2H, >NCH$_2$CH$_2$OH); 3.84 (s, 3H, =NOCH$_3$); 5.04 (d, J=4, 1H, H in the 6-position); 5.84 (dd, J=4 and 9, 1H, H in the 7-position); 6.77 (s, 1H, H of the thiazole); 6.96 (s, 1H, —CH(C$_6$H$_5$)$_2$); 6.96 and 7.09 (AB, J=16, 2×1H, —CH=CH—S—); 7.15 to 7.60 (Mt, 25H, aromatics);

8.72 (s, 1H, =NN=C—OH or =NNH—C—)
              |              ‖
                             O

Triethylamine (0.38 cc) and 4-N,N-dimethylaminopyridine (0.05 g), followed by a solution of formic anhydride (4.9 millimols) in methylene chloride (10 cc) (prepared according to G. A. OLAH et al., Angew. Chem. 91 649 (1979)) are added to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in dry tetrahydrofurane (100 cc), cooled to −10° C. The reaction mixture is stirred for 3 hours at about 20° C. and is then filtered, diluted with ethyl acetate (450 cc) and washed successively with 0.2 N hydrochloric acid (50 cc), distilled water (100 cc), a saturated sodium bicarbonate solution (100 cc) and a saturated sodium chloride solution (100 cc). The organic phase is dried over magnesium sulphate, filtered and concentrated under reduced pressure (30 mm Hg; 4 kPa) at 40° C. Crude 2-benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.7 g) is obtained in the form of a brown powder.

Rf=0.68 [silica gel chromatographic plate; eluant: an 80:20 (by volume) mixture of ethyl acetate and methanol].

The crude product (3.35 g) obtained above is dissolved in dry methylene chloride (50 cc). N,N-dimethylacetamide (1.42 cc) is added, the mixture is then cooled to −10° C. and phosphorus trichloride (0.67 cc) is introduced. The reaction mixture is stirred for 1 hour at about −10° C. and then treated with N,N-dimethylacetamide (0.2 cc) and phosphorus trichloride (0.1 cc). After 20 minutes at −10° C., the reaction mixture is diluted with ethyl acetate (500 cc) and a saturated sodium bicarbonate solution (150 cc). The organic phase is decanted, washed with distilled water (2×50 cc) and with a saturated sodium chloride solution (100 cc), dried over magnesium sulphate and filtered. Evaporation of the solvent under reduced pressure (35 mm Hg; 4.7 kPa) at 40° C. gives a residue (3.6 g) which is chromatographed on a column (column diameter: 5 cm, height: 30 cm) of Merck silica gel (0.063–0.04 mm), elution being carried out, under a pressure of 40 kPa, with a 40:60 (by volume) mixture of cyclohexane and ethyl acetate (4 liters), and fractions of about 50 cc being collected. Fractions 38 to 76 are evaporated to dryness under reduced pressure (35 mm Hg; 4.7 kPa) at 40° C. 2-Benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.3 g) is obtained in the form of a light yellow powder.

Proton nuclear magnetic resonance spectrum (350 MHz, DMSO d6, δ in ppm, J in Hz): 3.65 and 3.88 (AB, J=18, 2H, —SCH2—); 3.84 (s, 3H, =NOCH3); 4.10 and 4.32 (2t, J=5, 2×2H, >NCH2CH2OCHO); 5.21 (d, J=4, 1H, H in the 6-position); 5.75 (dd, J=4 and 9, 1H, H in the 7-position); 6.72 (s, 1H, H of the thiazole); 6.95 (s, 1H, —CH(C6H5)2); 6.93 and 7.02 (AB, J=16, 2H, —CH=CH—S—); 7.1 to 7.5 (Mt, 25H, aromatics); 8.80 (s broad, 1H, (C6H5)3CNH—); 9.60 (d, J=9, 1H, —CONH—C7);

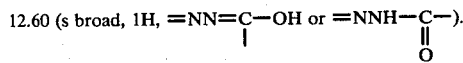

A solution of 2-benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.25 g) in formic acid (15 cc) is diluted with distilled water (4 cc) and heated for 25 minutes at 50° C., after which it is diluted with more distilled water (11 cc). After filtering off the insoluble matter, the filtrate is concentrated under reduced pressure (5 mm Hg; 0.67 kPa) at 30° C.; the residue is triturated in ethanol (50 cc), which is evaporated under reduced pressure (35 mm Hg; 4.7 kPa) at 40° C. This latter operation is repeated 4 times, after which the solid residue is taken up in ethanol (20 cc), filtered off, washed with diisopropyl ether (2×25 cc) and dried. The product is dissolved in pure formic acid (10 cc) and the solution is heated for 1 hour 30 minutes at 45° C. and then concentrated to dryness under reduced pressure (5 mm Hg; 0.67 kPa) at 40° C. The residue is triturated in anhydrous ethanol (30 cc) and the latter is then evaporated under reduced pressure (30 mm Hg; 4 kPa) at 40° C.; this operation is repeated twice more. 7-[2-(2-Amino-thiazol-4-yl)-2-methoxyimino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]-oct-2-ene (syn isomer, E-form) (0.54 g) is obtained in the form of a yellow powder.

Infra-red spectrum (KBr): characteristic bands in cm⁻¹ at 3400, 3200, 2200, 1775, 1710, 1680, 1530, 1040 and 945.

Proton nuclear magnetic resonance spectrum (350 MHz, DMSO d6, δ in ppm, J in Hz): 3.62 and 3.82 (AB, J=18, 2H, —SCH2—); 3.84 (s, 3H, =NOCH3); 4.15 and 4.32 (2t, J=5, 2×2H, >NCH2CH2—OCHO); 5.21 (d, J=4, 1H, H in the 6-position); 5.78 (dd, J=4 and 9, 1H, H in the 7-position); 6.73 (s, 1H, H of the thiazole); 6.89 and 7.10 (2d, J=16, 2H, —CH=CH—S—); 7.16 (s, broad, 2H, —NH2); 8.18 (s, 1H, HCOO—); 9.59 (d, J=9, 1H, —CONH—C7);

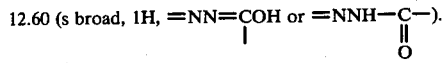

REFERENCE EXAMPLE 24

Sodium bicarbonate (0.64 g) is added to a solution of 2-benzhydryloxycarbonyl-3-{2-[4-(2-hydroxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.05 g) (obtained as described in reference example 2) in dry tetrahydrofurane (25 cc) at 22° C., after which a solution of acetic anhydride (0.4 cc) in dry tetrahydrofurane (5 cc) is introduced dropwise in the course of 15 minutes. 4-Dimethylaminopyridine (0.05 g) dissolved in dry tetrahydrofurane (1 cc) is then added and the reaction mixture is stirred for 10 minutes at 25° C. It is then diluted with distilled water (50 cc) and ethyl acetate (120 cc). The organic phase is decanted and washed successively with 0.5 N hydrochloric acid (80 cc), a saturated sodium bicarbonate solution (80 cc) and a saturated sodium chloride solution (100 cc). After drying over magnesium sulphate and filtering, the solution is concentrated to dryness under reduced pressure (30 mm Hg, 4 kPa) at 40° C. A crude product (2.05 g) is obtained in the form of a yellow powder.

The crude product (2.5 g) obtained as above is chromatographed on a column (column diameter: 4, cm height: 30 cm) of Merck silica (0.04–0.06 m), elution being carried out with a 40:60 (by volume) mixture of cyclohexane and ethyl acetate (3 liters) under a pressure of 40 kPa, and 100 cc fractions being collected. Fractions 11 to 26 are concentrated to dryness under reduced pressure (30 mm Hg; 4 kPa) at 40° C. 3-{2-[4-(2-Acetoxyethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.84 g) is obtained in the form of a light yellow froth.

Infra-red spectrum (CHBr3): characteristic bands in cm⁻¹ at 3400, 2820, 1790, 1720, 1685, 1590, 1495, 1450, 1050, 940, 760 and 740.

Proton nuclear magnetic resonance spectrum (350 MHz, DMSO d6, δ in ppm, J in Hz); 1.97 (s, 3H, CH3CO2—); 3.63 and 3.88 (AB, J=18, 2H, —SCH2—); 3.83 (s, 3H, =NOCH3); 4.06 (t, J=5, 2H, >N—CH2CH2OCOCH3); 4.23 (t, J=5, 2H, >NCH2—CH2OCOCH3); 5.21 (d, J=4, 1H, H in the 6-position); 5.76 (dd, J=4 and 9, 1H, H in the 7-position); 6.71 (s, 1H, H of the thiazole); 6.91 (d, J=16, 1H, —CH=CH—S—); 6.93 (s, 1H, —CH(C6H5)2); 7.0 (d, J=16, 1H, —CH=CH—S—); 7.2 to 7.5 (mt, 25H, aromatics); 9.60 (d, J=9, 1H, —CONH—);

12.58 (s broad, 1H, =NN=C—OH or =NNH—C—).

3-{2-[4-(2-Acetoxyethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form (1.8 g) is dissolved in formic acid (40 cc). After addition of distilled water (15 cc), the reaction mixture is heated at 60° C. for 30 minutes and then filtered and concentrated to dryness under reduced pressure (5 mm Hg; 0.67 kPa) at 40° C. The residue is triturated in ethanol (50 cc), which is then evaporated under reduced pressure (30 mm Hg; 4 kPa) at 40° C.

This operation is repeated twice more. The residue is dissolved in boiling ethanol (150 cc); after filtering the hot solution, the filtrate is allowed to cool and is kept for 2 days at 5° C. The solid is filtered off, washed with diethyl ether (20 cc) and then dried. 3-{2-[4-(2-Acetoxyethyl)-5,6-dioxo-1,4,5,6-tetrahydro-1,2,4-triazin-3-yl]-thiovinyl}-7-[2-(2-aminothiazol-4-yl)-2-methoxyimino-acetamido]-8-oxo-5-thia-1-aza-bicyclo[4.2.0]oct-2-ene (syn isomer, E-form) (0.65 g) is obtained in the form of a pale yellow powder.

Infra-red spectrum (KBr): characteristic bands in cm$^{-1}$ at 3320, 3220, 3150, 2300, 1780, 1740, 1720, 1680, 1636, 1590, 1535, 1375, 1210, 1040 and 950.

Proton nuclear magnetic resonance spectrum (350 MHz, DMSO d$_6$, δ in ppm, J in Hz): 2.0 (s, 3H, CH$_3$CO$_2$—); 3.63 and 3.82 (AB, J=18, 2H, —SCH$_2$—); 3.85 (s, 3H, =NOCH$_3$); 4.08 (t, J=5, 2H, >NCH$_2$CH$_2$OCOCH$_3$); 4.25 (t, J=5, 2H, >NCH$_2$CH$_2$OCOCH$_3$); 5.20 (d, J=4, 1H, H in the 6-position); 5.78 (dd, J=4 and 9, 1H, H in the 7-position); 6.73 (s, 1H, H of the thiazole); 6.90 (d, J=16, 1H, —CH=CH—S—); 7.12 (d, J=16, 1H, —CH=CHS—); 7.18 (s broad, 2H, —NH$_2$); 9.60 (s, J=9, 1H, —CONH—C$_7$);

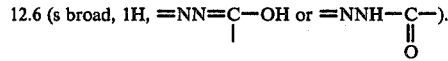

12.6 (s broad, 1H, =NN=C—OH or =NNH—C—).

REFERENCE EXAMPLE 25

A solution of N,N'-dicyclohexylcarbodiimide (0.72 g) in methylene chloride (20 cc) is added, in the course of 5 minutes, to N-tert.-butoxycarbonylglycine (1.12 g), dissolved in dry methylene chloride (30 cc), at 0° C. The reaction mixture is stirred for 30 minutes at a temperature of between 0° and 5° C. and is then filtered rapidly. The filtrate is added dropwise, in the course of 10 minutes, to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) (as obtained in reference example 23) in dry tetrahydrofuran (70 cc), which is cooled to 0° C. The reaction mixture is stirred for 45 minutes at 20° C. and is then diluted with ethyl acetate (500 cc) and washed successively with distilled water (200 cc), a saturated sodium bicarbonate solution (100 cc), distilled water (100 cc) and a saturated sodium chloride solution (50 cc). The organic phase is dried over sodium sulphate, filtered and concentrated under reduced pressure (30 mm Hg; 4 kPa) at 40° C. Crude 2-benzhydryloxycarbonyl-3-{2-[2-(2-N-tert.-butoxycarbonylglycyloxy-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2ene (syn isomer, E-form) (3.45 g) is obtained in the form of a brown powder.

This crude product (3.3 g) is dissolved in dry methylene chloride (45 cc). The solution, cooled to −10° C., is treated with N,N-dimethylacetamide (1.24 cc) and then with phosphorus trichloride (0.6 cc). After 1 hour 30 minutes at −10° C., the reaction mixture is diluted with ethyl acetate (600 cc) and washed successively with a saturated sodium bicarbonate solution (100 c), distilled water (2×100 cc) and a saturated sodium chloride solution (2×200 cc). After drying over sodium sulphate and filtering, the organic solution is concentrated to dryness under reduced pressure (30 mm Hg; 4 kPa) at 40° C. The residue is chromatographed on a column (column diameter: 4 cm, height: 30 cm) of Merck silica gel (0.04-0.62 mm), elution being carried out under a pressure of 40 kPa with a 10:90 (by volume) mixture of cyclohexane and ethyl acetate (1.5 liters) and 50 cc fractions being collected. Fractions 7 to 22 are combined and concentrated to dryness under reduced pressure (30 mm Hg; 4 kPa) at 30° C. 2-Benzhydryloxycarbonyl-3-{2-[4-(N-2-tert.-butoxycarbonylglycyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.44 g) is obtained in the form of a yellow powder.

Infra-red spectrum (KBr): characteristic bands in cm$^{-1}$ at 1785, 1715, 1685, 1530, 1495, 1445, 1160, 1030, 945, 755 and 700.

Proton nuclear magnetic resonance spectrum (350 MHz, DMSO d$_6$, δ in ppm, J in Hz): 1.36 (s, 9H, (CH$_3$)$_3$CO—); 3.25 and 3.86 (2d, J=18, 1H, —SCH$_2$—); 3.65 (d, J=9, 2H, —COCH$_2$NH—); 3.84 (s, 3H, =NOCH$_3$); 4.05 and 4.26 (2t, J=5, 2×2H, >NCH$_2$CH$_2$OCO—); 5.23 (d, J=4, 1H, H in the 6-position); 5.50 (d, J=9, 1H, —CH$_2$NHCO—); 5.76 (dd, J=4 and 9, 1H, H in the 7-position); 6.71 (s, 1H, H of the thiazole); 6.91 (s, 1H, —CH(C$_6$H$_5$)$_2$); 6.90 and 7 (2d, J=16, 2H, —CH=CH—S—); 7.15 to 7.5 (mt, 25H, aromatics); 8.78 (s broad, 1H, (C$_6$H$_5$)$_3$CNH—); 9.60 (d, J=9, 1H, —CONH—);

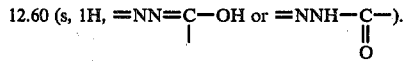

12.60 (s, 1H, =NN=C—OH or =NNH—C—).

A solution of 2-benzhydryloxycarbonyl-3-{2-[4-(N--2-tert.-butoxycarbonylglycyloxy-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.5 g) in formic acid (15 cc) is diluted with distilled water (4 cc) and heated at 50° C. for 30 minutes, after which it is diluted with distilled water (11 cc). After filtering off the insoluble matter, the filtrate is evaporated to dryness under reduced pressure (5 mm Hg; 0.67 kPa) at 30° C. The residue is triturated with dry ethanol (60 cc), which is then evaporated under reduced pressure (30 mm Hg; 4 kPa) at 40° C. This latter operation is repeated 3 times in total, after which the solid residue is taken up in isopropyl ether (50 cc), filtered off, washed with ethyl ether (3×20 cc) and dried. The formate of 7-[2-(2-amino-thiazol-4-yl)-2-methoxyimino-acetamido]-2-carboxy-3-{2-[5,6-dioxo-4-(2-glycyloxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.8 g) is obtained in the form of a light yellow powder.

Infra-red spectrum (KBr): characteristic bands in cm$^{-1}$ at 3550, 2200, 1755, 1705, 1675, 1580, 1530 and 1035.

Proton nuclear magnetic resonance spectrum (350 MHz, DMSO d$_6$, δ in ppm, J in Hz): 3.51 and 3.62 (AB, J=18, 2H, —SCH$_2$—); 3.72 (mt, 2H, —COCH$_2$NH$_2$); 3.82 (s, 3H, =NOCH$_3$); 4.12 and 4.40 (2 Mt, 2×2H, >NCH$_2$CH$_2$OCO—); 5.10 (d, J=4, 1H, H in the 6-position); 5.67 (dd, J=4 and 9, 1H, H in the 7-position); 6.44 (d, J=16, 1H, —CH=CH—S—); 6.72 (s, 1H, H of the thiazole); 7.18 (s broad, 3H, —NH$_3^+$ of the thiazole); 8.12 (s, 1H, HCO$_2$—); 9.56 (d, J=9, 1H, —CONH—C$_7$).

REFERENCE EXAMPLE 26

A solution of N,N'-dicyclohexylcarbodiimide (0.5 g) in methylene chloride (10 cc) is added dropwise, in the course of 10 minutes, to a solution, cooled to +5° C., of N-tert.-butoxycarbonylglycine (0.84 g) in methylene chloride (20 cc). The mixture is stirred for 30 minutes at 5° C. and is filtered, and the filtrate is poured dropwise, in the course of 20 minutes, into a solution, cooled to 5° C., of 3-{2-[4-(2-aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.04 g), triethylamine (0.34 cc) and dimethylaminopyridine (50 mg) in methylene chloride (100 cc). The temperature is allowed to rise to 20° C. whilst stirring, and after 1 hour the mixture is concentrated to about 30 cc under 20 mm Hg (2.7 kPa) at 20° C. The residue is diluted with ethyl acetate (70 cc) and this mixture is washed with a saturated sodium bicarbonate solution (2×50 cc) and water (3×50 cc), dried over sodium sulphate, filtered and concentrated to dryness under 20 mm Hg (2.7 kPa) at 20° C. The residue is taken up in tetrahydrofurane (10 cc) and the mixture is left at 4° C. for 48 hours. It is then filtered and the filtrate is concentrated to dryness under 20 mm Hg (2.7 kPa) at 20° C.; the residue is triturated in diethyl ether (50 cc), filtered off and dried. 2-Benzhydryloxycarbonyl-3-{2-[4-(2-tert.-butyoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (1.72 g) is obtained in the form of a brown powder.

Infra-red spectrum (KBr): characteristic bands in cm$^{-1}$ at 3380, 1800, 1710, 1690, 1590, 1515, 1495, 1450, 1210, 1165, 1050, 1040, 945, 755 and 700.

Proton nuclear magnetic resonance spectrum (350 MHz, DMSO d$_6$, δ in ppm, J in Hz): 1.35 (s, 9H, —C(CH$_3$)$_3$); 3.33 (m, 2H, >N—CH$_2$C$\underline{H}_2$NH—); 3.54 (t, J=5, 2H, >NC$\underline{H}_2$CH$_2$NH—); 3.63 (d, J=5, 2H, —COC$\underline{H}_2$NH—); 3.6 and 4.3 (2d, J=18, 2H, —SCH$_2$—); 3.86 (s, 3H, =NOCH$_3$); 5.06 (d, J=4, 1H, H$_6$); 5.86 (dd, J=4 and 9, 1H, H$_7$); 6.78 (s, 1H, H of the thiazole); 6.85 and 7.12 (2d, J=16, 2H, —CH=CH—); 6.97 (s, 1H, —COOC$\underline{H}$<); 7.18 (s, 1H, >N$\underline{H}$ of the thiazole); 8.0 (t, J=5, 1H, —COCH$_2$N$\underline{H}$—); 8.75 (s broad, 1H, >NCH$_2$CH$_2$N$\underline{H}$—); 9.03 (d, J=9, 1H, —CONH—); 12.6 (s, 1H, —NH— of the triazine).

A solution of 2-benzhydryloxycarbonyl-3-{2-[4-(2-tert.-butoxycarbonylglycylamino-ethyl)-5,6-dioxo-1,4,5,6-tetrahydro-1,2,4-triazin-3-yl]-thiovinyl}-2-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (1.65 g) in methylene chloride (30 cc) and dimethylacetamide (0.56 cc) is treated with phosphorus trichloride (0.5 cc) at −10° C. for 1 hour 30 minutes. The mixture is diluted with methylene chloride (150 cc), washed with a half-saturated sodium bicarbonate solution (2×100 cc) and a half-saturated sodium chloride solution (2×200 cc), dried over sodium sulphate, filtered and concentrated to dryness under 20 mm Hg (2.7 kPa) at 20° C.

The product is chromatographed on a column (column diameter: 2 cm, height: 34 cm) of Merck silica gel (0.6–0.2 mm) (50 g). Elution is carried out with a 50:50 (by volume) mixture of cyclohexane and ethyl acetate (250 cc) and with a 25:75 (by volume) mixture (500 cc), and with ethyl acetate (1.5 liters), 60 cc fractions being collected. Fractions 9 to 24 are concentrated to dryness and 2-benzhydryloxycarbonyl-3-{2-[4-(tert.-butoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.78 g) is obtained in the form of a cream-coloured froth.

Infra-red spectrum (KBr): characteristic bands in cm$^{-1}$ at 3400, 3300, 1785, 1710, 1680, 1590, 1530, 1495, 1450, 1200, 1165, 1050, 950, 755 and 700.

Proton nuclear magnetic resonance spectrum (350 MHz, DMSO d$_6$, δ in ppm, J in Hz): 1.38 (s, 9H, —C(CH$_3$)$_3$); 3.30 (m, 2H, >NCH$_2$C$\underline{H}_2$NH—); 3.45 (d, J=5, —COCH$_2$NH—); 3.65 and 3.88 (2d, J=16, 2H, —SCH$_2$—); 3.85 (t, J=6, 2H, >NC$\underline{H}_2$CH$_2$NH—); 3.85 (s, 3H, =NOCH$_3$); 5.24 (d, J=4, H$_6$); 5.76 (dd, J=4 and 9, H$_7$); 6.92 and 7.00 (2d, J=16, —C$\underline{H}$=C$\underline{H}$—); 6.93 (s, —COOCH<); 7.79 (t, J=5, 1H, —CH$_2$N$\underline{H}$ CO—) 8.80 (s, —N$\underline{H}$— of the thiazole); 9.59 (d, J=9, —CONH—); 12.53 (s, —NH— of the triazine).

A solution of 2-benzhydryloxycarbonyl-3-{2-[4-(2-tert.-butoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.73 g) in a mixture of formic acid (15 cc) and water (15 cc) is treated at 50° C. for 30 minutes. It is then concentrated to dryness under 0.05 mm Hg (0.007 kPa) at 50° C., and the residue is taken up in ethanol (3×150 cc), the mixture being evaporated each time under 20 mm Hg (2.7 kPa) at 20° C. Thereafter, the solid is taken up in ethanol (25 cc) at 45° C., and the mixture is stirred for 30 minutes, allowed to cool and filtered. After drying, 7-[2-(2-amino-thiazol-4-yl)-2-methoxyimino-acetamido]-2-carboxy-3-{2-[5,6-dioxo-4-(2-glycylaminoethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) formate (0.39 g) is obtained in the form of a yellow powder.

Infra-red spectrum (KBr): characteristic bands in cm$^{-1}$ at 3700 to 2200, 1765, 1705, 1675, 1610, 1585, 1530, 1035 and 930.

Proton nuclear magnetic resonance spectrum (350 MHz, DMSO d$_6$, δ in ppm, J in Hz): 3.2 to 3.6 (m, 8H, —SCH$_2$—, >NCH$_2$CH$_2$N< and —COCH$_2$N<); 3.85 (s, =NOCH$_3$); 5.12 (d, J=4, H$_6$); 5.67 (dd, J=4 and 9, H$_7$); 6.35 (d, J=16, —C$\underline{H}$=CHS—); 6.73 (s, H of the thiazole); 7.15 (s broad, —NH$_2$); 8.2 (s, H of the formate); 8.6 (m, —CH$_2$N$\underline{H}$CO—); 9.54 (d, J=9, —NH-CO—).

3-{2-[4-(2-Aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) can be obtained in the following manner:

A solution of hydrated p-toluenesulphonic acid (1.14 g) in acetonitrile (15 cc) is added dropwise, in the course of 10 minutes, to a solution, at 40° C., of 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5- thia-1-aza-bicyclo[4.2.0]oct-2-ene (syn isomer, E-form) (3.36 g) (prepared as described in Example 28) in acetonitrile (45 cc). The mixture is stirred for 2 hours at 40° C. and is then allowed to cool. A half-saturated sodium bicarbonate solution (100 cc) is introduced, and the batch is stirred vigorously for 1 hour and then filtered. After drying 3-{2-[4-(2-aminoethyl)-5,6-dioxo-1,4,5,6-tetrahydro-1,2,4-triazin-3-yl]-thiovinyl}2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.73 g) is obtained in the form of a brown powder.

Infra-red spectrum (KBr); characteristic bands in cm$^{-1}$ at 3250 to 2300, 1800, 1715, 1685, 1595, 1520, 1500, 1450, 1215, 1180, 1040, 945, 755 and 700.

Proton nuclear magnetic resonance spectrum (350 MHz, DMSO d$_6$, δ in ppm, J in Hz); 3.08 (m, 2H, >N—CH$_2$CH$_2$—NH$_2$); 3.63 and 4.30 (2d, J=18, 2H, —SCH$_2$—); 3.85 (s, 3H, =NOCH$_3$); 4.09 (t, J=6, 2H, >NCH$_2$CH$_2$NH$_2$); 5.07 (d, J=4, H$_6$); 5.87 (dd, J=4 and 9, H$_7$); 6.80 (s, H of the thiazole); 6.95 (s, —COOCH<); and 7.07 and 7.13 (2d, J=16, —CH=CH—); 9.0 (d, J=9, —NHCO—); 12.62 (s broad, —NH— of the triazine).

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10.04 g), dimethylformamide (200 cc), 4-(2-tert.-butoxycarbonylamino-ethyl)-5,6-dioxo-3-thioxo-perhydro-1,2,4-triazine (3.46 g) and N,N-diisopropylethylamine (2.1 cc) is stirred at 60° C. for 3 hours 30 minutes. It is then diluted with ethyl acetate (800 cc) and this mixture is washed with a half-saturated sodium chloride solution (400 cc), dried over sodium sulphate, filtered and concentrated to dryness at 30° C. under 20 mm Hg (2.7 kPa). The product, dissolved in methylene chloride (50 cc), is chromatographed on a column (column diameter: 3 cm, height: 30 cm) of Merck silica gel (0.06–0.2 mm) (100 g). Elution is carried out with a 50:50 (by volume) mixture of cyclohexane and ethyl acetate (500 cc), a 25:75 (by volume) mixture of cyclohexane and ethyl acetate (500 cc) and ethyl acetate alone (1.5 liters), 125 cc fractions being collected. Fractions 9 to 21 are concentrated to dryness (under 20 mm Hg; 2.7 kPa, at 20° C.) and 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)acetamido]-8-oxo-5-oxide-5-thia-1-aza-bicyclo[4.2.0]oct-2-ene (syn isomer, E-form) (7.69 g) is obtained in the form of a brown froth.

Infra-red spectrum (KBr): characteristic bands (cm$^{-1}$) at 3380, 1795, 1715, 1690, 1590, 1520, 1495, 1445, 1205, 1160, 1040, 940, 750 and 700.

Proton nuclear magnetic resonance spectrum (350 MHz, CDCl$_3$, δ in ppm, J in Hz): 1.36 (s, 9H, —C(CH$_3$)$_3$); 3.30 and 4.65 (2d, J=18, 2H, —SCH$_2$—); 3.38 (m, 2H, —CH$_2$NHCO—); 3.95 (m, 2H, —CH$_2$—CH$_2$NH—); 4.0 (s, 3H, CH$_3$OH=); 5.20 (d, J=4, H$_6$); 6.03 (dd, J=4 and 9, H$_7$); 6.70 (s, H of the thiazole); 6.86 (d, J=16, —CH=CHS—); 6.94 (s, —COOCH<); 11.7 (s broad, —NH— of the triazine).

4-(2-tert.-Butoxycarbonylamino-ethyl)-5,6-dioxo-3-thioxo-perhydro-1,2,4-triazine can be prepared in the following manner:

4-(2-tert.-Butoxycarbonylamino-ethyl)-thiosemicarbazide (9.37 g) is added to a solution of sodium (0.92 g) in methanol (40 cc) at 20° C., and diethyl oxalate (5.4 g) is then introduced dropwise in the course of 10 minutes. The mixture is heated under reflux for 3 hours. It is allowed to cool, water (100 cc) is added, concentrated hydrochloric acid (3 cc) is introduced dropwise, the mixture is extracted with ethyl acetate (2×100 cc) and the extract is washed with a saturated sodium chloride solution (2×50 cc), dried over sodium sulphate, filtered and concentrated to dryness at 20° C. under 20 mm Hg (2.7 kPa). The residue is taken up in methylene chloride (65 cc), the crystallisation is started, the batch is left for 2 hours at 20° C. and then filtered, and white crystals (4.59 g) of 4-(2-tert.-butoxycarbonylamino-ethyl)-5,6-dioxo-3-thioxo-perhydro-1,2,4-triazine, melting at 160° C., are obtained.

Infra-red spectrum (KBr): characteristic bands (cm$^{-1}$) at 3380, 3150, 1685, 1640, 1545 and 1370.

Proton nuclear magnetic resonance spectrum (80 MHz, DMSO, δ in ppm, J in Hz): 1.45 (s, 9H, —C(CH$_3$)$_3$); 3.32 (q, J=5, 2H, —CH$_2$CH$_2$NH—); 4.38 (t, J=5, 2H, —CH$_2$—CH$_2$—NH—); 6.72 (d, J=5, 1H, —CH$_2$CH$_2$NH—); 12.3 (s, broad, 1H, —NH— of the triazine).

4-(2-tert.-Butoxycarbonylamino-ethyl)-thiosemicarbazide can be prepared as follows:

A mixture of methyl N-(2-tert.-butoxycarbonylamino-ethyl)-dithiocarbamate (22.53 g), ethanol (90 cc) and hydrazine hydrate (4.4 cc) is heated under reflux for 1 hour 30 minutes. The solution is concentrated to dryness at 30° C. under 20 mm Hg (2.7 kPa) and the residue is triturated in the presence of diethyl ether (100 cc). Crystallisation starts in 5 minutes. The mixture is left for 1 hour at 20° C. and the product is then filtered off and dried. Pinkish white crystals (11.3 g) of 4-(2-tert.-butoxycarbonylamino-ethyl)-thiosemicarbazide, melting at 85° C., are obtained.

Infra-red spectrum (CHBr$_3$): characteristic bands (cm$^{-1}$) at 3450, 3350, 1700, 1620, 1545, 1510, 1390, 1370, 1250, 1225 and 1160.

Proton nuclear magnetic resonance spectrum (80 MHz, CDCl$_3$, δ in ppm, J in Hz): 1.48 (s, 9H, —C(CH$_3$)$_3$); 3.45 and 3.80 (2t, J=5, 4H, —CH$_2$CH$_2$—).

Triethylamine (15.5 cc) is added to a solution of 2-tert.-butoxycarbonylamino-ethylamine (17.62 g) in 95% strength ethanol (110 cc), and carbon disulphide (6.65 cc) is introduced dropwise in the course of 10 minutes, whilst maintaining the temperature at between 20° C. and 25° C. The mixture is stirred for 1 hour 30 minutes at 22° C. Methyl iodide (6.85 cc) is then added and the mixture is stirred for 1 hour 30 minutes at 22° C. It is then concentrated to dryness at 20° C. under 20 mm Hg (2.7 kPa), the residue is taken up in ethyl acetate (200 cc), and the organic phase is washed with water (3×100 cc), dried over sodium sulphate, filtered and concentrated to dryness at 20° C. under 20 mm Hg (2.7 kPa). Methyl N-(2-tert.-butoxycarbonylamino-ethyl)-dithiocarbamate (23.2 g) is obtained in the form of a yellow oil.

Infra-red spectrum (CHBr$_3$): characteristic bands (cm$^{-1}$) at 3440, 3370, 1700, 1505, 1430, 1380, 1370 and 945.

Proton nuclear magnetic resonance spectrum (60 MHz, CDCl$_3$, δ in ppm, J in Hz): 1.50 (s, 9H, —C(CH$_3$)$_3$); 2.65 (s, 3H, —CH$_3$); 3.50 and 3.80 (2t, J=5, 4H, —CH$_2$—CH$_2$—).

2-tert.-Butoxycarbonylamino-ethylamine is prepared by hydrazinolysis of N-tert.-butoxycarbonylphthalimidoethylamine:

Hydrazine hydrate (10.8 cc) is added to a suspension of 2-N-tert.-butoxycarbonyl-phthalimidoethylamine (53.7 g) in ethanol (540 cc), and the mixture is heated under reflux for 25 minutes. It is then cooled to 0° C. and filtered. The filtrate is concentrated to dryness under reduced pressure (20 mm Hg; 2.7 kPa). This gives 2-N-tert.-butoxycarbonylamino-ethylamine (19.6 g) in the form of a yellow oil.

Infra-red spectrum (CHCl$_3$): characteristic bands (cm$^{-1}$) at 3460, 3380, 3320, 1700, 1585, 1500, 1390, 1370, 1160 and 490.

Proton nuclear magnetic resonance spectrum (60 MHz, CDCl$_3$, δ in ppm, J in Hz): 1.48 (s, 9H, —C(C$\underline{H}_3$)$_3$; 2.20 (s broad, 2H, —NH$_2$); 2.80 (t, J=5, 2H, H$_2$N—C$\underline{H}_2$—CH$_2$—); 3.18 (t, J=5, 2H, H$_2$NCH$_2$C$\underline{H}_2$—); 5.50 (s broad, 1H, —NHCO—).

REFERENCE EXAMPLE 27

A mixture of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (2.9 g), tetrahydrofurane (50 cc) and methoxyamine hydrochloride (0.49 g) is heated under reflux for 24 hours. It is then concentrated to dryness under 20 mm Hg (2.7 kPa) at 30° C., the residue is triturated in water (20 cc) and the product is filtered off, washed with ethanol (2×10 cc) and dried. 2-Benzhydryloxycarbonyl-3-{2-[5,6-dioxo-4-(2-methoxyiminoethyl)-1,4,5,6-tetrahydro-1,2,4-triazin-3-yl]-thiovinyl}-7-[2-methoxyimino-2-(2-tritylamino-thiazol-4yl)-acetamido]-8-oxo-5-thia-1-azabicyclo[4.2.0]oct-2-ene (mixture of the syn, E, syn and anti, E, syn isomers) (0.92 g) is obtained.

Infra-red spectrum (KBr): characteristic bands in cm$^{-1}$ at 3700 to 2500, 1785, 1715, 1685, 1585, 1550, 1495, 1450, 1050, 950, 745 and 700.

Proton nuclear magnetic resonance spectrum (350 MHz, DMSO d$_6$, δ in ppm, J in Hz): 3.35 (s, 3H, —CH=N—O—CH$_3$); 3.70 and 3.90 (2d, J=18, 2H, —SCH$_2$—); 3.95 (s, 3H, =NOCH$_3$); 5.30 (d, J=4, 1H, H in the 6-position); 5.88 (dd, J=4 and 9, 1H, H in the 7-position); 6.95 and 7.05 (2d, J=16, 2H, —CH=CH—); 9.84 (d, J=9, 1H, —CONH—);

12.70 (s, 1H, =N NH CO— or =N N=C—).
                                              |
                                             OH

A solution of 2-benzhydryloxycarbonyl-3-{2-[5,6-dioxo-4-(2-methoxyiminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (mixture of the syn, E, syn and anti, E, syn isomers) (0.85 g) in formic acid (20 cc) and water (15 cc) is stirred for 30 minutes at 50° C. It is then concentrated to dryness under 0.05 mm Hg (0.007 kPa) at 45° C., and the residue is taken up in ethanol (40 cc), the mixture is evaporated to dryness under 20 mm Hg (2.7 kPa) at 20° C., and this operation is repeated twice. The yellow solid obtained is triturated in ethanol (20 cc) at 50° C., the mixture is allowed to cool and the product is filtered off. 7-[2-(2-Amino-thiazol-4-yl)-2-methoxyimino-acetamido]-2-carboxy-3-{2-[5,6-dioxo-4-(2-methoxyiminoethyl)-1,4,5,6-tetrahydro-1,2,4-triazin-3-yl]-thiovinyl}-8-oxo-5-thia-1-aza-bicyclo[4.2.0]oct-2-ene (mixture of the syn, syn, E and syn, anti, E isomers) (0.44 g) is obtained in the form of a yellow powder.

Infra-red spectrum (KBr): characteristic bands in cm$^{-1}$ at 3700 to 2000, 1775, 1710, 1690, 1630, 1585, 1550, 1050 and 945.

Proton nuclear magnetic resonance spectrum (350 MHz, DMSO d$_6$, δ in ppm, J in Hz): 5.24 (d, J=4, 1H, H in the 6-position); 5.80 (dd, J=4 and 9, 1H, H in the 7-position); 6.95 and 6.10 (2d, J=16, 2H, —CH=CH—); 9.77 (d, J=9, 1H, —CONH—).

REFERENCE EXAMPLES 28 to 58

Proceeding analogously, the products according to the invention are used to prepared the products of the general formula

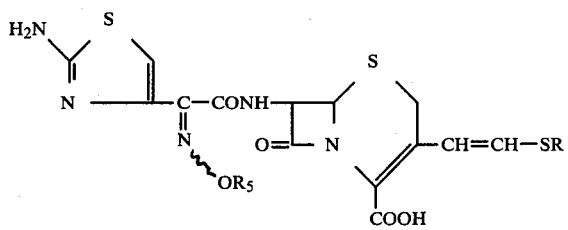

| Example | R | R$_5$ | Stereochemistry | (1) Infra-red spectrum (KBr): characteristic bands (cm$^{-1}$)<br>(2) Proton nuclear magnetic spectrum, 350 MHz, DMSO d$_6$, δ in ppm, J in Hz |
|---|---|---|---|---|
| 28 | —CH$_2$—CH—COOH<br>              \|<br>            NH$_2$ | —CH$_3$ | syn isomer<br>E-form | Product obtained as the formate<br>(1) 3500, 2000, 1750, 1660, 1530, 1035 and 940.<br>(2) 3 to 3.70 (hump, 4H, —SCH$_2$— of the cephalosporin and side chain); 3.87 (s, 3H, —OCH$_3$); 5.15 (d, J = 4, 1H, H in the 6-position); |

-continued

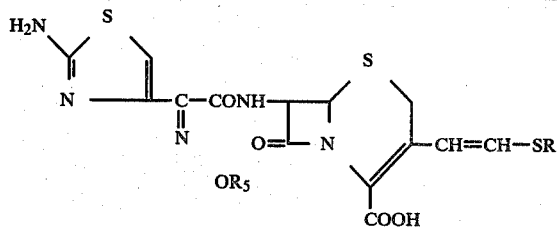

| Example | R | $R_5$ | Stereochemistry | (1) Infra-red spectrum (KBr): characteristic bands ($cm^{-1}$)<br>(2) Proton nuclear magnetic resonance spectrum, 350 MHz, DMSO $d_6$, δ in ppm, J in Hz |
|---|---|---|---|---|
| | | | | 5.65 to 5.72 (hump, 2H, H in the 7-position and $\diagdown$CHCOOH/); 6.77 (s, 1H, H of the thiazole); 6.92 (AB, 2H, —CH=CH—); 7.20 (s, 3H, —$NH_3^+$); 9.58 (d, J = 9, 1H, —CONH—). |
| 29 | $(CH_2)_2NHCOCH_3$ 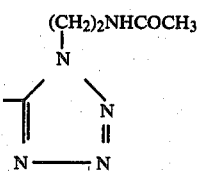 | —$CH_3$ | syn isomer E-form | (1) 3500, 2500, 1775, 1660, 1540, 1040 and 945 |
| | | | | (2) 1.90 (s, 3H, —$CH_3$); 3.44 (t, 2H, $\diagdown$N$CH_2$—/); 3.60 (q, 2H, —$CH_2$NHCO—); 3.64 and 3.76 (2d, J = 18, 2H, —$SCH_2$—); 4.0 (s, 3H, —$OCH_3$); 5.16 (d, J = 4, 1H, H in the 6-position); 5.82 (dd, J = 4 and 9, 1H, H in the 7-position); 6.60 (s, 3H, —$NH_3^+$); 6.78 (s, 1H, H of the thiazole); 6.96 (d, J = 16, 1H, —CH=CHS—); 7.37 (d, J = 16, 1H, =CHS—); 7.86 (t, J = 5, 1H, —NHCO$CH_3$); 9.50 (d, J = 9, 1H, —CONH—). |

| Example | R | $R_5$ | Stereochemistry | (1) Infra-red spectrum (KBr): characteristic bands ($cm^{-1}$)<br>(2) Proton nuclear magnetic resonance spectrum, 350 MHz, DMSO $d_6$, δ in ppm, J in Hz |
|---|---|---|---|---|
| 30 | 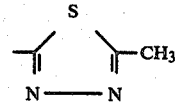 | —$CH_3$ | syn isomer E-form | (2) 2.57 (s, 3H, —$CH_3$); 3.65 and 3.95 (2d, J = 18, 2H, —$SCH_2$—); 3.86 (s, 3H, —$OCH_3$); 5.23 (d, J = 4, 1H, H in the 6-position); 5.82 (dd, J = 4 and 9, 1H, H in the 7-position); 6.75 (s, 1H, H of the thiazole); 7.04 |

-continued

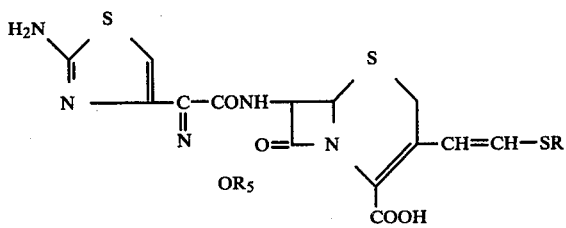

| | | | | |
|---|---|---|---|---|
| | | | | (d, J = 16, 1H, —CH=CHS—); 7.36 (d, J = 16, 1H, =CHS—); 9.63, (d, J = 9, 1H, —CONH—) |
| 31 | 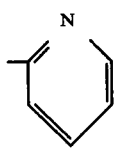 | —CH₃ | syn isomer E-form | (1) 3500, 2820, 2600, 1775, 1670, 1650, 1630, 1575, 1450, 1415, 1380, 1040, 940 and 765 |
| | | | | (2) 3.72 and 3.95 (2d, J = 18, 2H, H in the 4-position); 3.85 (s, 3H, —OCH₃); 5.20 (d, J = 4, 1H, H in the 6-position); 5.77 (dd, J = 4 and 9; 1H, H in the 7-position); 6.76 (s, 1H, H of the thiazole); 7.15 (d, J = 17, 1H, —CH=CHS—); 7.18 (s, 2H, amino); 7.44 (d, J = 16, 1H, —CH=CHS—); 7.75 and 8.2 (d, t, 1H, J = 8, H in the 4-position of the pyridine); 8.50 (t, 1H, J = 4, H₂ of the pyridine); 9.50 (d, J = 9, 1H, —CONH—). |
| 32 | 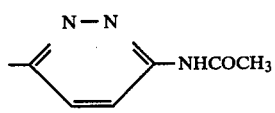 | —CH₃ | syn isomer E-form | (1) 3300, 1760, 1660, 1550, 1510, 1035 and 940 |
| | | | | (2) 2.10 (s, 3H, CH₃CONH—); 3.72 and 3.98 (AB, J = 17, 2H, —SCH₂—); 3.86 (s, 3H, =NOCH₃); 5.2 (d, J = 4, 1H, H in the 6-position); 5.78 (dd, J = 4 and 9, 1H, H in the 7-position); 6.76 (s, 1H, H of the thiazole); 7.20 (s, 2H, —NH₂); 7.19 (d, J = 10, 1H, —CH=CH—S—); 7.33 (d, J = 10, 1H, —CH=CH—S—); 7.78 (d, J = 9, 1H, H in the 5-position of the pyridazine); 8.12 (s, 1H, CH₃CONH—); 9.65 (d, J = 9, 1H, —CONH—); 8.27 (d, J = 9, 1H, H in the 4-position of the pyridazine); 11.1 (s broad, 1H, —CO₂H). |

-continued

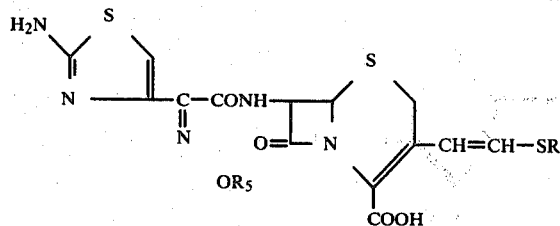

| | | | | |
|---|---|---|---|---|
| 33 | 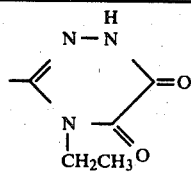 | —CH₃ | syn isomer E-form | (1) 3500, 2200, 1770, 1700, 1680, 1530, 1040 and 940 |
| | | | | (2) 1.22 (t, J = 7, 3H, —CH₃); 3.65 and 3.80 (2d, J = 18, 2H, —SCH₂—); 3.80 (q, J = 7, 2H, \NCH₂—); 3.86 (s, 3H, —OCH₃); 5.20 (d, J = 4, 1H, H in the 6-position); 5.78 (dd, J = 4 and 9, 1H, H in the 7-position); 6.75 (s, 1H, H of the thiazole); 6.95 (d, J = 16, 1H, —CH=CHS—); 7.13 (d, J = 16, 1H, =CHS—); 7.18 (s, 3H, —NH₃⁺); 9.63 (d, J = 9, 1H, —CONH—). |
| 34 | 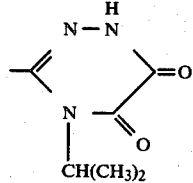 | —CH₃ | syn isomer E-form | (1) 3500, 2200, 1775, 1705, 1680, 1530, 1050 and 950 |
| | | | | (2) 1.48 (d, J = 7, 6H, —CH(CH₃)₂); 3.64 and 3.82 (2d, J = 18, 2H, —SCH₂—); 3.85 (s, 3H, —OCH₃); 4.42 (mt, 1H, —CH(CH₃)₂); 5.22 (d, J = 4, 1H, H in the 6-position); 5.78 (dd, J = 4 and 9, 1H, H in the 7-position); 6.74 (s, 1H, H of the thiazole); 6.93 (d, J = 16, 1H, —CH=CHS—); 7.07 (d, J = 16, 1H, =CHS—); 7.18 (s, 3H, —NH₃⁺); 9.62 (d, J = 9, 1H, —CONH—); 12.55 (s, 1H, =NNHCO— or =N—N=C—OH). |
| 35 | 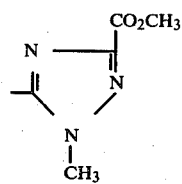 | —CH₃ | syn isomer E-form | (1) 3450, 3320, 2200, 1770, 1735, 1660, 1630, 1535, 1385, 1220, 1040 and 945 |
| | | | | (2) 3.66 and 3.90 (2d, J = 18, 2H, —SCH₂—); 3.85 (s, 3H, =NOCH₃); 3.87 (s, 3H, —CO₂CH₃); |

-continued

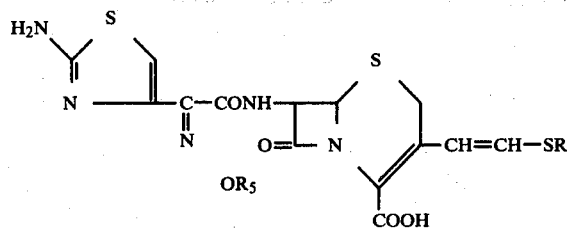

3.90 (s, 3H, \NCH₃ of
the triazole); 5.20
(d, J = 9, 1H, H in the
6-position); 5.79 (dd,
J = 4 and 9, 1H, H in
the 7-position); 6.74
(s, 1H, H of the thia-
zole); 6.98 and 7.03
(AB, J = 14, 2H,
—CH═CH—S—); 7.20 (s
broad, 2H, —NH₂);
9.63 (d, J = 9, 1H,
—CONH—C₇).

| 36 | 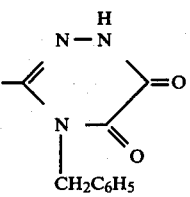 | —CH₃ | syn isomer E-form | (1) 3500, 2300, 1770, 1710, 1680, 1585, 1530, 1045 and 945 |

(2) 3.58 and 3.78 (2d, J =
18, 2H, —SCH₂—); 3.88
(s, 3H, —OCH₃); 5.10 (s,

2H, \NCH₂—); 5.18 (d, J

= 4, 1H, H in the 6-
position); 5.78 (dd, J
= 4 and 9, 1H, H in the
7-position); 6.75 (s,
1H, H of the thiazole);
6.86 (d, J = 16, 1H,
—CH═CHS—); 7.05 (d, J =
16, 1H, ═CHS—); 7.20 (s,
3H, —NH₃⁺); 9.60 (d,
J = 9, 1H, —CONH—);
12.69 (s, 1H, ═NNHCO—).

| 37 | 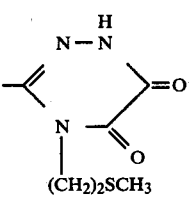 | —CH₃ | syn isomer E-form | (1) 3600, 2200, 1770, 1710, 1680, 1585, 1535, 1040 and 945 |

(2) 2.12 (s, 3H, —SCH₃);
2.73 (t, J = 7, 2H,
—CH₂S—CH₃); 3.64 and
3.82 (2d, J = 18, 2H,
—SCH₂—); 3.85 (s, 3H,
—OCH₃); 4.0 (t, J =

7, 2H, \NCH₂—); 5.20

(d, J = 4, 1H, H in
the 6-position);
5.78 (dd, J = 4 and
9, 1H, H in the 7-
position); 6.73 (s,
1H, H of the thiazole);
6.92 (d, J = 16, 1H, -continued

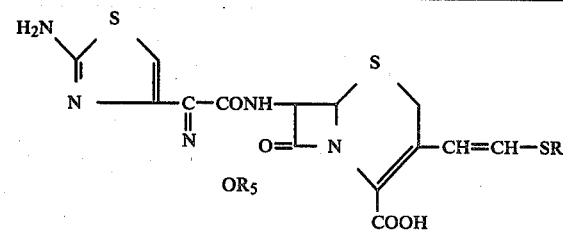

| | | | | |
|---|---|---|---|---|
| | | | | —CH=CHS—); 7.12 (d, J = 16, 1H, =CHS—); 7.15 (s, 3H, —NH$_3^+$); 9.66 (d, J = 9, 1H, —CONH—); 12.61 (s, 1H, \NNHCO—)./ |
| 38 | 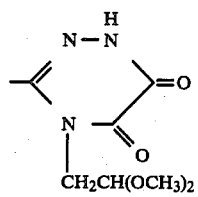<br>CH$_2$CH(OCH$_3$)$_2$ | —CH$_3$ | syn isomer E-form | (1) 3500, 3300, 1780, 1715, 1680, 1590, 1535, 1050 and 950 |
| | | | | (2) 3.62 and 3.81 (2d, J = 18, —SCH$_2$—); 3.84 (s, 3H, —OCH$_3$); 3.97 (d, J = 3, 2H, \NCH$_2$—); 4.58 (t, J =/ 3, 1H, —CH(OCH$_3$)$_2$); 5.20 (d, J = 4, 1H, H in the 6-position); 5.77 (dd, J = 4 and 9, 1H, H in the 7-position); 6.74 (s, 1H, H of the thiazole); 6.91 (d, J = 16, 1H, —CH=CHS—); 7.09 (d, J = 16, 1H, =CHS—); 7.17 (s, 3H, —NH$_3^+$); 9.60 (d, J = 9, 1H, —CONH—); 12.64 (s, 1H, =NNHCO—). |
| 39 | 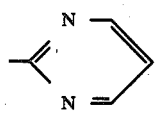 | —CH$_3$ | syn isomer E-form | (1) 3320, 3200, 3100 to 2100, 1770, 1665, 1560, 1550, 1040, 945, 770 and 750 |
| | | | | (2) 3.72 and 3.90 (2d, J = 18, 2H, —SCH$_2$— in the 4-position); 3.86 (s, 3H, =NOCH$_3$); 5.20 (d, J = 4, 1H, —H in the 6-position); 5.77 (dd, J = 4 and 9, 1H, —H in the 7-position); 6.74 (s, 1H, —H of the thiazole ring); 7.12 and 7.46 (2d, J = 16, 2H, trans vinyl protons); 7.14 (s, 2H, —NH$_2$ of thiazole ring); 7.27 (broad, 1H, —H in the 5-position of the pyrimidine ring); 8.66 (d, J = 5, 2H, —H in the 4- and 6-position of the pyrimidine ring); 9.60 (d, J = 9, 1H, —CONH—). Product obtained as the formate |

-continued

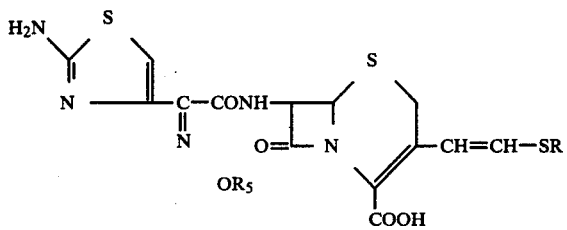

| Example | R | $R_5$ | Stereo-chemistry | (1) Infrared spectrum (KBr): Characteristic bands $(cm^{-1})$ (2) Proton nuclear magnetic resonance spectrum, 350 MHz, DMSO $d_6$, δ in ppm, J in Hz |
|---|---|---|---|---|
| 40 | 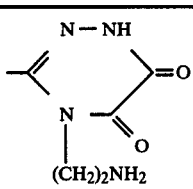 | —$CH_3$ | syn isomer E-form | (1) 3500, 2200, 1770, 1710, 1680, 1630, 1530, 1380, 1040 and 930 |

(2) 3.12 (m, 2H, —$CH_2$—$CH_2$—$NH_2$); 3.51 and 3.60 (2d, J = 18, 2H, —$SCH_2$—); 3.85 (s, 3H, $CH_3ON$=); 4.12 (t, J = 6, 2H,

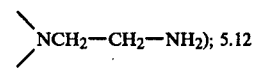$NCH_2$—$CH_2$—$NH_2$); 5.12

(d, J = 4, 1H, $H_6$); 5.67 (dd, J = 4 and 9, 1H, $H_7$); 6.44 (d, J = 8, 1H, —CH=CHS—); 6.73 (s, 1H, H of the thiazole); 7.2 (s broad, 2H, —$NH_2$); 8.18 (s, 1H, H of the formate); 9.55 (d, J = 9, 1H, —NHCO—)

| Example | R | $R_5$ | Stereo-chemistry | (1) Infrared spectrum (KBr): Characteristic bands $(cm^{-1})$ (2) Proton nuclear magnetic resonance spectrum, 350 MHz, DMSO $d_6$, δ in ppm, J in Hz |
|---|---|---|---|---|
| 41 | 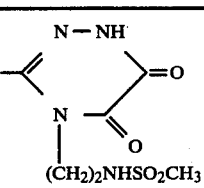 | —$CH_3$ | syn isomer E-form | (1) 3400, 3300, 3200, 1775, 1710, 1680, 1590, 1530, 1320, 1150, 1140 and 945 |

(2) 2.90 (s, 3H, —$SO_2CH_3$); 3.20 (mt, 2H, —$CH_2NH$—); 3.61 and 3.78 (2d, J = 18, 2H, —$SCH_2$—); 3.96 (s, 3H, =$NOCH_3$); 3.96

(t, J = 5, 2H, 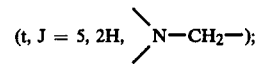N—$CH_2$—);

5.17 (d, J = 4, 1H, H in the 6-position); 5.73 (dd, J = 4 and 9, 1H, H in the 7-position); 6.74 (s, 1H, H of the thiazole); 6.79 (d, J = 16, 1H, —CH=CHS—); 7.17 (s, 2H, —$NH_2$); 9.60 (d, J = 9, 1H, —CONH—)

(1) Infrared spectrum (KBr): Characteristic bands $(cm^{-1})$
(2) Proton nuclear magnetic -continued

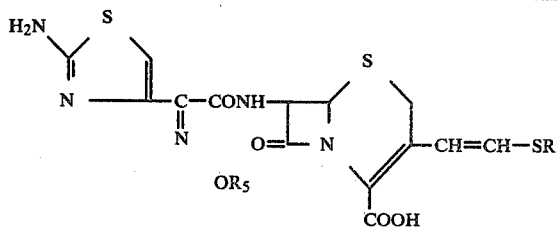

| Example | R | $R_5$ | Stereo-chemistry | resonance spectrum, 350 MHz, $CF_3COOD$, $\delta$ in ppm, J in Hz |
|---|---|---|---|---|
| 42 | ![N—NH structure with CH2CHO] | $-CH_3$ | anti isomer E-form | (1) 3700, 2300, 1770, 1715, 1685, 1630, 1590, 1525, 1060, 1030 and 940 |
| | | | | (2) 3.86 (s broad, 2H, $-SCH_2-$); 4.43 (s, 3H, $=NOCH_3$); 5.18 (s broad, 2H, $\backslash N-CH_2-/$); 5.35 (d, J = 4, 1H, H in the 6-position); 5.88 (d, J = 4, 1H, H in the 7-position); 7.24 and 7.74 (2d, J = 16, 2H, $-CH=CHS-$); 8.14 (s, 1H, H of the thiazole); 9.77 (s, 1H, $-CHO-$) |
| 43 | ![N—NH structure with CH2CHO] | $-CH_3$ | syn isomer Z-form | (1) 3700, 2200, 1770, 1715, 1680, 1590, 1530, 1045 |
| | | | | (2) 3.77 and 3.54 (2d, J = 18, 2H, $-SCH_2-$); 5.18 s, 2H, $\backslash N-CH_2-/$); 5.38 (d, J = 4. 1H, H in the 6-position); 6.02 (d, J = 4, 1H, H in the 7-position); 6.84 and 7.05 (2d, J = 10, 2H, $-CH=CHS-$); 7.48 (s, 1H, H of the thiazole); 9.72 (s, 1H, $-CHO$) |
| 44 | ![N—N structure with COOCH3 and CH2CH(OCH3)2] | $-CH_3$ | syn isomer E-form | (1) 3430, 3200, 1775, 1735, 1680, 1620, 1535, 1385, 1050, 945 |
| | | | | (2) 3.65 (s, 6H, $-CH(OCH_3)_2$); 4.21 (s, 3H, $-COOCH_3$); 4.29 (s, 3H, $=NOCH_3$); 5.38 (d, J = 4, 1H, H in the 6-position); 6.08 (d, J = 4, 1H, H in the 7-position); 7.07 and 7.95 (2d, J = 16, 2H, $-CH=CHS-$); 7.48 (s, 1H, H of the thiazole) |
| | | | | (1) Infrared spectrum (KBr): |

-continued

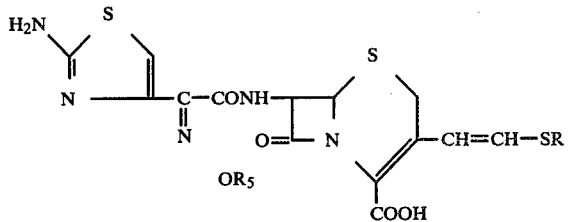

| Example | R | $R_5$ | Stereochemistry | Characteristic bands $(cm^{-1})$ (2) Proton nuclear magnetic resonance spectrum, 350 MHz, DMSO $d_6$, δ in ppm, J in Hz |
|---|---|---|---|---|
| 45 | ![thiadiazole S/N-N] | —$CH_3$ | syn isomer E-form | (1) 2820, 1775, 1675, 1630, 1530, 1490, 1450, 1370, 1040, 750, 700 |
| | | | | (2) 3.68 and 3.96 (2d, J = 18, 2H, —$SCH_2$—); 3.84 (s, 3H, =$NOCH_3$); 5.21 (d, J = 4, 1H, H in the 6-position); 5.80 (dd, J = 4 and 9, 1H, H in the 7-position); 6.73 (s, 1H, H of the thiazole); 7.18 to 7.22 (hump, 4H, —$NH_2$— and —CH=CH—); 9.03 (d, J = 9, 1H, —CONH—); 9.60 (s, 1H, H of the thiadiazole) |
| 46 | ![thiadiazole with NH2] | —$CH_3$ | syn isomer E-form | (1) 3320, 3200, 3100, 2820, 2000, 1770, 1670, 1610, 1380, 1040, 940 |
| | | | | (2) 3.83 (s, 3H, =$NOCH_3$); 5.12 (d, J = 4, 1H, H in the 6-position); 5.76 (dd, J = 4 and 9, 1H, H in the 7-position); 6.74 (s, 1H, H of the thiazole); 6.95 (d, J = 16, 1H, —CH=CHS—); 7.02 (d, J = 16, 1H, =CHS—); 7.18 (s broad, 2H, —$NH_2$ of the thiazole); 7.48 (s broad, 2H, —$NH_2$ of the thiadiazole); 9.60 (d, J = 9, 1H, —CONH—) Product obtained as the formate |
| 47 | ![thiadiazole with CH2N(CH3)2] | —$CH_3$ | syn isomer E-form | (1) 3400, 3330, 3250, 2000, 1765, 1665, 1600, 1530, 1035, 960 |
| | | | | (2) 2.36 (s, 6H, —$N(CH_3)_2$); 3.67 and 3.92 (2d, J = 18, 2H, —$SCH_2$—); 3.88 (s, 3H, =$NOCH_3$); 5.28 (d, J = 4, 1H, H in the 6-position); 5.80 (dd, J = 4 and 9, 1H, H in the 7-position); 6.76 (s, 1H, H of the thiazole); 7.10 (d, J = 16, 1H, —CH=CHS—); 7.20 (s, 2H, —$NH_2$); 7.25 (d, J = 16, 1H, =CHS—); 9.60 (d, J = 9, 1H, —CONH—) |
| 48 | ![N—NH ring with =O and (CH2)2NHCOOCH3] | —$CH_3$ | syn isomer E-form | (1) 3340, 3210, 3100, 2200, 1770, 1710, 1685, 1625, 1590, 1530, 1035, 945 |
| | | | | (2) 3.55 (s, 3H, —$COOCH_3$); |

-continued

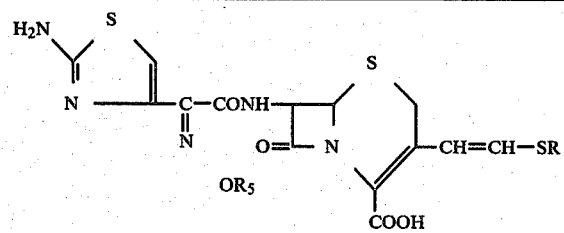

| | | | | |
|---|---|---|---|---|
| | | | | 3.62 and 3.79 (2d, J = 18, 2H, —SCH$_2$—); 3.85 to 3.93 (mt, 5H, =NOCH$_3$ and $\diagdown$NCH$_2$—); 5.19 (d, J = 4, 1H, H in the 6-position); 5.75 (dd, J = 4 and 9, 1H, H in the 7-position); 6.74 (s, 1H, H of the thiazole); 9.58 (d, J = 9, 1H, —CONH—); 12.53 (s broad, 1H, =NNHCO— or =NN=C—) $\quad\quad\quad\quad\quad\quad\quad\quad\quad\quad$ OH |
| 49 | 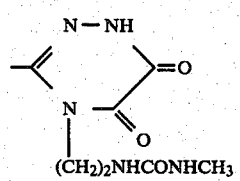 (CH$_2$)$_2$NHCONHCH$_3$ | —CH$_3$ | syn isomer E-form | (1) 3320, 3200, 1775, 1710, 1680, 1635, 1585, 1535, 1040, 945 |
| | | | | (2) 3.30 (m, 5H, —CH$_2$NH— and $\diagdown$NCH$_3$—); 3.60 and 3.78 (2d, J = 18, 2H, —SCH$_2$—); 3.85 (s broad, 5H, =NOCH$_3$ and $\diagdown$NCH$_2$—); 5.18 (d, J = 4, 1H, H$_6$); 5.74 (dd, J = 4 and 9, 1H, H$_7$); 6.09 (t, J = 6, 1H, —NH— CH$_2$—); 6.74 (s, 1H, H of the thiazole); 6.82 and 7.12 (2d, J = 16, 2H, —CH=CH—); 9.58 (d, J = 9, 1H, —CONH—); 12.52 (s, 1H, =N—NHCO— or =N—N=C—) $\quad\quad\quad\quad\quad\quad\quad\quad\quad\quad$ OH |
| 50 | 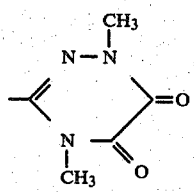 | —CH$_3$ | syn and anti isomers (50:50 mixture), E-form | (1) 3500, 2300, 1770, 1710, 1670, 1575, 1530, 1030, 940 |
| | | | | (2) syn isomer, E-form 3.35 and 3.48 (2s, 2 × 3H, 2-CH$_3$ of the triazine); 3.66 and 3.90 (2d, J = 18, 2H, —SCH$_2$—); 3.87 (s, 3H, =NOCH$_3$); 5.18 (d, J = 4, 1H, H in the 6-position); 5.82 (dd, J = 4 and 9, 1H, H in the 7-position); 6.74 (s, 1H, H of the thiazole); 6.95 |

-continued

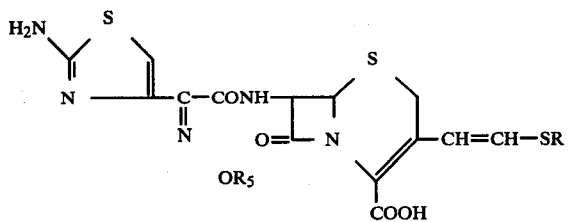

and 7.14 (2d, J = 16, 2H,
—CH=CH—S—); 7.18 (s
broad, 2H, —NH₂); 9.64
(d, J = 9, 1H, —CONH—).
anti isomer, E-form
3.35 and 3.48 (2s, 2 ×
3H, 2CH₃ of the tria-
zine); 3.66 and 3.90 (2d,
J = 18, 2H, —SCH₂—); 3.98
(s, 3H, =NOCH₃); 5.19
(d, J = 4, 1H, H in the
6-position); 5.81 (dd,
J = 4 and 9, 1H, H in the
7-position); 6.95 and
7.15 (2d, J = 16, 2H,
—CH=CH—S—); 7.09 (s
broad, 2H, —NH₂); 9.48
(d, J = 9, 1H, —CONH—)

| 51 | 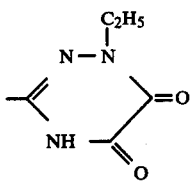 | —CH₃ | syn isomer E-form | (1) 3700, 2200, 1770, 1720, 1665, 1630, 1590, 1040, 945 |

(2) 1.25 (t, J = 7, 3H, —CH₂CH₃);
3.71 and 3.88 (2d, J = 18,
2H, —SCH₂—); 3.80 to 3.90
(hump, 5H, —CH₂CH₃ and
—OCH₃); 5.19 (d, J = 4, 1H,
H in the 6-position);
5.75 (dd, J = 4 and 9, 1H,
H in the 7-position);
6.77 (s, 1H, H of the
thiazole); 7.10 (s broad,
2H, —CH=CH—); 7.20 (s, 2H,
—NH₂); 9.62 (d, J = 9, 1H,
—CONH—)

| 52 | 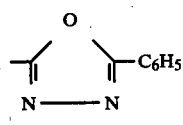 | —CH₃ | syn isomer E-form | (1) 3400 to 2000, 3330, 1760, 1630, 1540, 1380, 1055, 750, 710, 695 |

(2) 3.68 and 3.94 (2d, J = 18,
2H, —SCH₂—); 3.86 (s, 3H,
=NOCH₃); 5.22 (d, 1H, H in
the 6-position); 5.82 (dd,
1H, H in the 7-position);
6.74 (s, 1H, H of the thia-
zole ring); 7.10 (d, J = 16,
1H, —CH=CHS—); 7.18 (s,
2H, NH₂), 7.26 (d, J = 16,
1H, —CH=CHS—); 7.83 (mt,
3H, p and m protons of
—C₆H₅), 8.0 (d, J = 7, 2H,
o-protons of the —C₆H₅);
9.61 (d, J = 9, 1H,
—CONH—)

| 53 | 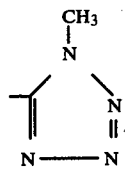 | —CH₂CN | syn isomer E-form | (1) 1770, 1680, 1620, 1530, 1380 |

(2) 3.66 and 3.88 (2d, J =
18, 2H, —SCH₂—); 4.02
(s, 3H, —CH₃); 5.0
(s, 2H, —OCH₂—); 5.22

-continued

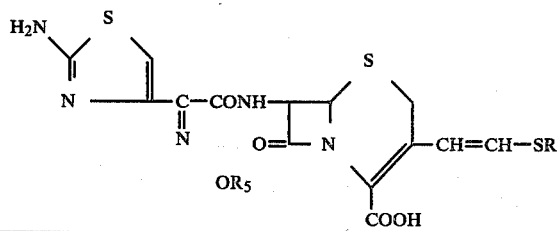

| Example | R | $R_5$ | Stereochemistry | (1) Infrared spectrum (KBr): Characteristic bands $(cm^{-1})$ (2) Proton nuclear magnetic resonance spectrum, 350 MHz, $CF_3COOD$, δ in ppm, J in HZ |
|---|---|---|---|---|
| | | | | (d, J = 4, 1H, H in the 6-position); 5.80 (dd, J = 4 and 9, 1H, H in the 7-position); 6.89 (s, 1H, H of the thiazole); 6.99 (d, J = 16, 1H, —CH=CHS—); 7.12 (d, J = 16, 1H, =CHS—); 9.82 (d, J = 9, 1H, —CONH—) Product obtained as the formate |
| 54 | 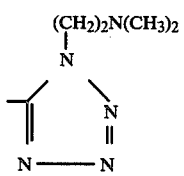 | —$CH_3$ | syn isomer E-form | (1) 3400, 3200, 2000, 1770, 1670, 1615, 1530, 1035 |
| | | | | (2) 2.70 (s, 6H, —$N(CH_3)_2$); 2.75 (t, J = 7, 2H, —$CH_2N\diagdown$ ); 3.85 (s, 3H, =$NOCH_3$); 3.95 (t, J = 7, 2H, —$CH_2CH_2N(CH_3)_2$); 5.16 (d, J = 4, 1H, H in the 6-position); 5.85 (dd, J = 4 and 9, 1H, H in the 7-position); 6.74 (s, 1H, H of the thiazole); 6.80 (d, J = 16, 1H, —CH=CHS—); 6.90 (d, J = 16, 1H, =CHS—); 7.20 (s, 2H, —$NH_2$); 9.63 (d, J = 9, 1H, —CONH—) |

| Example | R | $R_5$ | Stereochemistry | (1) Infrared spectrum (KBr): Characteristic bands $(cm^{-1})$ (2) Proton nuclear magnetic resonance spectrum, 350 MHz, $CF_3COOD$, δ in ppm, J in HZ |
|---|---|---|---|---|
| 55 | 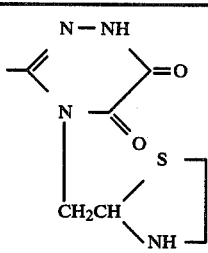 | —$CH_3$ | syn isomer E-form | (1) 3400, 3280, 3200, 2000, 1775, 1710, 1680, 1610, 1380, 1035, 750, 685 |
| | | | | (2) 4.32 (s, 3H, =$NOCH_3$); 5.40 (d, J = 4, 1H, H in the 6-position); 6.04 (d, J = 4, H in the 7-position); 7.25 and 7.78 (2d, J = 16, 2H, —CH=CH—); 7.50 (s, 1H, H of the thiazole) |

-continued

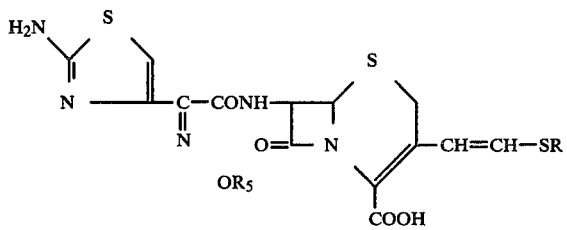

| Example | R | R$_5$ | Stereochemistry | (1) Infrared spectrum (KBr): Characteristics bands (cm$^{-1}$) (2) Proton nuclear magnetic resonance spectrum, 350 MHz, CDCL$_3$, δ in ppm, J in Hz |
|---|---|---|---|---|
| 56 | (structure with N—NH ring, =O, N-CH$_2$CH=N~OH) | —CH$_3$ | mixture of the syn, syn E and syn, anti E isomers | (1) 3700 to 3200, 1770, 1710, 1680, 1585, 1530, 1040, 940 (2) 3.89 (s, 2H, —SCH$_2$—); 4.30 (s, 3H, =NOCH$_3$); 5.39 (d, J = 4, 1H, H in the 6-position); 6.04 (d, J = 4, 1H, H in the 7-position); 7.28 and 7.77 (2d, J = 16, 2H, —CH=CHS—); 7.50 (s, 1H, H of the thiazole) |
| 57 | (structure with CH$_3$-N—NH ring, =O) | —CH$_3$ | syn isomer E-form | (1) 3600, 2300, 1765, 1720, 1670, 1600, 1525, 1280, 1075, 1040, 930 (2) 3.77 and 3.88 (2d, J = 18, 2H, —SCH$_2$—); 4.0 (s, 3H, —CH$_3$); 4.30 (s, 3H, =NOCH$_3$); 5.41 (d, J = 4, 1H, H in the 6-position); 6.0 (d, J = 4, 1H, H in the 7-position); 7.50 (s, 1H, H of the thiazole) |
| 58 | (oxazole structure with O, N, CH$_3$) | —CH$_3$ | syn isomer E-form | (1) 3300, 2940, 1770, 1675, 1530, 1380, 1040, 940, 730, 700 (2) 2.10 (s, 3H, —CH$_3$); 3.66 and 3.90 (2d, J = 18, 2H, —SCH$_2$—); 3.86 (s, 3H, =NOCH$_3$); 5.19 (d, 1H, H in the 6-position); 5.78 (dd, 1H, H in the 7-position); 6.74 (s, 1H, H of the thiazole ring); 7.0 (d, J = 16, 1H, —CH=CHS—); 7.14 (d, J = 16, 1H, —CH=CHS—); 7.20 (s, 2H, —NH$_2$); 7.94 (s, 1H, H of the oxazole ring); 9.72 (d, J = 9, 1H, —CONH—) |

The products according to the invention employed in accordance with the methods described above make it possible to prepare the products of the general formula (XXVI), which can be used for the preparation of the products of the general formula (XXI).

REFERENCE EXAMPLE 59

2-Benzhydryloxycarbonyl-7-tert.-butoxycarbonylamino-8-oxo-3-(2-oxo-ethyl)-5-oxide-5-thia-1-azabicyclo[4.2.0]oct-2-ene (52.4 mg) is dissolved in pyridine (2 cc). The solution is cooled to −15° C. and p- toluenesulphonyl chloride (21 mg) is then added. The reaction mixture is stirred for 5 minutes at −15° C. and then for 1 hour at between −15° C. and 0° C. It is then poured into distilled water (50 cc). The mixture is extracted with ethyl acetate (50 cc) and the organic phase is washed with 0.1 N hydrochloric acid (2×50 cc) and then with distilled water (2×50 cc). It is dried over sodium sulphate and filtered, and the solvent is evaporated under reduced pressure (20 mm Hg) at 30° C. A mixture (66 mg) of the Z- and E-forms of 2-benzhydryloxycarbonyl-7-tert.-butoxycarbonylamino-8-oxo-5-oxide-3-(2-tosyloxy-vinyl)-5-thia-1-aza-bicyclo[4.2.0]oct-2-ene is obtained in the form of an orange-coloured froth. Preparative chromatography on a silica gel chromatographic plate [solvent: a 50:50 (by volume) mixture of cyclohexane and ethyl acetate] is used to separate the two forms.

Z-form (10 mg): Infrared spectrum (CHBr$_3$): characteristic bands (cm$^{-1}$) at 3420, 1800, 1720, 1505, 1380, 1370, 1195, 1180, 1050, 1010 and 730.

Proton nuclear magnetic resonance spectrum (350 MHz, CDCl$_3$, δ in ppm, J in Hz): 1.49 (s, 9H, —C(CH$_3$)$_3$); 2,44 (s, 3H, —CH$_3$); 3.36 and 4.04 (2 d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —C$\underline{H}$=CH—OSO$_2$—); 6.46 (d, J=7, 1H, =CH—OSO$_2$—); 6.89 (s, 1H, —COOCH); 7.77 (d, J=9, 2H, H in the orthoposition of the tosyl).

E-form (40 mg): Infrared spectrum (CHBr$_3$): characteristic bands (cm$^{-1}$) at 3420, 1800, 1720, 1505, 1380, 1370, 1195, 1180, 1075, 935 and 745.

Proton nuclear magnetic resonance spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2 d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —C$\underline{H}$=CH—OSO$_2$—); 6.83 (s, 1H, —COOCH<); 7.08 (d, J=13, 1H, =CH—OSO$_2$—); 7.73 (d, J=9, 2H, H in the orthoposition of the tosyl).

A solution of 2-benzhydryloxycarbonyl-7-tert.butoxycarbonylamino-8-oxo-5-oxide-3-(2-tosyloxyvinyl)-5-thia-1-aza-bicyclo[4.2.0]oct-2-ene (mixture of the E- and Z-forms) (4.06 g) (obtained as described in Reference Example 2) in acetonitrile (150 cc) is stirred with p-toluenesulphonic acid monohydrate (2.28 g) at 20° C. for 16 hours. The mixture is concentrated under reduced pressure (20 mm Hg) at 20° C. to a volume of 10 cc and is diluted with ethyl acetate (150 cc), and this mixture is washed with a 2% strength sodium bicarbonate solution (100 cc) and then with saturated aqueous sodium chloride (2×150 cc), dried over sodium sulphate and concentrated to dryness under reduced pressure (20 mm Hg) at 20° C. 7-Amino-2-benzhydryloxycarbonyl-8-oxo-5-oxide-3-(2-tosyloxyvinyl)-5-thia-1-aza-bicyclo[4.2.0]oct-2-ene (mixture of the E- and Z-forms) (3.5 g) is obtained in the form of a crude brown solid.

Triethylamine (0.272 g) followed by thien-2-yl-acetyl chloride (0.433 g) is added to a solution, cooled to −10° C., of 7-amino-2-benzhydryloxycarbonyl-8-oxo-5-oxide-3-(2-tosyloxy-vinyl)-5-thia-1-aza-bicyclo[4.2.0]oct-2-ene (mixture of the E- and Z-forms) (1.56 g) in methylene chloride (40 cc), and the cooling bath is then removed. The mixture is stirred for a further 2 hours at 20° C., and is then washed successively with a 5% strength sodium bicarbonate solution (40 cc), 1 N hydrochloric acid (40 cc) and water (40 cc), dried over sodium sulphate, filtered and evaporated at 20° C. under reduced pressure (20 mm Hg). The residue is dissolved in a 50:50 (by volume) mixture of cyclohexane and ethyl acetate (30 cc) and the solution is chromatographed on a column (column diameter: 5 cm, height: 28 cm) of Merck silica gel (0.04–0.06 mm) (200 g). Elution is carried out with a 50:50 (by volume) mixture of cyclohexane and ethyl acetate (3 liters) under a pressure of 40 kPa, 60 cc fractions being collected.

Fractions 9 to 15 are evaporated to dryness under reduced pressure (20 mm Hg) at 20° C. 2-Benzhydryloxycarbonyl-8-oxo-5-oxide-7-(thien-2-yl-acetamido)-3-(2-tosyloxy-vinyl)-5-thia-1-aza-bicyclo[4.2.0]oct-2-ene, Z-form (0.60 g) is obtained.

Infrared spectrum (CHBr$_3$): characteristic bands (cm$^{-1}$) at 3400, 1805, 1725, 1685, 1510, 1500, 1450, 1380, 1195, 1180, 1060 and 610.

Proton nuclear magnetic resonance spectrum (350 MHz, CDCl$_3$, δ in ppm, J in Hz): 2.4 (s, 3H, —CH$_3$); 3.67 and 3.92 (2d, J=18, 2H, —S—CH$_2$—); 3.83 and 3.92 (2d, J=16, 2H, —CH$_2$CO—); 4.95 (d, J=4, 1H, H in the 6-position); 5.92 (dd, J=4 and 9, 1H, H in the 7-position); 6.16 (d, J=7, 1H, —C$\underline{H}$=CHOSO$_2$—); 6.65 (d, J=7, 1H, =CHOSO$_2$—); 6.86 (s, 1H, >CHOCO—); 6.96 (mt, 2H, H in the 3- and 4-position of the thiophene); 7.83 (d, J=8, 2H, H in the ortho-position of the tosyl group); 8.48 (d, J=9, 1H, —CONH—).

Fractions 16 to 32 were evaporated under reduced pressure (20 mm Hg) at 20° C. The E-form (0.8 g) of the same product as above is obtained.

Infrared spectrum (CHBr$_3$): characteristic bands (cm$^{-1}$) at 3310, 1795, 1710, 1670, 1540, 1500, 1450, 1375, 1195, 1180, 1075, 745, 700, 615 and 550.

Proton nuclear magnetic resonance spectrum (350 MHz, CDCl$_3$, δ in ppm, J in Hz): 2.43 (s, 3H, —CH$_3$); 3.54 and 4.36 (2d, J=17.5, 2H, —SCH$_2$—); 3.83 and 3.92 (2d, J=14, 2H, —CH$_2$CO—); 4.96 (d, J=4, 1H, H in the 6-position); 5.93 (dd, J=4 and 9, 1H, H in the 7-position); 6.72 (d, J=13, 1H, —C$\underline{H}$=CHOSO$_2$—); 6.91 (s, 1H, —COOCH<); 6.97 (mt, 2H, H in the 3- and 4-position of the thiophene); 7.37 (d, 1H, H in the 5-position of the thiophene); 7.48 (d, J=8, 2H, H in the metaposition of the tosyl group); 7.84 (d, J=8, 2H, H in the ortho-position of the tosyl group); 8.53 (d, J=9, 1H, —CONH—).

(a) Phosphorus trichloride (0.144 cc) is added to a solution, cooled to −10° C., of 2-benzhydryloxycarbonyl-8-oxo-5-oxide-7-(thien-2-yl-acetamido)-3-(2-tosyloxy-vinyl)-5-thia-1-aza-bicyclo[4.2.0]oct-2-ene (Z-form) (0.58 g) in methylene chloride (10 cc) and dimethylacetamide (0.328 cc) and the mixture is stirred for 50 minutes at the same temperature. It is taken up in ethyl acetate (150 cc), and this mixture is washed with a 2% strength sodium bicarbonate solution (2×80 cc) and a half-saturated sodium chloride solution (2×80 cc), dried over sodium sulphate and evaporated to dryness under reduced pressure (20 mm Hg) at 20° C. The residue is dissolved in an 80:20 (by volume) mixture of cyclohexane and ethyl acetate (3.5 cc) and is chromatographed on a column (column diameter: 2.5 cm, height: 20 cm) of Merck silica gel (0.05–0.2 mm) (25 g). Elution is carried out with the same mixture (200 cc); a first fraction of 50 cc is discarded; the next fraction, of 150 cc, is concentrated to dryness under reduced pressure (20 mm Hg) at 20° C. 2-Benzhydryloxycarbonyl-8-oxo-7-(thien-2-yl-acetamido)-3-(2-tosyloxy-vinyl)-5-thia-1-aza-bicyclo[4.2.0]oct-2-ene (Z-form) (0.42 g) is obtained in the form of a cream-coloured froth.

Rf=0.72; silica gel chromatographic plate; solvent: a 1:4 (by volume) mixture of cyclohexane and ethyl acetate.

2-Benzhydryloxycarbonyl-8-oxo-7-(thien-2-yl-acetamido)-3-(2-tosyloxy-vinyl)-5-thia-1-aza-bicyclo[4.2.0]oct-2-ene (Z-form) (0.42 g) and trifluoroacetic acid (10 cc) are left in contact for 30 minutes at 4° C. The mixture is evaporated to dryness under reduced pressure (20 mm Hg) at 20° C. The residue is taken up in a 1% strength sodium bicarbonate solution (150 cc) and this mixture is washed with ethyl acetate (150 cc). The aqueous phase is brought into contact with ethyl acetate (150 cc) and is acidified (so as to give a pH of about 2) with a 1 N hydrochloric acid solution, whilst stirring. The ethyl acetate phase is decanted, washed with a saturated sodium chloride solution (100 cc), dried over sodium sulphate and concentrated to dryness under reduced pressure (20 mm Hg) at 20° C. The residue is triturated in diethyl ether (20 cc) and after filtration and drying 2-carboxy-8-oxo-7-(thien-2-yl-acetamido)-3-(2-tosyloxy-vinyl)-5-thia-1-aza-bicyclo[4.2.0]oct-2-ene (Z-form) (90 mg) is obtained in the form of a cream-coloured powder.

Infrared spectrum (KBr): characteristic bands (cm$^{-1}$) at 3400, 2700, 2200, 1775, 1715, 1670, 1520, 1375, 1190, 1180, 815, 760 and 550.

Proton nuclear magnetic resonance spectrum (350 MHz, DMSO d$_6$, δ in ppm, J in Hz): in particular, the following signals are observed: 6.12 (d, J=17, —C$\underline{H}$=CHOSO$_2$—) and 6.62 (d, J=7, =CHOSO$_2$—).

(b) On following the same procedure as above in (a), but starting from the E-form of 2-benzhydryloxycarbonyl-8-oxo-5-oxide-7-(thien-2-yl-acetamido)-3-(2-tosyloxy-vinyl)-5-thia-1-aza-bicyclo[4.2.0]oct-2-ene (0.78 g), the product obtained after filtration over silica gel is 2-benzhydryloxycarbonyl-8-oxo-7-(thien-2-yl-acetamido)-3-(2-tosyloxy-vinyl)-5-thia-1-aza-bicyclo[4.2.0]oct-2-ene (E-form) (0.60 g) as a cream-coloured powder.

Rf=0.70; silica gel chromatographic plate; solvent: a 1:4 (by volume) mixture of cyclohexane and ethyl acetate.

On following the same procedure as above in (a), but starting from 2-benzhydryloxycarbonyl-8-oxo-7-(thien-2-yl-acetamido)-3-(2-tosyloxy-vinyl)-5-thia-1-aza-bicyclo[4.2.0]oct-2-ene (E-form) (600 mg), 2-carboxy-8-oxo-7-(thien-2-yl-acetamido)-3-(2-tosyloxy-vinyl)-5-thia-1-aza-bicyclo[4.2.0]oct-2-ene (E-form) (70 mg) is obtained in the form of a cream-coloured powder.

Infrared spectrum (KBr): characteristic bands (cm$^{-1}$) at 3380, 2700, 2200, 1775, 1715, 1675, 1525, 1370, 1190, 1180, 815 and 700.

Proton nuclear magnetic resonance spectrum (350 MHz, DMSO d$_6$, δ in ppm, J in Hz): in particular, the following signals are observed: 2.43 (s, 3H, —CH$_3$); 5.08 (d, J=4, 1H, H in the 6-position); 5.65 (dd, J=4 and 9, 1H, H in the 7-position); 6.65 (d, J=9, 1H, —C$\underline{H}$=CHOSO$_2$); 7.17 (d, J=9, =CHOSO$_2$—).

REFERENCE EXAMPLE 60

The product of Example 3 can be employed in the following manner:

The product (10.15 g) of Example 3 is dissolved in anhydrous pyridine (100 cc). The solution is cooled to −10° C. Acetyl chloride (1.57 g) is added dropwise in the course of 15 minutes, whilst stirring at −10° C. The reaction mixture is stirred for 3 hours at a temperature of between 0° and 13° C. and is then concentrated to dryness under reduced pressure (10 mm Hg) at 30° C. The residue is diluted with ethyl acetate (150 cc) and distilled water (100 cc). The aqueous phase is decanted and extracted with ethyl acetate (150 cc). The combined organic phases are washed with distilled water (100 cc), 1 N aqueous hydrochloric acid (2×100 cc) and distilled water (50 cc). They are dried over magnesium sulphate, filtered and concentrated under reduced pressure (20 mm Hg) at 50° C. The residue is dissolved in methylene chloride (200 cc). Silica gel (0.56–0.2 mm) (200 g) is added to the solution obtained and the solvent is evaporated under reduced pressure (20 mm Hg) at 30° C. The powder obtained is deposited at the top of a column (diameter=4.5 cm) of silica gel (0.56–0.2 mm) (200 g). Elution is carried out with a 90:10 (by volume) mixture of cyclohexane and ethyl acetate (500 cc). Thereafter the column is eluted with an 80:20 (by volume) mixture of cyclohexane and ethyl acetate (3 liters), 100 cc fractions being collected. Fractions 6 to 14 are combined and concentrated to dryness under reduced pressure (20 mm Hg) at 30° C. An orange-coloured froth (3.35 g) is obtained. This froth is dissolved in a mixture of cyclohexane (75 cc) and ethyl acetate (13 cc). The solution, when cooled to 4° C., deposits crystals which are filtered off and washed with a 90:10 (by volume) mixture of cyclohexane and ethyl acetate (10 cc) and then with cyclohexane (10 cc), and are dried under reduced pressure (10 mm Hg) at 30° C. 3-(2-Acetoxy-vinyl)-2-benzhydryloxycarbonyl-7-tert.-butoxycarbonylamino-8-oxo-5-thia-1-aza-bicylo[4.2.0]oct-2-ene (E-isomer) (2.3 g) is obtained in the form of beige yellow crystals.

Infrared spectrum (CHBr$_3$): characteristic bands (cm$^{-1}$) at 3420, 1780, 1765, 1720, 1635, 1500, 1450, 1395, 1370, 1200 and 605.

Proton nuclear magnetic resonance spectrum (350 MHz, CDCl$_3$, δ in ppm, J in Hz): 1.48 (s, 9H, (CH$_3$)$_3$C—; 2.15 (s, 3H, —COCH$_3$); 3.57 (AB, J=17, 2H, —S—CH$_2$—); 5.02 (d, J=4, 1H, H in the 5-position); 5.62 (dd, J=4 and 10, 1H, H in the 7-position); 5.75 (d, J=10, 1H, —CONH—); 6.95 (s, 1H, [C$_6$H$_5$]$_2$CH—); 7.02 (d, J=14, 1H, —C$\underline{H}$=CH—O—); 7.64 (d, J=14, 1H, =CH—O—).

The mother liquors give a mixture (1.25 g) of the preceding product and its Z-isomer in the form of a yellow froth.

The Z isomer can be isolated by again chromatographing the above product. Proton nuclear magnetic resonance spectrum (350 MHz, CDCl$_3$, δ in ppm, J in Hz): 1.48 (s, 9H, (CH$_3$)$_3$C—); 2.11 (s, 3H, —COCH$_3$); 3.25 and 3.32 (AB, J=17, 2H, —SCH$_2$—); 5.02 (d, J=4, 1H, H in the 6-position); 5.25 (d, J=10, 1H, —CONH—); 5.62 (dd, J=4 and 10, 1H, H in the 7-position); 6.01 (d, J=7, 1H, —C$\underline{H}$=CH—O—); 6.96 (s, 1H, (C$_6$H$_5$)$_2$CH—); 7.10 (d, J=7, 1H, =CH—O—).

Fractions 15 to 31, when combined and concentrated to dryness under reduced pressure (20 mm Hg) at 30° C., give a yellow froth (3.68 g) consisting of a mixture of 3-(2-acetoxy-vinyl)-2-benzhydryloxycarbonyl-2-tert.-butoxycarbonylamino-8-oxo-5-thia-1-aza-bicyclo[4.2.0]oct-2-ene and oct-3-ene (a mixture of the Z and E isomers).

A mixture of 3-(2-acetoxy-vinyl)-2-benzhydryloxycarbonyl-7-tert.-butoxycarbonylamino-8-oxo-5-thia-1-aza-bicyclo[4.2.0]oct-2-ene (E-form) (1.65 g) (obtained as described above in Example 5), p-toluenesulphonic acid monohydrate (1.14 g) and acetonitrile (50 cc) is stirred for 16 hours at 20° C. It is then taken up in a 5% strength sodium bicarbonate solution (50 cc) and extracted with ethyl acetate (50 cc) and the organic phase is washed with a saturated sodium chloride solution (2×20 cc), dried over sodium sulphate and then concentrated to dryness under reduced pressure (20 mm Hg) at 20° C. 3-(2-Acetoxy-vinyl)-7-amino-2-benzhydryloxycarbonyl-8-oxo-5-thia-1-aza-bicyclo[4.2.0]oct-2-ene (E-form) (1.26 g) is obtained in the form of a crude red oil.

Rf=0.62 [silica gel chromatographic plate, solvent: ethyl acetate].

Thien-2-yl-acetyl chloride (0.63 cc) is added, as a single shot, to a solution, cooled to −10° C., of crude 3-(2-acetoxy-vinyl)-7-amino-2-benzhydryloxycarbonyl-8-oxo-5-thia-1-aza-bicyclo[4.2.0]oct-2-ene (E-form) (2.3 g) in methylene chloride (40 cc) containing triethylamine (0.71 cc). The mixture is stirred for 30 minutes at 0° C. and is then diluted with methylene chloride (100 cc), and this mixture is washed with water (20 cc), a 5% strength sodium bicarbonate solution (20 cc), 1 N hydrochloric acid (20 cc) and water (40 cc), dried over sodium sulphate and evaporated to dryness under reduced pressure (20 mm Hg) at 20° C.

The product is dissolved in a 50:50 (by volume) mixture of cyclohexane and ethyl acetate (20 cc) and the solution is chromatographed on a column (column diameter: 2.5 cm, height: 43 cm) of Merck silica gel (0.05–0.2 mm) (50 g). Elution is carried out with the same mixture of solvents (700 cc), 30 cc fractions being collected. Fractions 6–7 are concentrated to dryness under reduced pressure (20 mm Hg) at 20° C. and a cream-coloured froth (1.60 g) is obtained.

This product is dissolved in hot ethyl acetate (2 cc) and the solution is diluted with cyclohexane (2 cc) and left to crystallise. After filtration and drying, 3-(2-acetoxy-vinyl)-2-benzhydryloxycarbonyl-8-oxo-7-(thien-2-yl-acetamido)-5-thia-1-aza-bicyclo[4.2.0]oct-2-ene (E-form) (0.59 g) is obtained; instantaneous m.p. (Kofler)=180° C.

Infrared spectrum (CHBr3): characteristic bands (cm⁻¹) at 3400, 3340, 1780, 1760, 1715, 1680, 1630, 1505, 1370 and 1195.

Proton nuclear magnetic resonance spectrum (350 MHz, CDCl3, δ in ppm, J in Hz): 2.15 (s, 3H, —OCOCH3); 3.45 (s, 2H, —SCH2—); 3.85 (s, 2H, —CH2CO—); 5 (d, J=5, 1H, H in the 6-position); 5.83 (dd, J=9 and 5, 1H, H in the 7-position); 6.43 (d, J=9, 1H —CONH—); 6.92 (s, 1H, (C6H5)2CH—); 6.95 to 7.05 (mt, 2H, H in the 3- and 4-position of the thiophene); 7 (d, J=13, —CH=CH—O—); 7.59 (d, J=13, =CH—O—).

A solution of 3-(2-acetoxy-vinyl)-2-benzhydryloxycarbonyl-8-oxo-7-(thien-2-yl-acetamido)-5-thia-1-aza-bicyclo[4.2.0]oct-2-ene (E-form) (0.78 g) in trifluoroacetic acid (8 cc) and anisole (0.8 cc) is stirred for 2 hours at +4° C. It is then concentrated to dryness at 20° C. under reduced pressure (20 mm Hg) and the residue is triturated in diethyl ether (20 cc), filtered off and dried. A crude chestnut-coloured solid (0.48 g) is obtained.

The product is purified by dissolving it in a 1% strength sodium bicarbonate solution (200 cc), washing the solution with diethyl ether (2×20 cc), acidifying it to pH 2 with a N hydrochloric acid solution and extracting it with ethyl acetate (3×15 cc). The organic phase is separated off, dried over sodium sulphate and then concentrated to dryness under reduced pressure (20 mm Hg) at 20° C. 3-(2-Acetoxy-vinyl)-2-carboxy-8-oxo-7-(thien-2-yl-acetamido)-5-thia-1-aza-bicyclo[4.2.0]oct-2-ene (E-form) (0.18 g) is obtained in the form of a cream-coloured powder.

Infrared spectrum (KBr): characteristic bands (cm⁻¹) at 3320, 1775, 1760, 1670, 1640, 1530, 1370, 1200 and 700.

Proton nuclear magnetic resonance spectrum (350 MHz, CDCl3, δ in ppm, J in Hz): 2.18 (s, 3H, —COCH3); 3.65 and 3.82 (2d, J=18, 2H, —SCH2—); 5.12 (d, J=4, 1H, H in the 6-position); 5.66 (dd, J=4 and 9, 1H, H in the 7-position); 6.33 (d, J=4, H in the 5-position of the thiophene); 6.81 (d, J=13, 1H, —CH=CH—O—); 6.94 (mt, 2H, H in 3- and 4-positions of the thiophene); 7.68 (d, J=13, 1H, =CH—O—); 9.12 (d, J=9, 1H, —CONH—).

REFERENCE EXAMPLE 61

Following the procedure in reference example 1, but starting from the brown froth (63.8 g) obtained under the conditions described above in Example 2 and tosyl chloride (20.5 g) in pyridine (180 cc), a mixture (68 g) consisting principally of 2-benzhydryloxycarbonyl-7-[D-α-tert.-butoxycarbonylaminophenylacetamido]-8-oxo-3-(2-tosyloxy-vinyl)-5-thia-1-aza-bicyclo[4.2.0]oct-2-ene (Z- and E-forms) is obtained.

A solution of m-chloroperbenzoic acid (3.66 g) in methylene chloride (30 cc) is added dropwise in the course of 30 minutes, with stirring, to a solution, cooled to −5° C., of 2-benzhydryloxycarbonyl-7-(tert.-butoxycarbonyl-D,α-phenylglycylamino)-8-oxo-3-(2-tosyloxy-vinyl)-5-thia-1-aza-bicyclo[4.2.0]oct-2-ene (or oct-3-ene) (a mixture of the E- and Z-forms) (14.3 g) in methylene chloride (120 cc). The mixture is then stirred for 30 minutes at 0° C., after which it is washed with a 2% strength sodium bicarbonate solution (2×250 cc) and distilled water (3×250 cc), dried over sodium sulphate, filtered and concentrated to dryness under reduced pressure (20 mm Hg) at 20° C.

The residue (15 g) is fixed on Merck silica gel (0.05–0.2 mm) (50 g) and the powder is deposited on a column (column height: 30 cm, diameter: 4.5 cm) of Merck silica gel (0.05–0.2 mm) (250 g) which has been prepared with an 80:20 (by volume) mixture of cyclohexane and ethyl acetate. Elution is carried out successively with the same mixture (1 liter) and with a 60:40 (by volume) mixture of cyclohexane and ethyl acetate (2 liters), 200 cc fractions being collected.

Fractions 8 to 12 are concentrated to dryness under reduced pressure. 2-Benzhydryloxycarbonyl-7-(tert-.butoxycarbonyl-D,α-phenylglycylamino)-8-oxo-5-oxide-3-(2-tosyloxy-vinyl)-5-thia-1-aza-bicyclo[4.2.0]oct-2-ene (a mixture of the E- and Z-forms) (8.9 g) is obtained.

Proton nuclear magnetic resonance spectrum (350 MHz, CDCl3, δ in ppm, J in Hz):

E-form: 1.48 (s, 9H, —C(CH3)3); 2.45 (s, 3H, —CH3); 3.49 and 4.34 (2d, J=19, 2H, —SCH2—); 4.93 (d, J=4, 1H, H in the 6-position); 5.37 (d, J=8, >CHC6H5); 5.97 (dd, J=4 and 9, 1H, H in the 7-position); 6.72 (d, J=12, 1H, —CH=CHOSO2—); 6.91 (s, 1H, —COOCH<); 8.38 (d, J=8, 1H, —CONH—); 7.83 (d, J=8, 2H, H in the ortho-position of the tosyl)

Z-form: 2.40 (s, 3H, —CH3); 3.62 and 3.85 (2d, J=19, 2H, —SCH2—); 4.98 (d, J=4, H in the 6-position); 5.87 (dd, J=4 and 9, H in the 7-position); 6.14 (d, J=6, 1H, —CH=CHSO2—); 6.64 (d, J=6, 1H, =CHOSO2—).

REFERENCE EXAMPLE 62

The product (12.9 g) resulting from the acid hydrolysis of the enamine (under the conditions described above) is dissolved in pyridine (50 cc). The solution is cooled to $-7°$ C. and methane sulphochloride (2.4 cc) is added, whilst stirring. The mixture is stirred for $1\frac{1}{2}$ hours at $-10°$ C. and 1 hour at 20° C. It is then poured into iced water (500 cc) and the precipitate is filtered off, washed with water (50 cc) and then dissolved in ethyl acetate (250 cc). The organic phase is washed with 1 N hydrochloric acid (2×100 cc) and with a saturated sodium chloride solution (2×100 cc), dried over sodium sulphate, filtered and evaporated to dryness under reduced pressure (20 mm Hg) at 20° C. The residue is taken up in an 80:20 (by volume) mixture of cyclohexane and ethyl acetate and the solution is chromatographed on a column (column diameter: 2.8 cm, height: 42 cm) of Merck silica gel (0.05-0.2 mm) (100 g). Elution is carried out with the preceding mixture (3 liters), 100 cc fractions being collected. Fractions 9 to 21 are evaporated to dryness under reduced pressure (20 mm Hg) at 20° C. 2-Benzhydryloxycarbonyl-7-tert.-butoxycarbonylamino-3-(2-mesyloxy-vinyl)-8-oxo-5-thia-1-aza-bicyclo[4.2.0]oct-2-ene (5.7 g) is obtained in the form of a yellow froth which consists of a mixture of the E- and Z-forms.

Crystallisation from diethyl ether (15 cc) gives a yellow crystalline product (1.85 g), the structure of which corresponds to that of the E-isomer.

Infrared spectrum (CHBr$_3$): characteristic bands (cm$^{-1}$) at 3420, 1790, 1720, 1510, 1380, 1370, 1185, 1085 and 770.

Proton nuclear magnetic resonance spectrum (350 MHz, CDCl$_3$, δ in ppm, J in Hz): 1.47 (s, 9H, (CH$_3$)$_3$C+); 3.04 (s, 3H, CH$_3$SO$_2$+); 3.48 and 3.57 (2d, J=17.5, 2H, —S—CH$_2$—); 5.02 (d, J=5, 1H, H in the 6-position); 5.25 (d, J=9, —CONH—); 5.66 (dd, J=5 and 9, 1H, H in the 7-position); 6.94 (s, 1H, —COOCH<); 6.96 and 7.04 (2d, J=13, 2H, —CH=CH—).

REFERENCE EXAMPLE 63

2-Benzhydryloxycarbonyl-7-tert.-butoxycarbonylamino-3-(2-dimethylamino-vinyl)-8-oxo-5-thia-1-aza-bicyclo[4.2.0]oct-2-ene (E-form) (42 g) obtained as described in Example 1 is hydrolysed in a mixture of tetrahydrofurane (770 cc), distilled water (391 cc) and pure formic acid (39.1 cc) in accordance with the method of Example 1. An orange-brown froth (39.1 g) is obtained, which is dissolved in pyridine (385 cc). Acetyl chloride (6.04 cc) is added dropwise, in the course of 15 minutes, to the solution, cooled to $-10°$ C. The reaction mixture is stirred for 30 minutes at $-10°$ C. and then for $2\frac{1}{2}$ hours at a temperature of between $-10°$ and $+20°$ C., after which it is poured into an ice/water mixture (3 liters). The precipitate is filtered off, washed with distilled water (2×1 liter) and then redissolved in methylene chloride (1050 cc). The organic solution is washed with distilled water (1 liter) and 1 N hydrochloric acid (2×200 cc) and is then dried over magnesium sulphate and filtered. The solution is partially concentrated, under reduced pressure (20 mm Hg at 30° C.), to a residual volume of 700 cc. This residue is cooled to $-10°$ C. and a solution of m-chloroperbenzoic acid (12.8 g) in dry methylene chloride (380 cc) is added dropwise in the course of 20 minutes. The reaction mixture is stirred for 40 minutes at 0° C. and then washed with a saturated sodium bicarbonate solution (2×200 cc) and with distilled water (250 cc). After drying the solution over magnesium sulphate, and filtering, the solvent is evaporated under reduced pressure (20 mm Hg) at 30° C. A chestnut-coloured froth (41.3 g) is obtained, which is then fixed on Merck silica (0.05-0.2 mm) (200 g) and deposited on a column (5 cm diameter) packed with Merck silica (0.05-0.2 mm) (400 g) in a 70:30 (by volume) mixture of cyclohexane and ethyl acetate. Elution is carried out with the same mixture (1.7 liters), 300 cc fractions being collected. Fractions 21 to 29 are concentrated to dryness, the residue (13.2 g) is triturated with isopropyl ether (100 cc) and the solid is filtered off and recrystallised from a 70:30 (by volume) mixture of cyclohexane and ethyl acetate (50 cc). 3-(2-Acetoxyvinyl)-2-benzhydryloxycarbonyl-7-tert.-butoxycarbonylamino-8-oxo-5-oxide-5-thia-1-aza-bicyclo[4.2.0]oct-2-ene (E-form) (7.8 g) is obtained in the form of white crystals.

M.p.=210° C.

Rf=0.38; silica gel chromatographic plate; eluant: a 50:50 (by volume) mixture of cyclohexane and ethyl acetate.

Proton nuclear magnetic resonance spectrum (350 MHz, CDCl$_3$, δ in ppm, J in Hz): 1.48 (s, 9H, (CH$_3$)$_3$C—); 2.15 (s, 3H, CH$_3$COO—); 3.24 and 3.96 (2d, J=19, 2H, —S(O)CH$_2$—); 4.53 (d, J=4, 1H, H in the 6-position); 5.72 (dd, J=4 and 9, 1H, H in the 7-position); 5.74 (d, J=9, 1H, >NH); 6.94 (s, 1H, —COOCH); 7.30 (d, J=13, 1H, —CH=CH—OCO—); 7.60 (d, J=13, 1H, —CH=CH—OCO—).

Thereafter, a mixture (7.5 g) of the 3-(2-acetoxyvinyl)-2-benzhydryloxycarbonyl-7-tert.-butoxycarbonylamino-8-oxo-5-oxide-1-aza-bicyclo[4.2.0]oct-2-enes (E- and Z-forms) is eluted in fractions 30 to 56.

Proton nuclear magnetic resonance spectrum (350 MHz, CDCl$_3$, δ in ppm, J in Hz): for the Z isomer, the following signals, inter alia, are observed: 2.14 (s, 3H, CH$_3$COO—); 3.41 and 4.30 (2d, J=21, 2H, —S(O)CH$_2$—); 6.95 (d, J=10, 1H, —CH=CHOCO—); 7.58 (d, J=10, 1H, —CH=CHOCO—).

REFERENCE EXAMPLE 64

The product of Example 5 can be employed in the following manner:

A solution of the syn isomer of 2-benzhydryloxycarbonyl-7-[2-methoxyimino-2-(2-tritylamino-thiazol-4-yl)-acetamido]-8-oxo-3-(2-oxo-ethyl)-5-thia-1-aza-bicyclo[4.2.0]oct-2-ene (0.833 g) and p-toluenesulphonyl chloride (0.228 g) in methylene chloride (16 cc) is cooled to 3° C. in an ice bath. A solution of triethylamine (0.155 cc) in methylene chloride (8 cc) is added in the course of 15 minutes, the mixture is left for a further 20 minutes at 3° C., and the temperature is then allowed to return to about 20° C. in the course of 30 minutes. Thereafter the reaction mixture is washed with a saturated sodium bicarbonate solution (2×20 cc) and a saturated sodium chloride solution (2×20 cc), dried over magnesium sulphate, filtered and evaporated to dryness under reduced pressure (20 mm Hg) at 30° C. The residue is dissolved in ethyl acetate (2 cc) and the solution is filtered in the presence of decolorising charcoal, diluted with isopropyl ether (15 cc) and filtered again. The precipitate (0.550 g) consists principally of a mixture of the syn isomer, E-form of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene [nuclear magnetic resonance spectrum (350 MHz, CDCl$_3$, δ in ppm) —characteristic bands at 3.37 and 3.49 (AB J=19 Hz, 2H, —S—CH2— cephem); 5.07 (d, J=4 Hz, H in the 6-position); 5.92 (dd, J=4 and 9 Hz, H in the 7-position)] and of the syn isomer, E-form of 2-benzhydryloxycarbonyl-7-[2-methoxyimino-2-(2-tritylamino-thiazol-4-yl)acetamido]-8-oxo-3-(2-tosyloxy-vinyl)-5-thia-1-azabicyclo[4.2.0]oct-3-ene [nuclear magnetic resonance spectrum (350 MHz, CDCl3, δ in ppm)—characteristic bands at 5.07 (s, 1H, H in the 2-position); 5.32 (d, J=4 Hz, H in the 6-position); 5.68 (dd, J=4 and 9 Hz, H in the 7-position); 6.19 (s, 1H, H in the 4-position)].

REFERENCE EXAMPLE 65

A solution of 2-benzhydryloxycarbonyl-8-oxo-3-(2-oxo-ethyl)-7-tritylamino-5-thia-1-aza-bicyclo[4.2.0]oct-2-ene (10 g) and p-toluenesulphonyl chloride (3.14 g) in tetrahydrofurane (80 cc) is cooled to −10° C. and then treated with triethylamine (2.1 cc); the reaction mixture is then stirred for 2 hours 30 minutes at a temperature of between 10° and 20° C., before being diluted with ethyl acetate (500 cc). The resulting solution is washed successively with distilled water (2×150 cc) and a saturated sodium chloride solution (200 cc) and is decanted and dried over magnesium sulphate. The residue obtained after concentration to dryness under reduced pressure (30 mm Hg; 4 kPa) at 30° C. is filtered over a column (height: 40 cm, diameter: 4 cm) of silica (0.067–0.2 mm), elution being carried out with a 1:1 (by volume) mixture of cyclohexane and ethyl acetate, and 125 cc fractions being collected. Fractions 2 to 7 are combined and concentrated under reduced pressure (30 mm Hg; 4 kPa) at 30° C. to give an orange-coloured froth (9 g) consisting principally of 2-benzhydryloxycarbonyl-8-oxo-3-(2-tosyloxy-vinyl)-7-tritylamino-5-thia-1-aza-bicyclo[4.2.0]oct-2-ene (a 2:1 mixture of the E- and Z-forms). This product is dissolved in dry methylene chloride (60 cc). After cooling to −10° C., a solution of 85% strength meta-chloroperbenzoic acid (2.25 g) in dry methylene chloride (25 cc) is added in the course of 5 minutes. After 30 minutes at −10° C., the reaction mixture is filtered and the filtrate is washed with a saturated sodium bicarbonate solution (150 cc) and a saturated sodium chloride solution (100 cc). The solvent is evaporated under reduced pressure (60 mm Hg; 8 kPa) at 40° C. and the residue is chromatographed on a column (height: 40 cm, diameter: 6 cm) of silica gel (0.04–0.06 mm), elution being carried out with a 25:75 (by volume) mixture of cyclohexane and ethyl acetate (4.5 liters) under a pressure of 0.5 bar, and 120 cc fractions being collected. The combined fractions 21 to 34 are concentrated to dryness under reduced pressure (30 mm Hg; 4 kPa) at 40° C., to give 2-benzhydryloxycarbonyl-8-oxo-5-oxide-3-(2-tosyloxy-vinyl)-7-tritylamino-5-thia-1-aza-bicyclo[4.2.0]oct-2-ene (a 70:30 mixture of the E- and Z-forms) (3.15 g) in the form of a cream-coloured solid.

Infrared spectrum (CHBr3): characteristic bands (cm$^{-1}$) at 3340, 1790, 1720, 1375, 1190, 1175, 1070, 1050 and 550.

Proton nuclear magnetic resonance spectrum (350 MHz, CDCl3, δ in ppm, J in Hz):

(a) E-form: 2.42 (s, 3H, CH3—); 2.77 and 3.45 (2d, J=18, 2H, —SOCH2—); 3.50 (d, J=12, 1H, NH); 3.52 (d, J=4, 1H, H in the 6-position); 4.84 (dd, J=4 and 12, 1H, H in the 7-position); 6.75 and 6.90 (2d, J=12, 2H, —CH=CH—O—); 6.88 (s, 1H, —CO2CH<); 7.2 to 7.60 (aromatics).

(b) Z-form: 2.42 (s, 3H, —CH3); 3.02 and 3.75 (2d, J=18, 2H, —SOCH2—); 3.49 (d, J=4, 1H, H in the 6-position); 3.50 (d, J=12, 1H, >NH); 4.84 (dd, J=4 and 12, 1H H in the 7-position); 6.23 and 6.31 (2d, J=7, 2H, —CH=CH—O—); 6.85 (s, 1H, —CO2CH<); 7.2 to 7.60 (aromatics).

A solution of 2-benzhydryloxycarbonyl-3-(2-dimethylaminovinyl)-8-oxo-7-tritylamino-5-thia-1-aza-bicyclo[4.2.0]oct-2-ene (E-form) (23.5 g) in ethyl acetate (500 cc) is stirred with 1 N hydrochloric acid (250 cc) for 90 minutes at 25° C. The organic phase is decanted, washed with distilled water (3×250 cc), a saturated sodium bicarbonate solution (100 cc) and a half-saturated sodium chloride solution (250 cc), then dried over sodium sulphate and concentrated to dryness under reduced pressure (40 mm Hg) at 40° C. 2-Benzhydryloxycarbonyl-8-oxo-3-(2-oxo-ethyl)-7-tritylamino-5-thia-1-aza-bicyclo[4.2.0]oct-2-ene (21 g) is obtained in the form of an orange-coloured froth.

Proton nuclear magnetic resonance spectrum (350 MHz, CDCl3, δ in ppm, J in Hz): 2.99 (d, J=9, 1H, NH); 3.07 and 3.33 (2d, J=18, 2H, —SCH2); 3.50 (AB, J=14, 2H, —CH2CHO); 4.30 (d, J=4, 1H, H in the 6-position); 4.75 (dd, J=4 and 9, 1H, H in the 7-position); 6.82 (s, 1H, —CO2CH(C6H5)2); 7.20 to 7.60 (hump, 25H, aromatics); 9.46 (s, 1H, —CHO).

tert.-Butoxy-bis-dimethylaminomethane (10.8 cc) is added to a solution of a mixture (21.8 g) of 2-benzhydryloxycarbonyl-3-methyl-8-oxo-7-tritylamino-5-thia-1-aza-bicyclo[4.2.0]oct-2-ene (40%) and its oct-3-ene isomer (60%) in dry N,N-dimethylformamide (120 cc) heated to 80° C. under nitrogen. After 5 minutes at 80° C., the reaction mixture is poured into ethyl acetate (500 cc). Distilled water (250 cc) is added, the mixture is stirred, and the organic phase is decanted, washed with distilled water (3×250 cc), then dried over magnesium sulphate and concentrated under reduced pressure (40 mm Hg) at 40° C. Examination, by thin layer chromatography, of the residue shows the presence of unchanged starting material. The product is redissolved in dry N,N-dimethylformamide (100 cc), the solution is heated to 80° C. under nitrogen, and after addition of tert.-butoxybis-dimethylaminoethane (6 cc) the reaction mixture is kept at 80° C. for 5 minutes. It is then diluted with ethyl acetate (500 cc) and treated as above, to give an orange froth (24 g) consisting principally of 2-benzhydryloxycarbonyl-3-(2-dimethylamino-vinyl)-8-oxo-7-tritylamino-5-thia-1-aza-bicyclo[4.2.0]oct-2-ene (E-form).

We claim:

1. A cephalosporin derivative of the formula

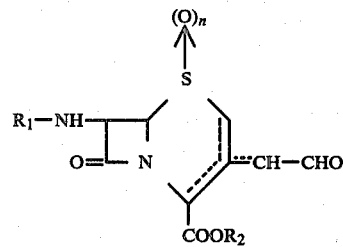

in which n is 0 or 1, (a) the symbol $R_1$ represents a radical of the formula

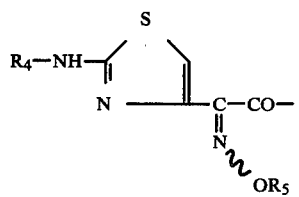

in the syn or anti form [in which R₄ is an amino protecting radical and R₅ is a hydrogen atom, an alkyl, vinyl or cyanomethyl radical or an oxime protecting group], a benzhydryl or trityl radical, an acyl radical of the formula

R₆CO— in which R₆ is a hydrogen atom or an alkyl radical [said alkyl being unsubstituted or substituted by one or more halogen atoms or by a phenyl or phenoxy radical] or phenyl, a radical of the formula

R₇OCO—

{in which R₇ is a branched unsubstituted alkyl radical or a straight or branched alkyl radical carrying one or more substituents [chosen from halogen atoms and cyano, trialkylsilyl, phenyl and substituted phenyl (the substituents being one or more alkoxy, nitro or phenyl radicals)], vinyl, allyl or quinolyl}, or a nitrophenylthio radical or R₁NH= is replaced by a methyleneimino radical, in dialkylamino or phenyl group (said phenyl being unsubstituted or substituted by one or more methoxy or nitro radicals) and the symbol R₂ represents an enzymatically easily removable radical of the formula

—CH—OCOR₈
  |
  R₉

[in which R₈ represents an alkyl radical or the cyclohexyl radical and R₉ represents a hydrogen atom or an alkyl radical] or a carboxyl protecting radical chosen from methoxymethyl, tert.-butyl, benzhydryl, p-nitrobenzyl or p-methoxybenzyl, or (b) the symbol R₁ represents an alkanoyl radical containing 1 to 8 carbon atoms, a substituted alkanoyl radical containing 2 to 8 carbon atoms (the substituents being chlorine or bromine atoms), an acyl radical of the formula

```
     Q
     |
AR—C—CO—
     |
     Q
``` in which each Q is H or methyl and Ar represents a thien-2-yl, thien-3-yl, fur-2-yl, fur-3-yl, pyrrol-2-yl, or pyrrol-3-yl radical or a phenyl radical [said phenyl being unsubstituted or substituted by halogen atoms or by hydroxyl, alkyl (containing 1 to 3 carbon atoms) or alkoxy (containing 1 to 3 carbon atoms) radicals, of which at least one is situated in the meta- or in the para-position of the phenyl radical], an acyl radical of the formula Ar—X—CH₂—CO— in which X is oxygen or sulphur and Ar is as hereinbefore defined, or Ar-X- represents pyrid-4-ylthio, an acyl radical of the formula Ar—CH—CO—
   |
   B in which Ar is as hereinbefore defined and B represents an amino radical which is protected [by a benzyloxycarbonyl, alkoxycarbonyl, cyclopentyloxy-carbonyl, cyclohexyloxycarbonyl, benzhydryloxycarbonyl, trityl or 2,2,2-trichloroethoxycarbonyl group], a sulpho radical, a hydroxyl radical or a carboxyl radical [said hydroxyl and carbonyl being unprotected or protected by esterification, respectively with an alkanoic acid or an alcohol (containing 1 to 6 carbon atoms)] or a 5-amino-adipyl radical [in which the amino group is protected by an alkanoyl radical (containing 1 to 3 carbon atoms and unsubstituted or substituted by a chlorine atom) and in which the carboxyl group is protected by a benzhydryl, 2,2,2-trichloroethyl, tert.-alkyl (containing 4 to 6 carbon atoms) or nitrobenzyl group] or R₁NH is replaced by a cyclic imide group of a dicarboxylic acid and the symbol R₂ represents a tert.-alkyl radical containing 4 to 6 carbon atoms, a tert.-alkenyl radical containing 6 or 7 carbon atoms, a tert.-alkynyl radical containing 6 or 7 carbon atoms, benzyl, methoxybenzyl, nitrobenzyl, 2,2,2-trichloroethyl benzhydryl, succinimidomethyl or phthalimidomethyl, the alkyl or acyl portions or radicals which have been referred to above being (unless stated to the contrary) straight or branched and containing 1 to 4 carbon atoms, and the product being in the 3-oxoethyl-bicyclooct-2-ene or 3-oxoethylbicyclooct-3-ene or 3-oxoethylidene-bicyclooctane form if n=0 and in the 3-oxoethyl-bicyclooct-2-ene or 3-oxoethylidene-bicyclooctane form if n=1, and the mixtures of their isomers.

2. A compound according to claim 1, in which n and R₂ are as defined in claim 1, and R₁ represents a radical of the formula

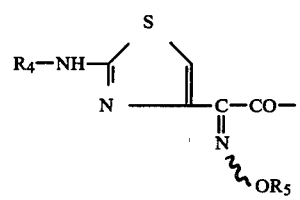

(in the syn or anti form), in which R₄ is a tert.-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl radical and R₅ is a hydrogen atom or an alkyl, trityl, tetrahydropyranyl or 2-methoxyprop-2-yl radical.

3. A compound according to claim 1 in which n is as defined in claim 1, (a) the symbol R₁ is a radical of the formula

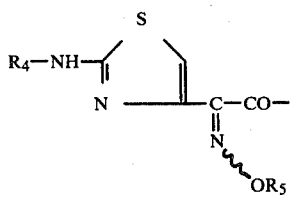

as defined in claim 1, a trityl radical, a radical of the formula

R₆CO— in which R₆ is an alkyl radical containing 1 or 2 carbon atoms (said alkyl being unsubstituted or substituted by a phenyl or phenoxy radical) or phenyl, or a radical of the formula

R₇OCO— in which R₇ is a branched unsubstituted alkyl radical, and the symbol R₂ is a carbonyl protective radical as defined in claim 10, or (b) the symbol R₁ is an acyl radical of the formula

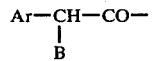

in which Ar represents a phenyl radical and B represents a protected amino radical and the symbol R₂ has the corresponding definition, given in claim 10, the product being in the bicyclooct-2-ene or bicyclooct-3-ene form if n=0 and in the bicyclooct-2-ene form if n=1, and the mixtures of their isomers.

4. A compound according to claim 1, in which n is as defined in claim 1, (a) the symbol R₁ is a radical of the formula

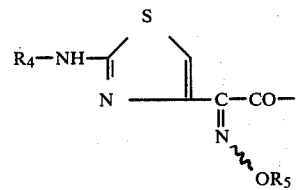

(in which R₅ is an alkyl or vinyl radical and R₄ is trityl), a trityl radical, a radical of the formula

R₆CO— in which R₆ is an alkyl radical containing 1 or 2 carbon atoms (said alkyl being unsubstituted or substituted by a phenyl or phenoxy radical) or phenyl, or a radical of the formula

R₇OCO—

[in which R₇ is a branched unsubstituted alkyl radical containing 3 or 4 carbon atoms] and the symbol R₂ is a benzhydryl or p-nitrobenzyl radical or (b) the symbol R₁ is an acyl radical of the formula

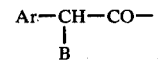

in which Ar is a phenyl radical and B is an amino radical protected by an alkoxycarbonyl group of which the alkyl part contains 1 to 4 carbon atoms and the symbol R₂ is a benzhydryl or nitrobenzyl radical, the product being in the bicyclooct-2-ene or bicyclooct-3-ene form if n=0 and in the bicyclooct-2-ene form if n=1, as well as the mixtures of their isomers.

5. A compound according to claim 3 in which R₁ represents a radical of the formula:

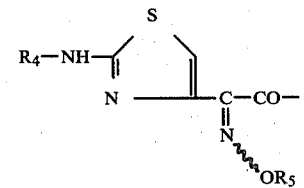

(in the syn or anti form), in which R₄ is a tert.-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl radical and R₅ is a hydrogen atom or an alkyl, trityl, tetrahydropyranyl or 2-methoxyprop-2-yl radical.

6. 2-Benzhydryloxycarbonyl-7-tert.-butoxycarbonylamino-8-oxo-3-(2-oxoethyl)-5-thia-1-azabicyclo[4.2.0]oct-2-ene.

7. 2-Benzhydryloxycarbonyl-8-oxo-3-(2-oxoethyl)-7-tritylamino-5-thia-1-aza-bicyclo[4.2.0]oct-2-ene.

8. 2-Benzhydryloxycarbonyl-8-oxo-3-(2-oxoethyl)-7-phenylacetamido-5-thia-1-aza-bicyclo[4.2.0]oct-2-ene.

9. 2-Benzhydryloxycarbonyl-8-oxo-3-(2-oxoethyl)-7-phenoxyacetamido-5-thia-1-aza-bicyclo[4.2.0]oct-2-ene.

10. 2-Benzhydryloxycarbonyl-7-[2-methoxyimino-2-(2-tritylamino-thiazol-4-yl)-acetamido[-8-oxo-3-(2-oxoethyl)-5-thia-1-aza-bicyclo[4.2.0]oct-2-ene.

* * * * *